US010239948B2

(12) United States Patent
Juillerat et al.

(10) Patent No.: US 10,239,948 B2
(45) Date of Patent: Mar. 26, 2019

(54) METHOD OF ENGINEERING MULTI-INPUT SIGNAL SENSITIVE T CELL FOR IMMUNOTHERAPY

(71) Applicant: CELLECTIS, Paris (FR)

(72) Inventors: Alexandre Juillerat, New York, NY (US); Claudia Bertonati, Saint Louis (FR); Julien Valton, New York, NY (US); Philippe Duchateau, Draveil (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/106,783

(22) PCT Filed: Dec. 19, 2014

(86) PCT No.: PCT/EP2014/078876
§ 371 (c)(1),
(2) Date: Jun. 20, 2016

(87) PCT Pub. No.: WO2015/092024
PCT Pub. Date: Jun. 25, 2015

(65) Prior Publication Data
US 2017/0073423 A1    Mar. 16, 2017

(30) Foreign Application Priority Data
Dec. 20, 2013    (DK) .................................. 2013 70806

(51) Int. Cl.
*C07K 14/47* (2006.01)
*C07K 16/30* (2006.01)
(Continued)

(52) U.S. Cl.
CPC .............. *C07K 16/30* (2013.01); *C07K 14/47* (2013.01); *C07K 16/2863* (2013.01);
(Continued)

(58) Field of Classification Search
CPC ................ C07K 14/47; C07K 16/2863; C07K 16/2866; C07K 16/2896; C07K 16/30;
(Continued)

(56) References Cited

U.S. PATENT DOCUMENTS 8,822,647 B2 *  9/2014  Jensen ................. A61K 48/005
                                                            424/93.21
2006/0233791 A1 * 10/2006 Tedder ............... C07K 16/2803
                                                            424/141.1

(Continued)

FOREIGN PATENT DOCUMENTS

WO        02/074981 A2    9/2002
WO     2006/016143 A1    2/2006
(Continued)

OTHER PUBLICATIONS

Ang et al, Mol. Therapy 17(Suppl 1): Abstract 62, S25-S26, May 2009.*

(Continued)

*Primary Examiner* — Kevin K Hill
(74) *Attorney, Agent, or Firm* — Arrigo, Lee, Guttman & Mouta-Bellum, LLP

(57) ABSTRACT

The present invention relates to a method to engineer immune cell for immunotherapy. In particular said immune cells are engineered with chimeric antigen receptors, which be activated by the combination of hypoxia and ligand extracellular binding as input signals. The invention also relates to new designed chimeric antigen receptors which are able to redirect immune cell specificity and reactivity toward a selected target exploiting the ligand-binding domain properties and the hypoxia condition. The present invention also relates to cells obtained by the present method, in particular (Continued)

Figure 1:
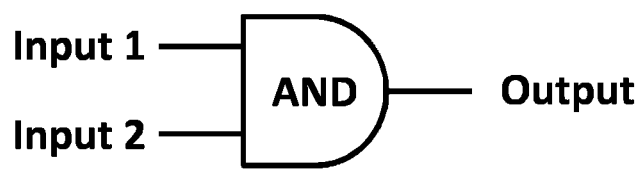

T-cells, comprising said chimeric antigen receptors for use in cancer treatments.

9 Claims, 38 Drawing Sheets

Specification includes a Sequence Listing.

(51) Int. Cl.
  *C07K 16/46* (2006.01)
  *C07K 16/28* (2006.01)
(52) U.S. Cl.
  CPC ...... *C07K 16/468* (2013.01); *C07K 2317/622* (2013.01); *C07K 2319/03* (2013.01); *C07K 2319/30* (2013.01); *C12N 2510/02* (2013.01)
(58) Field of Classification Search
  CPC .................. C07K 16/46; C07K 16/468; C07K 2317/622; C07K 2319/03; C07K 2319/30; C12N 2510/00; C12N 2510/02
  See application file for complete search history.

(56) References Cited

U.S. PATENT DOCUMENTS

| | | | |
|---|---|---|---|
| 2009/0148447 A1* | 6/2009 | Ledbetter | C07K 16/2803 424/134.1 |
| 2013/0315884 A1* | 11/2013 | Galetto | A61K 35/17 424/93.71 |
| 2014/0322183 A1* | 10/2014 | Milone | C07K 16/18 424/93.21 |
| 2015/0266973 A1* | 9/2015 | Jarjour | C07K 14/7056 424/93.21 |
| 2016/0145337 A1* | 5/2016 | Galetto | C12N 5/0636 424/93.21 |
| 2016/0215261 A1 | 7/2016 | Li et al. | |

FOREIGN PATENT DOCUMENTS

| | | | |
|---|---|---|---|
| WO | 2008/015675 A2 | | 2/2008 |
| WO | WO 12/079000 | * | 6/2012 |
| WO | 2012/099973 A2 | | 7/2012 |
| WO | WO 2013/123061 A1 | | 8/2013 |
| WO | WO 2013/176915 A1 | | 11/2013 |
| WO | WO 13/185552 | * | 12/2013 |
| WO | 2014/153270 A1 | | 9/2014 |
| WO | 2014/184143 A1 | | 11/2014 |

OTHER PUBLICATIONS

Karlos et al, Science Translational Medicine 3(95):95ra73, 12 pages, Aug. 10, 2011.*
Cooper, OMB#0704-0188, Grant# W81XWH-10-1-0765, Sep. 2011.*
Wang et al, GenBank Q16665, 1997.*
Jonnalagadda et al, Molecular Therapy 23(4): 757-768, 2015.*
Agnes Shuk Yee Lo et al., "Harnessing the tumor-derived cytokine, CSF-1 to co-stimulate T-cell growth and activation," Molecular Immunology, vol. 45, 2008, pp. 1276-1287.
Allen R. Buskirk et al., "Creating Small-Molecule-Dependent Switches to Modulate Biological Functions," Chemistry & Biology, vol. 12, Feb. 2005, pp. 151-161.
Christopher C. Kloss et al., "Combinatorial antigen recognition with balanced signaling promotes selective tumor eradication by engineered T cells," Nature Biotechnology, vol. 31, No. 1, Jan. 2013, pp. 71-76.
David Marc Davies et al., "Adoptive T-cell Immunotherapy of Cancer Using Chimeric Antigen Receptor-Grafted T Cells," Arch. Immunol. Ther. Exp., vol. 58, 2010, pp. 165-178.
Ernesto Andrianantoandro et al., "Synthetic Biology: new engineering rules for an emerging discipline," Molecular Systems Biology, XP-002456698, 2006, pp. 1-14.
International Search Report issued in International Patent Application No. PCT/EP2014/078876 dated Jun. 25, 2015.
Pawel Kalinski et al., "Polarized dendritic cells as cancer vaccines: Directing effector-type T cells to tumors," Seminars in Immunology, vol. 22, 2010, pp. 173-182.
Roy Gross, "Signal Transduction and virulence regulation in human and animal pathogens," FEMS Microbiology Reviews, vol. 104, 1993, pp. 301-326.
Sonny O. Ang et al., "Conditional Activation of T Cells of Specifically Target c-Met under Hypoxia," Molecular Therapy, vol. 17, XP009183317, May 2009, pp. 1-2.
Sonny O. Ang et al., "Conditional T-Cell Activation for Tumor Under Hypoxia," Blood (ASH Annual Meeting Abstracts) 2008, 112: Abstract 3906, XP009183313, pp. 1-2.
Sujan S. Shekhawat et al., "Split-protein systems: beyond binary protein-protein interactions," Current Opinion in Chemical Biology, vol. 15, 2011, pp. 789-797.
Tarik F Massoud et al., "A molecularly engineered split reporter for imaging protein-protein interactions with positron emission tomography," Nature Medicine, vol. 16, No. 8, Aug. 2010, pp. 921-926.
Terrence L. Geiger et al., "Development and Application of Receptor-Modified T Lymphocytes for Adoptive Immunotherapy," Transfusion Medicine Reviews, vol. 15, No. 1, Jan. 2001, pp. 21-34.
Wendell A. Lim, "Designing customized cell signaling circuits," Nature Reviews, Molecular Cell Biology, vol. 11, Jun. 2010, pp. 1-12.
Xiao-Song Zhong et al., "Chimeric Antigen Receptors Combining 4-1 BB and CD28 Signaling Domains Augment PI3 kinase/AKT/Bcl-XL Activation and CD8 + T Cell-mediated Tumor Eradication," Molecular Therapy, vol. 18, No. 2, Feb. 2010, pp. 413-420.
Zahra Sharifzadeh et al., "Genetically engineered T cells bearing chimeric nanoconstructed receptors harboring TAG-72-specific camelid single domain antibodies as targeting agents," Cancer Letters, vol. 334, 2013, pp. 237-244.

* cited by examiner

AND logic gate

| Input 1 | Input 2 | Output |
|---------|---------|--------|
| 0 | 0 | 0 |
| 1 | 0 | 0 |
| 0 | 1 | 0 |
| 1 | 1 | 1 |

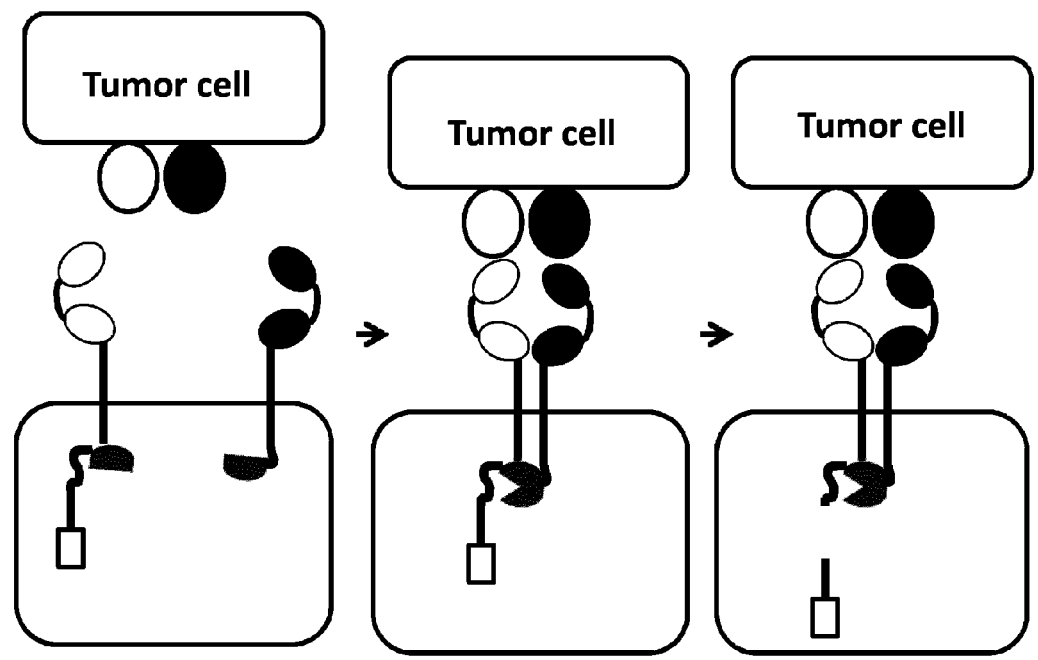
| 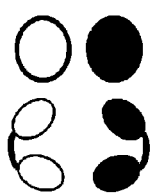 | Tumor cell ligand |
|---|---|
| 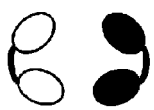 | Extracellular ligand-binding domain |
|  | N- and C-terminal domains of a split protease |
|  | Protease target sequence |
|  | Reconstituted protease "active" |
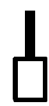 Signaling protein
Fig. 9

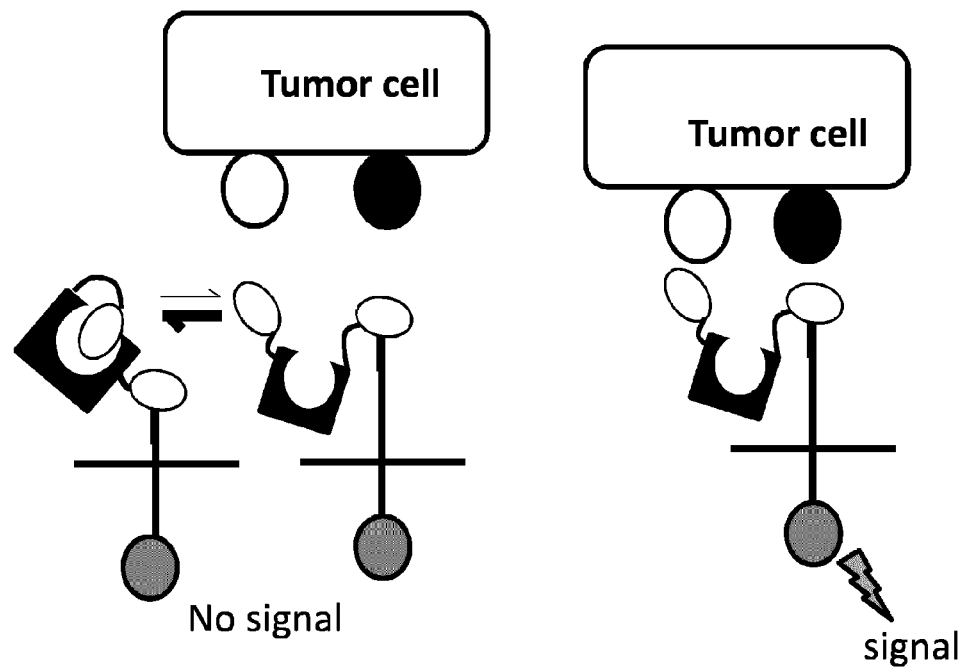
 Tumor cell ligand
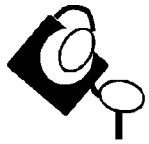 Extracellular ligand-binding domain "inactive"
 Extracellular ligand-binding domain "active"
 Transmitter domain
Fig. 18

AND logic gate

| Input 1 | Input 2 | Input 3 | Output |
|---|---|---|---|
| 0 | 0 | 0 | 0 |
| 1 | 0 | 0 | 0 |
| 0 | 1 | 0 | 0 |
| 0 | 0 | 1 | 0 |
| 1 | 1 | 0 | 1 |
| 1 | 0 | 1 | 0 |
| 0 | 1 | 1 | 0 |
| 1 | 1 | 1 | 0 |

A
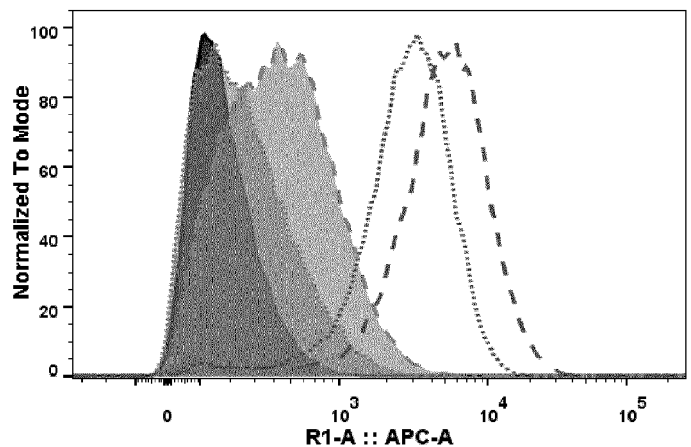
B
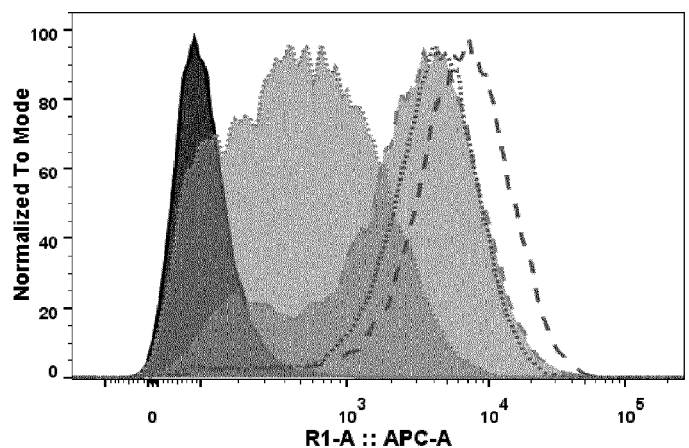
Fig. 24
| Sample | Conditions | Histogram |
|---|---|---|
| Isotype control | Hypoxia | solide line-dark Filled |
| α β γ | Normoxia | Dotted line |
| α β γ | Hypoxia | Dashed line |
| α-HIF β γ | Normoxia | Dotted line-Filled |
| α-HIF β γ | Hypoxia | Dashed line-Filled |

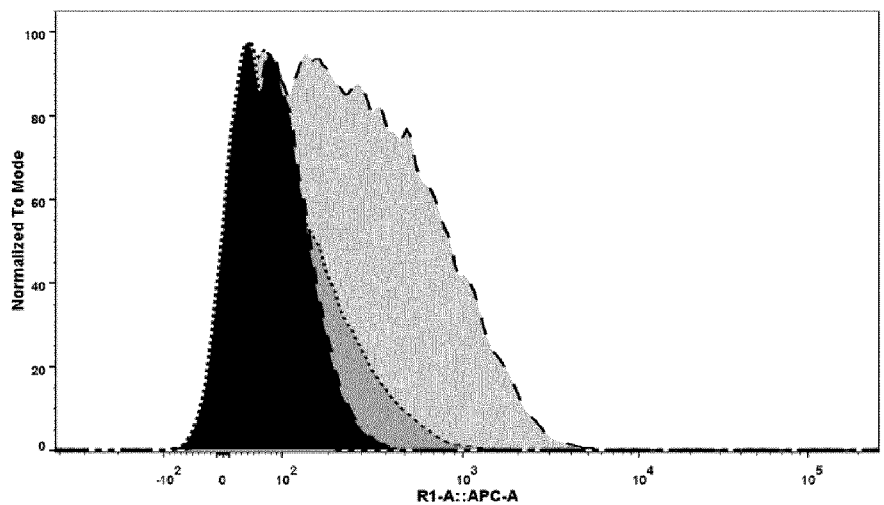
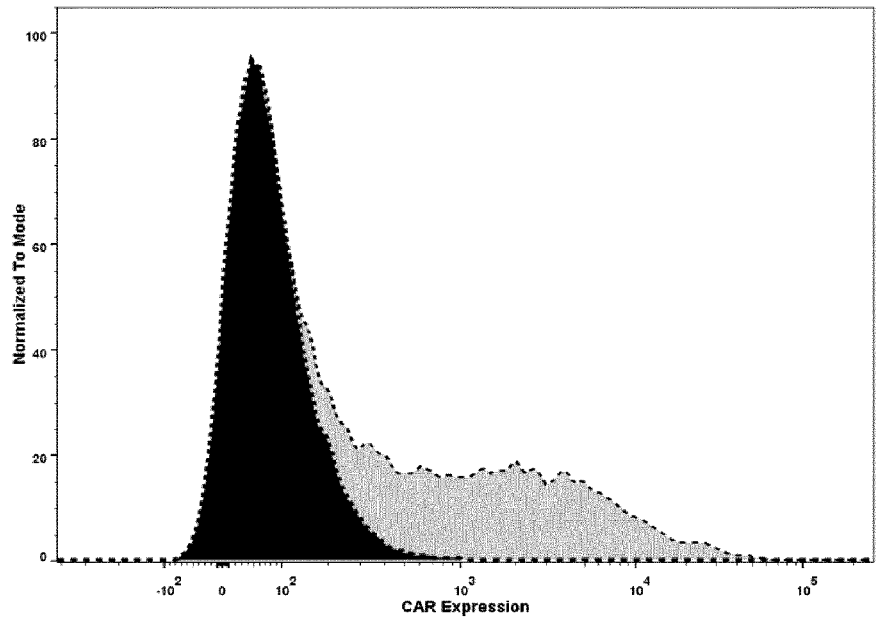
Fig. 25

A
B
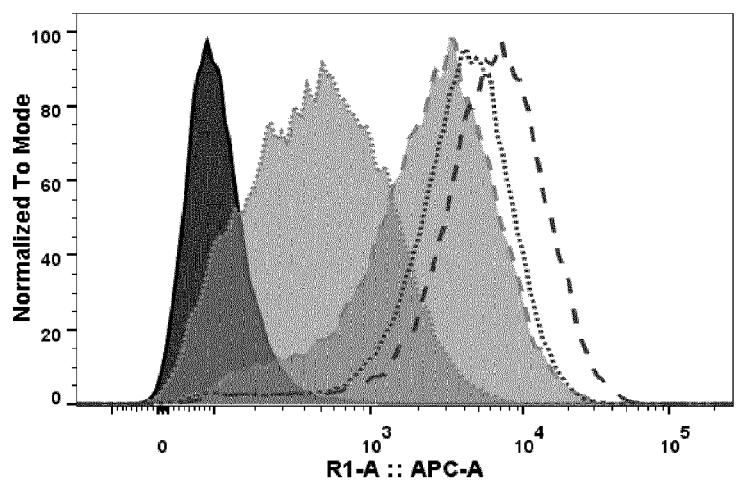
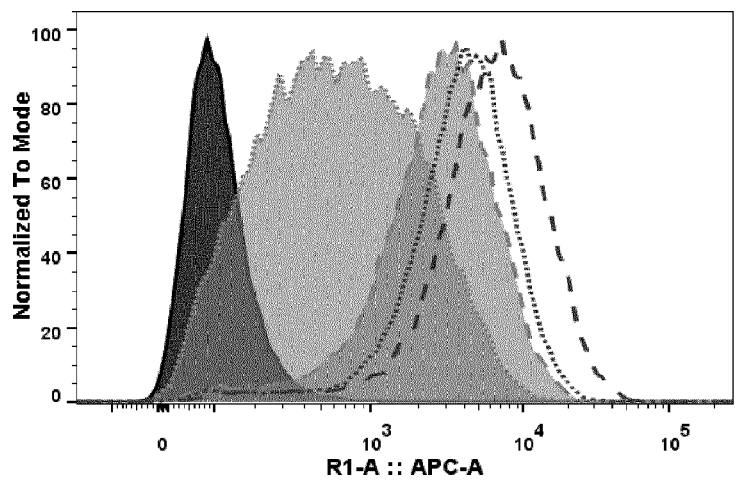
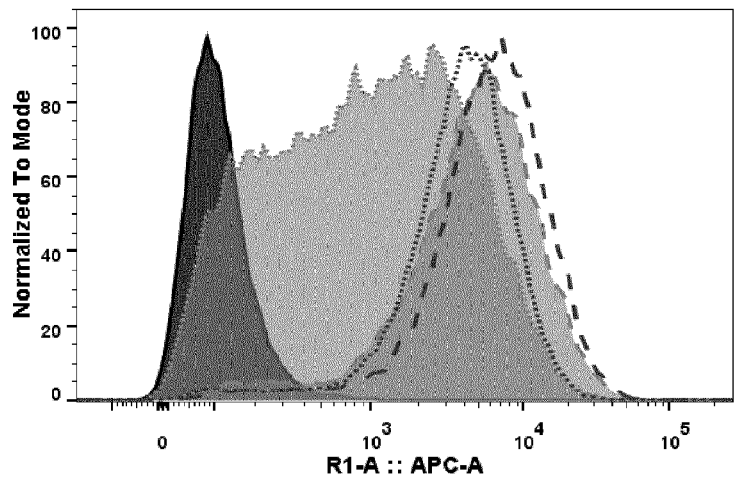
C
(The legends are inserted in the figures description)
Fig. 26A-C D 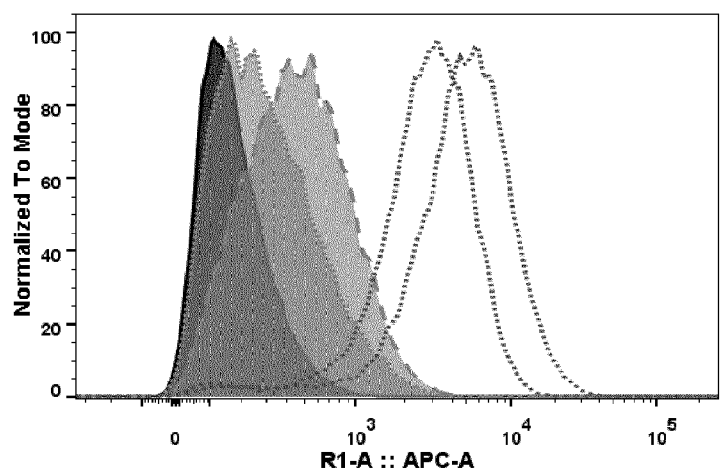
E 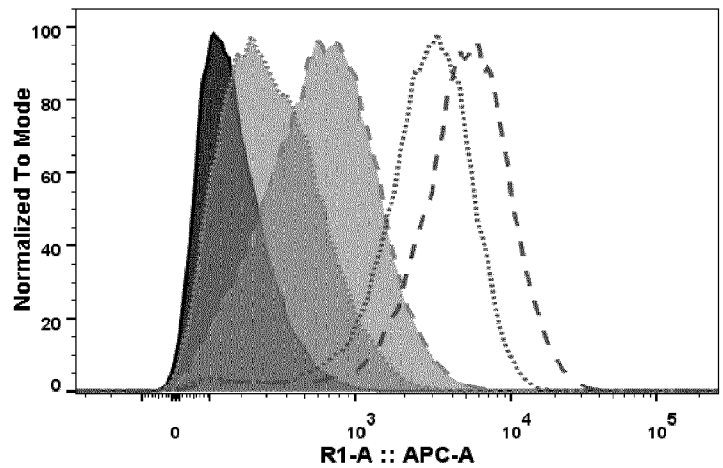
F 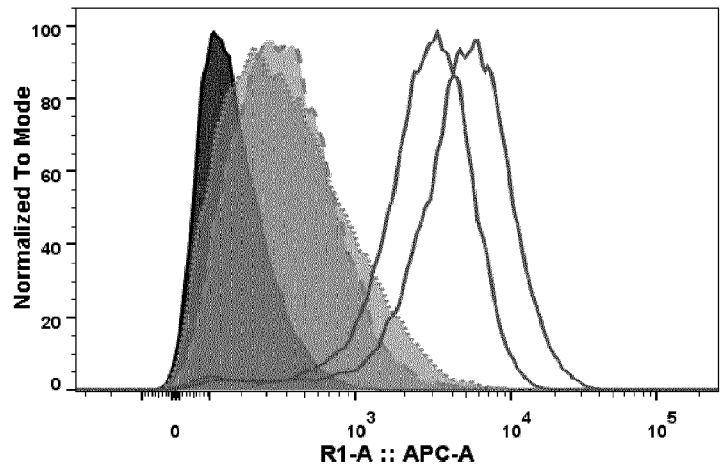
*(The legends are inserted in the figures description)*
Fig. 26D-F

| Membrane protein partner Name | Surface expression |
|---|---|
| GG83 | ++ |
| GG111 | ++ |
| GG121 | + |
| GG152 | + |
| GG153 | ++ |
| GG155 | ++ |
| GG156 | + |
| GG158 | + |

Fig. 30

|  | Reporter | |
|---|---|---|
| transactivator | Gal4 | TetO |
| Gal4_NF-Kb | + | - |
| GAL4_VP64 | ++ | - |
| TetR_NF-Kb | - | + |
| TetR_VP64 | - | ++ |

Fig. 31

SEQUENCE LISTING

```
<160> NUMBER OF SEQ ID NOS: 198

<210> SEQ ID NO 1
<211> LENGTH: 2541
<212> TYPE: DNA
<213> ORGANISM: artificial sequence
<220> FEATURE:
<223> OTHER INFORMATION: pCLS24707

<400> SEQUENCE: 1
atgatcccag ccgtggtcct gctgctgctg ctgctggtgg agcaggcagc tgcactggga      60
gaaccccagc tgtgctacat cctggacgcc attctgttcc tgtacggcat tgtgctgaca     120
ctgctgtatt gtaggctgaa gatccaggtc cgcaaagccg ctattacttc atatgagaag     180
agccgcgtga agttcagccg atccgctgac gcaccagcat accagcaggg acagaaccag     240
ctgtataacg agctgaatct gggacggaga gaggaatacg acgtcctgga taagaggcgc     300
ggcagggatc ctgaaatggg cgggaagcct cgacggaaaa acccacagga ggggctgtac     360
aatgaactgc agaaggacaa aatggctgag gcatatagtg aaatcggaat gaagggcgag     420
agaaggcgcg ggaaaggaca cgatggcctg taccaggggc tgtccaccgc cacaaaagac     480
acttatgatg cactgcatat gcaggccctg cccctcgcg gcagcgggc caccaacttc      540 tccctgctga gcaggctgg agacgtggag gaaaatcccg gcctatggc tcccgcaatg      600 gagtcccta cactgctgtg cgtggcactg ctgttctttg caccagatgg cgtgctggca     660
gaggtccagc tgcagcagtc aggaccagaa ctgatcaaac ccggagcatc tgtgaaaatg     720
agttgtaagg cctcaggcta tactttcacc tcttacgtga tgcactgggt caagcagaaa     780
cctggacagg gcctggagtg gatcggctat attaatccat acaacgacgg gaccaagtac     840
aacgaaaagt ttaaaggcaa ggcaacactg actagtgata gagctcctc tactgcttac     900 atggagctga gttcactgac cagcgaagac tccgctgtgt actattgcgc aagaggaacc     960
tactattacg gctctagggt gttcgattac tgggggcagg gaaccacact gacagtcagc    1020
tccggaggag gaggatccgg aggaggaggg tctggaggcg ggggaagtga catcgtgatg    1080
acacaggccg ctcctagcat tccagtgact cccgcgagt cagtcagcat ctcctgtcgg    1140
tctagtaaga gcctgctgaa ctccaatgga aacacatatc tgtactggtt tctgcagagg    1200
cctggccagt ccccacagct gctgatctat cgcatgtcta acctggccag tggcgtgccc    1260
gatcggttct ctggcagtgg gtcaggaacc gcctttacac tgaggattag ccgcgtcgag    1320
gctgaagacg tggggtcta ttactgcatg cagcatctgg agtacccttt cacatttggc    1380
gccgggacta aactggaact gaagcgcgcc gatactacca caccagctcc acgaccacct    1440
actcctgcac caaccattgc ttcacagcct ctgagcctgc gaccagaagc ttgccggcca    1500
gcagcaggag gagcagtgca caccagaggc ctggacttcg cctgtgatt ctttatcccc     1560 ctgctggtgg tcattctgtt cgccgtggac actgggctgt ttatctccac ccagcagcag    1620
gtcacattcc tgctgaaaat taagcggacc agaaagggct tccggctgct gaatccccat    1680
cctaaaccaa accccaagaa caatggaagc ggagagggac gaggatccct gctgacctgc    1740
ggggacgtgg aggaaaaccc aggacctatg gacactgagt ctaaccggag agccaatctg    1800
gctctgccac aggaacccag ctccgtgccc gcattcgagg tcctggaaat ctctcctcag    1860
```

-continued

```
gaggtgtcta gtgggcgcct gctgaagagt gcctcaagcc cccctctgca cacttggctg    1920
accgtgctga agaaagagca ggaattcctg ggagtcaccc agatcctgac agctatgatt    1980
tgcctgtgtt ttggcacagt ggtctgcagt gtgctggaca tctcacatat tgagggggat    2040
atcttctcct cttttaaggc tgggtacccc ttttggggag caatcttctt tagcatttcc    2100
ggaatgctgt caatcattag cgaaaggcgc aacgcaacat atctggtgcg aggaagcctg    2160
ggcgcaaata ctgccagttc aatcgccggc gggacaggca tcactattct gatcattaac    2220
ctgaagaaaa gcctggctta catccacatt cattcctgcc agaagttctt tgagactaaa    2280
tgtttcatgg cctcttttag taccgaaatc gtggtcatga tgctgttcct gaccattctg    2340
gggctgggat ccgccgtgtc tctgacaatc tgcggcgctg gggaggaact gaagggcaac    2400
aaggtcccag agaagcgagg gcggaagaaa ctgctgtata ttttcaaaca gccttttatg    2460
agaccagtgc agaccacaca ggaggaagat ggctgctcct gtaggtttcc cgaggaagag    2520
gaaggaggct gtgagctgtg a                                               2541
```

<210> SEQ ID NO 2
<211> LENGTH: 373
<212> TYPE: PRT
<213> ORGANISM: artificial sequence
<220> FEATURE:
<223> OTHER INFORMATION: alpha-chain

<400> SEQUENCE: 2

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240
```

```
Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn
    370
```

<210> SEQ ID NO 3
<211> LENGTH: 257
<212> TYPE: PRT
<213> ORGANISM: artificial sequence
<220> FEATURE:
<223> OTHER INFORMATION: beta-chain

<400> SEQUENCE: 3

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Lys Arg Gly Arg Lys Lys Leu Leu Tyr
    210                 215                 220
```

```
Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Gly Gly Cys Glu
                245                 250                 255

Leu

<210> SEQ ID NO 4
<211> LENGTH: 173
<212> TYPE: PRT
<213> ORGANISM: artificial sequence
<220> FEATURE:
<223> OTHER INFORMATION: gamma-chain

<400> SEQUENCE: 4

Met Ile Pro Ala Val Val Leu Leu Leu Leu Leu Val Glu Gln Ala
1                 5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
                35                  40                  45

Gln Val Arg Lys Ala Ala Ile Thr Ser Tyr Glu Lys Ser Arg Val Lys
50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
                100                 105                 110

Lys Asn Pro Gln Glu Gly Leu Tyr Asn Glu Leu Gln Lys Asp Lys Met
            115                 120                 125

Ala Glu Ala Tyr Ser Glu Ile Gly Met Lys Gly Glu Arg Arg Arg Gly
            130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg
                165                 170

<210> SEQ ID NO 5
<211> LENGTH: 224
<212> TYPE: PRT
<213> ORGANISM: homo sapiens
<220> FEATURE:
<223> OTHER INFORMATION: Hypoxia-inducible factor 1-alpha 380-603

<400> SEQUENCE: 5

Ser Glu Asp Thr Ser Ser Leu Phe Asp Lys Leu Lys Lys Glu Pro Asp
1               5                   10                  15

Ala Leu Thr Leu Leu Ala Pro Ala Ala Gly Asp Thr Ile Ile Ser Leu
                20                  25                  30

Asp Phe Gly Ser Asn Asp Thr Glu Thr Asp Asp Gln Gln Leu Glu Glu
                35                  40                  45

Val Pro Leu Tyr Asn Asp Val Met Leu Pro Ser Pro Asn Glu Lys Leu
            50                  55                  60

Gln Asn Ile Asn Leu Ala Met Ser Pro Leu Pro Thr Ala Glu Thr Pro
65                  70                  75                  80

Lys Pro Leu Arg Ser Ser Ala Asp Pro Ala Leu Asn Gln Glu Val Ala
                85                  90                  95
```

-continued

```
Leu Lys Leu Glu Pro Asn Pro Glu Ser Leu Glu Leu Ser Phe Thr Met
            100                 105                 110

Pro Gln Ile Gln Asp Gln Thr Pro Ser Pro Ser Asp Gly Ser Thr Arg
        115                 120                 125

Gln Ser Ser Pro Glu Pro Asn Ser Pro Ser Glu Tyr Cys Phe Tyr Val
    130                 135                 140

Asp Ser Asp Met Val Asn Glu Phe Lys Leu Glu Leu Val Glu Lys Leu
145                 150                 155                 160

Phe Ala Glu Asp Thr Glu Ala Lys Asn Pro Phe Ser Thr Gln Asp Thr
                165                 170                 175

Asp Leu Asp Leu Glu Met Leu Ala Pro Tyr Ile Pro Met Asp Asp Asp
            180                 185                 190

Phe Gln Leu Arg Ser Phe Asp Gln Leu Ser Pro Leu Glu Ser Ser Ser
        195                 200                 205

Ala Ser Pro Glu Ser Ala Ser Pro Gln Ser Thr Val Thr Val Phe Gln
    210                 215                 220

<210> SEQ ID NO 6
<211> LENGTH: 8
<212> TYPE: PRT
<213> ORGANISM: artificial sequence
<220> FEATURE:
<223> OTHER INFORMATION: -GS- linker

<400> SEQUENCE: 6

Ser Ser Gly Ser Gly Ser Gly Ser
1               5

<210> SEQ ID NO 7
<211> LENGTH: 605
<212> TYPE: PRT
<213> ORGANISM: artificial sequence
<220> FEATURE:
<223> OTHER INFORMATION: pCLS26580

<400> SEQUENCE: 7

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175
```

```
Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
            195                 200                 205

Ser Pro Gln Leu Leu Ile Tyr Arg Met Ser Asn Leu Ala Ser Gly Val
        210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Ser Ser Gly Ser Gly Ser Gly Ser Ser Glu Asp
370                 375                 380

Thr Ser Ser Leu Phe Asp Lys Leu Lys Lys Glu Pro Asp Ala Leu Thr
385                 390                 395                 400

Leu Leu Ala Pro Ala Ala Gly Asp Thr Ile Ile Ser Leu Asp Phe Gly
                405                 410                 415

Ser Asn Asp Thr Glu Thr Asp Asp Gln Gln Leu Glu Glu Val Pro Leu
            420                 425                 430

Tyr Asn Asp Val Met Leu Pro Ser Pro Asn Glu Lys Leu Gln Asn Ile
        435                 440                 445

Asn Leu Ala Met Ser Pro Leu Pro Thr Ala Glu Thr Pro Lys Pro Leu
450                 455                 460

Arg Ser Ser Ala Asp Pro Ala Leu Asn Gln Glu Val Ala Leu Lys Leu
465                 470                 475                 480

Glu Pro Asn Pro Glu Ser Leu Glu Leu Ser Phe Thr Met Pro Gln Ile
                485                 490                 495

Gln Asp Gln Thr Pro Ser Pro Ser Asp Gly Ser Thr Arg Gln Ser Ser
            500                 505                 510

Pro Glu Pro Asn Ser Pro Ser Glu Tyr Cys Phe Tyr Val Asp Ser Asp
        515                 520                 525

Met Val Asn Glu Phe Lys Leu Glu Leu Val Glu Lys Leu Phe Ala Glu
530                 535                 540

Asp Thr Glu Ala Lys Asn Pro Phe Ser Thr Gln Asp Thr Asp Leu Asp
545                 550                 555                 560

Leu Glu Met Leu Ala Pro Tyr Ile Pro Met Asp Asp Asp Phe Gln Leu
                565                 570                 575

Arg Ser Phe Asp Gln Leu Ser Pro Leu Glu Ser Ser Ser Ala Ser Pro
            580                 585                 590
```

```
Glu Ser Ala Ser Pro Gln Ser Thr Val Thr Val Phe Gln
        595                 600             605
```

<210> SEQ ID NO 8
<211> LENGTH: 55
<212> TYPE: DNA
<213> ORGANISM: artificial sequence
<220> FEATURE:
<223> OTHER INFORMATION: alpha-chain-F

<400> SEQUENCE: 8
gcatcgtaat acgactcact atagggcagg ccaccatggc tcccgcaatg gagtc    55

<210> SEQ ID NO 9
<211> LENGTH: 22
<212> TYPE: DNA
<213> ORGANISM: artificial sequence
<220> FEATURE:
<223> OTHER INFORMATION: alpha-chain-R

<400> SEQUENCE: 9
tcaattgttc ttggggtttg gt                                         22

<210> SEQ ID NO 10
<211> LENGTH: 54
<212> TYPE: DNA
<213> ORGANISM: artificial sequence
<220> FEATURE:
<223> OTHER INFORMATION: beta-chain-F

<400> SEQUENCE: 10
gcatcgtaat acgactcact atagggcagg ccaccatgga cactgagtct aacc     54

<210> SEQ ID NO 11
<211> LENGTH: 20
<212> TYPE: DNA
<213> ORGANISM: artificial sequence
<220> FEATURE:
<223> OTHER INFORMATION: beta-chain-R

<400> SEQUENCE: 11
tcacagctca cagcctcctt                                            20

<210> SEQ ID NO 12
<211> LENGTH: 55
<212> TYPE: DNA
<213> ORGANISM: artificial sequence
<220> FEATURE:
<223> OTHER INFORMATION: gamma-chain-F

<400> SEQUENCE: 12
gcatcgtaat acgactcact atagggcagg ccaccatgat cccagccgtg gtcct    55

<210> SEQ ID NO 13
<211> LENGTH: 20
<212> TYPE: DNA
<213> ORGANISM: artificial sequence
<220> FEATURE:
<223> OTHER INFORMATION: gamma-chain-R

<400> SEQUENCE: 13
tcagcgaggg ggcagggcct                                            20

<210> SEQ ID NO 14
<211> LENGTH: 44
<212> TYPE: DNA

```
<213> ORGANISM: artificial sequence
<220> FEATURE:
<223> OTHER INFORMATION: alpha-chain-HIF-R

<400> SEQUENCE: 14
acgtaagctt cggccgctat cactgaaaca cagtgacggt tgac                44

<210> SEQ ID NO 15
<211> LENGTH: 22
<212> TYPE: DNA
<213> ORGANISM: artificial sequence
<220> FEATURE:
<223> OTHER INFORMATION: GAalpha-chain-F

<400> SEQUENCE: 15
atggctcccg caatggagtc cc                                        22

<210> SEQ ID NO 16
<211> LENGTH: 46
<212> TYPE: DNA
<213> ORGANISM: artificial sequence
<220> FEATURE:
<223> OTHER INFORMATION: GAalpha-chain-HIF-R

<400> SEQUENCE: 16
ggatcctcgt ccctctccgc ttccctgaaa cacagtgacg gttgac               46

<210> SEQ ID NO 17
<211> LENGTH: 24
<212> TYPE: DNA
<213> ORGANISM: artificial sequence
<220> FEATURE:
<223> OTHER INFORMATION: GAbeta-chain-F

<400> SEQUENCE: 17
ggaagcggag agggacgagg atcc                                      24

<210> SEQ ID NO 18
<211> LENGTH: 25
<212> TYPE: DNA
<213> ORGANISM: artificial sequence
<220> FEATURE:
<223> OTHER INFORMATION: GAbeta-chain-R

<400> SEQUENCE: 18
gatatcaagc ttgcatgcct gcagg                                     25

<210> SEQ ID NO 19
<211> LENGTH: 22
<212> TYPE: DNA
<213> ORGANISM: artificial sequence
<220> FEATURE:
<223> OTHER INFORMATION: GAgamma-chain-F

<400> SEQUENCE: 19
gagctcacaa ccnctcactc gg                                        22

<210> SEQ ID NO 20
<211> LENGTH: 25
<212> TYPE: DNA
<213> ORGANISM: artificial sequence
<220> FEATURE:
<223> OTHER INFORMATION: GAgamma-chain-R

<400> SEQUENCE: 20
gggactccat tgcgggagcc atagg                                     25
```

<210> SEQ ID NO 21
<211> LENGTH: 3734
<212> TYPE: DNA
<213> ORGANISM: artificial sequence
<220> FEATURE:
<223> OTHER INFORMATION: pCLS26949

<400> SEQUENCE: 21

| | | | | | |
|---|---|---|---|---|---|
| gataaaataa | aagattttat | ttagtctcca | gaaaaagggg | ggaatgaaag | acccccacctg | 60 |
| taggtttggc | aagctagctg | cagtaacgcc | attttgcaag | gcatggaaaa | ataccaaacc | 120 |
| aagaatagag | aagttcagat | caagggcggg | tacatgaaaa | tagctaacgt | tgggccaaac | 180 |
| aggatatctg | cggtgagcag | tttcggcccc | ggcccggggc | caagaacaga | tggtcaccgc | 240 |
| agtttcggcc | ccggcccgag | gccaagaaca | gatggtcccc | agatatggcc | caaccctcag | 300 |
| cagtttctta | agacccatca | gatgtttcca | ggctccccca | aggacctgaa | atgaccctgc | 360 |
| gccttatttg | aattaaccaa | tcagcctgct | tctcgcttct | gttcgcgcgc | ttctgcttcc | 420 |
| cgagctctat | aaaagagctc | acaaccccctc | actcggcgcg | ccagtcctcc | gacagactga | 480 |
| gtcgcccggg | ggccaccatg | atcccagccg | tggtcctgct | gctgctgctg | ctggtggagc | 540 |
| aggcagctgc | actgggagaa | ccccagctgt | gctacatcct | ggacgccatt | ctgttcctgt | 600 |
| acggcattgt | gctgacactg | ctgtattgta | ggctgaagat | ccaggtccgc | aaagccgcta | 660 |
| ttacttcata | tgagaagagc | cgcgtgaagt | tcagccgatc | cgctgacgca | ccagcatacc | 720 |
| agcagggaca | gaaccagctg | tataacgagc | tgaatctggg | acggagagag | gaatacgacg | 780 |
| tcctggataa | gaggcgcggc | agggatcctg | aaatgggcgg | gaagcctcga | cggaaaaacc | 840 |
| cacaggaggg | gctgtacaat | gaactgcaga | aggacaaaat | ggctgaggca | tatagtgaaa | 900 |
| tcggaatgaa | gggcgagaga | aggcgcggga | aggacacga | tggcctgtac | cagggggctgt | 960 |
| ccaccgccac | aaaagacact | tatgatgcac | tgcatatgca | ggccctgccc | cctcgcggca | 1020 |
| gcggggccac | caacttctcc | ctgctgaagc | aggctggaga | cgtggaggaa | atcccggcc | 1080 |
| ctatggctcc | cgcaatggag | tccccctacac | tgctgtgcgt | ggcactgctg | ttcttttgcac | 1140 |
| cagatggcgt | gctggcagag | gtccagctgc | agcagtcagg | accagaactg | atcaaacccg | 1200 |
| gagcatctgt | gaaaatgagt | tgtaaggcct | caggctatac | tttcacctct | tacgtgatgc | 1260 |
| actgggtcaa | gcagaaacct | ggacaggcc | tggagtggat | cggctatatt | aatccataca | 1320 |
| acgacgggac | caagtacaac | gaaaagttta | aaggcaaggc | aacactgact | agtgataaga | 1380 |
| gctcctctac | tgcttacatg | gagctgagtt | cactgaccag | cgaagactcc | gctgtgtact | 1440 |
| attgcgcaag | aggaacctac | tattacggct | ctagggtgtt | cgattactgg | gggcagggaa | 1500 |
| ccacactgac | agtcagctcc | ggaggaggag | gatccggagg | aggagggtct | ggaggcgggg | 1560 |
| gaagtgacat | cgtgatgaca | caggccgctc | ctagcattcc | agtgactccc | ggcgagtcag | 1620 |
| tcagcatctc | ctgtcggtct | agtaagagcc | tgctgaactc | caatgaaaac | acatatctgt | 1680 |
| actggtttct | gcagaggcct | ggccagtccc | cacagctgct | gatctatcgc | atgtctaacc | 1740 |
| tggccagtgg | cgtgcccgat | cggttctctg | gcagtgggtc | aggaaccgcc | tttacactga | 1800 |
| ggattagccg | cgtcgaggct | gaagacgtgg | gggtctatta | ctgcatgcag | catctggagt | 1860 |
| acccttcac | atttggcgcc | gggactaaac | tggaactgaa | gcgcgccgat | actaccacac | 1920 |
| cagctccacg | accacctact | cctgcaccaa | ccattgcttc | acagcctctg | agcctgcgac | 1980 |
| cagaagcttg | ccggccagca | gcaggaggag | cagtgcacac | cagaggcctg | gacttcgcct | 2040 |

```
gtgatttctt tatccccctg ctggtggtca ttctgttcgc cgtggacact gggctgttta    2100
tctccaccca gcagcaggtc acattcctgc tgaaaattaa gcggaccaga aagggcttcc    2160
ggctgctgaa tccccatcct aaaccaaacc ccaagaacaa ctcgagcggt agcggctctg    2220
gatcctcaga agatacaagt agcctctttg acaaacttaa gaaggaacct gatgctttaa    2280 cttttgctggc cccagccgct ggagacacaa tcatatcttt agattttggc agcaacgaca    2340
cagaaactga tgaccagcaa cttgaggaag taccattata taatgatgta atgctccccct   2400 cacccaacga aaaattacag aatataaatt tggcaatgtc tccattaccc accgctgaaa    2460
cgccaaagcc acttcgaagt agtgctgacc ctgcactcaa tcaagaagtt gcattaaaat    2520
tagaaccaaa tccagagtca ctggaacttt cttttaccat gccccagatt caggatcaga    2580
cacctagtcc ttccgatgga agcactagac aaagttcacc tgagcctaat agtcccagtg    2640
aatattgttt ttatgtggat agtgatatgg tcaatgaatt taaactggag ctcgtggaga    2700
agctcttcgc cgaggacacc gaggcaaaga acccttctc cacccaggac accgaccttg    2760
acctggagat gctggcacct tacatcccta tggacgacga cttccagctg aggtccttcg    2820
accagctttc cccactggag tcctctagcg cttcccctga atccgctagt ccacagtcaa    2880
ccgtcactgt gtttcaggga agcggagagg gacgaggatc cctgctgacc tgcggggacg    2940
tggaggaaaa cccaggacct atggacactg agtctaaccg gagagccaat ctggctctgc    3000
cacaggaacc cagctccgtg cccgcattcg aggtcctgga atctctcct caggaggtgt    3060 ctagtgggcg cctgctgaag agtgcctcaa gcccccctct gcacacttgg ctgaccgtgc    3120
tgaagaaaga gcaggaattc ctgggagtca cccagatcct gacagctatg atttgcctgt    3180
gttttggcac agtggtctgc agtgtgctgg acatctcaca tattgagggg gatatcttct    3240
cctcttttaa ggctgggtac cctttttggg gagcaatctt cttttagcatt tccggaatgc    3300 tgtcaatcat tagcgaaagg cgcaacgcaa catatctggt gcgaggaagc ctgggcgcaa    3360
atactgccag ttcaatcgcc ggcgggacag gcatcactat tctgatcatt aacctgaaga    3420
aaagcctggc ttacatccac attcattcct gccagaagtt ctttgagact aaatgtttca    3480
tggcctcttt tagtaccgaa atcgtggtca tgatgctgtt cctgaccatt ctggggctgg    3540
gatccgccgt gtctctgaca atctgcggcg ctggggagga actgaagggc aacaaggtcc    3600
cagagaagcg agggcggaag aaactgctgt atattttcaa acagccttt atgagaccag    3660 tgcagaccac acaggaggaa gatggctgct cctgtaggtt tcccgaggaa gaggaaggag    3720
gctgtgagct gtga                                                      3734
```

```
<210> SEQ ID NO 22
<211> LENGTH: 74
<212> TYPE: PRT
<213> ORGANISM: homo sapiens
<220> FEATURE:
<223> OTHER INFORMATION: 344-417 HIF1

<400> SEQUENCE: 22

Gly Ile Ile Gln His Asp Leu Ile Phe Ser Leu Gln Gln Thr Glu Cys
1               5                   10                  15

Val Leu Lys Pro Val Glu Ser Ser Asp Met Lys Met Thr Gln Leu Phe
            20                  25                  30

Thr Lys Val Glu Ser Glu Asp Thr Ser Ser Leu Phe Asp Lys Leu Lys
        35                  40                  45

Lys Glu Pro Asp Ala Leu Thr Leu Leu Ala Pro Ala Ala Gly Asp Thr
    50                  55                  60
```

```
Ile Ile Ser Leu Asp Phe Gly Ser Asn Asp
65                  70
```

<210> SEQ ID NO 23
<211> LENGTH: 123
<212> TYPE: PRT
<213> ORGANISM: homo sapiens
<220> FEATURE:
<223> OTHER INFORMATION: 530-652 HIF1

<400> SEQUENCE: 23

```
Glu Phe Lys Leu Glu Leu Val Glu Lys Leu Phe Ala Glu Asp Thr Glu
1               5                   10                  15

Ala Lys Asn Pro Phe Ser Thr Gln Asp Thr Asp Leu Asp Leu Glu Met
                20                  25                  30

Leu Ala Pro Tyr Ile Pro Met Asp Asp Asp Phe Gln Leu Arg Ser Phe
            35                  40                  45

Asp Gln Leu Ser Pro Leu Glu Ser Ser Ser Ala Ser Pro Glu Ser Ala
        50                  55                  60

Ser Pro Gln Ser Thr Val Thr Val Phe Gln Gln Thr Gln Ile Gln Glu
65                  70                  75                  80

Pro Thr Ala Asn Ala Thr Thr Thr Thr Ala Thr Thr Asp Glu Leu Lys
                85                  90                  95

Thr Val Thr Lys Asp Arg Met Glu Asp Ile Lys Ile Leu Ile Ala Ser
            100                 105                 110

Pro Ser Pro Thr His Ile His Lys Glu Thr Thr
        115                 120
```

<210> SEQ ID NO 24
<211> LENGTH: 455
<212> TYPE: PRT
<213> ORGANISM: artificial sequence
<220> FEATURE:
<223> OTHER INFORMATION: pCLS26959

<400> SEQUENCE: 24

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
        130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
```

```
            165                 170                 175
Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Ser Ser Gly Ser Gly Ser Gly Ser Gly Ile Ile
    370                 375                 380

Gln His Asp Leu Ile Phe Ser Leu Gln Gln Thr Glu Cys Val Leu Lys
385                 390                 395                 400

Pro Val Glu Ser Ser Asp Met Lys Met Thr Gln Leu Phe Thr Lys Val
                405                 410                 415

Glu Ser Glu Asp Thr Ser Ser Leu Phe Asp Lys Leu Lys Lys Glu Pro
            420                 425                 430

Asp Ala Leu Thr Leu Leu Ala Pro Ala Gly Asp Thr Ile Ile Ser
        435                 440                 445

Leu Asp Phe Gly Ser Asn Asp
    450                 455

<210> SEQ ID NO 25
<211> LENGTH: 504
<212> TYPE: PRT
<213> ORGANISM: artificial sequence
<220> FEATURE:
<223> OTHER INFORMATION: pCLS26960

<400> SEQUENCE: 25

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
```

```
                65                  70                  75                  80
Asp Gly Thr Lys Tyr Asn Glu Lys Phe Lys Gly Lys Ala Thr Leu Thr
                        85                  90                  95

Ser Asp Lys Ser Ser Ser Thr Ala Tyr Met Glu Leu Ser Ser Leu Thr
                100                 105                 110

Ser Glu Asp Ser Ala Val Tyr Tyr Cys Ala Arg Gly Thr Tyr Tyr
                115                 120                 125

Gly Ser Arg Val Phe Asp Tyr Trp Gly Gln Gly Thr Thr Leu Thr Val
            130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                    165                 170                 175

Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
            195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
            290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Ser Ser Gly Ser Gly Ser Glu Phe Lys
    370                 375                 380

Leu Glu Leu Val Glu Lys Leu Phe Ala Glu Asp Thr Glu Ala Lys Asn
385                 390                 395                 400

Pro Phe Ser Thr Gln Asp Thr Asp Leu Asp Leu Glu Met Leu Ala Pro
            405                 410                 415

Tyr Ile Pro Met Asp Asp Asp Phe Gln Leu Arg Ser Phe Asp Gln Leu
        420                 425                 430

Ser Pro Leu Glu Ser Ser Ser Ala Ser Pro Glu Ser Ala Ser Pro Gln
            435                 440                 445

Ser Thr Val Thr Val Phe Gln Gln Thr Gln Ile Gln Glu Pro Thr Ala
    450                 455                 460

Asn Ala Thr Thr Thr Thr Ala Thr Thr Asp Glu Leu Lys Thr Val Thr
465                 470                 475                 480

Lys Asp Arg Met Glu Asp Ile Lys Ile Leu Ile Ala Ser Pro Ser Pro
            485                 490                 495
```

Thr His Ile His Lys Glu Thr Thr
            500

<210> SEQ ID NO 26
<211> LENGTH: 92
<212> TYPE: PRT
<213> ORGANISM: homo sapiens
<220> FEATURE:
<223> OTHER INFORMATION: 480-571 HIF3

<400> SEQUENCE: 26

Gln Asp Ala Asp Ala Leu Asp Leu Glu Met Leu Ala Pro Tyr Ile Ser
1               5                   10                  15

Met Asp Asp Asp Phe Gln Leu Asn Ala Ser Glu Gln Leu Pro Arg Ala
                20                  25                  30

Tyr His Arg Pro Leu Gly Ala Val Pro Arg Pro Ala Arg Ser Phe
            35                  40                  45

His Gly Leu Ser Pro Pro Ala Leu Glu Pro Ser Leu Leu Pro Arg Trp
    50                  55                  60

Gly Ser Asp Pro Arg Leu Ser Cys Ser Ser Pro Ser Arg Gly Asp Pro
65                  70                  75                  80

Ser Ala Ser Ser Pro Met Ala Gly Ala Arg Lys Arg
                85                  90

<210> SEQ ID NO 27
<211> LENGTH: 106
<212> TYPE: PRT
<213> ORGANISM: homo sapiens
<220> FEATURE:
<223> OTHER INFORMATION: 466-571 HIF3

<400> SEQUENCE: 27

Gly Lys Asp Thr Glu Ala Val Glu Thr Asp Leu Asp Ile Ala Gln Asp
1               5                   10                  15

Ala Asp Ala Leu Asp Leu Glu Met Leu Ala Pro Tyr Ile Ser Met Asp
                20                  25                  30

Asp Asp Phe Gln Leu Asn Ala Ser Glu Gln Leu Pro Arg Ala Tyr His
            35                  40                  45

Arg Pro Leu Gly Ala Val Pro Arg Pro Ala Arg Ser Phe His Gly
    50                  55                  60

Leu Ser Pro Pro Ala Leu Glu Pro Ser Leu Leu Pro Arg Trp Gly Ser
65                  70                  75                  80

Asp Pro Arg Leu Ser Cys Ser Ser Pro Ser Arg Gly Asp Pro Ser Ala
                85                  90                  95

Ser Ser Pro Met Ala Gly Ala Arg Lys Arg
            100                 105

<210> SEQ ID NO 28
<211> LENGTH: 473
<212> TYPE: PRT
<213> ORGANISM: artificial sequence
<220> FEATURE:
<223> OTHER INFORMATION: pCLS26961

<400> SEQUENCE: 28

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

-continued

```
Gly Pro Glu Leu Ile Lys Pro Gly Ala Ser Val Lys Met Ser Cys Lys
             35                  40                  45

Ala Ser Gly Tyr Thr Phe Thr Ser Tyr Val Met His Trp Val Lys Gln
 50                  55                  60

Lys Pro Gly Gln Gly Leu Glu Trp Ile Gly Tyr Ile Asn Pro Tyr Asn
 65                  70                  75                  80

Asp Gly Thr Lys Tyr Asn Glu Lys Phe Lys Gly Lys Ala Thr Leu Thr
                 85                  90                  95

Ser Asp Lys Ser Ser Thr Ala Tyr Met Glu Leu Ser Ser Leu Thr
                100                 105                 110

Ser Glu Asp Ser Ala Val Tyr Tyr Cys Ala Arg Gly Thr Tyr Tyr Tyr
                115                 120                 125

Gly Ser Arg Val Phe Asp Tyr Trp Gly Gln Gly Thr Thr Leu Thr Val
130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
                195                 200                 205

Ser Pro Gln Leu Leu Ile Tyr Arg Met Ser Asn Leu Ala Ser Gly Val
                210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
                260                 265                 270

Lys Arg Ala Asp Thr Thr Thr Pro Ala Pro Arg Pro Pro Thr Pro Ala
                275                 280                 285

Pro Thr Ile Ala Ser Gln Pro Leu Ser Leu Arg Pro Glu Ala Cys Arg
290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
                340                 345                 350

Lys Arg Thr Arg Lys Gly Phe Arg Leu Leu Asn Pro His Pro Lys Pro
                355                 360                 365

Asn Pro Lys Asn Asn Ser Ser Gly Ser Gly Ser Gln Asp Ala
370                 375                 380

Asp Ala Leu Asp Leu Glu Met Leu Ala Pro Tyr Ile Ser Met Asp Asp
385                 390                 395                 400

Asp Phe Gln Leu Asn Ala Ser Glu Gln Leu Pro Arg Ala Tyr His Arg
                405                 410                 415

Pro Leu Gly Ala Val Pro Arg Pro Ala Arg Ser Phe His Gly Leu
                420                 425                 430

Ser Pro Pro Ala Leu Glu Pro Ser Leu Leu Pro Arg Trp Gly Ser Asp
                435                 440                 445

Pro Arg Leu Ser Cys Ser Ser Pro Ser Arg Gly Asp Pro Ser Ala Ser
```

```
                450             455             460
Ser Pro Met Ala Gly Ala Arg Lys Arg
465                 470

<210> SEQ ID NO 29
<211> LENGTH: 487
<212> TYPE: PRT
<213> ORGANISM: artificial sequence
<220> FEATURE:
<223> OTHER INFORMATION: pCLS26962

<400> SEQUENCE: 29

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
```

```
                    340                 345                 350
Lys Arg Thr Arg Lys Gly Phe Arg Leu Leu Asn Pro His Pro Lys Pro
                355                 360                 365

Asn Pro Lys Asn Asn Ser Ser Gly Ser Gly Ser Gly Ser Gly Lys Asp
            370                 375                 380

Thr Glu Ala Val Glu Thr Asp Leu Asp Ile Ala Gln Asp Ala Asp Ala
385                 390                 395                 400

Leu Asp Leu Glu Met Leu Ala Pro Tyr Ile Ser Met Asp Asp Asp Phe
                405                 410                 415

Gln Leu Asn Ala Ser Glu Gln Leu Pro Arg Ala Tyr His Arg Pro Leu
            420                 425                 430

Gly Ala Val Pro Arg Pro Arg Ala Arg Ser Phe His Gly Leu Ser Pro
                435                 440                 445

Pro Ala Leu Glu Pro Ser Leu Leu Pro Arg Trp Gly Ser Asp Pro Arg
            450                 455                 460

Leu Ser Cys Ser Ser Pro Ser Arg Gly Asp Pro Ser Ala Ser Ser Pro
465                 470                 475                 480

Met Ala Gly Ala Arg Lys Arg
                485

<210> SEQ ID NO 30
<211> LENGTH: 10
<212> TYPE: PRT
<213> ORGANISM: artificial sequence
<220> FEATURE:
<223> OTHER INFORMATION: -EA- linker

<400> SEQUENCE: 30

Glu Ala Ala Ala Arg Glu Ala Ala Ala Arg
1               5                   10

<210> SEQ ID NO 31
<211> LENGTH: 609
<212> TYPE: PRT
<213> ORGANISM: artificial sequence
<220> FEATURE:
<223> OTHER INFORMATION: pCLS26784

<400> SEQUENCE: 31

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140
```

```
Ser Ser Gly Gly Gly Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn Ser Arg Glu Ala Ala Arg Glu Ala Ala Ala
    370                 375                 380

Arg Ser Glu Asp Thr Ser Ser Leu Phe Asp Lys Leu Lys Lys Glu Pro
385                 390                 395                 400

Asp Ala Leu Thr Leu Leu Ala Pro Ala Ala Gly Asp Thr Ile Ile Ser
                405                 410                 415

Leu Asp Phe Gly Ser Asn Asp Thr Glu Thr Asp Asp Gln Gln Leu Glu
            420                 425                 430

Glu Val Pro Leu Tyr Asn Asp Val Met Leu Pro Ser Pro Asn Glu Lys
        435                 440                 445

Leu Gln Asn Ile Asn Leu Ala Met Ser Pro Leu Pro Thr Ala Glu Thr
    450                 455                 460

Pro Lys Pro Leu Arg Ser Ser Ala Asp Pro Ala Leu Asn Gln Glu Val
465                 470                 475                 480

Ala Leu Lys Leu Glu Pro Asn Pro Glu Ser Leu Glu Leu Ser Phe Thr
                485                 490                 495

Met Pro Gln Ile Gln Asp Gln Thr Pro Ser Pro Ser Asp Gly Ser Thr
            500                 505                 510

Arg Gln Ser Ser Pro Glu Pro Asn Ser Pro Ser Glu Tyr Cys Phe Tyr
        515                 520                 525

Val Asp Ser Asp Met Val Asn Glu Phe Lys Leu Glu Leu Val Glu Lys
    530                 535                 540

Leu Phe Ala Glu Asp Thr Glu Ala Lys Asn Pro Phe Ser Thr Gln Asp
545                 550                 555                 560

Thr Asp Leu Asp Leu Glu Met Leu Ala Pro Tyr Ile Pro Met Asp Asp
```

565                 570                 575

Asp Phe Gln Leu Arg Ser Phe Asp Gln Leu Ser Pro Leu Glu Ser Ser
            580                 585                 590

Ser Ala Ser Pro Glu Ser Ala Ser Pro Gln Ser Thr Val Thr Val Phe
            595                 600                 605

Gln

<210> SEQ ID NO 32
<211> LENGTH: 273
<212> TYPE: PRT
<213> ORGANISM: artificial sequence
<220> FEATURE:
<223> OTHER INFORMATION: CD19-scFv-a

<400> SEQUENCE: 32

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255

Pro Phe Thr Phe Gly Ala Gly Thr Lys Leu Glu Leu Lys Arg Ser Asp
            260                 265                 270

Pro

<210> SEQ ID NO 33
<211> LENGTH: 267
<212> TYPE: PRT
<213> ORGANISM: artificial sequence
<220> FEATURE:

<223> OTHER INFORMATION: 5T4-scFv

<400> SEQUENCE: 33

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Asp Leu
            20                  25                  30

Val Lys Pro Gly Ala Ser Val Lys Ile Ser Cys Lys Ala Ser Gly Tyr
        35                  40                  45

Ser Phe Thr Gly Tyr Tyr Met His Trp Val Lys Gln Ser His Gly Lys
    50                  55                  60

Ser Leu Glu Trp Ile Gly Arg Ile Asn Pro Asn Asn Gly Val Thr Leu
65                  70                  75                  80

Tyr Asn Gln Lys Phe Lys Asp Lys Ala Ile Leu Thr Val Asp Lys Ser
                85                  90                  95

Ser Thr Thr Ala Tyr Met Glu Leu Arg Ser Leu Thr Ser Glu Asp Ser
            100                 105                 110

Ala Val Tyr Tyr Cys Ala Arg Ser Thr Met Ile Thr Asn Tyr Val Met
        115                 120                 125

Asp Tyr Trp Gly Gln Val Thr Ser Val Thr Val Ser Ser Gly Gly Gly
    130                 135                 140

Gly Ser Gly Gly Gly Gly Ser Gly Gly Gly Gly Ser Ser Ile Val Met
145                 150                 155                 160

Thr Gln Thr Pro Thr Phe Leu Leu Val Ser Ala Gly Asp Arg Val Thr
                165                 170                 175

Ile Thr Cys Lys Ala Ser Gln Ser Val Ser Asn Asp Val Ala Trp Tyr
            180                 185                 190

Gln Gln Lys Pro Gly Gln Ser Pro Thr Leu Leu Ile Ser Tyr Thr Ser
        195                 200                 205

Ser Arg Tyr Ala Gly Val Pro Asp Arg Phe Ile Gly Ser Gly Tyr Gly
    210                 215                 220

Thr Asp Phe Thr Phe Thr Ile Ser Thr Leu Gln Ala Glu Asp Leu Ala
225                 230                 235                 240

Val Tyr Phe Cys Gln Gln Asp Tyr Asn Ser Pro Pro Thr Phe Gly Gly
                245                 250                 255

Gly Thr Lys Leu Glu Ile Lys Arg Ser Asp Pro
            260                 265

<210> SEQ ID NO 34
<211> LENGTH: 265
<212> TYPE: PRT
<213> ORGANISM: artificial sequence
<220> FEATURE:
<223> OTHER INFORMATION: RORI-scFv

<400> SEQUENCE: 34

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ala Ser Val Thr Leu Ser Cys Lys Ala Ser Gly Tyr
        35                  40                  45

Thr Phe Ser Asp Tyr Glu Met His Trp Val Ile Gln Thr Pro Val His
    50                  55                  60

Gly Leu Glu Trp Ile Gly Ala Ile Asp Pro Glu Thr Gly Gly Thr Ala
65                  70                  75                  80

Tyr Asn Gln Lys Phe Lys Gly Lys Ala Ile Leu Thr Ala Asp Lys Ser
            85                  90                  95

Ser Ser Thr Ala Tyr Met Glu Leu Arg Ser Leu Thr Ser Glu Asp Ser
            100                 105                 110

Ala Val Tyr Tyr Cys Thr Gly Tyr Tyr Asp Tyr Asp Ser Phe Thr Tyr
            115                 120                 125

Trp Gly Gln Gly Thr Leu Val Thr Val Ser Ala Gly Gly Gly Gly Ser
130                 135                 140

Gly Gly Gly Gly Ser Gly Gly Gly Ser Asp Ile Val Met Thr Gln
145                 150                 155                 160

Ser Gln Lys Ile Met Ser Thr Thr Val Gly Asp Arg Val Ser Ile Thr
            165                 170                 175

Cys Lys Ala Ser Gln Asn Val Asp Ala Ala Val Ala Trp Tyr Gln Gln
            180                 185                 190

Lys Pro Gly Gln Ser Pro Lys Leu Leu Ile Tyr Ser Ala Ser Asn Arg
            195                 200                 205

Tyr Thr Gly Val Pro Asp Arg Phe Thr Gly Ser Gly Ser Gly Thr Asp
            210                 215                 220

Phe Thr Leu Thr Ile Ser Asn Met Gln Ser Glu Asp Leu Ala Asp Tyr
225                 230                 235                 240

Phe Cys Gln Gln Tyr Asp Ile Tyr Pro Tyr Thr Phe Gly Gly Gly Thr
            245                 250                 255

Lys Leu Glu Ile Lys Arg Ser Asp Pro
            260                 265

<210> SEQ ID NO 35
<211> LENGTH: 270
<212> TYPE: PRT
<213> ORGANISM: artificial sequence
<220> FEATURE:
<223> OTHER INFORMATION: CD19-scFv-b

<400> SEQUENCE: 35

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Gly Leu
            20                  25                  30

Val Ala Pro Ser Gln Ser Leu Ser Val Thr Cys Thr Val Ser Gly Val
            35                  40                  45

Ser Leu Pro Asp Tyr Gly Val Ser Trp Ile Arg Gln Pro Pro Arg Lys
    50                  55                  60

Gly Leu Glu Trp Leu Gly Val Ile Trp Gly Ser Glu Thr Thr Tyr Tyr
65                  70                  75                  80

Asn Ser Ala Leu Lys Ser Arg Leu Thr Ile Ile Lys Asp Asn Ser Lys
            85                  90                  95

Ser Gln Val Phe Leu Lys Met Asn Ser Leu Gln Thr Asp Asp Thr Ala
            100                 105                 110

Ile Tyr Tyr Cys Ala Lys His Tyr Tyr Tyr Gly Gly Ser Tyr Ala Met
            115                 120                 125

Asp Tyr Trp Gly Gln Gly Thr Ser Val Thr Val Ser Ser Gly Gly Gly
            130                 135                 140

Gly Ser Gly Gly Gly Gly Ser Gly Gly Gly Gly Ser Asp Ile Gln Met
145                 150                 155                 160

Thr Gln Thr Thr Ser Ser Leu Ser Ala Ser Leu Gly Asp Arg Val Thr
            165                 170                 175

```
Ile Ser Cys Arg Ala Ser Gln Asp Ile Ser Lys Tyr Leu Asn Trp Tyr
            180                 185                 190

Gln Gln Lys Pro Asp Gly Thr Val Lys Leu Leu Ile Tyr His Thr Ser
            195                 200                 205

Arg Leu His Ser Gly Val Pro Ser Arg Phe Ser Gly Ser Gly Ser Gly
            210                 215                 220

Thr Asp Tyr Ser Leu Thr Ile Ser Asn Leu Glu Gln Glu Asp Ile Ala
225                 230                 235                 240

Thr Tyr Phe Cys Gln Gln Gly Asn Thr Leu Pro Tyr Thr Phe Gly Gly
            245                 250                 255

Gly Thr Lys Leu Glu Ile Thr Arg Ser Asp Pro Thr Ser Ser
            260                 265                 270

<210> SEQ ID NO 36
<211> LENGTH: 282
<212> TYPE: PRT
<213> ORGANISM: artificial sequence
<220> FEATURE:
<223> OTHER INFORMATION: CD123-scFV

<400> SEQUENCE: 36

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
        115                 120                 125

Tyr Ser Pro Glu Gly Ala Met Asp Tyr Trp Gly Gln Gly Thr Ser Val
    130                 135                 140

Thr Val Ser Ser Gly Gly Gly Ser Gly Gly Gly Ser Gly Gly Gly Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
            180                 185                 190

Ala Ser Gln Asn Val Asp Ser Ala Val Ala Trp Tyr Gln Gln Lys Pro
        195                 200                 205

Gly Gln Ser Pro Lys Ala Leu Ile Tyr Ser Ala Ser Tyr Arg Tyr Ser
    210                 215                 220

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
                245                 250                 255

Gln Gln Tyr Tyr Ser Thr Pro Trp Thr Phe Gly Gly Gly Thr Lys Leu
            260                 265                 270
```

```
Glu Ile Lys Arg Ser Asp Pro Thr Ser Ser
        275                 280
```

<210> SEQ ID NO 37
<211> LENGTH: 267
<212> TYPE: PRT
<213> ORGANISM: artificial sequence
<220> FEATURE:
<223> OTHER INFORMATION: CD33-scFV

<400> SEQUENCE: 37

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Thr Phe Thr Asp Tyr Asn Met His Trp Val Lys Gln Ser His Gly Lys
    50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

Gln Gly Thr Ser Val Thr Val Ser Ser Gly Gly Gly Gly Ser Gly Gly
    130                 135                 140

Gly Gly Ser Gly Gly Gly Gly Ser Asp Ile Val Leu Thr Gln Ser Pro
145                 150                 155                 160

Ala Ser Leu Ala Val Ser Leu Gly Gln Arg Ala Thr Ile Ser Cys Arg
                165                 170                 175

Ala Ser Glu Ser Val Asp Asn Tyr Gly Ile Ser Phe Met Asn Trp Phe
            180                 185                 190

Gln Gln Lys Pro Gly Gln Pro Pro Lys Leu Leu Ile Tyr Ala Ala Ser
        195                 200                 205

Asn Gln Gly Ser Gly Val Pro Ala Arg Phe Ser Gly Ser Gly Ser Gly
    210                 215                 220

Thr Asp Phe Ser Leu Asn Ile His Pro Met Glu Glu Asp Asp Thr Ala
225                 230                 235                 240

Met Tyr Phe Cys Gln Gln Ser Lys Glu Val Pro Trp Thr Phe Gly Gly
                245                 250                 255

Gly Thr Lys Leu Glu Ile Lys Arg Ser Asp Pro
            260                 265
```

<210> SEQ ID NO 38
<211> LENGTH: 277
<212> TYPE: PRT
<213> ORGANISM: artificial sequence
<220> FEATURE:
<223> OTHER INFORMATION: CD19-scFv-c

<400> SEQUENCE: 38

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
```

-continued

```
                20                  25                  30
Gly Pro Glu Leu Ile Lys Pro Gly Ala Ser Val Lys Met Ser Cys Lys
             35                  40                  45
Ala Ser Gly Tyr Thr Phe Thr Ser Tyr Val Met His Trp Val Lys Gln
 50                  55                  60
Lys Pro Gly Gln Gly Leu Glu Trp Ile Gly Tyr Ile Asn Pro Tyr Asn
 65                  70                  75                  80
Asp Gly Thr Lys Tyr Asn Glu Lys Phe Lys Gly Lys Ala Thr Leu Thr
                 85                  90                  95
Ser Asp Lys Ser Ser Ser Thr Ala Tyr Met Glu Leu Ser Ser Leu Thr
            100                 105                 110
Ser Glu Asp Ser Ala Val Tyr Tyr Cys Ala Arg Gly Thr Tyr Tyr Tyr
        115                 120                 125
Gly Ser Arg Val Phe Asp Tyr Trp Gly Gln Gly Thr Thr Leu Thr Val
    130                 135                 140
Ser Ser Gly Gly Gly Gly Ser Gly Gly Gly Gly Ser Gly Gly Gly Gly
145                 150                 155                 160
Ser Asp Ile Val Met Thr Gln Ala Ala Pro Ser Ile Pro Val Thr Pro
                165                 170                 175
Gly Glu Ser Val Ser Ile Ser Cys Arg Ser Ser Lys Ser Leu Leu Asn
                180                 185                 190
Ser Asn Gly Asn Thr Tyr Leu Tyr Trp Phe Leu Gln Arg Pro Gly Gln
            195                 200                 205
Ser Pro Gln Leu Leu Ile Tyr Arg Met Ser Asn Leu Ala Ser Gly Val
        210                 215                 220
Pro Asp Arg Phe Ser Gly Ser Gly Ser Gly Thr Ala Phe Thr Leu Arg
225                 230                 235                 240
Ile Ser Arg Val Glu Ala Glu Asp Val Gly Val Tyr Tyr Cys Met Gln
                245                 250                 255
His Leu Glu Tyr Pro Phe Thr Phe Gly Ala Gly Thr Lys Leu Glu Leu
                260                 265                 270
Lys Arg Ser Asp Pro
        275
```

<210> SEQ ID NO 39
<211> LENGTH: 45
<212> TYPE: PRT
<213> ORGANISM: homo sapiens
<220> FEATURE:
<223> OTHER INFORMATION: CD8a TM

<400> SEQUENCE: 39

```
Thr Thr Thr Pro Ala Pro Arg Pro Pro Thr Pro Ala Pro Thr Ile Ala
 1               5                  10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45
```

<210> SEQ ID NO 40
<211> LENGTH: 233
<212> TYPE: PRT
<213> ORGANISM: homo sapiens
<220> FEATURE:
<223> OTHER INFORMATION: IgG1 TM

<400> SEQUENCE: 40

-continued

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys Lys Asp
225                 230

<210> SEQ ID NO 41
<211> LENGTH: 101
<212> TYPE: PRT
<213> ORGANISM: homo sapiens
<220> FEATURE:
<223> OTHER INFORMATION: EpoR_D2 TM

<400> SEQUENCE: 41

Ala Pro Val Gly Leu Val Ala Arg Leu Ala Asp Glu Ser Gly His Val
1               5                   10                  15

Val Leu Arg Trp Leu Pro Pro Pro Glu Thr Pro Met Thr Ser His Ile
            20                  25                  30

Arg Tyr Glu Val Asp Val Ser Ala Gly Asn Gly Ala Gly Ser Val Gln
            35                  40                  45

Arg Val Glu Ile Leu Glu Gly Arg Thr Glu Cys Val Leu Ser Asn Leu
        50                  55                  60

Arg Gly Arg Thr Arg Tyr Thr Phe Ala Val Arg Ala Arg Met Ala Glu
65                  70                  75                  80

Pro Ser Phe Gly Gly Phe Trp Ser Ala Trp Ser Glu Pro Val Ser Leu
                85                  90                  95

Leu Thr Pro Ser Asp
            100

<210> SEQ ID NO 42
<211> LENGTH: 25
```

```
<212> TYPE: PRT
<213> ORGANISM: homo sapiens
<220> FEATURE:
<223> OTHER INFORMATION: CD8a TM

<400> SEQUENCE: 42

Ile Tyr Ile Trp Ala Pro Leu Ala Gly Thr Cys Gly Val Leu Leu
1               5                   10                  15

Ser Leu Val Ile Thr Leu Tyr Cys Arg
            20                  25

<210> SEQ ID NO 43
<211> LENGTH: 31
<212> TYPE: PRT
<213> ORGANISM: homo sapiens
<220> FEATURE:
<223> OTHER INFORMATION: 4-1BB TM

<400> SEQUENCE: 43

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val Lys Arg Gly Arg
            20                  25                  30

<210> SEQ ID NO 44
<211> LENGTH: 27
<212> TYPE: PRT
<213> ORGANISM: homo sapiens
<220> FEATURE:
<223> OTHER INFORMATION: DAP10 TM

<400> SEQUENCE: 44

Ile Leu Leu Ala Gly Leu Val Ala Ala Asp Ala Val Ala Ser Leu Leu
1               5                   10                  15

Ile Val Gly Ala Val Phe Leu Cys Ala Arg Arg
            20                  25

<210> SEQ ID NO 45
<211> LENGTH: 33
<212> TYPE: PRT
<213> ORGANISM: homo sapiens
<220> FEATURE:
<223> OTHER INFORMATION: CD28 TM

<400> SEQUENCE: 45

Ile Phe Trp Val Leu Val Val Gly Gly Val Leu Ala Cys Tyr Ser
1               5                   10                  15

Leu Leu Val Thr Val Ala Phe Ile Ile Phe Trp Val Arg Ser Lys Arg
            20                  25                  30

Arg

<210> SEQ ID NO 46
<211> LENGTH: 54
<212> TYPE: PRT
<213> ORGANISM: homo sapiens
<220> FEATURE:
<223> OTHER INFORMATION: FceRIa TM

<400> SEQUENCE: 46

Asp Ile Phe Ile Pro Leu Leu Val Ile Leu Phe Ala Val Asp Thr
1               5                   10                  15

Gly Leu Phe Ile Ser Thr Gln Gln Val Thr Phe Leu Leu Lys Ile
            20                  25                  30
```

```
Lys Arg Thr Arg Lys Gly Phe Arg Leu Leu Asn Pro His Pro Lys Pro
            35                  40                  45

Asn Pro Lys Asn Asn Arg
        50

<210> SEQ ID NO 47
<211> LENGTH: 119
<212> TYPE: PRT
<213> ORGANISM: artificial sequence
<220> FEATURE:
<223> OTHER INFORMATION: CD3z linker

<400> SEQUENCE: 47

Val Lys Phe Ser Arg Ser Ala Asp Ala Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
            35                  40                  45

Arg Arg Lys Asn Pro Gln Glu Gly Leu Tyr Asn Glu Leu Gln Lys Asp
        50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg Gly
            100                 105                 110

Ser Gly Ser Gly Ser Gly Ser
        115

<210> SEQ ID NO 48
<211> LENGTH: 49
<212> TYPE: PRT
<213> ORGANISM: artificial sequence
<220> FEATURE:
<223> OTHER INFORMATION: FceRIg linker

<400> SEQUENCE: 48

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln Gly Ser Gly Ser Gly Ser Gly
            35                  40                  45

Ser

<210> SEQ ID NO 49
<211> LENGTH: 45
<212> TYPE: PRT
<213> ORGANISM: artificial sequence
<220> FEATURE:
<223> OTHER INFORMATION: CD28 linker

<400> SEQUENCE: 49

Ser Arg Leu Leu His Ser Asp Tyr Met Asn Met Thr Pro Arg Arg Pro
1               5                   10                  15

Gly Pro Thr Arg Lys His Tyr Gln Pro Tyr Ala Pro Pro Arg Asp Phe
            20                  25                  30

Ala Ala Tyr Arg Ser Gly Ser Gly Ser Gly Ser Gly Ser
            35                  40                  45
```

```
<210> SEQ ID NO 50
<211> LENGTH: 48
<212> TYPE: PRT
<213> ORGANISM: artificial sequence
<220> FEATURE:
<223> OTHER INFORMATION: 4-1BB linker

<400> SEQUENCE: 50

Gly Arg Lys Lys Leu Leu Tyr Ile Phe Lys Gln Pro Phe Met Arg Pro
1               5                   10                  15

Val Gln Thr Thr Gln Glu Glu Asp Gly Cys Ser Cys Arg Phe Pro Glu
            20                  25                  30

Glu Glu Glu Gly Gly Cys Glu Leu Gly Ser Gly Ser Gly Ser Gly Ser
        35                  40                  45

<210> SEQ ID NO 51
<211> LENGTH: 50
<212> TYPE: PRT
<213> ORGANISM: artificial sequence
<220> FEATURE:
<223> OTHER INFORMATION: OX40 linker

<400> SEQUENCE: 51

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile Gly Ser Gly Ser Gly Ser
        35                  40                  45

Gly Ser
    50

<210> SEQ ID NO 52
<211> LENGTH: 28
<212> TYPE: PRT
<213> ORGANISM: artificial sequence
<220> FEATURE:
<223> OTHER INFORMATION: DAP10 linker

<400> SEQUENCE: 52

Pro Arg Arg Ser Pro Ala Gln Glu Asp Gly Lys Val Tyr Ile Asn Met
1               5                   10                  15

Pro Gly Arg Gly Gly Ser Gly Ser Gly Ser Gly Ser
            20                  25

<210> SEQ ID NO 53
<211> LENGTH: 54
<212> TYPE: PRT
<213> ORGANISM: artificial sequence
<220> FEATURE:
<223> OTHER INFORMATION: CD18 linker

<400> SEQUENCE: 53

Lys Ala Leu Ile His Leu Ser Asp Leu Arg Glu Tyr Arg Arg Phe Glu
1               5                   10                  15

Lys Glu Lys Leu Lys Ser Gln Trp Asn Asn Asp Asn Pro Leu Phe Lys
            20                  25                  30

Ser Ala Thr Thr Thr Val Met Asn Pro Lys Phe Ala Glu Ser Gly Ser
        35                  40                  45

Gly Ser Gly Ser Gly Ser
    50
```

<210> SEQ ID NO 54
<211> LENGTH: 49
<212> TYPE: PRT
<213> ORGANISM: artificial sequence
<220> FEATURE:
<223> OTHER INFORMATION: CD28 linker

<400> SEQUENCE: 54

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser Gly Ser Gly Ser Gly Ser Gly
                35                  40                  45

Ser

<210> SEQ ID NO 55
<211> LENGTH: 33
<212> TYPE: PRT
<213> ORGANISM: artificial sequence
<220> FEATURE:
<223> OTHER INFORMATION: CD275 linker

<400> SEQUENCE: 55

Arg Asp Arg Cys Leu Gln His Ser Tyr Ala Gly Ala Trp Ala Val Ser
1               5                   10                  15

Pro Glu Thr Glu Leu Thr Gly His Val Gly Ser Gly Ser Gly Ser Gly
                20                  25                  30

Ser

<210> SEQ ID NO 56
<211> LENGTH: 68
<212> TYPE: PRT
<213> ORGANISM: artificial sequence
<220> FEATURE:
<223> OTHER INFORMATION: HVEM linker

<400> SEQUENCE: 56

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
                20                  25                  30

Glu Ala Leu Gln Ala Pro Pro Asp Val Thr Thr Val Ala Val Glu Glu
                35                  40                  45

Thr Ile Pro Ser Phe Thr Gly Arg Ser Pro Asn His Gly Ser Gly Ser
        50                  55                  60

Gly Ser Gly Ser
65

<210> SEQ ID NO 57
<211> LENGTH: 45
<212> TYPE: PRT
<213> ORGANISM: artificial sequence
<220> FEATURE:
<223> OTHER INFORMATION: LIGHT linker

<400> SEQUENCE: 57

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser

```
                   20                  25                  30

Cys Ser Val Ala Arg Gly Ser Gly Ser Gly Ser
           35                  40                  45

<210> SEQ ID NO 58
<211> LENGTH: 30
<212> TYPE: PRT
<213> ORGANISM: artificial sequence
<220> FEATURE:
<223> OTHER INFORMATION: CD40L linker

<400> SEQUENCE: 58

Met Ile Glu Thr Tyr Asn Gln Thr Ser Pro Arg Ser Ala Ala Thr Gly
1               5                   10                  15

Leu Pro Ile Ser Met Lys Gly Ser Gly Ser Gly Ser Gly Ser
            20                  25                  30

<210> SEQ ID NO 59
<211> LENGTH: 66
<212> TYPE: PRT
<213> ORGANISM: artificial sequence
<220> FEATURE:
<223> OTHER INFORMATION: GITR linker

<400> SEQUENCE: 59

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Arg Gly Glu Arg Ser Ala Glu
        35                  40                  45

Glu Lys Gly Arg Leu Gly Asp Leu Trp Val Gly Ser Gly Ser Gly Ser
    50                  55                  60

Gly Ser
65

<210> SEQ ID NO 60
<211> LENGTH: 56
<212> TYPE: PRT
<213> ORGANISM: artificial sequence
<220> FEATURE:
<223> OTHER INFORMATION: TIM1 linker

<400> SEQUENCE: 60

Lys Lys Tyr Phe Phe Lys Lys Glu Val Gln Gln Leu Ser Val Ser Phe
1               5                   10                  15

Ser Ser Leu Gln Ile Lys Ala Leu Gln Asn Ala Val Glu Lys Glu Val
            20                  25                  30

Gln Ala Glu Asp Asn Ile Tyr Ile Glu Asn Ser Leu Tyr Ala Thr Asp
        35                  40                  45

Gly Ser Gly Ser Gly Ser Gly Ser
    50                  55

<210> SEQ ID NO 61
<211> LENGTH: 85
<212> TYPE: PRT
<213> ORGANISM: artificial sequence
<220> FEATURE:
<223> OTHER INFORMATION: SLAM linker

<400> SEQUENCE: 61

Gln Leu Arg Arg Arg Gly Lys Thr Asn His Tyr Gln Thr Thr Val Glu
```

```
                1               5                  10                 15
Lys Lys Ser Leu Thr Ile Tyr Ala Gln Val Gln Lys Pro Gly Pro Leu
                20                 25                 30

Gln Lys Lys Leu Asp Ser Phe Pro Ala Gln Asp Pro Cys Thr Thr Ile
                35                 40                 45

Tyr Val Ala Ala Thr Glu Pro Val Pro Glu Ser Val Gln Glu Thr Asn
                50                 55                 60

Ser Ile Thr Val Tyr Ala Ser Val Thr Leu Pro Glu Ser Gly Ser Gly
65                 70                 75                 80

Ser Gly Ser Gly Ser
                85

<210> SEQ ID NO 62
<211> LENGTH: 124
<212> TYPE: PRT
<213> ORGANISM: artificial sequence
<220> FEATURE:
<223> OTHER INFORMATION: CD2 linker

<400> SEQUENCE: 62

Lys Arg Lys Lys Gln Arg Ser Arg Arg Asn Asp Glu Glu Leu Glu Thr
1               5                  10                 15

Arg Ala His Arg Val Ala Thr Glu Glu Arg Gly Arg Lys Pro His Gln
                20                 25                 30

Ile Pro Ala Ser Thr Pro Gln Asn Pro Ala Thr Ser Gln His Pro Pro
                35                 40                 45

Pro Pro Pro Gly His Arg Ser Gln Ala Pro Ser His Arg Pro Pro Pro
                50                 55                 60

Pro Gly His Arg Val Gln His Gln Pro Gln Lys Arg Pro Pro Ala Pro
65                 70                 75                 80

Ser Gly Thr Gln Val His Gln Gln Lys Gly Pro Pro Leu Pro Arg Pro
                85                 90                 95

Arg Val Gln Pro Lys Pro Pro His Gly Ala Ala Glu Asn Ser Leu Ser
                100                105                110

Pro Ser Ser Asn Gly Ser Gly Ser Gly Ser Gly Ser
                115                120

<210> SEQ ID NO 63
<211> LENGTH: 40
<212> TYPE: PRT
<213> ORGANISM: artificial sequence
<220> FEATURE:
<223> OTHER INFORMATION: TLT-2 linker

<400> SEQUENCE: 63

Lys Lys Arg His Met Ala Ser Tyr Ser Met Cys Ser Asp Pro Ser Thr
1               5                  10                 15

Arg Asp Pro Pro Gly Arg Pro Glu Pro Tyr Val Glu Val Tyr Leu Ile
                20                 25                 30

Gly Ser Gly Ser Gly Ser Gly Ser
                35                 40

<210> SEQ ID NO 64
<211> LENGTH: 62
<212> TYPE: PRT
<213> ORGANISM: artificial sequence
<220> FEATURE:
<223> OTHER INFORMATION: LAG3 linker

<400> SEQUENCE: 64
```

-continued

His Leu Trp Arg Arg Gln Trp Arg Pro Arg Phe Ser Ala Leu Glu
1               5                   10                  15

Gln Gly Ile His Pro Pro Gln Ala Gln Ser Lys Ile Glu Glu Leu Glu
                20                  25                  30

Gln Glu Pro Glu Pro Glu Pro Glu Pro Glu Pro Glu Pro Glu Pro Glu
            35                  40                  45

Pro Glu Pro Glu Gln Leu Gly Ser Gly Ser Gly Ser Gly Ser
        50                  55                  60

<210> SEQ ID NO 65
<211> LENGTH: 60
<212> TYPE: PRT
<213> ORGANISM: artificial sequence
<220> FEATURE:
<223> OTHER INFORMATION: DAP12 linker

<400> SEQUENCE: 65

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
                20                  25                  30

Leu Gln Gly Gln Arg Ser Asp Val Tyr Ser Asp Leu Asn Thr Gln Arg
            35                  40                  45

Pro Tyr Tyr Lys Gly Ser Gly Ser Gly Ser Gly Ser
        50                  55                  60

<210> SEQ ID NO 66
<211> LENGTH: 107
<212> TYPE: PRT
<213> ORGANISM: artificial sequence
<220> FEATURE:
<223> OTHER INFORMATION: CD84 linker

<400> SEQUENCE: 66

Arg Leu Phe Lys Arg Arg Gln Gly Arg Ile Phe Pro Glu Gly Ser Cys
1               5                   10                  15

Leu Asn Thr Phe Thr Lys Asn Pro Tyr Ala Ala Ser Lys Lys Thr Ile
                20                  25                  30

Tyr Thr Tyr Ile Met Ala Ser Arg Asn Thr Gln Pro Ala Glu Ser Arg
            35                  40                  45

Ile Tyr Asp Glu Ile Leu Gln Ser Lys Val Leu Pro Ser Lys Glu Glu
        50                  55                  60

Pro Val Asn Thr Val Tyr Ser Glu Val Gln Phe Ala Asp Lys Met Gly
65                  70                  75                  80

Lys Ala Ser Thr Gln Asp Ser Lys Pro Pro Gly Thr Ser Ser Tyr Glu
                85                  90                  95

Ile Val Ile Gly Ser Gly Ser Gly Ser Gly Ser
            100                 105

<210> SEQ ID NO 67
<211> LENGTH: 113
<212> TYPE: PRT
<213> ORGANISM: artificial sequence
<220> FEATURE:
<223> OTHER INFORMATION: CD244 linker

<400> SEQUENCE: 67

Glu Phe Leu Thr Ile Tyr Glu Asp Val Lys Asp Leu Lys Thr Arg Arg
1               5                   10                  15

Asn His Glu Gln Glu Gln Thr Phe Pro Gly Gly Ser Thr Ile Tyr
                20                  25                  30

Ser Met Ile Gln Ser Gln Ser Ser Ala Pro Thr Ser Gln Glu Pro Ala
            35                  40                  45

Tyr Thr Leu Tyr Ser Leu Ile Gln Pro Ser Arg Lys Ser Gly Ser Arg
 50                  55                  60

Lys Arg Asn His Ser Pro Ser Phe Asn Ser Thr Ile Tyr Glu Val Ile
 65                  70                  75                  80

Gly Lys Ser Gln Pro Lys Ala Gln Asn Pro Ala Arg Leu Ser Arg Lys
                85                  90                  95

Glu Leu Glu Asn Phe Asp Val Tyr Ser Gly Ser Gly Gly Ser Gly
            100                 105                 110

Ser

<210> SEQ ID NO 68
<211> LENGTH: 157
<212> TYPE: PRT
<213> ORGANISM: artificial sequence
<220> FEATURE:
<223> OTHER INFORMATION: CD229 linker

<400> SEQUENCE: 68

Leu Tyr Ser Val Leu Ser Gln Gly Tyr Glu Lys Leu Asp Thr Pro Leu
1                5                  10                  15

Arg Pro Ala Arg Gln Gln Pro Thr Pro Thr Ser Asp Ser Ser Ser Asp
                20                  25                  30

Ser Asn Leu Thr Thr Glu Glu Asp Glu Asp Arg Pro Glu Val His Lys
            35                  40                  45

Pro Ile Ser Gly Arg Tyr Glu Val Phe Asp Gln Val Thr Gln Glu Gly
 50                  55                  60

Ala Gly His Asp Pro Ala Pro Glu Gly Gln Ala Asp Tyr Asp Pro Val
 65                  70                  75                  80

Thr Pro Tyr Val Thr Glu Val Glu Ser Val Val Gly Glu Asn Thr Met
                85                  90                  95

Tyr Ala Gln Val Phe Asn Leu Gly Lys Thr Pro Val Ser Gln Lys
            100                 105                 110

Glu Glu Ser Ser Ala Thr Ile Tyr Cys Ser Ile Arg Lys Pro Gln Val
            115                 120                 125

Val Pro Pro Gln Gln Asn Asp Leu Glu Ile Pro Glu Ser Pro Thr
            130                 135                 140

Tyr Glu Asn Phe Thr Gly Ser Gly Ser Gly Ser Gly Ser
145                 150                 155

<210> SEQ ID NO 69
<211> LENGTH: 151
<212> TYPE: PRT
<213> ORGANISM: artificial sequence
<220> FEATURE:
<223> OTHER INFORMATION: LTBR linker

<400> SEQUENCE: 69

Lys Ala His Pro Tyr Phe Pro Asp Leu Val Gln Pro Leu Leu Pro Ile
1                5                  10                  15

Ser Gly Asp Val Ser Pro Val Ser Thr Gly Leu Pro Ala Ala Pro Val
                20                  25                  30

Leu Glu Ala Gly Val Pro Gln Gln Gln Ser Pro Leu Asp Leu Thr Arg
            35                  40                  45

```
Glu Pro Gln Leu Glu Pro Gly Glu Gln Ser Gln Val Ala His Gly Thr
 50                  55                  60

Asn Gly Ile His Val Thr Gly Gly Ser Met Thr Ile Thr Gly Asn Ile
 65                  70                  75                  80

Tyr Ile Tyr Asn Gly Pro Val Leu Gly Gly Pro Pro Gly Pro Gly Asp
                 85                  90                  95

Leu Pro Ala Thr Pro Glu Pro Pro Tyr Pro Ile Pro Glu Glu Gly Asp
                100                 105                 110

Pro Gly Pro Pro Gly Leu Ser Thr Pro His Gln Glu Asp Gly Lys Ala
                115                 120                 125

Trp His Leu Ala Glu Thr Glu His Cys Gly Ala Thr Pro Ser Asn Gly
130                 135                 140

Ser Gly Ser Gly Ser Gly Ser
145                 150

<210> SEQ ID NO 70
<211> LENGTH: 46
<212> TYPE: PRT
<213> ORGANISM: artificial sequence
<220> FEATURE:
<223> OTHER INFORMATION: CD278 linker

<400> SEQUENCE: 70

Cys Trp Leu Thr Lys Lys Lys Tyr Ser Ser Ser Val His Asp Pro Asn
  1               5                  10                  15

Gly Glu Tyr Met Phe Met Arg Ala Val Asn Thr Ala Lys Lys Ser Arg
                 20                  25                  30

Leu Thr Asp Val Thr Leu Gly Ser Gly Ser Gly Ser Gly Ser
             35                  40                  45

<210> SEQ ID NO 71
<211> LENGTH: 249
<212> TYPE: PRT
<213> ORGANISM: Tobacco etch virus
<220> FEATURE:
<223> OTHER INFORMATION: TEV Interactor 1

<400> SEQUENCE: 71

Ser Gly Ser Gly Ser Gly Gly Glu Ser Leu Phe Lys Gly Pro Arg Asp
  1               5                  10                  15

Tyr Asn Pro Ile Ser Ser Thr Ile Cys His Leu Thr Asn Glu Ser Asp
                 20                  25                  30

Gly His Thr Thr Ser Leu Tyr Gly Ile Gly Phe Gly Pro Phe Ile Ile
                 35                  40                  45

Thr Asn Lys His Leu Phe Arg Arg Asn Asn Gly Thr Leu Leu Val Gln
 50                  55                  60

Ser Leu His Gly Val Phe Lys Val Lys Asn Thr Thr Thr Leu Gln Gln
 65                  70                  75                  80

His Leu Ile Asp Gly Arg Asp Met Ile Ile Arg Met Pro Lys Asp
                 85                  90                  95

Phe Pro Pro Phe Pro Gln Lys Leu Lys Phe Arg Glu Pro Gln Arg Glu
                100                 105                 110

Glu Arg Ile Cys Leu Val Thr Thr Asn Phe Gln Thr Lys Ser Met Ser
                115                 120                 125

Ser Met Val Ser Asp Thr Ser Cys Thr Phe Pro Ser Ser Asp Gly Ile
                130                 135                 140

Phe Trp Lys His Trp Ile Gln Thr Lys Asp Gly Gln Cys Gly Ser Pro
145                 150                 155                 160
```

```
Leu Val Ser Thr Arg Asp Gly Phe Ile Val Gly Ile His Ser Ala Ser
                165                 170                 175

Asn Phe Thr Asn Thr Asn Asn Tyr Phe Thr Ser Val Pro Lys Asn Phe
            180                 185                 190

Met Glu Leu Leu Thr Asn Gln Glu Ala Gln Trp Val Ser Gly Trp
        195                 200                 205

Arg Leu Asn Ala Asp Ser Val Leu Trp Gly His Lys Val Phe Met
    210                 215                 220

Ser Lys Pro Glu Glu Pro Phe Gln Pro Val Lys Glu Ala Thr Gln Leu
225                 230                 235                 240

Met Asn Glu Leu Val Tyr Ser Glu Glu
                245

<210> SEQ ID NO 72
<211> LENGTH: 40
<212> TYPE: PRT
<213> ORGANISM: homo sapiens
<220> FEATURE:
<223> OTHER INFORMATION: Nub_Human Interactor 1

<400> SEQUENCE: 72

Ser Gly Ser Gly Ser Gly Met Gln Ile Phe Val Lys Thr Leu Thr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu
        35                  40

<210> SEQ ID NO 73
<211> LENGTH: 40
<212> TYPE: PRT
<213> ORGANISM: homo sapiens
<220> FEATURE:
<223> OTHER INFORMATION: Nub-I13A_Human Interactor 1

<400> SEQUENCE: 73

Ser Gly Ser Gly Ser Gly Met Gln Ile Phe Val Lys Thr Leu Thr Gly
1               5                   10                  15

Lys Thr Ala Thr Leu Glu Val Glu Pro Ser Asp Thr Ile Glu Asn Val
            20                  25                  30

Lys Ala Lys Ile Gln Asp Lys Glu
        35                  40

<210> SEQ ID NO 74
<211> LENGTH: 40
<212> TYPE: PRT
<213> ORGANISM: homo sapiens
<220> FEATURE:
<223> OTHER INFORMATION: Nub-I13G_Human Interactor 1

<400> SEQUENCE: 74

Ser Gly Ser Gly Ser Gly Met Gln Ile Phe Val Lys Thr Leu Thr Gly
1               5                   10                  15

Lys Thr Gly Thr Leu Glu Val Glu Pro Ser Asp Thr Ile Glu Asn Val
            20                  25                  30

Lys Ala Lys Ile Gln Asp Lys Glu
        35                  40

<210> SEQ ID NO 75
<211> LENGTH: 40
```

```
<212> TYPE: PRT
<213> ORGANISM: Saccharomyces cerevisiae
<220> FEATURE:
<223> OTHER INFORMATION: Nub_Yeast Interactor 1

<400> SEQUENCE: 75

Ser Gly Ser Gly Ser Gly Met Gln Ile Phe Val Lys Thr Leu Thr Gly
1               5                   10                  15

Lys Thr Ile Thr Leu Glu Val Glu Ser Ser Asp Thr Ile Asp Asn Val
            20                  25                  30

Lys Ser Lys Ile Gln Asp Lys Glu
        35                  40

<210> SEQ ID NO 76
<211> LENGTH: 40
<212> TYPE: PRT
<213> ORGANISM: Saccharomyces cerevisiae
<220> FEATURE:
<223> OTHER INFORMATION: Nub-I13A_Yeast Interactor 1

<400> SEQUENCE: 76

Ser Gly Ser Gly Ser Gly Met Gln Ile Phe Val Lys Thr Leu Thr Gly
1               5                   10                  15

Lys Thr Ala Thr Leu Glu Val Glu Ser Ser Asp Thr Ile Asp Asn Val
            20                  25                  30

Lys Ser Lys Ile Gln Asp Lys Glu
        35                  40

<210> SEQ ID NO 77
<211> LENGTH: 40
<212> TYPE: PRT
<213> ORGANISM: Saccharomyces cerevisiae
<220> FEATURE:
<223> OTHER INFORMATION: Nub-I13G_Yeast Interactor 1

<400> SEQUENCE: 77

Ser Gly Ser Gly Ser Gly Met Gln Ile Phe Val Lys Thr Leu Thr Gly
1               5                   10                  15

Lys Thr Gly Thr Leu Glu Val Glu Ser Ser Asp Thr Ile Asp Asn Val
            20                  25                  30

Lys Ser Lys Ile Gln Asp Lys Glu
        35                  40

<210> SEQ ID NO 78
<211> LENGTH: 20
<212> TYPE: PRT
<213> ORGANISM: Tobacco etch virus
<220> FEATURE:
<223> OTHER INFORMATION: TEV cleavage site Interactor 2

<400> SEQUENCE: 78

Ser Gly Ser Gly Ser Gly Glu Asn Leu Tyr Phe Gln Ser Gly Ser Gly
1               5                   10                  15

Ser Gly Ser Gly
            20

<210> SEQ ID NO 79
<211> LENGTH: 61
<212> TYPE: PRT
<213> ORGANISM: homo sapiens
<220> FEATURE:
<223> OTHER INFORMATION: Cub_Human Interactor 2

<400> SEQUENCE: 79
```

Ser Gly Ser Gly Ser Gly Gly Ile Pro Pro Asp Gln Gln Arg Leu Ile
1               5                   10                  15

Phe Ala Gly Lys Gln Leu Glu Asp Gly Arg Thr Leu Ser Asp Tyr Asn
                20                  25                  30

Ile Gln Lys Glu Ser Thr Leu His Leu Val Leu Arg Leu Arg Gly Gly
            35                  40                  45

Met His Arg Ser Ala Cys Gly Arg Met Ala Gly Ser Gly
    50                  55                  60

<210> SEQ ID NO 80
<211> LENGTH: 207
<212> TYPE: PRT
<213> ORGANISM: homo sapiens
<220> FEATURE:
<223> OTHER INFORMATION: tetR DNA binding

<400> SEQUENCE: 80

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 81
<211> LENGTH: 147
<212> TYPE: PRT
<213> ORGANISM: homo sapiens
<220> FEATURE:
<223> OTHER INFORMATION: Gal4 DNA binding

<400> SEQUENCE: 81

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro

```
                    35                  40                  45
Leu Thr Arg Ala His Leu Thr Glu Val Glu Ser Arg Leu Glu Arg Leu
 50                  55                  60
Glu Gln Leu Phe Leu Leu Ile Phe Pro Arg Glu Asp Leu Asp Met Ile
 65                  70                  75                  80
Leu Lys Met Asp Ser Leu Gln Asp Ile Lys Ala Leu Leu Thr Gly Leu
                 85                  90                  95
Phe Val Gln Asp Asn Val Asn Lys Asp Ala Val Thr Asp Arg Leu Ala
                100                 105                 110
Ser Val Glu Thr Asp Met Pro Leu Thr Leu Arg Gln His Arg Ile Ser
                115                 120                 125
Ala Thr Ser Ser Ser Glu Glu Ser Ser Asn Lys Gly Gln Arg Gln Leu
                130                 135                 140
Thr Val Ser
145

<210> SEQ ID NO 82
<211> LENGTH: 128
<212> TYPE: PRT
<213> ORGANISM: homo sapiens
<220> FEATURE:
<223> OTHER INFORMATION: VP16 Transactivator

<400> SEQUENCE: 82

Ala Tyr Ser Arg Ala Arg Thr Lys Asn Asn Tyr Gly Ser Thr Ile Glu
 1               5                  10                  15
Gly Leu Leu Asp Leu Pro Asp Asp Asp Ala Pro Glu Glu Ala Gly Leu
                 20                  25                  30
Ala Ala Pro Arg Leu Ser Phe Leu Pro Ala Gly His Thr Arg Arg Leu
                 35                  40                  45
Ser Thr Ala Pro Pro Thr Asp Val Ser Leu Gly Asp Glu Leu His Leu
 50                  55                  60
Asp Gly Glu Asp Val Ala Met Ala His Ala Asp Ala Leu Asp Asp Phe
 65                  70                  75                  80
Asp Leu Asp Met Leu Gly Asp Gly Asp Ser Pro Gly Pro Gly Phe Thr
                 85                  90                  95
Pro His Asp Ser Ala Pro Tyr Gly Ala Leu Asp Met Ala Asp Phe Glu
                100                 105                 110
Phe Glu Gln Met Phe Thr Asp Ala Leu Gly Ile Asp Glu Tyr Gly Gly
                115                 120                 125

<210> SEQ ID NO 83
<211> LENGTH: 245
<212> TYPE: PRT
<213> ORGANISM: homo sapiens
<220> FEATURE:
<223> OTHER INFORMATION: NF-kB Transactivator

<400> SEQUENCE: 83

Glu Thr Phe Lys Ser Ile Met Lys Lys Ser Pro Phe Ser Gly Pro Thr
 1               5                  10                  15
Asp Pro Arg Pro Pro Arg Arg Ile Ala Val Pro Ser Arg Ser Ser
                 20                  25                  30
Ala Ser Val Pro Lys Pro Ala Pro Gln Pro Tyr Pro Phe Thr Ser Ser
                 35                  40                  45
Leu Ser Thr Ile Asn Tyr Asp Glu Phe Pro Thr Met Val Phe Pro Ser
 50                  55                  60
```

```
Gly Gln Ile Ser Gln Ala Ser Ala Leu Ala Pro Pro Gln Val
65                  70                  75                  80

Leu Pro Gln Ala Pro Ala Pro Ala Pro Ala Met Val Ser Ala
                85                  90                  95

Leu Ala Gln Ala Pro Ala Pro Val Pro Val Leu Ala Pro Gly Pro Pro
            100                 105                 110

Gln Ala Val Ala Pro Pro Ala Pro Lys Pro Thr Gln Ala Gly Glu Gly
            115                 120                 125

Thr Leu Ser Glu Ala Leu Leu Gln Leu Gln Phe Asp Asp Glu Asp Leu
            130                 135                 140

Gly Ala Leu Leu Gly Asn Ser Thr Asp Pro Ala Val Phe Thr Asp Leu
145                 150                 155                 160

Ala Ser Val Asp Asn Ser Glu Phe Gln Gln Leu Leu Asn Gln Gly Ile
                165                 170                 175

Pro Val Ala Pro His Thr Thr Glu Pro Met Leu Met Glu Tyr Pro Glu
            180                 185                 190

Ala Ile Thr Arg Leu Val Thr Gly Ala Gln Arg Pro Pro Asp Pro Ala
            195                 200                 205

Pro Ala Pro Leu Gly Ala Pro Gly Leu Pro Asn Gly Leu Leu Ser Gly
210                 215                 220

Asp Glu Asp Phe Ser Ser Ile Ala Asp Met Asp Phe Ser Ala Leu Leu
225                 230                 235                 240

Ser Gln Ile Ser Ser
                245

<210> SEQ ID NO 84
<211> LENGTH: 57
<212> TYPE: PRT
<213> ORGANISM: homo sapiens
<220> FEATURE:
<223> OTHER INFORMATION: VP64 Transactivator

<400> SEQUENCE: 84

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn
        50                  55

<210> SEQ ID NO 85
<211> LENGTH: 296
<212> TYPE: PRT
<213> ORGANISM: homo sapiens
<220> FEATURE:
<223> OTHER INFORMATION: HIF1a Transactivator

<400> SEQUENCE: 85

Phe Lys Leu Glu Leu Val Glu Lys Leu Phe Ala Glu Asp Thr Glu Ala
1               5                   10                  15

Lys Asn Pro Phe Ser Thr Gln Asp Thr Asp Leu Asp Leu Glu Met Leu
            20                  25                  30

Ala Pro Tyr Ile Pro Met Asp Asp Asp Phe Gln Leu Arg Ser Phe Asp
        35                  40                  45

Gln Leu Ser Pro Leu Glu Ser Ser Ser Ala Ser Pro Glu Ser Ala Ser
        50                  55                  60
```

```
Pro Gln Ser Thr Val Thr Val Phe Gln Gln Thr Gln Ile Gln Glu Pro
 65                  70                  75                  80

Thr Ala Asn Ala Thr Thr Thr Ala Thr Asp Glu Leu Lys Thr
             85                  90                  95

Val Thr Lys Asp Arg Met Glu Asp Ile Lys Ile Leu Ile Ala Ser Pro
            100                 105                 110

Ser Pro Thr His Ile His Lys Glu Thr Thr Ser Ala Thr Ser Ser Pro
            115                 120                 125

Tyr Arg Asp Thr Gln Ser Arg Thr Ala Ser Pro Asn Arg Ala Gly Lys
            130                 135                 140

Gly Val Ile Glu Gln Thr Glu Lys Ser His Pro Arg Ser Pro Asn Val
145                 150                 155                 160

Leu Ser Val Ala Leu Ser Gln Arg Thr Thr Val Pro Glu Glu Glu Leu
                165                 170                 175

Asn Pro Lys Ile Leu Ala Leu Gln Asn Ala Gln Arg Lys Arg Lys Met
            180                 185                 190

Glu His Asp Gly Ser Leu Phe Gln Ala Val Gly Ile Gly Thr Leu Leu
            195                 200                 205

Gln Gln Pro Asp Asp His Ala Ala Thr Thr Ser Leu Ser Trp Lys Arg
210                 215                 220

Val Lys Gly Cys Lys Ser Ser Glu Gln Asn Gly Met Glu Gln Lys Thr
225                 230                 235                 240

Ile Ile Leu Ile Pro Ser Asp Leu Ala Cys Arg Leu Leu Gly Gln Ser
                245                 250                 255

Met Asp Glu Ser Gly Leu Pro Gln Leu Thr Ser Tyr Asp Cys Glu Val
            260                 265                 270

Asn Ala Pro Ile Gln Gly Ser Arg Asn Leu Leu Gln Gly Glu Glu Leu
            275                 280                 285

Leu Arg Ala Leu Asp Gln Val Asn
            290                 295

<210> SEQ ID NO 86
<211> LENGTH: 22
<212> TYPE: DNA
<213> ORGANISM: artificial sequence
<220> FEATURE:
<223> OTHER INFORMATION: pUC57-F

<400> SEQUENCE: 86
cccagtcacg acgttgtaaa ac                                           22

<210> SEQ ID NO 87
<211> LENGTH: 23
<212> TYPE: DNA
<213> ORGANISM: artificial sequence
<220> FEATURE:
<223> OTHER INFORMATION: pUC57-R

<400> SEQUENCE: 87
cacaggaaac agctatgacc atg                                          23

<210> SEQ ID NO 88
<211> LENGTH: 23
<212> TYPE: DNA
<213> ORGANISM: artificial sequence
<220> FEATURE:
<223> OTHER INFORMATION: pJET-F

<400> SEQUENCE: 88
```

```
cgactcacta tagggagagc ggc                                           23

<210> SEQ ID NO 89
<211> LENGTH: 24
<212> TYPE: DNA
<213> ORGANISM: artificial sequence
<220> FEATURE:
<223> OTHER INFORMATION: pJET-R

<400> SEQUENCE: 89
aagaacatcg attttccatg gcag                                          24

<210> SEQ ID NO 90
<211> LENGTH: 142
<212> TYPE: DNA
<213> ORGANISM: artificial sequence
<220> FEATURE:
<223> OTHER INFORMATION: Assembly plasmid pCLS26146

<400> SEQUENCE: 90
gaattcgcca ctagcgctgt cacgcgccag cggtctccca tggacgtctt ccggttctag    60
atctggaagc ggaagacagg aatgagacct aactcgagcg atcctctaga cgagctcctc   120
gagcctgcag cagctgaagc tt                                            142

<210> SEQ ID NO 91
<211> LENGTH: 144
<212> TYPE: DNA
<213> ORGANISM: artificial sequence
<220> FEATURE:
<223> OTHER INFORMATION: Assembly plasmid pCLS26147

<400> SEQUENCE: 91
gaattcgcca ctagcgctgt cacgcgccag ggtctcccca tggacgtctt ccggttctag    60
atctggaagc ggaagacagg aatgagagac taactcgag cgatcctcta gacgagctcc   120
tcgagcctgc agcagctgaa gctt                                          144

<210> SEQ ID NO 92
<211> LENGTH: 1830
<212> TYPE: DNA
<213> ORGANISM: artificial sequence
<220> FEATURE:
<223> OTHER INFORMATION: GG78

<400> SEQUENCE: 92
atggctttgc ctgtcactgc cttgctgctt ccacttgctc tgttgttgca cgccgcaaga    60
cccgaggtgc agttgcagca gtcagggcca gagttgatta agcccggagc ctccgtcaag   120
atgtcctgca aggccagcgg gtacactttc accagctacg tcatgcattg ggtgaagcag   180
aagccaggcc aggggcttga gtggattggg tacatcaacc cctacaacga cggaccaaa    240 tacaacgaga aattcaaggg caaagccaca ctcacctccg ataagtcctc ctctaccgcc   300
tacatggagc tcagctccct gacctccgag gatagcgctg tgtattactg cgcaaggggc   360
acatactact atggctctag ggtgttcgac tactgggggc agggcactac tctcacagtg   420
agctcaggcg gaggaggcag tggcggaggg ggaagtgggg gcggcggcag cgatattgtc   480
atgacccagg cagcccctag tatccctgtg actccaggcg agagcgtgag catcagctgc   540
cggtccagca gagcctgct gaacagtaac ggaaacacat acctctactg gtttctgcag   600
aggcccggcc agagccctca gctgctgatt taccgcatgt caaatcttgc ctctggggtg   660
```

```
cccgatagat ttagtgggag cggctccggc acagctttta cattgcggat ctccagagtc    720
gaggccgaag atgtgggggt ctattactgt atgcaacacc tggaataccc ctttaccttc    780
ggagccggca caaagctgga gctgaagcgg tcggatcccg agcccaaatc tcctgacaaa    840
actcacacat gcccaccgtg cccagcacct ccgtggccg gccgtcagt gttcctcttc      900
ccccaaaac ccaaggacac cctcatgatc gcccggaccc ctgaggtcac atgcgtggtg    960
gtggacgtga gccacgagga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtg   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat cccagcgaca tcgccgtgga gtgggagagc   1320
aatgggcaac cggagaacaa ctacaagacc acgcctcccg tgctggactc cgacggctcc   1380
ttcttcctct acagcaagct caccgtggac aagagcaggt ggcagcaggg gaacgtgttc   1440
tcatgctccg tgatgcatga ggccctgcac aatcactata cccagaaatc tctgagtctg   1500
agcccaggca agaggatat cttttgggtg ctggtggtgg ttggtggagt cctggcttgc   1560
tatagcttgc tagtaacagt ggcctttatt attttctggg tgaggagtaa gcgcagaagg   1620
gaccgatgcc tccaacacag ctatgcaggt gcctgggctg tgagtccgga cagagctc    1680
actggccacg ttggatcagg gagcggctct gggagcggta gtggatctgg tatgcaaatc   1740
ttcgtgaaaa ccctgaccgg gaaaacaatc actctcgaag tcgagcccag cgatacaatt   1800
gagaacgtga aggccaagat tcaggacaag                                    1830
```

<210> SEQ ID NO 93
<211> LENGTH: 1917
<212> TYPE: DNA
<213> ORGANISM: artificial sequence
<220> FEATURE:
<223> OTHER INFORMATION: GG80

<400> SEQUENCE: 93

```
atggctttgc ctgtcactgc cttgctgctt ccacttgctc tgttgttgca cgccgcaaga    60
cccgaggtcc agcttcagca gtctggacct gacctggtga agcctggggc ttcagtgaag   120
atatcctgca aggcttctgg ttactcattc actggctact acatgcactg ggtgaagcag   180
agtcatggaa agagccttga gtggattgga cgtattaatc ctaacaatgg tgttactctc   240
tacaaccaga aattcaagga caaggccata ttaactgtag acaagtcatc caccacagcc   300
tacatggagc tccgcagcct gacatctgag gactctgcgg tctattactg tgcaagatca   360
actatgatta cgaactatgt tatggactac tggggtcaag taacctcagt caccgtttcc   420
tcaggcggag gaggcagtgg cggaggggga agtggggggcg gcggcagcag tattgtgatg   480
acccagactc ccacattcct gcttgtttca gcaggagaca gggttaccat aacctgcaag   540
gccagtcaga gtgtgagtaa tgatgtagct tggtaccaac agaagccagg gcagtctcct   600
acactgctca tatcctatac atccagtcgc tacgctggag tccctgatcg cttcattggc   660
agtggatatg ggacggattt cactttcacc atcagcactt gcaggctgaa ggacctggca   720
gtttatttct gtcagcaaga ttataattct cctccgacgt tcggtggagg caccaagctg   780
gaaatcaaac ggtcggatcc cgagcccaaa tctcctgaca aaactcacac atgcccaccg   840
tgcccagcac ctcccgtggc cggccccgtca gtgttcctct tccccccaaa acccaaggac   900
```

```
accctcatga tcgcccggac ccctgaggtc acatgcgtgg tggtggacgt gagccacgag    960
gaccctgagg tcaagttcaa ctggtacgtg gacggcgtgg aggtgcataa tgccaagaca   1020
aagccgcggg aggagcagta acagcacg taccgtgtgg tcagcgtcct caccgtcctg    1080
caccaggact ggctgaatgg caaggagtac aagtgcaagg tgtccaacaa agccctccca   1140
gcccccatcg agaaaaccat ctccaaagcc aagggcagc cccgagaacc acaggtgtac    1200
accctgcccc catcccggga tgagctgacc aagaaccagg tcagcctgac ctgcctggtc   1260
aaaggcttct atcccagcga catcgccgtg gagtgggaga gcaatgggca accggagaac   1320
aactacaaga ccacgcctcc cgtgctggac tccgacggct ccttcttcct ctacagcaag   1380
ctcaccgtgg acaagagcag gtggcagcag gggaacgtgt tctcatgctc cgtgatgcat   1440
gaggccctgc acaatcacta cccagaaaa tctctgagtc tgagcccagg caagaaggat    1500
atcttttggg tgctggtggt ggttggtgga gtcctggctt gctatagctt gctagtaaca   1560
gtggccttta ttatttttctg ggtgaggagt aagcgcagat gtgtgaaaag aagaaagcca   1620
aggggtgatg tagtcaaggt gattgtctcc gtccagcgga aaagacagga ggcagaaggt    1680
gaggccacag tcattgaggc cctgcaagcc cctccggacg tcaccacggt ggccgtggag   1740
gagacaatac cctcattcac ggggaggagc ccaaaccacg gatcagggag cggctctggg   1800
agcggtagtg gatctggtat gcaaatcttc gtgaaaaccc tgaccgggaa acaatcact    1860 ctcgaagtcg agcccagcga tacaattgag aacgtgaagg ccaagattca ggacaag     1917
```

<210> SEQ ID NO 94
<211> LENGTH: 1893
<212> TYPE: DNA
<213> ORGANISM: artificial sequence
<220> FEATURE:
<223> OTHER INFORMATION: GG81

<400> SEQUENCE: 94

```
atggctttgc ctgtcactgc cttgctgctt ccacttgctc tgttgttgca cgccgcaaga     60
cccgaggtcc agcttcagca gtctggacct gacctggtga agcctggggc ttcagtgaag    120
atatcctgca aggcttctgg ttactcattc actggctact acatgcactg ggtgaagcag    180
agtcatggaa agagccttga gtggattgga cgtattaatc ctaacaatgg tgttactctc    240
tacaaccaga aattcaagga caaggccata ttaactgtag acaagtcatc caccacagcc    300
tacatggagc tccgcagcct gacatctgag gactctgcgg tctattactg tgcaagatca    360
actatgatta cgaactatgt tatggactac tgggtcaag taacctcagt caccgttttcc   420 tcaggcggag gaggcagtgg cggaggggga agtgggggcg gcggcagcag tattgtgatg   480
acccagactc ccacattcct gcttgtttca gcaggagaca gggttaccat aacctgcaag   540
gccagtcaga gtgtgagtaa tgatgtagct tggtaccaac agaagccagg gcagtctcct   600
acactgctca tatcctatac atccagtcgc tacgctggag tccctgatcg cttcattggc   660
agtggatatg ggacggattt cactttcacc atcagcactt gcaggctga ggacctggca    720 gtttatttct gtcagcaaga ttataattct cctccgacgt tcggtggagg caccaagctg   780
gaaatcaaac ggtcggatcc cgagcccaaa tctcctgaca aaactcacac atgcccaccg   840
tgcccagcac ctcccgtggc cggccccgtca gtgttcctct tcccccccaaa acccaaggac   900 accctcatga tcgcccggac ccctgaggtc acatgcgtgg tggtggacgt gagccacgag   960
gaccctgagg tcaagttcaa ctggtacgtg gacggcgtgg aggtgcataa tgccaagaca  1020
```

| | |
|---|---:|
| aagccgcggg aggagcagta caacagcacg taccgtgtgg tcagcgtcct caccgtcctg | 1080 |
| caccaggact ggctgaatgg caaggagtac aagtgcaagg tgtccaacaa agccctccca | 1140 |
| gcccccatcg agaaaaccat ctccaaagcc aagggcagc cccgagaacc acaggtgtac | 1200 |
| accctgcccc catcccggga tgagctgacc aagaaccagg tcagcctgac ctgcctggtc | 1260 |
| aaaggcttct atcccagcga catcgccgtg gagtgggaga gcaatgggca accggagaac | 1320 |
| aactacaaga ccacgcctcc cgtgctggac tccgacggct ccttcttcct ctacagcaag | 1380 |
| ctcaccgtgg acaagagcag gtggcagcag gggaacgtgt tctcatgctc cgtgatgcat | 1440 |
| gaggccctgc acaatcacta tacccagaaa tctctgagtc tgagcccagg caagaaggat | 1500 |
| attctcctgg caggcctcgt ggctgctgat gcggtggcat cgctgctcat cgtggggcg | 1560 |
| gtgttcctgt gcgcacgcag acagcttgga ctgcacatct ggcagctgag gagtcagtgc | 1620 |
| atgtggcccc gagagacaca gctgctgctg gaggtgccgc cgtcgaccga ggacgccaga | 1680 |
| agctgccagt tccccgagga agagcggggc gagcgatcgg cagaggagaa ggggcggctg | 1740 |
| ggagatctgt gggtgggatc agggagcggc tctgggagcg gtagtggatc tggtatgcaa | 1800 |
| atcttcgtga aaccctgac cgggaaaaca atcactctcg aagtcgagcc cagcgataca | 1860 |
| attgagaacg tgaaggccaa gattcaggac aag | 1893 |

<210> SEQ ID NO 95
<211> LENGTH: 1842
<212> TYPE: DNA
<213> ORGANISM: artificial sequence
<220> FEATURE:
<223> OTHER INFORMATION: GG82

<400> SEQUENCE: 95

| | |
|---|---:|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga gttcaaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccggtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat atacccctac accttcggcg gaggcacaaa gctcgaaata | 780 |
| aagcggtcgg atcccgagcc caatctcct gacaaaactc acacatgccc accgtgccca | 840 |
| gcacctcccg tggccggccc gtcagtgttc ctcttccccc caaaacccaa ggacaccctc | 900 |
| atgatcgccc ggacccctga ggtcacatgc gtggtggtgg acgtgagcca cgaggaccct | 960 |
| gaggtcaagt tcaactggta cgtggacggc gtggaggtgc ataatgccaa gacaaagccg | 1020 |
| cgggaggagc agtacaacag cacgtaccgt gtggtcagcg tcctcaccgt cctgcaccag | 1080 |
| gactggctga atggcaagga gtacaagtgc aaggtgtcca acaaagccct ccagccccca | 1140 |
| atcgagaaaa ccatctccaa agccaagggg cagccccgag aaccacaggt gtacaccctg | 1200 |

```
ccccatccc gggatgagct gaccaagaac caggtcagcc tgacctgcct ggtcaaaggc    1260
ttctatccca gcgacatcgc cgtggagtgg gagagcaatg gcaaccgga gaacaactac    1320 aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc aggcaagaa ggatatcttt    1500 tgggtgctgg tggtggttgg tggagtcctg gcttgctata gcttgctagt aacagtggcc    1560
tttattattt tctgggtgag gagtaagcgc agaatggagg agagtgtcgt acggccctca    1620
gtgtttgtgg tggatggaca gaccgacatc ccattcacga ggctgggacg aagccaccgg    1680
agacagtcgt gcagtgtggc ccggggatca gggagcggct ctgggagcgg tagtggatct    1740
ggtatgcaaa tcttcgtgaa accctgaccg ggaaaacaa tcactctcga agtcgagccc    1800
agcgatacaa ttgagaacgt gaaggccaag attcaggaca ag                      1842

<210> SEQ ID NO 96
<211> LENGTH: 1782
<212> TYPE: DNA
<213> ORGANISM: artificial sequence
<220> FEATURE:
<223> OTHER INFORMATION: GG83

<400> SEQUENCE: 96
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaagg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccctac accttcggcg gaggcacaaa gctcgaaata    780
aagcggtcgg atcccgagcc caaatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtgtcca acaaagccct cccagccccc   1140
atcgagaaaa ccatctccaa agccaaaggg cagccccgag aaccacaggt gtacaccctg   1200 ccccatccc gggatgagct gaccaagaac caggtcagcc tgacctgcct ggtcaaaggc   1260
ttctatccca gcgacatcgc cgtggagtgg gagagcaatg gcaaccgga gaacaactac   1320 aagaccacgc ctcccgtgct ggactccgac ggctccttct tcctctacag caagctcacc   1380
```

| | |
|---|---|
| gtggacaaga gcaggtggca gcaggggaac gtgttctcat gctccgtgat gcatgaggcc | 1440 |
| ctgcacaatc actatacgca gaaatctctg agtctgagcc caggcaagaa ggatatttac | 1500 |
| atctgggcac ccctcgccgg cacctgcggg gtgcttctcc tctccctggt gattaccctg | 1560 |
| tattgcagaa gggaccgatg cctccaacac agctatgcag gtgcctgggc tgtgagtccg | 1620 |
| gagacagagc tcactggcca cgttggatca gggagcggct ctgggagcgg tagtggatct | 1680 |
| ggtatgcaaa tcttcgtgaa aaccctgacc gggaaaacaa tcactctcga agtcgagccc | 1740 |
| agcgatacaa ttgagaacgt gaaggccaag attcaggaca ag | 1782 |

<210> SEQ ID NO 97
<211> LENGTH: 1245
<212> TYPE: DNA
<213> ORGANISM: artificial sequence
<220> FEATURE:
<223> OTHER INFORMATION: GG102

<400> SEQUENCE: 97

| | |
|---|---|
| atggccctgc ctgtcactgc tctgctgctg cctctggctc tgctgctgca cgctgcccga | 60 |
| cctgaagtca aactggtgga gtctggggga ggactggtgc agccaggagg ctcactgagc | 120 |
| ctgtcctgcg ccgcttccgg cttcaccttc accgactact atatgtcttg ggtccgccag | 180 |
| ccacctggga aggctctgga gtggctggca ctgatccgga gcaaagcaga tggatacacc | 240 |
| acagaatatt ctgccagtgt gaagggccgc ttcacactgt cccgagacga ttcacagagc | 300 |
| attctgtacc tgcagatgaa cgctctgagg cctgaggact ctgccactta ctattgcgct | 360 |
| agggatgcag cctactattc ttactatagt ccagaaggcg ctatggacta ctgggggcag | 420 |
| ggaacaagcg tgactgtcag ctccggagga ggaggatccg aggaggagg atctggagga | 480 |
| ggaggaagta tggctgacta taaggatatc gtgatgaccc agagccacaa gttcatgtcc | 540 |
| acatctgtgg gcgaccgcgt caacattacc tgtaaggcct cacagaatgt ggatagcgcc | 600 |
| gtcgcttggt accagcagaa gcctggacag agcccaaaag cactgatcta tagtgcctca | 660 |
| taccggtata gtggcgtgcc agacagattc acaggcaggg ggtcaggaac tgatttttacc | 720 |
| ctgacaattt ctagtgtgca ggccgaggat ctggctgtct actattgcca gcagtactat | 780 |
| tccacccccct ggacattcgg gggaggcaca aagctggaaa tcaaacgatc ggatcccacc | 840 |
| acaaccccccg ctccaaggcc cctaccccc gcaccaacta ttgcctccca gccactctca | 900 |
| ctgcggcctg aggcctgtcg gcccgctgct ggaggcgcag tgcatacaag gggcctcgat | 960 |
| ttcgcctgcg atatttacat ctgggcaccc ctcgccggca cctgcggggt gcttctcctc | 1020 |
| tccctggtga ttaccctgta ttgcagacca cgccgcagcc ccgcccaaga agatggcaaa | 1080 |
| gtctacatca acatgccagg caggggcgga tcagggagcg gctctgggag cggtagtgga | 1140 |
| tctggtatgc aaatcttcgt gaaaaccctg accgggaaaa caatcactct cgaagtcgag | 1200 |
| cccagcgata caattgagaa cgtgaaggcc aagattcagg acaag | 1245 |

<210> SEQ ID NO 98
<211> LENGTH: 1245
<212> TYPE: DNA
<213> ORGANISM: artificial sequence
<220> FEATURE:
<223> OTHER INFORMATION: GG103

<400> SEQUENCE: 98

| | |
|---|---|
| atggccctgc ctgtcactgc tctgctgctg cctctggctc tgctgctgca cgctgcccga | 60 |
| cctgaagtca aactggtgga gtctggggga ggactggtgc agccaggagg ctcactgagc | 120 |

```
ctgtcctgcg ccgcttccgg cttcaccttc accgactact atatgtcttg ggtccgccag    180
ccacctggga aggctctgga gtggctggca ctgatccgga gcaaagcaga tggatacacc    240
acagaatatt ctgccagtgt gaagggccgc ttcacactgt cccgagacga ttcacagagc    300
attctgtacc tgcagatgaa cgctctgagg cctgaggact ctgccactta ctattgcgct    360
agggatgcag cctactattc ttactatagt ccagaaggcg ctatggacta ctggggcag    420 ggaacaagcg tgactgtcag ctccggagga ggaggatccg aggaggagg atctggagga    480 ggaggaagta tggctgacta taaggatatc gtgatgaccc agagccacaa gttcatgtcc    540
acatctgtgg gcgaccgcgt caacattacc tgtaaggcct cacagaatgt ggatagcgcc    600
gtcgcttggt accagcagaa gcctggacag agcccaaaag cactgatcta tagtgcctca    660
taccggtata gtggcgtgcc agacagattc acaggcaggg ggtcaggaac tgattttacc    720
ctgacaattt ctagtgtgca ggccgaggat ctggctgtct actattgcca gcagtactat    780
tccaccccct ggacattcgg ggaggcaca aagctgaaaa tcaaacgatc ggatcccacc    840 acaaccccg ctccaaggcc ccctaccccc gcaccaacta ttgcctccca gccactctca    900
ctgcggcctg aggcctgtcg gcccgctgct ggaggcgcag tgcatacaag gggcctcgat    960
ttcgcctgcg atatttacat ctgggcaccc ctcgccggca cctgcggggt gcttctcctc    1020
tccctggtga ttaccctgta ttgcagacca cgccgcagcc ccgccaaga gatggcaaa    1080 gtctacatca acatgccagg caggggcgga tcagggagcg gctctgggag cggtagtgga    1140
tctggtatgc aaatcttcgt gaaaaccctg accgggaaaa caatcactct cgaagtcgag    1200
cccagcgata caattgagaa cgtgaaggcc aagattcagg acaag    1245

<210> SEQ ID NO 99
<211> LENGTH: 1851
<212> TYPE: DNA
<213> ORGANISM: artificial sequence
<220> FEATURE:
<223> OTHER INFORMATION: GG104

<400> SEQUENCE: 99
atggccctgc ccgtcaccgc tctgctgctg cccctggctc tgctgctgca cgccgcaaga     60
cccgaagtcc agctgcagca gtccggaccc gagctggtga agcctggggc ttctgtcaaa    120
atcagttgca aggcatcagg atatactttc accgactaca catgcactg ggtcaaacag    180 agccacggaa agtccctgga atggatcggc tacatctacc catcaacgg cgggaccggc    240 tataatcaga agtttaaatc caaggcaaca ctgactgtgg ataatagctc ctctactgct    300
tacatggacg tgagatccct gaccagtgag gattcagccg tctactattg cgctcgaggc    360
cggcccgcaa tggactactg gggacagggc actagcgtga ccgtcagttc cggaggagga    420
ggatccggag gaggaggatc tggaggaggc gggagtgata ttgtgctgac tcagagccca    480
gcctccctgg ctgtctcact gggacagagg gcaaccatca gctgtcgcgc cagcgaatcc    540
gtggacaact atggaattag cttcatgaat tggtttcagc agaaacctgg ccagcccct    600 aagctgctga tctacgccgc ttctaaccag gggagtggag tccctgccag gttctctggc    660
agtgggtcag gaaccgattt ttcccctgaat attcacccaa tggaggagga cgatacagcc    720
atgtatttct gccagcagtc taaggaggtg ccctggacct tggaggcgg acaaaactg    780 gaaatcaagc gatcggatcc cgagcccaaa tctcctgaca aaactcacac atgcccaccg    840
tgcccagcac ctcccgtggc cggccgtca gtgttcctct tccccccaaa acccaaggac    900
```

```
accctcatga tcgcccggac ccctgaggtc acatgcgtgg tggtggacgt gagccacgag    960
gaccctgagg tcaagttcaa ctggtacgtg gacggcgtgg aggtgcataa tgccaagaca   1020
aagccgcggg aggagcagta caacagcacg taccgtgtgg tcagcgtcct caccgtcctg   1080
caccaggact ggctgaatgg caaggagtac aagtgcaagg tgtccaacaa agccctccca   1140
gcccccatcg agaaaaccat ctccaaagcc aagggcagc cccgagaacc acaggtgtac    1200
accctgcccc catcccggga tgagctgacc aagaaccagg tcagcctgac ctgcctggtc   1260
aaaggcttct atcccagcga catcgccgtg gagtgggaga gcaatgggca accggagaac   1320
aactacaaga ccacgcctcc cgtgctggac tccgacggct ccttcttcct ctacagcaag   1380
ctcaccgtgg acaagagcag gtggcagcag gggaacgtgt tctcatgctc cgtgatgcat   1440
gaggccctgc acaatcacta cccagaaaa tctctgagtc tgagcccagg caagaaggat    1500
atcatctcct tctttcttgc gctcacgtcg actgcgttgc tcttcctgct gttcttcctc   1560
acgctccgtt tctctgttgt taaacggggc agaggcagaa agaaactcct gtatatattc   1620
aaacaaccat ttatgcgacc agtacaaact actcaagagg aagatggctg tagctgccga   1680
tttccagaag aagaagaagg aggatgtgaa ctgggatcag ggagcggctc tgggagcggt   1740
agtggatctg gtatgcaaat cttcgtgaaa accctgaccg ggaaaacaat cactctcgaa   1800
gtcgagccca gcgatacaat tgagaacgtg aaggccaaga ttcaggacaa g            1851
```

<210> SEQ ID NO 100
<211> LENGTH: 1851
<212> TYPE: DNA
<213> ORGANISM: artificial sequence
<220> FEATURE:
<223> OTHER INFORMATION: GG105

<400> SEQUENCE: 100

```
atggccctgc ccgtcaccgc tctgctgctg ccctggctc tgctgctgca cgccgcaaga     60
cccgaagtcc agctgcagca gtccggaccc gagctggtga agcctggggc ttctgtcaaa    120
atcagttgca aggcatcagg atatactttc accgactaca catgcactg gtcaaacag     180 agccacggaa agtccctgga atggatcggc tacatctacc catacaacgg cgggaccggc    240
tataatcaga agttaaatc caaggcaaca ctgactgtgg ataatagctc ctctactgct    300
tacatggacg tgagatccct gaccagtgag gattcagccg tctactattg cgctcgaggc    360
cggcccgcaa tggactactg gggacagggc actagcgtga ccgtcagttc cggaggagga    420
ggatccggag gaggaggatc tggaggaggc gggagtgata ttgtgctgac tcagagccca    480
gcctccctgg ctgtctcact gggacagagg gcaaccatca gctgtcgcgc cagcgaatcc    540
gtggacaact atggaattag cttcatgaat tggtttcagc agaaacctgg ccagcccct    600 aagctgctga tctacgccgc ttctaaccag gggagtggag tccctgccag gttctctggc    660
agtgggtcag gaaccgattt tccctgaat attcacccaa tggaggagga cgatacagcc    720
atgtatttct gccagcagtc taaggaggtg ccctggacct ttggaggcgg acaaaactg    780 gaaatcaagc gatcggatcc cgagcccaaa tctcctgaca aaactcacac atgcccaccg   840
tgcccagcac ctcccgtggc cggccgtca gtgttcctct ccccccaaa acccaaggac     900 accctcatga tcgcccggac ccctgaggtc acatgcgtgg tggtggacgt gagccacgag    960
gaccctgagg tcaagttcaa ctggtacgtg gacggcgtgg aggtgcataa tgccaagaca   1020
aagccgcggg aggagcagta caacagcacg taccgtgtgg tcagcgtcct caccgtcctg   1080
caccaggact ggctgaatgg caaggagtac aagtgcaagg tgtccaacaa agccctccca   1140
```

| | |
|---|---|
| gcccccatcg agaaaaccat ctccaaagcc aaagggcagc cccgagaacc acaggtgtac | 1200 |
| accctgcccc catcccggga tgagctgacc aagaaccagg tcagcctgac ctgcctggtc | 1260 |
| aaaggcttct atcccagcga catcgccgtg gagtgggaga gcaatgggca accggagaac | 1320 |
| aactacaaga ccacgcctcc cgtgctggac tccgacggct ccttcttcct ctacagcaag | 1380 |
| ctcaccgtgg acaagagcag gtggcagcag gggaacgtgt tctcatgctc cgtgatgcat | 1440 |
| gaggccctgc acaatcacta tacccagaaa tctctgagtc tgagcccagg caagaaggat | 1500 |
| atcatctcct tctttcttgc gctcacgtcg actgcgttgc tcttcctgct gttcttcctc | 1560 |
| acgctccgtt tctctgttgt taaacggggc agaggcagaa agaaactcct gtatatattc | 1620 |
| aaacaaccat ttatgcgacc agtacaaact actcaagagg aagatggctg tagctgccga | 1680 |
| tttccagaag aagaagaagg aggatgtgaa ctgggatcag ggagcggctc tgggagcggt | 1740 |
| agtggatctg gtatgcaaat cttcgtgaaa accctgaccg gaaaacaat cactctcgaa | 1800 |
| gtcgagccca gcgatacaat tgagaacgtg aaggccaaga ttcaggacaa g | 1851 |

<210> SEQ ID NO 101
<211> LENGTH: 1209
<212> TYPE: DNA
<213> ORGANISM: artificial sequence
<220> FEATURE:
<223> OTHER INFORMATION: GG106

<400> SEQUENCE: 101

| | |
|---|---|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccgtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat ataccctac accttcggcg gaggcacaaa gctcgaaata | 780 |
| aagcggtcgg atcccaccac aaccccgct ccaaggcccc ctaccccgc accaactatt | 840 |
| gcctcccagc cactctcact gcggcctgag gcctgtcggc ccgctgctgg aggcgcagtg | 900 |
| catacaaggg gcctcgattt cgcctgcgat attctcctgg caggcctcgt ggctgctgat | 960 |
| gcggtggcat cgctgctcat cgtggggcg gtgttcctgt gcgcacgcag accacgccgc | 1020 |
| agccccgccc aagaagatgg caaagtctac atcaacatgc caggcagggg cggatcaggg | 1080 |
| agcggctctg ggagcggtag tggatctggt atgcaaatct tcgtgaaaac cctgaccggg | 1140 |
| aaaacaatca ctctcgaagt cgagcccagc gatacaattg agaacgtgaa ggccaagatt | 1200 |
| caggacaag | 1209 |

<210> SEQ ID NO 102

```
<211> LENGTH: 1209
<212> TYPE: DNA
<213> ORGANISM: artificial sequence
<220> FEATURE:
<223> OTHER INFORMATION: GG107

<400> SEQUENCE: 102
atggctttgc ctgtcactgc cttgctgctt ccacttgctc tgttgttgca cgccgcaaga      60
ccccaagtgc agcttcaaca gtctggggca gaactcgtaa gaccaggagc atcagtgaca     120
ctgtcttgta aagcctccgg ctataccttc tctgactacg agatgcattg ggtcatccag     180
acaccagtac atgggctcga atggatagga gccatagatc cagagacagg cggaacagca     240
tacaaccaga gttcaaagg caaggccatt ctcacagcgg acaagagcag tagcaccgct      300
tacatggagt tgcgatccct gaccagtgag gactctgcag tctactattg tacagggtac     360
tatgactacg actcattcac atattggggg cagggtacct tggtgactgt ctccgctggc     420
ggaggaggca gtggcggagg gggaagtggg ggcggcggca gcgatatagt gatgacgcag     480
tcccagaaga tcatgtccac gaccgtcggg gatcgggtca gtataacatg taaggcatcc     540
cagaacgtgg acgcggccgt ggcttggtat caacagaaac ccggtcaatc cccaaagctc     600
ctcatctact ctgcgagcaa tagatatacc ggtgtgcctg ataggttcac cggaagcggc     660
tccggaacag atttcaccct gactatcagc aatatgcaat ccgaggactt ggctgactac     720
ttttgccagc aatacgacat ataccccctac accttcggcg aggcacaaa gctcgaaata      780
aagcggtcgg atcccaccac aaccccgct ccaaggcccc ctaccccgc accaactatt       840
gcctcccagc cactctcact gcggcctgag gcctgtcggc cgctgctgg aggcgcagtg      900
catacaaggg gcctcgattt cgcctgcgat attctcctgg caggcctcgt ggctgctgat     960
gcggtggcat cgctgctcat cgtggggcg tgttcctgt gcgcacgcag accacgccgc      1020
agccccgccc aagaagatgg caaagtctac atcaacatgc caggcagggg cggatcaggg    1080
agcggctctg ggagcggtag tggatctggt atgcaaatct cgtgaaaac cctgaccggg     1140
aaaacaatca ctctcgaagt cgagcccagc gatacaattg agaacgtgaa ggccaagatt    1200
caggacaag                                                            1209

<210> SEQ ID NO 103
<211> LENGTH: 1320
<212> TYPE: DNA
<213> ORGANISM: artificial sequence
<220> FEATURE:
<223> OTHER INFORMATION: GG108

<400> SEQUENCE: 103
atggccctgc ctgtcactgc tctgctgctg cctctggctc tgctgctgca cgctgcccga      60
cctgaagtca aactggtgga gtctggggga ggactggtgc agccaggagg ctcactgagc     120
ctgtcctgcg ccgcttccgg cttcaccttc accgactact atatgtcttg ggtccgccag     180
ccacctggga aggctctgga gtggctggca ctgatccgga gcaaagcaga tggatacacc     240
acagaatatt ctgccagtgt gaagggccgc ttcacactgt cccgagacga ttcacagagc     300
attctgtacc tgcagatgaa cgctctgagg cctgaggact ctgccactta ctattgcgct     360
agggatgcag cctactattc ttactatagt ccagaaggcg ctatggacta ctgggggcag     420
ggaacaagcg tgactgtcag ctccggagga ggaggatccg aggaggagg atctggagga      480
ggaggaagta tggctgacta taaggatatc gtgatgaccc agagccacaa gttcatgtcc    540
acatctgtgg gcgaccgcgt caacattacc tgtaaggcct cacagaatgt ggatagcgcc    600
```

```
gtcgcttggt accagcagaa gcctggacag agcccaaaag cactgatcta tagtgcctca    660
taccggtata gtggcgtgcc agacagattc acaggcaggg ggtcaggaac tgattttacc    720
ctgacaattt ctagtgtgca ggccgaggat ctggctgtct actattgcca gcagtactat    780 tccacccct ggacattcgg gggaggcaca aagctggaaa tcaaacgatc ggatcccacc     840 acaaccccg ctccaaggcc cctaccccc gcaccaacta ttgcctccca gccactctca     900
ctgcggcctg aggcctgtcg gcccgctgct ggaggcgcag tgcatacaag gggcctcgat    960
ttcgcctgcg atatcttttg ggtgctggtg gtggttggtg gagtcctggc ttgctatagc   1020
ttgctagtaa cagtggcctt tattattttc tgggtgagga gtaagcgcag aagcaggctc   1080
ctgcacagtg actacatgaa catgactccc cgccgccccg ggcccacccg caagcattac   1140
cagccctatg ccccaccacg cgacttcgca gcctatcgct ccggatcagg gagcggctct   1200
gggagcggta gtggatctgg tatgcaaatc ttcgtgaaaa ccctgaccgg gaaaacaatc   1260
actctcgaag tcgagcccag cgatacaatt gagaacgtga aggccaagat tcaggacaag   1320
```

<210> SEQ ID NO 104
<211> LENGTH: 1320
<212> TYPE: DNA
<213> ORGANISM: artificial sequence
<220> FEATURE:
<223> OTHER INFORMATION: GG109

<400> SEQUENCE: 104

```
atggccctgc ctgtcactgc tctgctgctg cctctggctc tgctgctgca cgctgcccga     60
cctgaagtca aactggtgga gtctggggga ggactggtgc agccaggagg ctcactgagc    120
ctgtcctgcg ccgcttccgg cttcaccttc accgactact atatgtcttg ggtccgccag    180
ccacctggga aggctctgga gtggctggca ctgatccgga gcaaagcaga tggatacacc    240
acagaatatt ctgccagtgt gaagggccgc ttcacactgt cccgagacga ttcacagagc    300
attctgtacc tgcagatgaa cgctctgagg cctgaggact ctgccactta ctattgcgct    360
agggatgcag cctactattc ttactatagt ccagaaggcg ctatggacta ctggggggcag   420 ggaacaagcg tgactgtcag ctccggagga ggaggatccg gaggaggagg atctggagga   480
ggaggaagta tggctgacta taaggatatc gtgatgaccc agagccacaa gttcatgtcc    540
acatctgtgg gcgaccgcgt caacattacc tgtaaggcct cacagaatgt ggatagcgcc    600
gtcgcttggt accagcagaa gcctggacag agcccaaaag cactgatcta tagtgcctca    660
taccggtata gtggcgtgcc agacagattc acaggcaggg ggtcaggaac tgattttacc    720
ctgacaattt ctagtgtgca ggccgaggat ctggctgtct actattgcca gcagtactat    780 tccacccct ggacattcgg gggaggcaca aagctggaaa tcaaacgatc ggatcccacc     840 acaaccccg ctccaaggcc cctaccccc gcaccaacta ttgcctccca gccactctca     900
ctgcggcctg aggcctgtcg gcccgctgct ggaggcgcag tgcatacaag gggcctcgat    960
ttcgcctgcg atatcttttg ggtgctggtg gtggttggtg gagtcctggc ttgctatagc   1020
ttgctagtaa cagtggcctt tattattttc tgggtgagga gtaagcgcag aagcaggctc   1080
ctgcacagtg actacatgaa catgactccc cgccgccccg ggcccacccg caagcattac   1140
cagccctatg ccccaccacg cgacttcgca gcctatcgct ccggatcagg gagcggctct   1200
gggagcggta gtggatctgg tatgcaaatc ttcgtgaaaa ccctgaccgg gaaaacaatc   1260
actctcgaag tcgagcccag cgatacaatt gagaacgtga aggccaagat tcaggacaag   1320
```

<210> SEQ ID NO 105
<211> LENGTH: 1839
<212> TYPE: DNA
<213> ORGANISM: artificial sequence
<220> FEATURE:
<223> OTHER INFORMATION: GG110

<400> SEQUENCE: 105

| | | | | | | |
|---|---|---|---|---|---|---|
| atggccctgc | cgtcaccgc | tctgctgctg | cccctggctc | tgctgctgca | cgccgcaaga | 60 |
| cccgaagtcc | agctgcagca | gtccggaccc | gagctggtga | agcctggggc | ttctgtcaaa | 120 |
| atcagttgca | aggcatcagg | atatactttc | accgactaca | acatgcactg | ggtcaaacag | 180 |
| agccacggaa | agtccctgga | atggatcggc | tacatctacc | catacaacgg | cgggaccggc | 240 |
| tataatcaga | agtttaaatc | caaggcaaca | ctgactgtgg | ataatagctc | ctctactgct | 300 |
| tacatggacg | tgagatccct | gaccagtgag | gattcagccg | tctactattg | cgctcgaggc | 360 |
| cggcccgcaa | tggactactg | gggacagggc | actagcgtga | ccgtcagttc | cggaggagga | 420 |
| ggatccggag | gaggaggatc | tggaggaggc | gggagtgata | ttgtgctgac | tcagagccca | 480 |
| gcctccctgg | ctgtctcact | gggacagagg | gcaaccatca | gctgtcgcgc | cagcgaatcc | 540 |
| gtggacaact | atggaattag | cttcatgaat | tggtttcagc | agaaacctgg | ccagcccct | 600 |
| aagctgctga | tctacgccgc | ttctaaccag | gggagtggag | tccctgccag | gttctctggc | 660 |
| agtgggtcag | gaaccgattt | ttccctgaat | attcacccaa | tggaggagga | cgatacagcc | 720 |
| atgtatttct | gccagcagtc | taaggaggtg | ccctggacct | ttggaggcgg | acaaaaactg | 780 |
| gaaatcaagc | gatcggatcc | cgagcccaaa | tctcctgaca | aaactcacac | atgcccaccg | 840 |
| tgcccagcac | ctcccgtggc | cggcccgtca | gtgttcctct | tccccccaaa | acccaaggac | 900 |
| accctcatga | tctcccggac | ccctgaggtc | acatgcgtgg | tggtggacgt | gagccacgag | 960 |
| gaccctgagg | tcaagttcaa | ctggtacgtg | gacggcgtgg | aggtgcataa | tgccaagaca | 1020 |
| aagccgcggg | aggagcagta | caacagcacg | taccgtgtgg | tcagcgtcct | caccgtcctg | 1080 |
| caccaggact | ggctgaatgg | caaggagtac | aagtgcaagg | tgtccaacaa | agccctccca | 1140 |
| gcccccatcg | agaaaaccat | ctccaaagcc | aaagggcagc | cccgagaacc | acaggtgtac | 1200 |
| accctgcccc | catcccggga | tgagctgacc | aagaaccagg | tcagcctgac | ctgcctggtc | 1260 |
| aaaggcttct | atcccagcga | catcgccgtg | gagtgggaga | gcaatgggca | accggagaac | 1320 |
| aactacaaga | ccacgcctcc | cgtgctggac | tccgacggct | ccttcttcct | ctacagcaag | 1380 |
| ctcaccgtgg | acaagagcag | gtggcagcag | gggaacgtgt | tctcatgctc | cgtgatgcat | 1440 |
| gaggccctgc | acaatcacta | cacccagaaa | tctctgagtc | tgagcccagg | caagaaggat | 1500 |
| atttacatct | gggcaccct | cgccggcacc | tgcggggtgc | ttctcctctc | cctggtgatt | 1560 |
| accctgtatt | gcagagccct | gtacctgctc | cggagggacc | agaggctgcc | cccgatgcc | 1620 |
| cacaagcccc | ctgggggagg | cagtttccgg | accccatcc | aagaggagca | ggccgacgcc | 1680 |
| cactccaccc | tggccaagat | cggatcaggg | agcggctctg | gagcggtag | tggatctggt | 1740 |
| atgcaaatct | tcgtgaaaac | cctgaccggg | aaaacaatca | ctctcgaagt | cgagcccagc | 1800 |
| gatacaattg | agaacgtgaa | ggccaagatt | caggacaag | | | 1839 |

<210> SEQ ID NO 106
<211> LENGTH: 1839
<212> TYPE: DNA
<213> ORGANISM: artificial sequence
<220> FEATURE:
<223> OTHER INFORMATION: GG111

<400> SEQUENCE: 106

```
atggccctgc ccgtcaccgc tctgctgctg ccctggctc tgctgctgca cgccgcaaga      60
cccgaagtcc agctgcagca gtccggaccc gagctggtga agcctggggc ttctgtcaaa    120
atcagttgca aggcatcagg atatactttc accgactaca catgcactg ggtcaaacag     180
agccacggaa agtccctgga atggatcggc tacatctacc catacaacgg cgggaccggc    240
tataatcaga agtttaaatc caaggcaaca ctgactgtgg ataatagctc ctctactgct    300
tacatggacg tgagatccct gaccagtgag gattcagccg tctactattg cgctcgaggc    360
cggcccgcaa tggactactg gggacagggc actagcgtga ccgtcagttc cggaggagga    420
ggatccggag gaggaggatc tggaggaggc gggagtgata ttgtgctgac tcagagccca    480
gcctccctgg ctgtctcact gggacagagg gcaaccatca gctgtcgcgc agcgaatcc    540
gtggacaact atggaattag cttcatgaat tggtttcagc agaaacctgg ccagccccct    600
aagctgctga tctacgccgc ttctaaccag gggagtggag tccctgccag gttctctggc    660
agtgggtcag gaaccgattt ttccctgaat attcacccaa tggaggagga cgatacagcc    720
atgtatttct gccagcagtc taaggaggtg ccctggacct ttggaggcgg gacaaaactg    780
gaaatcaagc gatcggatcc cgagcccaaa tctcctgaca aaactcacac atgcccaccg    840
tgcccagcac ctcccgtggc cggccgtca gtgttcctct ccccccaaa cccaaggac      900
accctcatga tcgcccggac ccctgaggtc acatgcgtgg tggtggacgt gagccacgag    960
gaccctgagg tcaagttcaa ctggtacgtg gacggcgtgg aggtgcataa tgccaagaca   1020
aagccgcggg aggagcagta caacagcacg taccgtgtgg tcagcgtcct caccgtcctg   1080
caccaggact ggctgaatgg caaggagtac aagtgcaagg tgtccaacaa agccctccca   1140
gcccccatcg agaaaaccat ctccaaagcc aaagggcagc cccgagaacc acaggtgtac   1200
accctgcccc catcccggga tgagctgacc aagaaccagg tcagcctgac ctgcctggtc   1260
aaaggcttct atcccagcga catcgccgtg gagtgggaga gcaatgggca accggagaac   1320
aactacaaga ccacgcctcc cgtgctggac tccgacggct ccttcttcct ctacagcaag   1380
ctcaccgtgg acaagagcag gtggcagcag gggaacgtgt tctcatgctc cgtgatgcat   1440
gaggccctgc acaatcacta cccagaaa tctctgagtc tgagcccagg caagaaggat     1500
atttacatct gggcacccct cgccggcacc tgcggggtgc ttctcctctc cctggtgatt   1560
accctgtatt gcagagccct gtacctgctc cgagggacc agaggctgcc ccccgatgcc    1620
cacaagcccc tgggggagg cagtttccgg acccccatcc aagaggagca ggccgacgcc    1680
cactccaccc tggccaagat cggatcaggg agcggctctg ggagcggtag tggatctggt   1740
atgcaaatct tcgtgaaaac cctgaccggg aaaacaatca ctctcgaagt cgagcccagc   1800
gatacaattg agaacgtgaa ggccaagatt caggacaag                          1839
```

<210> SEQ ID NO 107
<211> LENGTH: 1281
<212> TYPE: DNA
<213> ORGANISM: artificial sequence
<220> FEATURE:
<223> OTHER INFORMATION: GG112

<400> SEQUENCE: 107

```
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca   120
```

```
ctgtcttgta aagcctccgg ctataccttc tctgactacg agatgcattg ggtcatccag      180
acaccagtac atgggctcga atggatagga gccatagatc cagagacagg cggaacagca      240
tacaaccaga agttcaaagg caaggccatt ctcacagcgg acaagagcag tagcaccgct      300
tacatggagt tgcgatccct gaccagtgag gactctgcag tctactattg tacagggtac      360
tatgactacg actcattcac atattggggg cagggtacct tggtgactgt ctccgctggc      420
ggaggaggca gtggcggagg gggaagtggg ggcggcggca gcgatatagt gatgacgcag      480
tcccagaaga tcatgtccac gaccgtcggg gatcgggtca gtataacatg taaggcatcc      540
cagaacgtgg acgcggccgt ggcttggtat caacagaaac ccggtcaatc cccaaagctc      600
ctcatctact ctgcgagcaa tagatatacc ggtgtgcctg ataggttcac cggaagcggc      660
tccggaacag atttcaccct gactatcagc aatatgcaat ccgaggactt ggctgactac      720
ttttgccagc aatacgacat ataccctac accttcggcg gaggcacaaa gctcgaaata      780
aagcggtcgg atcccaccac aaccccgct ccaaggcccc ctaccccgc accaactatt      840 gcctcccagc cactctcact gcggcctgag gcctgtcggc ccgctgctgg aggcgcagtg      900
catacaaggg gcctcgattt cgcctgcgat atcatctcct tctttcttgc gctcacgtcg      960
actgcgttgc tcttcctgct gttcttcctc acgctccgtt tctctgttgt taaacggggc     1020
agaggcagaa agaaactcct gtatatattc aaacaaccat ttatgcgacc agtacaaact     1080
actcaagagg aagatggctg tagctgccga tttccagaag aagaagaagg aggatgtgaa     1140
ctgggatcag ggagcggctc tgggagcggt agtggatctg gtatgcaaat cttcgtgaaa     1200
accctgaccg gaaaaacaat cactctcgaa gtcgagccca gcgatacaat tgagaacgtg     1260
aaggccaaga ttcaggacaa g                                               1281
```

<210> SEQ ID NO 108
<211> LENGTH: 1281
<212> TYPE: DNA
<213> ORGANISM: artificial sequence
<220> FEATURE:
<223> OTHER INFORMATION: GG113

<400> SEQUENCE: 108

```
atggctttgc ctgtcactgc cttgctgctt ccacttgctc tgttgttgca cgccgcaaga       60
ccccaagtgc agcttcaaca gtctggggca gaactcgtaa gaccaggagc atcagtgaca      120
ctgtcttgta aagcctccgg ctataccttc tctgactacg agatgcattg ggtcatccag      180
acaccagtac atgggctcga atggatagga gccatagatc cagagacagg cggaacagca      240
tacaaccaga agttcaaagg caaggccatt ctcacagcgg acaagagcag tagcaccgct      300
tacatggagt tgcgatccct gaccagtgag gactctgcag tctactattg tacagggtac      360
tatgactacg actcattcac atattggggg cagggtacct tggtgactgt ctccgctggc      420
ggaggaggca gtggcggagg gggaagtggg ggcggcggca gcgatatagt gatgacgcag      480
tcccagaaga tcatgtccac gaccgtcggg gatcgggtca gtataacatg taaggcatcc      540
cagaacgtgg acgcggccgt ggcttggtat caacagaaac ccggtcaatc cccaaagctc      600
ctcatctact ctgcgagcaa tagatatacc ggtgtgcctg ataggttcac cggaagcggc      660
tccggaacag atttcaccct gactatcagc aatatgcaat ccgaggactt ggctgactac      720
ttttgccagc aatacgacat ataccctac accttcggcg gaggcacaaa gctcgaaata      780
aagcggtcgg atcccaccac aaccccgct ccaaggcccc ctaccccgc accaactatt      840 gcctcccagc cactctcact gcggcctgag gcctgtcggc ccgctgctgg aggcgcagtg      900
```

```
catacaaggg gcctcgattt cgcctgcgat atcatctcct tctttcttgc gctcacgtcg    960
actgcgttgc tcttcctgct gttcttcctc acgctccgtt tctctgttgt taaacggggc   1020
agaggcagaa agaaactcct gtatatattc aaacaaccat ttatgcgacc agtacaaact   1080
actcaagagg aagatggctg tagctgccga tttccagaag aagaagaagg aggatgtgaa   1140
ctgggatcag ggagcggctc tgggagcggt agtggatctg gtatgcaaat cttcgtgaaa   1200
accctgaccg ggaaaacaat cactctcgaa gtcgagccca gcgatacaat tgagaacgtg   1260
aaggccaaga ttcaggacaa g                                            1281
```

<210> SEQ ID NO 109
<211> LENGTH: 1860
<212> TYPE: DNA
<213> ORGANISM: artificial sequence
<220> FEATURE:
<223> OTHER INFORMATION: GG120

<400> SEQUENCE: 109

```
atggctttgc ctgtcactgc cttgctgctt ccacttgctc tgttgttgca cgccgcaaga     60
cccgaggtgc agttgcagca gtcagggcca gagttgatta gcccggagc ctccgtcaag    120 atgtcctgca aggccagcgg gtacactttc accagctacg tcatgcattg ggtgaagcag    180
aagccaggcc aggggcttga gtggattggg tacatcaacc cctacaacga cgggaccaaa    240
tacaacgaga attcaagggc aaagccaca ctcacctccg ataagtcctc ctctaccgcc    300
tacatggagc tcagctccct gacctccgag gatagcgctg tgtattactg cgcaaggggc    360
acatactact atggctctag ggtgttcgac tactgggggc agggcactac tctcacagtg    420
agctcaggcg gaggaggcag tggcggaggg ggaagtgggg gcggcggcag cgatattgtc    480
atgacccagg cagcccctag tatccctgtg actccaggcg agagcgtgag catcagctgc    540
cggtccagca gagcctgct gaacagtaac ggaaacacat acctctactg gtttctgcag    600
aggcccggcc agagccctca gctgctgatt taccgcatgt caaatcttgc ctctggggtg    660
cccgatagat ttagtgggag cggctccggc acagctttta cattgcggat ctccagagtc    720
gaggccgaag atgtgggggt ctattactgt atgcaacacc tggaataccc ctttaccttc    780
ggagccggca aaagctgga gctgaagcgg tcggatcccg agcccaaatc tcctgacaaa    840
actcacacat gcccaccgtg cccagcacct cccgtggccg gccgtcagt gttcctcttc    900 ccccaaaac caaggacac cctcatgatc gcccggaccc ctgaggtcac atgcgtggtg    960
gtggacgtga gccacgagga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtg   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat cccagcgaca tcgccgtgga gtgggagagc   1320
aatgggcaac cggagaacaa ctacaagacc acgcctcccg tgctggactc cgacggctcc   1380
ttcttcctct acagcaagct caccgtggac aagagcaggt ggcagcaggg gaacgtgttc   1440
tcatgctccg tgatgcatga ggccctgcac aatcactata cccagaaatc tctgagtctg   1500
agcccaggca gaaggatat catctccttc tttcttgcgc tcacgtcgac tgcgttgctc   1560
ttcctgctgt tcttcctcac gctccgtttc tctgttgtta acggggcag aatggaggag   1620
```

-continued

| | |
|---|---|
| agtgtcgtac ggccctcagt gtttgtggtg gatggacaga ccgacatccc attcacgagg | 1680 |
| ctgggacgaa gccaccggag acagtcgtgc agtgtggccc ggggatcagg gagcggctct | 1740 |
| gggagcggta gtggatctgg tatgcaaatc ttcgtgaaaa ccctgaccgg gaaaacaatc | 1800 |
| actctcgaag tcgagcccag cgatacaatt gagaacgtga aggccaagat tcaggacaag | 1860 |

<210> SEQ ID NO 110
<211> LENGTH: 2688
<212> TYPE: DNA
<213> ORGANISM: artificial sequence
<220> FEATURE:
<223> OTHER INFORMATION: GG121

<400> SEQUENCE: 110

| | |
|---|---|
| atggctttgc ctgtcactgc cttgctgctt ccacttgctc tgttgttgca cgccgcaaga | 60 |
| cccgaggtgc agttgcagca gtcagggcca gagttgatta gcccggagc ctccgtcaag | 120 |
| atgtcctgca aggccagcgg gtacactttc accagctacg tcatgcattg ggtgaagcag | 180 |
| aagccaggcc aggggcttga gtggattggg tacatcaacc cctacaacga cggaccaaa | 240 |
| tacaacgaga aattcaaggg caaagccaca ctcacctccg ataagtcctc ctctaccgcc | 300 |
| tacatggagc tcagctccct gacctccgag gatagcgctg tgtattactg cgcaaggggc | 360 |
| acatactact atggctctag ggtgttcgac tactgggggc agggcactac tctcacagtg | 420 |
| agctcaggcg gaggaggcag tggcggaggg ggaagtgggg cggcggcag cgatattgtc | 480 |
| atgacccagg cagcccctag tatccctgtg actccaggcg agagcgtgag catcagctgc | 540 |
| cggtccagca gagcctgct gaacagtaac ggaaacacat acctctactg gtttctgcag | 600 |
| aggcccggcc agagccctca gctgctgatt taccgcatgt caaatcttgc ctctggggtg | 660 |
| cccgatagat ttagtgggag cggctccggc acagctttta cattgcggat ctccagagtc | 720 |
| gaggccgaag atgtgggggt ctattactgt atgcaacacc tggaataccc ctttaccttc | 780 |
| ggagccggca caaagctgga gctgaagcgg tcggatcccg agcccaaatc tcctgacaaa | 840 |
| actcacacat gcccaccgtg cccagcacct cccgtggccg gcccgtcagt gttcctcttc | 900 |
| cccccaaaac ccaaggacac cctcatgatc gcccggaccc ctgaggtcac atgcgtggtg | 960 |
| gtggacgtga gccacgagga ccctgaggtc aagttcaact ggtacgtgga cggcgtggag | 1020 |
| gtgcataatg ccaagacaaa gccgcgggag gagcagtaca acagcacgta ccgtgtggtc | 1080 |
| agcgtcctca ccgtcctgca ccaggactgg ctgaatggca aggagtacaa gtgcaaggtg | 1140 |
| tccaacaaag ccctcccagc ccccatcgag aaaaccatct ccaaagccaa agggcagccc | 1200 |
| cgagaaccac aggtgtacac cctgccccca tcccgggatg agctgaccaa gaaccaggtc | 1260 |
| agcctgacct gcctggtcaa aggcttctat cccagcgaca tcgccgtgga gtgggagagc | 1320 |
| aatgggcaac cggagaacaa ctacaagacc acgcctcccg tgctggactc cgacggctcc | 1380 |
| ttcttcctct acagcaagct caccgtggac aagagcaggt ggcagcaggg gaacgtgttc | 1440 |
| tcatgctccg tgatgcatga ggccctgcac aatcactata cccagaaatc tctgagtctg | 1500 |
| agcccaggca gaaggatat cttttgggtg ctggtggtgg ttggtggagt cctggcttgc | 1560 |
| tatagcttgc tagtaacagt ggcctttatt attttctggg tgaggagtaa gcgcagaagg | 1620 |
| gaccgatgcc tccaacacag ctatgcaggt gcctgggctg tgagtccgga cagagctc | 1680 |
| actggccacg ttggatcagg gagcggctct gggagcggta gtggatctgg tggcatccct | 1740 |
| cccgatcaac agcgccttat cttcgcagga aagcagctgg aggacggccg gacattgtct | 1800 |
| gactacaaca ttcagaaaga atccacctc cacctggtgc tgaggctccg ggggggatg | 1860 |

```
cataggagcg cctgcgggag aatggctggc tctggaatgt ccagactcga caagagcaaa   1920
gtgatcaaca gcgccctgga gctcctgaac gaggtgggaa tcgagggcct gactaccaga   1980
aagctcgcac agaagctggg ggtcgagcag ccaaccttgt actggcacgt gaagaacaag   2040
agggccctcc ttgacgctct tgcaatcgag atgctggaca ggcaccacac ccacttctgc   2100
cctcttgagg gagagtcctg gcaggatttc ctgaggaaca acgctaagag cttccggtgc   2160
gctctgctgt cccacaggga tggggccaaa gtgcatttgg ggacacgccc tacagaaaag   2220
cagtacgaga ctctggagaa ccagctggcc ttcctgtgcc agcaggggtt tagcctcgaa   2280
aatgccctct atgccctctc tgccgtcggc catttcaccc tcgggtgtgt cttggaagat   2340
caggagcacc aggtggccaa ggaagagcgg gagacaccaa caactgacag tatgcccccc   2400
ttgttgcggc aagccattga gctgtttgat catcagggcg ccgagcccgc ctttctgttt   2460
ggcctggagc tgattatttg cggcctggag aagcagctga agtgcgagtc aggtagcggg   2520
tctggacggg cagatgcttt ggatgatttc gaccttgaca tgctggggag cgatgccttg   2580
gatgacttcg atctggacat gctcggctca gatgccctgg atgattttga cctggacatg   2640
ctgggctccg atgccctgga cgactttgac ctcgacatgc tcatcaac                2688
```

<210> SEQ ID NO 111
<211> LENGTH: 3084
<212> TYPE: DNA
<213> ORGANISM: artificial sequence
<220> FEATURE:
<223> OTHER INFORMATION: GG122

<400> SEQUENCE: 111

```
atggctttgc ctgtcactgc cttgctgctt ccacttgctc tgttgttgca cgccgcaaga     60
cccgaggtgc agttgcagca gtcagggcca gagttgatta agcccggagc ctccgtcaag    120
atgtcctgca aggccagcgg gtacactttc accagctacg tcatgcattg ggtgaagcag    180
aagccaggcc aggggcttga gtggattggg tacatcaacc cctacaacga cgggaccaaa    240
tacaacgaga aattcaaggg caaagccaca ctcacctccg ataagtcctc ctctaccgcc    300
tacatggagc tcagctccct gacctccgag gatagcgctg tgtattactg cgcaaggggc    360
acatactact atggctctag ggtgttcgac tactgggggc agggcactac tctcacagtg    420
agctcaggcg gaggaggcag tggcggaggg ggaagtgggg gcggcggcag cgatattgtc    480
atgacccagg cagcccctag tatccctgtg actccaggcg agagcgtgag catcagctgc    540
cggtccagca agagcctgct gaacagtaac ggaaacacat acctctactg gtttctgcag    600
aggcccggcc agagccctca gctgctgatt taccgcatgt caaatcttgc ctctggggtg    660
cccgatagat ttagtgggag cggctccggc acagctttta cattgcggat ctccagagtc    720
gaggccgaag atgtgggggt ctattactgt atgcaacacc tggaataccc ctttaccttc    780
ggagccggca caaagctgga gctgaagcgg tcggatcccg agcccaaatc tcctgacaaa    840
actcacacat gcccaccgtg cccagcacct cccgtggccg gcccgtcagt gttcctcttc    900
cccccaaaac ccaaggacac cctcatgatc gcccggaccc ctgaggtcac atgcgtggtg    960
gtggacgtga gccacgagga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtg   1140
tccaacaaag ccctcccagc ccccatcgag aaaaccatct ccaaagccaa agggcagccc   1200
```

| | |
|---|---:|
| cgagaaccac aggtgtacac cctgccccca tcccgggatg agctgaccaa gaaccaggtc | 1260 |
| agcctgacct gcctggtcaa aggcttctat cccagcgaca tcgccgtgga gtgggagagc | 1320 |
| aatgggcaac cggagaacaa ctacaagacc acgcctcccg tgctggactc cgacggctcc | 1380 |
| ttcttcctct acagcaagct caccgtggac aagagcaggt ggcagcaggg gaacgtgttc | 1440 |
| tcatgctccg tgatgcatga ggccctgcac aatcactata cccagaaatc tctgagtctg | 1500 |
| agcccaggca agaaggatat ttacatctgg gcacccctcg ccggcacctg cggggtgctt | 1560 |
| ctcctctccc tggtgattac cctgtattgc agaatggagg agagtgtcgt acggccctca | 1620 |
| gtgtttgtgg tggatggaca gaccgacatc ccattcacga ggctgggacg aagccaccgg | 1680 |
| agacagtcgt gcagtgtggc ccggggatca gggagcggct ctgggagcgg tagtggatct | 1740 |
| ggtggcatcc ctcccgatca acagcgcctt atcttcgcag gaaagcagct ggaggacggc | 1800 |
| cggacattgt ctgactacaa cattcagaaa gaatccaccc tccacctggt gctgaggctc | 1860 |
| cgggggggga tgcataggag cgcctgcggg agaatggctg gctctggaat gaagctcctg | 1920 |
| tcctctatcg agcaggcatg cgacatctgc agactcaaga agctgaagtg cagcaaggag | 1980 |
| aagcccaagt gcgccaagtg ccttaagaac aactgggagt gtaggtactc ccctaagacc | 2040 |
| aagaggtccc ctctgaccag agctcacctt actgaggtgg agtccaggtt ggagcggttg | 2100 |
| gaacaactgt tcctgttgat cttccccagg gaggacctcg atatgattct gaaaatggac | 2160 |
| tccctccagg acattaaggc cctgctgacc gggctctttg tgcaggacaa tgtgaacaaa | 2220 |
| gatgccgtca cagatcggct cgccagcgtc gagactgata tgccactgac actgcggcag | 2280 |
| catcggatta gcgccacaag ctcaagcgag gaaagttcta acaaaggcca gcgccagctg | 2340 |
| acagttagcg aaaccttcaa gtccatcatg aagaagtccc ccttcagcgg accaaccgac | 2400 |
| ccaaggcccc cacctcgcag gatcgccgtg ccctccagat cctccgcctc cgtgcctaag | 2460 |
| cctgcccctc agccatacc tttcacctcc agcctgtcca ccatcaacta cgacgagttc | 2520 |
| ccaactatgg tgttccccag cggccagatt agccaggcaa cgccctcgc acctgcccct | 2580 |
| ccccaggtgc tccctcaggc acctgcacct gctcctgctc cagctatggt cagcgccctc | 2640 |
| gctcaggctc ctgctcccgt cccagtgctt gctccaggac caccaagc cgtcgcccca | 2700 |
| cccgccccca aacccacaca agccggagaa ggcactcttt ctgaggcctt gttgcagttg | 2760 |
| cagtttgacg acgaggacct gggggccctg ctgggcaatt caacagaccc cgccgtgttt | 2820 |
| actgacctcg ccagcgtgga taacagcgag tttcagcagc tgctcaacca gggcatcccc | 2880 |
| gtcgccccc acaccacaga gcccatgctc atggagtatc ccgaggccat tacacggctg | 2940 |
| gtgacagggg cccagcggcc ccccgatccc gcccccgccc cctgggggc cccagggctg | 3000 |
| cccaacggcc tgctgagtgg ggatgaggat ttttcatcta ttgccgatat ggattttagt | 3060 |
| gccctgctgt ctcagattag ctcg | 3084 |

<210> SEQ ID NO 112
<211> LENGTH: 3321
<212> TYPE: DNA
<213> ORGANISM: artificial sequence
<220> FEATURE:
<223> OTHER INFORMATION: GG123

<400> SEQUENCE: 112

| | |
|---|---:|
| atggctttgc ctgtcactgc cttgctgctt ccacttgctc tgttgttgca cgccgcaaga | 60 |
| cccgaggtcc agcttcagca gtctggacct gacctggtga agcctggggc ttcagtgaag | 120 |
| atatcctgca aggcttctgg ttactcattc actggctact acatgcactg ggtgaagcag | 180 |

```
agtcatggaa agagccttga gtggattgga cgtattaatc ctaacaatgg tgttactctc    240
tacaaccaga aattcaagga caaggccata ttaactgtag acaagtcatc caccacagcc    300
tacatggagc tccgcagcct gacatctgag gactctgcgg tctattactg tgcaagatca    360
actatgatta cgaactatgt tatggactac tggggtcaag taacctcagt caccgtttcc    420
tcaggcggag gaggcagtgg cggaggggga agtgggggcg gcggcagcag tattgtgatg    480
acccagactc ccacattcct gcttgtttca gcaggagaca gggttaccat aacctgcaag    540
gccagtcaga gtgtgagtaa tgatgtagct tggtaccaac agaagccagg gcagtctcct    600
acactgctca tatcctatac atccagtcgc tacgctggag tccctgatcg cttcattggc    660
agtggatatg ggacggattt cactttcacc atcagcactt tgcaggctga ggacctggca    720
gtttatttct gtcagcaaga ttataattct cctccgacgt tcggtggagg caccaagctg    780
gaaatcaaac ggtcggatcc cgagcccaaa tctcctgaca aaactcacac atgcccaccg    840
tgcccagcac ctcccgtggc cggcccgtca gtgttcctct tccccccaaa acccaaggac    900
accctcatga tcgcccggac ccctgaggtc acatgcgtgg tggtggacgt gagccacgag    960
gaccctgagg tcaagttcaa ctggtacgtg gacggcgtgg aggtgcataa tgccaagaca    1020
aagccgcggg aggagcagta caacagcacg taccgtgtgg tcagcgtcct caccgtcctg    1080
caccaggact ggctgaatgg caaggagtac aagtgcaagg tgtccaacaa agccctccca    1140
gcccccatcg agaaaaccat ctccaaagcc aaagggcagc ccgagaacc acaggtgtac    1200 accctgcccc catcccggga tgagctgacc aagaaccagg tcagcctgac ctgcctggtc    1260
aaaggcttct atcccagcga catcgccgtg gagtgggaga gcaatgggca accggagaac    1320
aactacaaga ccacgcctcc cgtgctggac tccgacggct ccttcttcct ctacagcaag    1380
ctcaccgtgg acaagagcag gtggcagcag gggaacgtgt tctcatgctc cgtgatgcat    1440
gaggccctgc acaatcacta cccagaaaa tctctgagtc tgagcccagg caagaaggat    1500
attctcctgg caggcctcgt ggctgctgat gcggtggcat cgctgctcat cgtggggcg    1560 gtgttcctgt gcgcacgcag atgtgtgaaa agaagaaagc caaggggtga tgtagtcaag    1620
gtgattgtct ccgtccagcg gaaaagacag gaggcagaag tgaggccac agtcattgag    1680 gccctgcaag cccctccgga cgtcaccacg gtggccgtgg aggagacaat accctcattc    1740
acggggagga gcccaaacca cggatcaggg agcggctctg ggagcggtag tggatctggt    1800
ggcatccctc ccgatcaaca gcgccttatc ttcgcaggaa agcagctgga ggacggccgg    1860
acattgtctg actacaacat tcagaaagaa tccacccctcc acctggtgct gaggctccgg    1920 gggggatgc ataggagcgc ctgcgggaga atggctggct ctggaatgtc cagactcgac    1980
aagagcaaag tgatcaacag cgccctggag ctcctgaacg aggtgggaat cgagggcctg    2040
actaccagaa agctcgcaca gaagctgggg gtcgagcagc aaccttgta ctggcacgtg    2100 aagaacaaga gggccctcct tgacgctctt gcaatcgaga tgctggacag gccaccacc    2160 cacttctgcc ctcttgaggg agagtcctgg caggattcc tgaggaacaa cgctaagagc    2220
ttccggtgcg ctctgctgtc ccacagggat ggggccaaag tgcatttggg gacacgccct    2280
acagaaaagc agtacgagac tctggagaac cagctgcct cctgtgcca gcaggggttt    2340 agcctcgaaa atgccctcta tgccctctct gccgtcggcc atttcacct cgggtgtgtc    2400 ttggaagatc aggagcacca ggtggccaag gaagagcggg agacaccaac aactgacagt    2460 atgccccct tgttgcggca agccattgag ctgtttgatc atcagggcgc cgagcccgcc    2520
```

-continued

| | |
|---|---|
| tttctgtttg gcctggagct gattatttgc ggcctggaga agcagctgaa gtgcgagtca | 2580 |
| ggtagcgaaa ccttcaagtc catcatgaag aagtcccct tcagcggacc aaccgaccca | 2640 |
| aggcccccac ctcgcaggat cgccgtgccc tccagatcct ccgcctccgt gcctaagcct | 2700 |
| gcccctcagc catacccttt cacctccagc ctgtccacca tcaactacga cgagttccca | 2760 |
| actatggtgt tccccagcgg ccagattagc caggcaagcg ccctcgcacc tgcccctccc | 2820 |
| caggtgctcc ctcaggcacc tgcacctgct cctgctccag ctatggtcag cgccctcgct | 2880 |
| caggctcctg ctcccgtccc agtgcttgct ccaggaccac acaagccgt cgccccaccc | 2940 |
| gcccccaaac ccacacaagc cggagaaggc actctttctg aggccttgtt gcagttgcag | 3000 |
| tttgacgacg aggacctggg ggccctgctg ggcaattcaa cagaccccgc cgtgtttact | 3060 |
| gacctcgcca gcgtggataa cagcgagttt cagcagctgc tcaaccaggg catccccgtc | 3120 |
| gccccccaca ccacagagcc catgctcatg gagtatcccg aggccattac acggctggtg | 3180 |
| acagggcc agcggccccc cgatcccgcc ccgccccc tggggccc agggctgccc | 3240 |
| aacggctgc tgagtgggga tgaggatttt tcatctattg ccgatatgga ttttagtgcc | 3300 |
| ctgctgtctc agattagctc g | 3321 |

<210> SEQ ID NO 113
<211> LENGTH: 2484
<212> TYPE: DNA
<213> ORGANISM: artificial sequence
<220> FEATURE:
<223> OTHER INFORMATION: GG124

<400> SEQUENCE: 113

| | |
|---|---|
| atggctttgc ctgtcactgc cttgctgctt ccacttgctc tgttgttgca cgccgcaaga | 60 |
| cccccaagtgc agcttcaaca gtctggggca gaactcgtaa gaccaggagc atcagtgaca | 120 |
| ctgtcttgta agcctccgg ctataccttc tctgactacg agatgcattg ggtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccgtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat ataccctac accttcggcg gaggcacaaa gctcgaaata | 780 |
| aagcggtcgg atcccgagcc caaatctcct gacaaaactc acacatgccc accgtgccca | 840 |
| gcacctcccg tggccggccc gtcagtgttc ctcttccccc caaaacccaa ggacaccctc | 900 |
| atgatcgccc ggacccctga ggtcacatgc gtggtggtgg acgtgagcca cgaggaccct | 960 |
| gaggtcaagt tcaactggta cgtggacggc gtggaggtgc ataatgccaa gacaaagccg | 1020 |
| cgggaggagc agtacaacag cacgtaccgt gtggtcagcg tcctcaccgt cctgcaccag | 1080 |
| gactggctga atggcaagga gtacaagtgc aaggtgtcca acaaagccct cccagccccc | 1140 |
| atcgagaaaa ccatctccaa agccaaaggg cagccccgag aaccacaggt gtacaccctg | 1200 |
| cccccatccc gggatgagct gaccaagaac caggtcagcc tgacctgcct ggtcaaaggc | 1260 |

```
ttctatccca gcgacatcgc cgtggagtgg gagagcaatg ggcaaccgga gaacaactac   1320
aagaccacgc ctcccgtgct ggactccgac ggctccttct tcctctacag caagctcacc   1380
gtggacaaga gcaggtggca gcaggggaac gtgttctcat gctccgtgat gcatgaggcc   1440
ctgcacaatc actataccca gaaatctctg agtctgagcc caggcaagaa ggatatcttt   1500
tgggtgctgg tggtggttgg tggagtcctg gcttgctata gcttgctagt aacagtggcc   1560
tttattattt tctgggtgag gagtaagcgc agaagggacc gatgcctcca acacagctat   1620
gcaggtgcct gggctgtgag tccggagaca gagctcactg gccacgttgg atcagggagc   1680
ggctctggga gcgtagtgg atctggtggc atccctcccg atcaacagcg ccttatcttc   1740
gcaggaaagc agctggagga cggccggaca ttgtctgact acaacattca gaaagaatcc   1800
accctccacc tggtgctgag gctccggggg gggatgcata ggagcgcctg cgggagaatg   1860
gctggctctg gaatgaagct cctgtcctct atcgagcagg catgcgacat ctgcagactc   1920
aagaagctga gtgcagcaa ggagaagccc aagtgcgcca agtgccttaa gaacaactgg   1980
gagtgtaggt actcccctaa gaccaagagg tcccctctga ccagagctca ccttactgag   2040
gtggagtcca ggttggagcg gttggaacaa ctgttcctgt tgatcttccc cagggaggac   2100
ctcgatatga ttctgaaaat ggactccctc caggacatta aggccctgct gaccgggctc   2160
tttgtgcagg acaatgtgaa caaagatgcc gtcacagatc ggctcgccag cgtcgagact   2220
gatatgccac tgacactgcg gcagcatcgg attagcgcca caagctcaag cgaggaaagt   2280
tctaacaaag gccagcgcca gctgacagtt agcgggtctg gacgggcaga tgctttggat   2340
gatttcgacc ttgacatgct ggggagcgat gccttggatg acttcgatct ggacatgctc   2400
ggctcagatg ccctggatga ttttgacctg gacatgctgg gctccgatgc cctggacgac   2460
tttgacctcg acatgctcat caac   2484
```

<210> SEQ ID NO 114
<211> LENGTH: 2490
<212> TYPE: DNA
<213> ORGANISM: artificial sequence
<220> FEATURE:
<223> OTHER INFORMATION: GG125

<400> SEQUENCE: 114

```
atggctttgc ctgtcactgc cttgctgctt ccacttgctc tgttgttgca cgccgcaaga    60
cccgaggtcc agcttcagca gtctggacct gacctggtga agcctggggc ttcagtgaag   120
atatcctgca aggcttctgg ttactcattc actggctact acatgcactg ggtgaagcag   180
agtcatggaa agagccttga gtggattgga cgtattaatc ctaacaatgg tgttactctc   240
tacaaccaga aattcaagga caaggccata ttaactgtag acaagtcatc caccacagcc   300
tacatggagc tccgcagcct gacatctgag gactctgcgg tctattactg tgcaagatca   360
actatgatta cgaactatgt tatggactac tggggtcaag taacctcagt caccgtttcc   420
tcaggcggag gaggcagtgg cggaggggga agtgggggcg gcggcagcag tattgtgatg   480
acccagactc ccacattcct gcttgtttca gcaggagaca gggttaccat aacctgcaag   540
gccagtcaga gtgtgagtaa tgatgtagct tggtaccaac agaagccagg cagtctcct    600 acactgctca tatcctatac atccagtcgc tacgctggag tccctgatcg cttcattggc   660
agtggatatg ggacggattt cactttcacc atcagcactt tgcaggctga ggacctggca   720
gtttatttct gtcagcaaga ttataattct cctccgacgt tcggtggagg caccaagctg   780
```

```
gaaatcaaac ggtcggatcc cgagcccaaa tctcctgaca aaactcacac atgcccaccg      840
tgcccagcac ctcccgtggc cggcccgtca gtgttcctct tccccccaaa acccaaggac      900
accctcatga tcgcccggac ccctgaggtc acatgcgtgg tggtggacgt gagccacgag      960
gaccctgagg tcaagttcaa ctggtacgtg gacggcgtgg aggtgcataa tgccaagaca     1020
aagccgcggg aggagcagta acagcacg taccgtgtgg tcagcgtcct caccgtcctg       1080
caccaggact ggctgaatgg caaggagtac aagtgcaagg tgtccaacaa agccctccca     1140
gcccccatcg agaaaaccat ctccaaagcc aagggcagc cccgagaacc acaggtgtac      1200
accctgcccc catcccggga tgagctgacc aagaaccagg tcagcctgac ctgcctggtc     1260
aaaggcttct atcccagcga catcgccgtg gagtgggaga gcaatgggca accggagaac     1320
aactacaaga ccacgcctcc cgtgctggac tccgacggct ccttcttcct ctacagcaag     1380
ctcaccgtgg acaagagcag gtggcagcag gggaacgtgt tctcatgctc cgtgatgcat     1440
gaggccctgc acaatcacta cccagaaa tctctgagtc tgagcccagg caagaaggat       1500
atcttttggg tgctggtggt ggttggtgga gtcctggctt gctatagctt gctagtaaca     1560
gtggccttta ttattttctg ggtgaggagt aagcgcagaa gggaccgatg cctccaacac     1620
agctatgcag gtgcctgggc tgtgagtccg gagacagagc tcactggcca cgttggatca     1680
gggagcggct ctgggagcgg tagtggatct ggtggcatcc ctcccgatca acagcgcctt     1740
atcttcgcag gaaagcagct ggaggacggc cggacattgt ctgactacaa cattcagaaa     1800
gaatccaccc tccacctggt gctgaggctc cggggggga tgcataggag cgcctgcggg      1860
agaatggctg gctctggaat gaagctcctg tcctctatcg agcaggcatg cgacatctgc     1920
agactcaaga agctgaagtg cagcaaggag aagcccaagt gcgccaagtg ccttaagaac     1980
aactgggagt gtaggtactc ccctaagacc aagaggtccc ctctgaccag agctcacctt     2040
actgaggtgg agtccaggtt ggagcggttg gaacaactgt tcctgttgat cttccccagg     2100
gaggacctcg atatgattct gaaaatggac tccctccagg acattaaggc cctgctgacc     2160
gggctctttg tgcaggacaa tgtgaacaaa gatgccgtca cagatcggct cgccagcgtc     2220
gagactgata tgccactgac actgcggcag catcggatta gcgccacaag ctcaagcgag     2280
gaaagttcta acaaaggcca gcgccagctg acagttagcg ggtctggacg ggcagatgct     2340
ttggatgatt tcgaccttga catgctgggg agcgatgcct ggatgacttt cgatctggac     2400
atgctcggct cagatgccct ggatgatttt gacctggaca tgctgggctc cgatgccctg     2460
gacgactttg acctcgacat gctcatcaac                                      2490
```

<210> SEQ ID NO 115
<211> LENGTH: 3321
<212> TYPE: DNA
<213> ORGANISM: artificial sequence
<220> FEATURE:
<223> OTHER INFORMATION: GG126

<400> SEQUENCE: 115

```
atggctttgc ctgtcactgc cttgctgctt ccacttgctc tgttgttgca cgccgcaaga       60
ccccaagtgc agcttcaaca gtctggggca gaactcgtaa gaccaggagc atcagtgaca      120
ctgtcttgta aagcctccgg ctataccttc tctgactacg agatgcattg ggtcatccag      180
acaccagtac atgggctcga atggatagga gccatagatc cagagacagg cggaacagca      240
tacaaccaga agttcaaagg caaggccatt ctcacagcgg acaagagcag tagcaccgct      300
tacatggagt tgcgatccct gaccagtgag gactctgcag tctactattg tacagggtac      360
```

```
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat aacagaaac ccggtcaatc cccaaagctc    600
ctcatctact ctgcgagcaa tagatatacc ggtgtgcctg ataggttcac cggaagcggc    660 tccgaacag atttcaccct gactatcagc aatatgcaat ccgaggactt ggctgactac    720
ttttgccagc aatacgacat ataccctac accttcggcg gaggcacaaa gctcgaaata    780
aagcggtcgg atcccgagcc caaatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg    1020
cgggaggagc agtacaacag cacgtaccgt gtggtcagcg tcctcaccgt cctgcaccag    1080
gactggctga atggcaagga gtacaagtgc aaggtgtcca acaaagccct cccagccccc    1140
atcgagaaaa ccatctccaa agccaaaggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg ggcaaccgga gaacaactac    1320
aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc caggcaagaa ggatatcatc    1500
tccttctttc ttgcgctcac gtcgactgcg ttgctcttcc tgctgttctt cctcacgctc    1560
cgtttctctg ttgttaaacg gggcagacag cttggactgc acatctggca gctgaggagt    1620
cagtgcatgt ggccccgaga gacacagctg ctgctggagg tgccgccgtc gaccgaggac    1680
gccagaagct gccagttccc cgaggaagag cggggcgagc gatcggcaga ggagaagggg    1740
cggctgggag atctgtgggt gggatcaggg agcggctctg ggagcggtag tggatctggt    1800
ggcatccctc ccgatcaaca gcgccttatc ttcgcaggaa agcagctgga ggacggccgg    1860
acattgtctg actacaacat tcagaaagaa tccacccctc cacctggtgct gaggctccgg    1920 gggggggatgc ataggagcgc ctgcgggaga atggctggct ctggaatgtc cagactcgac    1980
aagagcaaag tgatcaacag cgccctggag ctcctgaacg aggtgggaat cgagggcctg    2040
actaccagaa agctcgcaca gaagctgggg gtcgagcagc caaccttgta ctggcacgtg    2100
aagaacaaga gggccctcct tgacgctctt gcaatcgaga tgctggacag gcaccacacc    2160
cacttctgcc ctcttgaggg agagtcctgg caggatttcc tgaggaacaa cgctaagagc    2220
ttccggtgcg ctctgctgtc ccacagggat ggggccaaag tgcatttggg gacacgccct    2280
acagaaaagc agtacgagac tctgagaaac cagctgcct tcctgtgcca gcaggggttt    2340
agcctcgaaa atgccctcta tgccctctct gccgtcggcc atttcacccc tgggtgtgtc    2400
ttggaagatc aggagcacca ggtggccaag aagagcggg agacaccaac aactgacagt    2460 atgccccct tgttgcggca agccattgag ctgtttgatc atcagggcgc cgagcccgcc    2520
tttctgtttg gcctggagct gattatttgc ggcctggaga gcagctgaa gtgcgagtca    2580 ggtagcgaaa ccttcaagtc catcatgaag aagtcccct tcagcggacc aaccgaccca    2640 aggccccac ctcgcaggat cgccgtgccc tccagatcct ccgcctccgt gcctaagcct    2700
```

```
gcccctcagc catacccttt cacctccagc ctgtccacca tcaactacga cgagttccca    2760
actatggtgt tccccagcgg ccagattagc caggcaagcg ccctcgcacc tgcccctccc    2820
caggtgctcc ctcaggcacc tgcacctgct cctgctccag ctatggtcag cgccctcgct    2880
caggctcctg ctcccgtccc agtgcttgct ccaggaccac cacaagccgt cgccccaccc    2940
gcccccaaac ccacacaagc cggagaaggc actctttctg aggccttgtt gcagttgcag    3000
tttgacgacg aggacctggg ggccctgctg ggcaattcaa cagacccgc cgtgtttact      3060 gacctcgcca gcgtggataa cagcgagttt cagcagctgc tcaaccaggg catcccgtc     3120 gccccccaca ccacagagcc catgctcatg gagtatcccg aggccattac acggctggtg    3180
acaggggccc agcggccccc cgatcccgcc cccgccccc tggggccc agggctgccc       3240 aacggcctgc tgagtgggga tgaggatttt tcatctattg ccgatatgga ttttagtgcc    3300
ctgctgtctc agattagctc g                                              3321
```

<210> SEQ ID NO 116
<211> LENGTH: 1941
<212> TYPE: DNA
<213> ORGANISM: artificial sequence
<220> FEATURE:
<223> OTHER INFORMATION: GG127

<400> SEQUENCE: 116

```
atggctttgc ctgtcactgc cttgctgctt ccacttgctc tgttgttgca cgccgcaaga      60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga agttcaaagg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccctac accttcggcg gaggcacaaa gctcgaaata    780
aagcggtcgg atcccaccac aacccccgct ccaaggcccc ctaccccgc accaactatt     840 gcctcccagc cactctcact gcggcctgag gctgtcggc ccgctgctgg aggcgcagtg      900
catacaaggg gcctcgattt cgcctgcgat atttacatct gggcaccct cgccggcacc     960 tgcggggtgc ttctcctctc cctggtgatt accctgtatt gcagaggcag aaagaaactc    1020
ctgtatatat tcaaacaacc atttatgcga ccagtacaaa ctactcaaga ggaagatggc    1080
tgtagctgcc gatttccaga agaagaagaa ggaggatgtg aactgggatc agggagcggc    1140
tctgggagcg gtagtggatc tggtggcatc cctcccgatc aacagcgcct tatcttcgca    1200
ggaaagcagc tggaggacgg ccggacattg tctgactaca cattcagaa agaatccacc    1260 ctccacctgg tgctgaggct ccgggggggg atgcatagga gcgcctgcgg gagaatggct    1320
ggctctggaa tgaagctcct gtcctctatc gagcaggcat gcgacatctg cagactcaag    1380
aagctgaagt gcagcaagga aagcccaag tgcgccaagt gccttaagaa caactgggag      1440
```

| | | |
|---|---|---|
| tgtaggtact ccccctaagac caagaggtcc cctctgacca gagctcacct tactgaggtg | 1500 | |
| gagtccaggt tggagcggtt ggaacaactg ttcctgttga tcttccccag ggaggacctc | 1560 | |
| gatatgattc tgaaaatgga ctccctccag gacattaagg ccctgctgac cgggctcttt | 1620 | |
| gtgcaggaca atgtgaacaa agatgccgtc acagatcggc tcgccagcgt cgagactgat | 1680 | |
| atgccactga cactgcggca gcatcggatt agcgccacaa gctcaagcga ggaaagttct | 1740 | |
| aacaaaggcc agcgccagct gacagttagc gggtctggac gggcagatgc tttgatgat | 1800 | |
| ttcgaccttg acatgctggg gagcgatgcc ttggatgact tcgatctgga catgctcggc | 1860 | |
| tcagatgccc tggatgattt tgacctggac atgctgggct ccgatgccct ggacgacttt | 1920 | |
| gacctcgaca tgctcatcaa c | 1941 | |

<210> SEQ ID NO 117
<211> LENGTH: 1956
<212> TYPE: DNA
<213> ORGANISM: artificial sequence
<220> FEATURE:
<223> OTHER INFORMATION: GG128

<400> SEQUENCE: 117

| | | |
|---|---|---|
| atggctttgc ctgtcactgc cttgctgctt ccacttgctc tgttgttgca cgccgcaaga | 60 | |
| cccgaggtca agctccagga aagcggacca gggctggtgg cccctagtca gtcattgagc | 120 | |
| gtcacttgca ccgtcagcgg cgtgtctctg cccgattacg gcgtgagctg gatcagacag | 180 | |
| cccccaagga agggactgga gtggctgggc gtcatctggg ggagcgagac tacctactac | 240 | |
| aacagcgccc tgaagagcag gctgaccatc attaaggaca actccaagtc ccaggtcttt | 300 | |
| ctgaaaatga acagcctgca gactgatgac actgccatct actactgcgc caagcattac | 360 | |
| tactacgggg gcagctacgc tatggactac tggggccagg ggacctctgt cacagtgtca | 420 | |
| agtggcggag gaggcagtgg cggaggggga agtgggggcg gcggcagcga catccagatg | 480 | |
| acccagacaa catccagcct ctccgcctct ctgggcgaca gagtgacaat cagctgccgg | 540 | |
| gccagtcagg acatcagcaa gtatctcaat tggtaccagc agaaaccaga cgggacagtg | 600 | |
| aaattgctga tctaccacac atccaggctg cactcaggag tccccagcag gttttccggc | 660 | |
| tccggctccg ggacagatta cagtctgacc atttccaacc tggagcagga ggatattgcc | 720 | |
| acatactttt gccagcaagg caacactctg ccctatacct cggcggagg cacaaaactg | 780 | |
| gagattactc ggtcggatcc caccacaacc cccgctccaa ggccccctac ccccgcacca | 840 | |
| actattgcct cccagccact ctcactgcgg cctgaggcct gtcggcccgc tgctggaggc | 900 | |
| gcagtgcata aaggggcct cgatttcgcc tgcgatatca tctccttctt tcttgcgctc | 960 | |
| acgtcgactg cgttgctctt cctgctgttc ttcctcacgc tccgtttctc tgttgttaaa | 1020 | |
| cggggcagaa gcaggctcct gcacagtgac tacatgaaca tgactccccg ccgccccggg | 1080 | |
| cccacccgca agcattacca gccctatgcc ccaccacgcg acttcgcagc ctatcgctcc | 1140 | |
| ggatcaggga gcggctctgg gagcggtagt ggatctggtg gcatccctcc cgatcaacag | 1200 | |
| cgccttatct tcgcaggaaa gcagctggag gacggccgga cattgtctga ctacaacatt | 1260 | |
| cagaaagaat ccaccctcca cctggtgctg aggctccggg ggggatgca taggagcgcc | 1320 | |
| tgcgggagaa tggctggctc tggaatgaag ctcctgtcct ctatcgagca ggcatgcgac | 1380 | |
| atctgcagac tcaagaagct gaagtgcagc aaggagaagc caagtgcgc caagtgcctt | 1440 | |
| aagaacaact gggagtgtag gtactcccct aagaccaaga ggtcccctct gaccagagct | 1500 | |

-continued

| | |
|---|---|
| caccttactg aggtggagtc caggttggag cggttggaac aactgttcct gttgatcttc | 1560 |
| cccagggagg acctcgatat gattctgaaa atggactccc tccaggacat taaggccctg | 1620 |
| ctgaccgggc tctttgtgca ggacaatgtg aacaaagatg ccgtcacaga tcggctcgcc | 1680 |
| agcgtcgaga ctgatatgcc actgacactg cggcagcatc ggattagcgc cacaagctca | 1740 |
| agcgaggaaa gttctaacaa aggccagcgc cagctgacag ttagcgggtc tggacgggca | 1800 |
| gatgctttgg atgatttcga ccttgacatg ctggggagcg atgccttgga tgacttcgat | 1860 |
| ctggacatgc tcggctcaga tgccctggat gattttgacc tggacatgct gggctccgat | 1920 |
| gccctggacg actttgacct cgacatgctc atcaac | 1956 |

<210> SEQ ID NO 118
<211> LENGTH: 2541
<212> TYPE: DNA
<213> ORGANISM: artificial sequence
<220> FEATURE:
<223> OTHER INFORMATION: GG129

<400> SEQUENCE: 118

| | |
|---|---|
| atggctttgc ctgtcactgc cttgctgctt ccacttgctc tgttgttgca cgccgcaaga | 60 |
| cccgaggtgc agttgcagca gtcagggcca gagttgatta gcccggagc ctccgtcaag | 120 |
| atgtcctgca aggccagcgg gtacactttc accagctacg tcatgcattg ggtgaagcag | 180 |
| aagccaggcc aggggcttga gtggattggg tacatcaacc cctacaacga cgggaccaaa | 240 |
| tacaacgaga aattcaaggg caaagccaca ctcacctccg ataagtcctc ctctaccgcc | 300 |
| tacatggagc tcagctccct gacctccgag gatagcgctg tgtattactg cgcaaggggc | 360 |
| acatactact atggctctag ggtgttcgac tactgggggc agggcactac tctcacagtg | 420 |
| agctcaggcg gaggaggcag tggcggaggg ggaagtgggg cggcggcag cgatattgtc | 480 |
| atgacccagg cagcccctag tatccctgtg actccaggcg agagcgtgag catcagctgc | 540 |
| cggtccagca gagcctgct gaacagtaac ggaaacacat acctctactg gtttctgcag | 600 |
| aggcccggcc agagccctca gctgctgatt taccgcatgt caaatcttgc ctctggggtg | 660 |
| cccgatagat ttagtgggag cggctccggc acagctttta cattgcggat ctccagagtc | 720 |
| gaggccgaag atgtgggggt ctattactgt atgcaacacc tggaataccc ctttaccttc | 780 |
| ggagccggca caaagctgga gctgaagcgg tcggatcccg agcccaaatc tcctgacaaa | 840 |
| actcacacat gcccaccgtg cccagcacct cccgtggccg gccgtcagt gttcctcttc | 900 |
| cccccaaaac ccaaggacac cctcatgatc gcccggaccc ctgaggtcac atgcgtggtg | 960 |
| gtggacgtga gccacgagga ccctgaggtc aagttcaact ggtacgtgga cggcgtggag | 1020 |
| gtgcataatg ccaagacaaa gccgcgggag gagcagtaca acagcacgta ccgtgtggtc | 1080 |
| agcgtcctca ccgtcctgca ccaggactgg ctgaatggca aggagtacaa gtgcaaggtg | 1140 |
| tccaacaaag ccctcccagc ccccatcgag aaaaccatct ccaaagccaa agggcagccc | 1200 |
| cgagaaccac aggtgtacac cctgccccca tcccgggatg agctgaccaa gaaccaggtc | 1260 |
| agcctgacct gcctggtcaa aggcttctat cccagcgaca tcgccgtgga gtgggagagc | 1320 |
| aatgggcaac cggagaacaa ctacaagacc acgcctcccg tgctggactc cgacggctcc | 1380 |
| ttcttcctct acagcaagct caccgtggac aagagcaggt ggcagcaggg gaacgtgttc | 1440 |
| tcatgctccg tgatgcatga ggccctgcac aatcactata cccagaaatc tctgagtctg | 1500 |
| agcccaggca gaaggatat tctcctggca ggcctcgtgg ctgctgatgc ggtggcatcg | 1560 |
| ctgctcatcg tgggggcggt gttcctgtgc gcacgcagag ccctgtacct gctccggagg | 1620 |

```
gaccagaggc tgcccccga tgcccacaag ccccctgggg gaggcagttt ccggacccc      1680 atccaagagg agcaggccga cgcccactcc accctggcca agatcggatc agggagcggc    1740
tctgggagcg gtagtggatc tggtggcatc cctcccgatc aacagcgcct tatcttcgca    1800
ggaaagcagc tggaggacgg ccggacattg tctgactaca acattcagaa agaatccacc    1860
ctccacctgg tgctgaggct ccggggggg atgcatagga gcgcctgcgg gagaatggct     1920
ggctctggaa tgaagctcct gtcctctatc gagcaggcat gcgacatctg cagactcaag    1980
aagctgaagt gcagcaagga gaagcccaag tgcgccaagt gccttaagaa caactgggag    2040
tgtaggtact cccctaagac caagaggtcc cctctgacca gagctcacct tactgaggtg    2100
gagtccaggt tggagcggtt ggaacaactg ttcctgttga tcttcccag ggaggacctc     2160 gatatgattc tgaaaatgga ctccctccag gacattaagg ccctgctgac cgggctcttt    2220
gtgcaggaca atgtgaacaa agatgccgtc acagatcggc tcgccagcgt cgagactgat    2280
atgccactga cactgcggca gcatcggatt agcgccacaa gctcaagcga ggaaagttct    2340
aacaaaggcc agcgccagct gacagttagc gggtctggac gggcagatgc tttggatgat    2400
ttcgaccttg acatgctggg gagcgatgcc ttggatgact cgatctgga catgctcggc     2460 tcagatgccc tggatgattt tgacctggac atgctgggct ccgatgccct ggacgacttt    2520
gacctcgaca tgctcatcaa c                                              2541

<210> SEQ ID NO 119
<211> LENGTH: 2475
<212> TYPE: DNA
<213> ORGANISM: artificial sequence
<220> FEATURE:
<223> OTHER INFORMATION: GG130

<400> SEQUENCE: 119
atggctttgc ctgtcactgc cttgctgctt ccacttgctc tgttgttgca cgccgcaaga      60
cccgaggtcc agcttcagca gtctggacct gacctggtga agcctggggc ttcagtgaag     120
atatcctgca aggcttctgg ttactcattc actggctact acatgcactg ggtgaagcag     180
agtcatggaa agagccttga gtggattgga cgtattaatc ctaacaatgg tgttactctc     240
tacaaccaga aattcaagga caaggccata ttaactgtag acaagtcatc caccacagcc     300
tacatggagc tccgcagcct gacatctgag gactctgcgg tctattactg tgcaagatca    360
actatgatta cgaactatgt tatggactac tggggtcaag taacctcagt caccgtttcc     420
tcaggcggag gaggcagtgg cggaggggga agtgggggcg gcggcagcag tattgtgatg     480
acccagactc ccacattcct gcttgtttca gcaggagaca gggttaccat aacctgcaag    540
gccagtcaga gtgtgagtaa tgatgtagct tggtaccaac agaagccagg cagtctcct      600 acactgctca tatcctatac atccagtcgc tacgctggag tccctgatcg cttcattggc    660
agtggatatg ggacggattt cactttcacc atcagcactt gcaggctga ggacctggca      720 gtttatttct gtcagcaaga ttataattct cctccgacgt tcggtggagg caccaagctg    780
gaaatcaaac ggtcggatcc cgagcccaaa tctcctgaca aaactcacac atgcccaccg    840
tgcccagcac ctcccgtggc cggccctca gtgttcctct ccccccaaa acccaaggac       900 accctcatga tcgcccggac ccctgaggtc acatgcgtgg tggtggacgt gagccacgag    960
gaccctgagg tcaagttcaa ctggtacgtg acggcgtgg aggtgcataa tgccaagaca     1020
aagccgcggg aggagcagta caacagcacg taccgtgtgg tcagcgtcct caccgtcctg    1080
```

```
caccaggact ggctgaatgg caaggagtac aagtgcaagg tgtccaacaa agccctccca    1140
gcccccatcg agaaaaccat ctccaaagcc aaagggcagc cccgagaacc acaggtgtac    1200
accctgcccc catcccggga tgagctgacc aagaaccagg tcagcctgac ctgcctggtc    1260
aaaggcttct atcccagcga catcgccgtg gagtgggaga gcaatgggca accggagaac    1320
aactacaaga ccacgcctcc cgtgctggac tccgacggct ccttcttcct ctacagcaag    1380
ctcaccgtgg acaagagcag gtggcagcag gggaacgtgt tctcatgctc cgtgatgcat    1440
gaggccctgc acaatcacta tacccagaaa tctctgagtc tgagcccagg caagaaggat    1500
atcttttggg tgctggtggt ggttggtgga gtcctggctt gctatagctt gctagtaaca    1560
gtggccttta ttattttctg ggtgaggagt aagcgcagac cacgccgcag ccccgcccaa    1620
gaagatggca aagtctacat caacatgcca ggcaggggcg gatcaggagc ggctctggg     1680 agcggtagtg gatctggtgg catccctccc gatcaacagc gccttatctt cgcaggaaag    1740
cagctggagg acggccggac attgtctgac tacaacattc agaaagaatc caccctccac    1800
ctggtgctga ggctccgggg ggggatgcat aggagcgcct gcgggagaat ggctggctct    1860
ggaatgaagc tcctgtcctc tatcgagcag gcatgcgaca tctgcagact caagaagctg    1920
aagtgcagca aggagaagcc caagtgcgcc aagtgcctta agaacaactg ggagtgtagg    1980
tactccccta agaccaagag gtcccctctg accagagctc accttactga ggtggagtcc    2040
aggttggagc ggttggaaca actgttcctg ttgatcttcc ccaggaggga cctcgatatg    2100
attctgaaaa tggactccct ccaggacatt aaggccctgc tgaccgggct ctttgtgcag    2160
gacaatgtga acaagatgc cgtcacagat cggctcgcca gcgtcgagac tgatatgcca    2220
ctgacactgc ggcagcatcg gattagcgcc acaagctcaa gcgaggaaag ttctaacaaa    2280
ggccagcgcc agctgacagt tagcgggtct ggacgggcag atgctttgga tgatttcgac    2340
cttgacatgc tggggagcga tgccttggat gacttcgatc tggacatgct cggctcagat    2400
gccctggatg attttgacct ggacatgctg ggctccgatg ccctggacga ctttgacctc    2460
gacatgctca tcaac                                                     2475

<210> SEQ ID NO 120
<211> LENGTH: 2664
<212> TYPE: DNA
<213> ORGANISM: artificial sequence
<220> FEATURE:
<223> OTHER INFORMATION: GG131

<400> SEQUENCE: 120
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaagg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtga acgcggccgt ggcttggtat caacagaaac ccgtcaatc cccaaagctc    600 ctcatctact ctgcgagcaa tagatatacc ggtgtgcctg ataggttcac cggaagcggc    660
```

```
tccggaacag atttcaccct gactatcagc aatatgcaat ccgaggactt ggctgactac    720
ttttgccagc aatacgacat atacccctac accttcggcg gaggcacaaa gctcgaaata    780
aagcggtcgg atcccgcccc cgtggggctg gtggcgcggt tggctgacga gagcggccac    840
gtagtgttgc gctggctccc gccgcctgag acacccatga cgtctcacat ccgctacgag    900
gtggacgtct cggccggcaa cggcgcaggg agcgtacaga gggtggagat cctggagggc    960
cgcaccgagt gtgtgctgag caacctgcgg ggccggacgc gctacacctt cgccgtccgc   1020
gcgcgtatgg ctgagccgag cttcggcggc ttctggagcg cctggtcgga gcctgtgtcg   1080
ctgctgacgc ctagcgatat ttacatctgg gcacccctcg ccggcacctg cggggtgctt   1140
ctcctctccc tggtgattac cctgtattgc agaatggagg agagtgtcgt acggccctca   1200
gtgtttgtgg tggatggaca gaccgacatc ccattcacga ggctgggacg aagccaccgg   1260
agacagtcgt gcagtgtggc ccggggatca gggagcggct ctgggagcgg tagtggatct   1320
ggtggcatcc ctcccgatca acagcgcctt atcttcgcag gaaagcagct ggaggacggc   1380
cggacattgt ctgactacaa cattcagaaa gaatccaccc tccacctggt gctgaggctc   1440
cgggggggga tgcataggag cgcctgcggg agaatggctg gctctggaat gaagctcctg   1500
tcctctatcg agcaggcatg cgacatctgc agactcaaga agctgaagtg cagcaaggag   1560
aagcccaagt gcgccaagtg ccttaagaac aactgggagt gtaggtactc ccctaagacc   1620
aagaggtccc ctctgaccag agctcacctt actgaggtgg agtccaggtt ggagcggttg   1680
gaacaactgt tcctgttgat cttccccagg gaggacctcg atatgattct gaaaatggac   1740
tccctccagg acattaaggc cctgctgacc gggctctttg tgcaggacaa tgtgaacaaa   1800
gatgccgtca cagatcggct cgccagcgtc gagactgata tgccactgac actgcggcag   1860
catcggatta gcgccacaag ctcaagcgag gaaagttcta acaaaggcca gcgccagctg   1920
acagttagcg aaaccttcaa gtccatcatg aagaagtccc ccttcagcgg accaaccgac   1980
ccaaggcccc cacctcgcag gatcgccgtg ccctccagat cctccgcctc cgtgcctaag   2040
cctgcccctc agccataccc ттттcacctcc agcctgtcca ccatcaacta cgacgagttc   2100
ccaactatgg tgttccccag cggccagatt agccaggcaa gcgccctcgc acctgcccct   2160
ccccaggtgc tccctcaggc acctgcacct gctcctgctc cagctatggt cagcgccctc   2220
gctcaggctc ctgctcccgt cccagtgctt gctccaggac caccacaagc cgtcgcccca   2280
cccgccccca acccacaca agccggagaa ggcactcttt ctgaggcctt gttgcagttg   2340
cagtttgacg acgaggacct gggggccctg ctgggcaatt caacagaccc cgccgtgttt   2400
actgacctcg ccagcgtgga taacagcgag tttcagcagc tgctcaacca gggcatcccc   2460
gtcgcccccc acaccacaga gcccatgctc atggagtatc cgaggccat acacggctg   2520 gtgacagggg cccagcggcc ccccgatccc gcccccgccc cctgggggc cccagggctg   2580 cccaacggcc tgctgagtgg ggatgaggat ttttcatcta tgccgatat ggattttagt   2640 gccctgctgt ctcagattag ctcg                                          2664
```

<210> SEQ ID NO 121
<211> LENGTH: 2652
<212> TYPE: DNA
<213> ORGANISM: artificial sequence
<220> FEATURE:
<223> OTHER INFORMATION: GG132

<400> SEQUENCE: 121

-continued

| | |
|---|---|
| atggctttgc ctgtcactgc cttgctgctt ccacttgctc tgttgttgca cgccgcaaga | 60 |
| cccgaggtca agctccagga aagcggacca gggctggtgg cccctagtca gtcattgagc | 120 |
| gtcacttgca ccgtcagcgg cgtgtctctg cccgattacg gcgtgagctg atcagacag | 180 |
| cccccaagga agggactgga gtggctgggc gtcatctggg ggagcgagac tacctactac | 240 |
| aacagcgccc tgaagagcag gctgaccatc attaaggaca actccaagtc ccaggtcttt | 300 |
| ctgaaaatga acagcctgca gactgatgac actgccatct actactgcgc aagcattac | 360 |
| tactacgggg gcagctacgc tatggactac tgggggcagg ggacctctgt cacagtgtca | 420 |
| agtggcggag gaggcagtgg cggaggggga agtgggggcg gcggcagcga catccagatg | 480 |
| acccagacaa catccagcct ctccgcctct ctgggcgaca gagtgacaat cagctgccgg | 540 |
| gccagtcagg acatcagcaa gtatctcaat tggtaccagc agaaaccaga cgggacagtg | 600 |
| aaattgctga tctaccacac atccaggctg cactcaggag tccccagcag gttttccggc | 660 |
| tccggctccg ggacagatta cagtctgacc atttccaacc tggagcagga ggatattgcc | 720 |
| acatactttt gccagcaagg caacactctg ccctatacct cggcggagg cacaaaactg | 780 |
| gagattactc ggtcggatcc cgcccccgtg gggctggtgg cgcggttggc tgacgagagc | 840 |
| ggccacgtag tgttgcgctg gctcccgccg cctgagacac ccatgacgtc tcacatccgc | 900 |
| tacgaggtgg acgtctcggc cggcaacggc gcagggagcg tacagagggt ggagatcctg | 960 |
| gagggccgca ccgagtgtgt gctgagcaac ctgcggggcc ggacgcgcta cacccttcgcc | 1020 |
| gtccgcgcgc gtatggctga ccgagcttc ggcggcttct ggagcgcctg gtcggagcct | 1080 |
| gtgtcgctgc tgacgcctag cgatatcatc tccttctttc ttgcgctcac gtcgactgcg | 1140 |
| ttgctcttcc tgctgttctt cctcacgctc cgtttctctg ttgttaaacg gggcagaagg | 1200 |
| gaccgatgcc tccaacacag ctatgcaggt gcctgggctg tgagtccgga cagagagctc | 1260 |
| actggccacg ttggatcagg gagcggctct gggagcggta gtggatctgg tggcatccct | 1320 |
| cccgatcaac agcgccttat cttcgcagga aagcagctgg aggacggccg acattgtct | 1380 |
| gactacaaca ttcagaaaga atccacctc cacctggtgc tgaggctccg ggggggatg | 1440 |
| cataggagcg cctgcgggag aatggctggc tctggaatga agctcctgtc ctctatcgag | 1500 |
| caggcatgcg acatctgcag actcaagaag ctgaagtgca gcaaggagaa gcccaagtgc | 1560 |
| gccaagtgcc ttaagaacaa ctgggagtgt aggtactccc ctaagaccaa gaggtccccct | 1620 |
| ctgaccagag ctcaccttac tgaggtggag tccaggttgg agcggttgga caactgttc | 1680 |
| ctgttgatct cccccaggga ggacctcgat atgattctga aaatggactc cctccaggac | 1740 |
| attaaggccc tgctgaccgg gctctttgtg caggacaatg tgaacaaaga tgccgtcaca | 1800 |
| gatcggctcg ccagcgtcga gactgatatg ccactgacac tgcggcagca tcggattagc | 1860 |
| gccacaagct caagcgagga aagttctaac aaaggccagc gccagctgac agttagcgaa | 1920 |
| accttcaagt ccatcatgaa gaagtccccc ttcagcggac caaccgaccc aaggccccca | 1980 |
| cctcgcagga tcgccgtgcc ctccagatcc tccgcctccg tgcctaagcc tgcccctcag | 2040 |
| ccatacccctt tcacctccag cctgtccacc atcaactacg acgagttccc aactatggtg | 2100 |
| ttccccagcg gccagattag ccaggcaagc gccctcgcac ctgcccctcc ccaggtgctc | 2160 |
| cctcaggcac ctgcacctgc tcctgctcca gctatggtca gcgccctcgc tcaggctcct | 2220 |
| gctcccgtcc cagtgcttgc tccaggacca ccacaagccg tcgccccacc cgcccccaaa | 2280 |
| cccacacaag ccggagaagg cactctttct gaggccttgt tgcagttgca gtttgacgac | 2340 |
| gaggacctgg gggccctgct gggcaattca acagacccg ccgtgtttac tgacctcgcc | 2400 |

```
agcgtggata acagcgagtt tcagcagctg ctcaaccagg gcatcccgt cgcccccac      2460 accacagagc ccatgctcat ggagtatccc gaggccatta cacggctggt gacagggggcc   2520 cagcggcccc ccgatcccgc ccccgccccc ctggggggccc cagggctgcc caacggcctg   2580
ctgagtgggg atgaggattt ttcatctatt gccgatatgg attttagtgc cctgctgtct   2640
cagattagct cg                                                         2652
```

<210> SEQ ID NO 122
<211> LENGTH: 2763
<212> TYPE: DNA
<213> ORGANISM: artificial sequence
<220> FEATURE:
<223> OTHER INFORMATION: GG133

<400> SEQUENCE: 122

```
atggctttgc ctgtcactgc cttgctgctt ccacttgctc tgttgttgca cgccgcaaga     60
cccgaggtgc agttgcagca gtcagggcca gagttgatta gcccggagc ctccgtcaag    120 atgtcctgca aggccagcgg gtacactttc accagctacg tcatgcattg ggtgaagcag   180
aagccaggcc aggggcttga gtggattggg tacatcaacc cctacaacga cgggaccaaa   240
tacaacgaga aattcaaggg caaagccaca ctcacctccg ataagtcctc ctctaccgcc   300
tacatggagc tcagctccct gacctccgag gatagcgctg tgtattactg cgcaaggggc   360
acatactact atggctctag ggtgttcgac tactgggggc agggcactac tctcacagtg   420
agctcaggcg gaggaggcag tggcggaggg ggaagtgggg gcggcggcag cgatattgtc   480
atgacccagg cagcccctag tatccctgtg actccaggcg agagcgtgag catcagctgc   540
cggtccagca gagcctgct gaacagtaac ggaaacacat acctctactg gtttctgcag   600
aggcccggcc agagccctca gctgctgatt taccgcatgt caaatcttgc ctctggggtg   660
cccgatagat ttagtgggag cggctccggc acagctttta cattgcggat ctccagagtc   720
gaggccgaag atgtgggggt ctattactgt atgcaacacc tggaataccc ctttaccttc   780
ggagccggca caaagctgga gctgaagcgg tcggatcccg cccccgtggg gctggtggcg   840
cggttggctg acgagagcgg ccacgtagtg ttgcgctggc tcccgccgcc tgagacaccc   900
atgacgtctc acatccgcta cgaggtggac gtctcggccg gcaacggcgc agggagcgta   960
cagagggtgg agatcctgga gggccgcacc gagtgtgtgc tgagcaacct gcggggccgg  1020
acgcgctaca ccttcgccgt ccgcgcgcgt atggctgagc cgagcttcgg cggcttctgg  1080
agcgcctggt cggagcctgt gtcgctgctg acgcctagcg atattctcct ggcaggcctc  1140
gtggctgctg atgcggtggc atcgctgctc atcgtggggg cggtgttcct gtgcgcacgc  1200
agatgtgtga aagaagaaa gccaagggg gatgtagtca aggtgattgt ctccgtccag  1260
cggaaaagac aggaggcaga aggtgaggcc acagtcattg aggccctgca gccccctccg  1320
gacgtcacca cggtggccgt ggaggagaca ataccctcat tcacggggag agcccaaac  1380 cacggatcag ggagcggctc tgggagcggt agtggatctg gtggcatccc tcccgatcaa  1440
cagcgcctta tcttcgcagg aaagcagctg gaggacggcc ggacattgtc tgactacaac  1500
attcagaaag aatccaccct ccacctggtg ctgaggctcc gggggggat gcataggagc  1560 gcctgcggga gaatggctgg ctctggaatg aagctcctgt cctctatcga gcaggcatgc  1620
gacatctgca gactcaagaa gctgaagtgc agcaaggaga gcccaagtg cgccaagtgc  1680 cttaagaaca actgggagtg taggtactcc cctaagacca gaggtccccc tctgaccaga  1740
```

```
gctcacctta ctgaggtgga gtccaggttg gagcggttgg aacaactgtt cctgttgatc    1800
ttccccaggg aggacctcga tatgattctg aaaatggact ccctccagga cattaaggcc    1860
ctgctgaccg ggctctttgt gcaggacaat gtgaacaaag atgccgtcac agatcggctc    1920
gccagcgtcg agactgatat gccactgaca ctgcggcagc atcggattag cgccacaagc    1980
tcaagcgagg aaagttctaa caaaggccag cgccagctga cagttagcga aaccttcaag    2040
tccatcatga agaagtcccc cttcagcgga ccaaccgacc caaggccccc acctcgcagg    2100
atcgccgtgc cctccagatc ctccgcctcc gtgcctaagc ctgcccctca gccatacccct   2160 ttcacctcca gcctgtccac catcaactac gacgagttcc aactatggt gttccccagc    2220 ggccagatta gccaggcaag cgccctcgca cctgcccctc ccaggtgct ccctcaggca    2280 cctgcacctg ctcctgctcc agctatggtc agcgccctcg ctcaggctcc tgctcccgtc    2340
ccagtgcttg ctccaggacc accacaagcc gtcgccccac ccgcccccaa acccacacaa    2400
gccggagaag gcactctttc tgaggccttg ttgcagttgc agtttgacga cgaggacctg    2460
ggggccctgc tgggcaattc aacagacccc gccgtgttta ctgacctcgc cagcgtggat    2520
aacagcgagt tcagcagct gctcaaccag ggcatccccg tcgcccccca caccacagag    2580
cccatgctca tggagtatcc cgaggccatt acacggctgg tgacaggggc ccagcggccc    2640
cccgatcccg ccccgccc cctgggggcc cagggctgc ccaacggcct gctgagtggg     2700
gatgaggatt tttcatctat tgccgatatg gattttagtg ccctgctgtc tcagattagc    2760
tcg                                                                  2763
```

<210> SEQ ID NO 123
<211> LENGTH: 2589
<212> TYPE: DNA
<213> ORGANISM: artificial sequence
<220> FEATURE:
<223> OTHER INFORMATION: GG134

<400> SEQUENCE: 123

```
atggctttgc ctgtcactgc cttgctgctt ccacttgctc tgttgttgca cgccgcaaga      60
cccgaggtcc agcttcagca gtctggacct gacctggtga agcctggggc ttcagtgaag     120
atatcctgca aggcttctgg ttactcattc actggctact acatgcactg ggtgaagcag     180
agtcatggaa agagccttga gtggattgga cgtattaatc ctaacaatgg tgttactctc     240
tacaaccaga aattcaagga caaggccata ttaactgtag acaagtcatc caccacagcc     300
tacatggagc tccgcagcct gacatctgag actctgcgg tctattactg tgcaagatca     360
actatgatta cgaactatgt tatggactac tggggtcaag taacctcagt caccgtttcc     420
tcaggcggag gaggcagtgg cggaggggga agtgggggcg gcggcagcag tattgtgatg     480
acccagactc ccacattcct gcttgtttca gcaggagaca gggttaccat aacctgcaag     540
gccagtcaga gtgtgagtaa tgatgtagct tggtaccaac agaagccagg gcagtctcct     600
acactgctca tatcctatac atccagtcgc tacgctggag tccctgatcg cttcattggc     660
agtggatatg ggacggattt cactttcacc atcagcactt tgcaggctga ggacctggca    720
gtttatttct gtcagcaaga ttataattct cctccgacgt tcggtggagg caccaagctg    780
gaaatcaaac ggtcggatcc caccacaacc cccgctccaa ggccccctac cccgcacca    840 actattgcct cccagccact ctcactgcgg cctgaggcct gtcggccgc tgctggaggc     900 gcagtgcata aagggggcct cgattccgcc tgcgatatct tttgggtgct ggtggtggtt     960
ggtggagtcc tggcttgcta tagcttgcta gtaacagtgg cctttattat tttctgggtg   1020
```

```
aggagtaagc gcagacagct tggactgcac atctggcagc tgaggagtca gtgcatgtgg    1080
ccccgagaga cacagctgct gctggaggtg ccgccgtcga ccgaggacgc cagaagctgc    1140
cagttccccg aggaagagcg gggcgagcga tcggcagagg agaaggggcg gctgggagat    1200
ctgtgggtgg gatcagggag cggctctggg agcggtagtg gatctggtgg catccctccc    1260
gatcaacagc gccttatctt cgcaggaaag cagctggagg acggccggac attgtctgac    1320
tacaacattc agaaagaatc caccctccac ctggtgctga ggctccgggg ggggatgcat    1380
aggagcgcct gcgggagaat ggctggctct ggaatgaagc tcctgtcctc tatcgagcag    1440
gcatgcgaca tctgcagact caagaagctg aagtgcagca aggagaagcc caagtgcgcc    1500
aagtgcctta agaacaactg ggagtgtagg tactccccta agaccaagag gtcccctctg    1560
accagagctc accttactga ggtggagtcc aggttggagc ggttggaaca actgttcctg    1620
ttgatcttcc ccagggagga cctcgatatg attctgaaaa tggactccct ccaggacatt    1680
aaggccctgc tgaccgggct ctttgtgcag gacaatgtga acaaagatgc cgtcacagat    1740
cggctcgcca gcgtcgagac tgatatgcca ctgacactgc ggcagcatcg gattagcgcc    1800
acaagctcaa gcgaggaaag ttctaacaaa ggccagcgcc agctgacagt tagcgaaacc    1860
ttcaagtcca tcatgaagaa gtccccctcc agcggaccaa ccgacccaag gcccccacct    1920
cgcaggatcg ccgtgccctc cagatcctcc gcctccgtgc ctaagcctgc ccctcagcca    1980
tacccttcca cctccagcct gtccaccatc aactacgacg agttcccaac tatggtgttc    2040
cccagcggcc agattagcca ggcaagcgcc ctcgcacctg cccctcccca ggtgctccct    2100
caggcacctg cacctgctcc tgctccagct atggtcagcg ccctcgctca ggctcctgct    2160
cccgtcccag tgcttgctcc aggaccacca caagccgtcg ccccacccgc ccccaaaccc    2220
acacaagccg gagaaggcac tctttctgag gccttgttgc agttgcagtt tgacgacgag    2280 gacctgggg ccctgctggg caattcaaca gaccccgccg tgtttactga cctcgccagc    2340
gtggataaca gcgagtttca gcagctgctc aaccagggca tccccgtcgc cccccacacc    2400
acagagccca tgctcatgga gtatcccgag gccattacac ggctggtgac aggggcccag    2460 cggcccccg atcccgcccc cgcccccctg ggggcccag ggctgcccaa cggcctgctg    2520
agtggggatg aggattttc atctattgcc gatatggatt ttagtgccct gctgtctcag    2580
attagctcg                                                          2589
```

<210> SEQ ID NO 124
<211> LENGTH: 1800
<212> TYPE: DNA
<213> ORGANISM: artificial sequence
<220> FEATURE:
<223> OTHER INFORMATION: GG151

<400> SEQUENCE: 124

```
atggctttgc ctgtcactgc cttgctgctt ccacttgctc tgttgttgca cgccgcaaga    60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaagg caaggccatt ctcacagcgg acaagagcag tagcaccgct    300
tacatggagt tgcgatccct gaccagtgag gactctgcag tctactattg tacagggtac    360
tatgactacg actcattcac atattgggg cagggtacct tggtgactgt ctccgctggc    420
```

```
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccccctac accttcggcg gaggcacaaa gctcgaaata    780
aagcggtcgg atcccgagcc caaatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtgtcca acaaagccct cccagccccc   1140
atcgagaaaa ccatctccaa agccaaaggg cagccccgag aaccacaggt gtacaccctg   1200
cccccatccc gggatgagct gaccaagaac caggtcagcc tgacctgcct ggtcaaaggc   1260
ttctatccca gcgacatcgc cgtggagtgg gagagcaatg ggcaaccgga gaacaactac   1320
aagaccacgc ctcccgtgct ggactccgac ggctccttct tcctctacag caagctcacc   1380
gtggacaaga gcaggtggca gcaggggaac gtgttctcat gctccgtgat gcatgaggcc   1440
ctgcacaatc actatacccca gaaatctctg agtctgagcc caggcaagaa ggatatcatc   1500
tccttctttc ttgcgctcac gtcgactgcg ttgctcttcc tgctgttctt cctcacgctc   1560
cgtttctctg ttgttaaacg gggcagaagg gaccgatgcc tccaacacag ctatgcaggt   1620
gcctgggctg tgagtccgga gacagagctc actggccacg ttggatcagg gagcggctct   1680
gggagcggta gtggatctgg tatgcaaatc ttcgtgaaaa ccctgaccgg gaaaacaatc   1740
actctcgaag tcgagcccag cgatacaatt gagaacgtga aggccaagat tcaggacaag   1800

<210> SEQ ID NO 125
<211> LENGTH: 1788
<212> TYPE: DNA
<213> ORGANISM: artificial sequence
<220> FEATURE:
<223> OTHER INFORMATION: GG152

<400> SEQUENCE: 125
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggataggg gccatagatc cagagacagg cggaacagca    240
tacaaccaga agttcaaagg caaggccatt tcacagcggg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
```

```
ttttgccagc aatacgacat ataccctac accttcggcg gaggcacaaa gctcgaaata       780
aagcggtcgg atcccgagcc caaatctcct gacaaaactc acacatgccc accgtgccca       840
gcacctcccg tggccggccc gtcagtgttc ctcttccccc caaaacccaa ggacaccctc       900
atgatcgccc ggacccctga ggtcacatgc gtggtggtgg acgtgagcca cgaggaccct       960
gaggtcaagt tcaactggta cgtggacggc gtggaggtgc ataatgccaa gacaaagccg      1020
cgggaggagc agtacaacag cacgtaccgt gtggtcagcg tcctcaccgt cctgcaccag      1080
gactggctga atggcaagga gtacaagtgc aaggtgtcca acaaagccct cccagccccc      1140
atcgagaaaa ccatctccaa agccaaaggg cagccccgag aaccacaggt gtacaccctg      1200
cccccatccc gggatgagct gaccaagaac caggtcagcc tgacctgcct ggtcaaaggc      1260
ttctatccca gcgacatcgc cgtggagtgg gagagcaatg gcaaccggga gaacaactac      1320
aagaccacgc ctcccgtgct ggactccgac ggctccttct tcctctacag caagctcacc      1380
gtggacaaga gcaggtggca gcaggggaac gtgttctcat gctccgtgat gcatgaggcc      1440
ctgcacaatc actatacccca gaaatctctg agtctgagcc caggcaagaa ggatattctc      1500
ctggcaggcc tcgtggctgc tgatgcggtg gcatcgctgc tcatcgtggg ggcggtgttc      1560
ctgtgcgcac gcagaaggga ccgatgcctc caacacagct atgcaggtgc ctgggctgtg      1620
agtccggaga cagagctcac tggccacgtt ggatcaggga gcggctctgg agcggtagt      1680 ggatctggta tgcaaatctt cgtgaaaacc ctgaccggga aaacaatcac tctcgaagtc      1740
gagcccagcg atacaattga aacgtgaag gccaagattc aggacaag                     1788

<210> SEQ ID NO 126
<211> LENGTH: 1806
<212> TYPE: DNA
<213> ORGANISM: artificial sequence
<220> FEATURE:
<223> OTHER INFORMATION: GG153

<400> SEQUENCE: 126
atggctttgc ctgtcactgc cttgctgctt ccacttgctc tgttgttgca cgccgcaaga       60 cccccaagtgc agcttcaaca gtctggggca gaactcgtaa gaccaggagc atcagtgaca      120
ctgtcttgta aagcctccgg ctataccttc tctgactacg agatgcattg ggtcatccag      180
acaccagtac atgggctcga atggatagga gccatagatc cagagacagg cggaacagca      240
tacaaccaga agttcaaagg caaggccatt ctcacagcgg acaagagcag tagcaccgct      300
tacatggagt tgcgatccct gaccagtgag gactctgcag tctactattg tacagggtac      360
tatgactacg actcattcac atattggggg cagggtacct tggtgactgt ctccgctggc      420
ggaggaggca gtggcggagg gggaagtggg gcggcggca gcgatatagt gatgacgcag      480
tcccagaaga tcatgtccac gaccgtcggg gatcgggtca gtataacatg taaggcatcc      540
cagaacgtgg acgcggccgt ggcttggtat caacagaaac ccggtcaatc cccaaagctc      600
ctcatctact ctgcgagcaa tagatatacc ggtgtgcctg ataggttcac cggaagcggc      660
tccggaacag atttcaccct gactatcagc aatatgcaat ccgaggactt ggctgactac      720
ttttgccagc aatacgacat ataccctac accttcggcg gaggcacaaa gctcgaaata      780
aagcggtcgg atcccgagcc caaatctcct gacaaaactc acacatgccc accgtgccca      840
gcacctcccg tggccggccc gtcagtgttc ctcttccccc caaaacccaa ggacaccctc      900
atgatcgccc ggacccctga ggtcacatgc gtggtggtgg acgtgagcca cgaggaccct      960
```

```
gaggtcaagt tcaactggta cgtggacggc gtggaggtgc ataatgccaa gacaaagccg    1020
cgggaggagc agtacaacag cacgtaccgt gtggtcagcg tcctcaccgt cctgcaccag    1080
gactggctga atggcaagga gtacaagtgc aaggtgtcca acaaagccct cccagccccc    1140
atcgagaaaa ccatctccaa agccaaaggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg ggcaaccgga gaacaactac    1320
aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc caggcaagaa ggatatcttt    1500
tgggtgctgg tggtggttgg tggagtcctg gcttgctata gcttgctagt aacagtggcc    1560
tttattattt tctgggtgag gagtaagcgc agaagggacc gatgcctcca acacagctat    1620
gcaggtgcct gggctgtgag tccggagaca gagctcactg gccacgttgg atcagggagc    1680
ggctctggga gcggtagtgg atctggtatg caaatcttcg tgaaaccct gaccgggaaa     1740
acaatcactc tcgaagtcga gcccagcgat acaattgaga acgtgaaggc caagattcag    1800
gacaag                                                              1806
```

<210> SEQ ID NO 127
<211> LENGTH: 1386
<212> TYPE: DNA
<213> ORGANISM: artificial sequence
<220> FEATURE:
<223> OTHER INFORMATION: GG154

<400> SEQUENCE: 127

```
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaaggg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccccctac accttcggcg gaggcacaaa gctcgaaata    780
aagcggtcgg atcccgcccc cgtggggctg gtggcgcggt ggctgacga gagcggccac    840
gtagtgttgc gctggctccc gccgcctgag acacccatga cgtctcacat ccgctacgag    900
gtggacgtct cggccggcaa cggcgcaggg agcgtacaga gggtggagat cctggagggc    960
cgcaccgagt gtgtgctgag caacctgcgg ggccggacgc gctacacctt cgccgtccgc    1020
gcgcgtatgg ctgagccgag cttcggcggc ttctggagcg cctggtcgga gcctgtgtcg    1080
ctgctgacgc ctagcgatat ttacatctgg gcaccctcg ccggcacctg cggggtgctt    1140
ctcctctccc tggtgattac cctgtattgc agaagggacc gatgcctcca acacagctat    1200
```

```
gcaggtgcct gggctgtgag tccggagaca gagctcactg gccacgttgg atcagggagc    1260
ggctctggga gcggtagtgg atctggtatg caaatcttcg tgaaaaccct gaccgggaaa    1320
acaatcactc tcgaagtcga gcccagcgat acaattgaga acgtgaaggc caagattcag    1380
gacaag                                                               1386
```

<210> SEQ ID NO 128
<211> LENGTH: 1218
<212> TYPE: DNA
<213> ORGANISM: artificial sequence
<220> FEATURE:
<223> OTHER INFORMATION: GG155

<400> SEQUENCE: 128

```
atggctttgc ctgtcactgc cttgctgctt ccacttgctc tgttgttgca cgccgcaaga      60
ccccaagtgc agcttcaaca gtctggggca gaactcgtaa gaccaggagc atcagtgaca     120
ctgtcttgta aagcctccgg ctataccttc tctgactacg agatgcattg ggtcatccag     180
acaccagtac atgggctcga atggatagga gccatagatc cagagacagg cggaacagca     240
tacaaccaga agttcaaagg caaggccatt ctcacagcgg acaagagcag tagcaccgct     300
tacatggagt tgcgatccct gaccagtgag gactctgcag tctactattg tacagggtac     360
tatgactacg actcattcac atattggggg cagggtacct tggtgactgt ctccgctggc     420
ggaggaggca gtggcggagg gggaagtggg ggcggcggca gcgatatagt gatgacgcag     480
tcccagaaga tcatgtccac gaccgtcggg gatcgggtca gtataacatg taaggcatcc     540
cagaacgtgg acgcggccgt ggcttggtat caacagaaac ccggtcaatc cccaaagctc     600
ctcatctact ctgcgagcaa tagatatacc ggtgtgcctg ataggttcac cggaagcggc     660
tccggaacag atttcaccct gactatcagc aatatgcaat ccgaggactt ggctgactac     720
ttttgccagc aatacgacat ataccccctac accttcggcg gaggcacaaa gctcgaaata     780
aagcggtcgg atcccaccac aaccccccgct ccaaggcccc ctaccccgc accaactatt     840 gcctcccagc cactctcact gcggcctgag gcctgtcggc ccgctgctgg aggcgcagtg     900
catacaaggg gcctcgattt cgcctgcgat atttacatct gggcacccct cgccggcacc     960 tgcgggggtgc ttctcctctc cctggtgatt accctgtatt gcagaaggga ccgatgcctc    1020 caaacacagct atgcaggtgc ctgggctgtg agtccggaga cagagctcac tggccacgtt    1080
ggatcaggga gcggctctgg gagcggtagt ggatctggta tgcaaatctt cgtgaaaacc    1140
ctgaccggga aaacaatcac tctcgaagtc gagcccagcg atacaattga aacgtgaag    1200 gccaagattc aggacaag                                                  1218
```

<210> SEQ ID NO 129
<211> LENGTH: 3024
<212> TYPE: DNA
<213> ORGANISM: artificial sequence
<220> FEATURE:
<223> OTHER INFORMATION: GG156

<400> SEQUENCE: 129

```
atggctttgc ctgtcactgc cttgctgctt ccacttgctc tgttgttgca cgccgcaaga      60
ccccaagtgc agcttcaaca gtctggggca gaactcgtaa gaccaggagc atcagtgaca     120
ctgtcttgta aagcctccgg ctataccttc tctgactacg agatgcattg ggtcatccag     180
acaccagtac atgggctcga atggatagga gccatagatc cagagacagg cggaacagca     240
```

```
tacaaccaga agttcaaagg caaggccatt ctcacagcgg acaagagcag tagcaccgct      300
tacatggagt tgcgatccct gaccagtgag gactctgcag tctactattg tacagggtac      360
tatgactacg actcattcac atattggggg cagggtacct tggtgactgt ctccgctggc      420
ggaggaggca gtggcggagg gggaagtggg ggcggcggca gcgatatagt gatgacgcag      480
tcccagaaga tcatgtccac gaccgtcggg gatcgggtca gtataacatg taaggcatcc      540
cagaacgtgg acgcggccgt ggcttggtat aacagaaac ccggtcaatc cccaaagctc       600
ctcatctact ctgcgagcaa tagatatacc ggtgtgcctg ataggttcac cggaagcggc      660
tccggaacag atttcaccct gactatcagc aatatgcaat ccgaggactt ggctgactac      720
ttttgccagc aatacgacat ataccctac accttcggcg gaggcacaaa gctcgaaata       780
aagcggtcgg atcccgagcc caaatctcct gacaaaactc acacatgccc accgtgccca      840
gcacctcccg tggccggccc gtcagtgttc ctcttccccc caaaacccaa ggacaccctc      900
atgatcgccc ggacccctga ggtcacatgc gtggtggtgg acgtgagcca cgaggaccct      960
gaggtcaagt tcaactggta cgtggacggc gtggaggtgc ataatgccaa gacaaagccg     1020
cgggaggagc agtacaacag cacgtaccgt gtggtcagcg tcctcaccgt cctgcaccag     1080
gactggctga atggcaagga gtacaagtgc aaggtgtcca acaaagccct cccagccccc     1140
atcgagaaaa ccatctccaa agccaaaggg cagccccgag aaccacaggt gtacaccctg     1200
cccccatccc gggatgagct gaccaagaac caggtcagcc tgacctgcct ggtcaaaggc     1260
ttctatccca gcgacatcgc cgtggagtgg gagagcaatg ggcaaccgga gaacaactac     1320
aagaccacgc ctcccgtgct ggactccgac ggctccttct tcctctacag caagctcacc     1380
gtggacaaga gcaggtggca gcaggggaac gtgttctcat gctccgtgat gcatgaggcc     1440
ctgcacaatc actataccca gaaatctctg agtctgagcc caggcaagaa ggatatttac     1500
atctgggcac cctcgccgg cacctgcggg gtgcttctcc tctccctggt gattaccctg     1560
tattgcagaa gggaccgatg cctccaacac agctatgcag gtgcctgggc tgtgagtccg     1620
gagacagagc tcactggcca cgttggatca gggagcggct ctgggagcgg tagtggatct     1680
ggtggcatcc ctcccgatca acagcgcctt atcttcgcag gaaagcagct ggaggacggc     1740
cggacattgt ctgactacaa cattcagaaa gaatccaccc tccacctggt gctgaggctc     1800
cgggggggga tgcataggag cgcctgcggg agaatggctg gctctggaat gaagctcctg     1860
tcctctatcg agcaggcatg cgacatctgc agactcaaga agctgaagtg cagcaaggag     1920
aagcccaagt gcgccaagtg ccttaagaac aactgggagt gtaggtactc ccctaagacc     1980
aagaggtccc ctctgaccag agctcacctt actgaggtgg agtccaggtt ggagcggttg     2040
gaacaactgt tcctgttgat cttccccagg gaggacctcg atatgattct gaaaatggac     2100
tccctccagg acattaaggc cctgctgacc gggctctttg tgcaggacaa tgtgaacaaa     2160
gatgccgtca cagatcggct cgccagcgtc gagactgata tgccactgac actgcggcag     2220
catcggatta gcgccacaag ctcaagcgag gaaagttcta caaaggcca gcgccagctg     2280
acagttagcg aaaccttcaa gtccatcatg aagaagtccc ccttcagcgg accaaccgac     2340
ccaaggcccc cacctcgcag gatcgccgtg ccctccagat cctccgcctc cgtgcctaag     2400
cctgcccctc agccataccc tttcacctcc agcctgtcca ccatcaacta cgacgagttc     2460
ccaactatgg tgttccccag cggccagatt agccaggcaa gcgccctcgc acctgcccct     2520
ccccaggtgc tccctcaggc acctgcacct gctcctgctc cagctatggt cagcgccctc     2580
gctcaggctc ctgctcccgt cccagtgctt gctccaggac caccacaagc cgtcgcccca     2640
```

```
cccgccccca aacccacaca agccggagaa ggcactcttt ctgaggcctt gttgcagttg    2700
cagtttgacg acgaggacct gggggccctg ctgggcaatt caacagaccc cgccgtgttt    2760
actgacctcg ccagcgtgga taacagcgag tttcagcagc tgctcaacca gggcatcccc    2820 gtcgccccc acaccacaga gcccatgctc atggagtatc ccgaggccat tacacggctg     2880
gtgacagggg cccagcggcc ccccgatccc gccccgccc cctgggggc cccagggctg      2940 cccaacggcc tgctgagtgg ggatgaggat ttttcatcta ttgccgatat ggattttagt    3000
gccctgctgt ctcagattag ctcg                                            3024
```

<210> SEQ ID NO 130
<211> LENGTH: 2460
<212> TYPE: DNA
<213> ORGANISM: artificial sequence
<220> FEATURE:
<223> OTHER INFORMATION: GG157

<400> SEQUENCE: 130

```
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaagg caaggccatt ctcacagcgg acaagagcag tagcaccgct     300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat aacagaaac ccggtcaatc cccaaagctc     600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccccac accttcggcg gaggcacaaa gctcgaaata    780
aagcggtcgg atcccgagcc caaatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg    1020
cgggaggagc agtacaacag cacgtaccgt gtggtcagcg tcctcaccgt cctgcaccag    1080
gactggctga atggcaagga gtacaagtgc aaggtgtcca acaaagccct cccagccccc    1140
atcgagaaaa ccatctccaa agccaaaggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg ggcaaccgga gaacaactac    1320
aagaccacgc ctcccgtgct ggactccgac ggctccttct cctctacag caagctcacc    1380 gtggacaaga gcaggtggca gcaggggaac gtgttctcat gctccgtgat gcatgaggc    1440 ctgcacaatc actatacccca gaaatctctg agtctgagcc caggcaagaa ggatatttac    1500
atctgggcac ccctcgccgg cacctgcggg gtgcttctcc tctccctggt gattacctg     1560 tattgcagaa gggaccgatg cctccaacac agctatcag gtgcctgggc tgtgagtccg     1620
```

| | | |
|---|---|---|
| gagacagagc tcactggcca cgttggatca gggagcggct ctgggagcgg tagtggatct | 1680 | |
| ggtggcatcc ctcccgatca acagcgcctt atcttcgcag gaaagcagct ggaggacggc | 1740 | |
| cggacattgt ctgactacaa cattcagaaa gaatccaccc tccacctggt gctgaggctc | 1800 | |
| cgggggggga tgcataggag cgcctgcggg agaatggctg gctctggaat gaagctcctg | 1860 | |
| tcctctatcg agcaggcatg cgacatctgc agactcaaga agctgaagtg cagcaaggag | 1920 | |
| aagcccaagt gcgccaagtg ccttaagaac aactgggagt gtaggtactc ccctaagacc | 1980 | |
| aagaggtccc ctctgaccag agctcacctt actgaggtgg agtccaggtt ggagcggttg | 2040 | |
| gaacaactgt tcctgttgat cttccccagg gaggacctcg atatgattct gaaaatggac | 2100 | |
| tccctccagg acattaaggc cctgctgacc gggctctttg tgcaggacaa tgtgaacaaa | 2160 | |
| gatgccgtca cagatcggct cgccagcgtc gagactgata tgccactgac actgcggcag | 2220 | |
| catcggatta gcgccacaag ctcaagcgag gaaagttcta acaaaggcca gcgccagctg | 2280 | |
| acagttagcg ggtctggacg ggcagatgct ttggatgatt tcgaccttga catgctgggg | 2340 | |
| agcgatgcct tggatgactt cgatctggac atgctcggct cagatgccct ggatgatttt | 2400 | |
| gacctggaca tgctgggctc cgatgccctg gacgactttg acctcgacat gctcatcaac | 2460 | |

<210> SEQ ID NO 131
<211> LENGTH: 3204
<212> TYPE: DNA
<213> ORGANISM: artificial sequence
<220> FEATURE:
<223> OTHER INFORMATION: GG158

<400> SEQUENCE: 131

| | | |
|---|---|---|
| atggctttgc ctgtcactgc cttgctgctt ccacttgctc tgttgttgca cgccgcaaga | 60 | |
| cccccaagtgc agcttcaaca gtctggggca gaactcgtaa gaccaggagc atcagtgaca | 120 | |
| ctgtcttgta aagcctccgg ctataccttc tctgactacg agatgcattg ggtcatccag | 180 | |
| acaccagtac atgggctcga atggatagga gccatagatc cagagacagg cggaacagca | 240 | |
| tacaaccaga agttcaaagg caaggccatt ctcacagcgg acaagagcag tagcaccgct | 300 | |
| tacatggagt tgcgatccct gaccagtgag gactctgcag tctactattg tacagggtac | 360 | |
| tatgactacg actcattcac atattggggg cagggtacct tggtgactgt ctccgctggc | 420 | |
| ggaggaggca gtggcggagg gggaagtggg ggcggcggca gcgatatagt gatgacgcag | 480 | |
| tcccagaaga tcatgtccac gaccgtcggg gatcgggtca gtataacatg taaggcatcc | 540 | |
| cagaacgtgg acgcggccgt ggcttggtat caacagaaac ccggtcaatc cccaaagctc | 600 | |
| ctcatctact ctgcgagcaa tagatatacc ggtgtgcctg ataggttcac cggaagcggc | 660 | |
| tccggaacag atttcaccct gactatcagc aatatgcaat ccgaggactt ggctgactac | 720 | |
| ttttgccagc aatacgacat ataccctac accttcggcg gaggcacaaa gctcgaaata | 780 | |
| aagcggtcgg atcccgagcc caaatctcct gacaaaactc acacatgccc accgtgccca | 840 | |
| gcacctcccg tggccggccc gtcagtgttc ctcttccccc caaaacccaa ggacaccctc | 900 | |
| atgatcgccc ggacccctga ggtcacatgc gtggtggtgg acgtgagcca cgaggaccct | 960 | |
| gaggtcaagt tcaactggta cgtggacggc gtggaggtgc ataatgccaa gacaaagccg | 1020 | |
| cgggaggagc agtacaacag cacgtaccgt gtggtcagcg tcctcaccgt cctgcaccag | 1080 | |
| gactggctga atggcaagga gtacaagtgc aaggtgtcca acaaagccct cccagccccc | 1140 | |
| atcgagaaaa ccatctccaa agccaaaggg cagccccgag aaccacaggt gtacaccctg | 1200 | |
| cccccatccc gggatgagct gaccaagaac caggtcagcc tgacctgcct ggtcaaaggc | 1260 | |

```
ttctatccca gcgacatcgc cgtggagtgg gagagcaatg ggcaaccgga gaacaactac    1320
aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc caggcaagaa ggatatttac    1500
atctgggcac ccctcgccgg cacctgcggg gtgcttctcc tctccctggt gattaccctg    1560
tattgcagaa gggaccgatg cctccaacac agctatgcag gtgcctgggc tgtgagtccg    1620
gagacagagc tcactggcca cgttggatca gggagcggct ctgggagcgg tagtggatct    1680
ggtggcatcc ctcccgatca acagcgcctt atcttcgcag gaaagcagct ggaggacggc    1740
cggacattgt ctgactacaa cattcagaaa gaatccaccc tccacctggt gctgaggctc    1800
cgggggggga tgcataggag cgcctgcggg agaatggctg gctctggaat gtccagactc    1860
gacaagagca aagtgatcaa cagcgccctg gagctcctga cgaggtgggg aatcgagggc    1920
ctgactacca gaaagctcgc cagaagctg ggggtcgagc agccaaccct gtactggcac    1980
gtgaagaaca gagggcccct ccttgacgct cttgcaatcg agatgctgga caggcaccac    2040
acccacttct gccctcttga gggagagtcc tggcaggatt tcctgaggaa caacgctaag    2100
agcttccggt gcgctctgct gtcccacagg gatgggccaa agtgcattt gggacacgc    2160 cctacagaaa agcagtacga gactctggag aaccagctgg ccttcctgtg ccagcagggg    2220
tttagcctcg aaaatgccct ctatgccctc tctgccgtcg gccatttcac cctcgggtgt    2280
gtcttggaag atcaggagca ccaggtggcc aaggaagagc gggagacacc aacaactgac    2340
agtatgcccc ccttgttgcg gcaagccatt gagctgtttg atcatcaggg cgccgagccc    2400
gcctttctgt ttggcctgga gctgattatt tgcggcctgg agaagcagct gaagtgcgag    2460
tcaggtagcg aaaccttcaa gtccatcatg aagaagtccc ccttcagcgg accaaccgac    2520
ccaaggcccc cacctcgcag gatcgccgtg ccctccagat cctccgcctc cgtgcctaag    2580
cctgcccctc agccataccc tttcacctcc agcctgtcca ccatcaacta cgacgagttc    2640
ccaactatgg tgttcccag cggccagatt agccaggcaa gcgccctcgc acctgcccct    2700
ccccaggtgc tccctcaggc acctgcacct gctcctgctc cagctatggt cagcgccctc    2760
gctcaggctc ctgctcccgt cccagtgctt gctccaggac caccacaagc cgtcgcccca    2820
cccgccccca aacccacaca agccggagaa ggcactcttt ctgaggcctt gttgcagttg    2880
cagtttgacg acgaggacct gggggccctg ctgggcaatt caacagaccc cgccgtgttt    2940
actgacctcg ccagcgtgga taacagcgag tttcagcagc tgctcaacca gggcatcccc    3000
gtcgcccccc acaccacaga gcccatgctc atggagtatc ccgaggccat tacacggctg    3060
gtgacagggg cccagcggcc ccccgatccc gcccccgccc cctgggggc ccagggctg    3120 cccaacggcc tgctgagtgg ggatgaggat ttttcatcta ttgccgatat ggattttagt    3180
gccctgctgt ctcagattag ctcg                                            3204
```

<210> SEQ ID NO 132
<211> LENGTH: 2640
<212> TYPE: DNA
<213> ORGANISM: artificial sequence
<220> FEATURE:
<223> OTHER INFORMATION: GG159

<400> SEQUENCE: 132

```
atggctttgc ctgtcactgc cttgctgctt ccacttgctc tgttgttgca cgccgcaaga    60
```

```
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga agttcaaagg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccccta ccttcggcg gaggcacaaa gctcgaaata    780
aagcggtcgg atcccgagcc caaatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtgtcca acaaagccct cccagccccc   1140
atcgagaaaa ccatctccaa agccaaaggg cagccccgag aaccacaggt gtacaccctg   1200
cccccatccc gggatgagct gaccaagaac caggtcagcc tgacctgcct ggtcaaaggc   1260
ttctatccca gcgacatcgc cgtggagtgg gagagcaatg ggcaaccgga gaacaactac   1320
aagaccacgc ctcccgtgct ggactccgac ggctccttct tcctctacag caagctcacc   1380
gtggacaaga gcaggtggca gcaggggaac gtgttctcat gctccgtgat gcatgaggcc   1440
ctgcacaatc actataccca gaaatctctg agtctgagcc caggcaagaa ggatatttac   1500
atctgggcac ccctcgccgg cacctgcggg gtgcttctcc tctccctggt gattaccctg   1560
tattgcagaa gggaccgatg cctccaacac agctatcag gtgcctgggc tgtgagtccg   1620
gagacagagc tcactggcca cgttggatca gggagcggct ctgggagcgg tagtggatct   1680
ggtggcatcc ctcccgatca acagcgcctt atcttcgcag gaaagcagct ggaggacggc   1740
cggacattgt ctgactacaa cattcagaaa gaatccaccc tccacctggt gctgaggctc   1800
cggggggga tgcataggag cgcctgcggg agaatggctg gctctggaat gtccagactc   1860
gacaagagca agtgatcaa cagcgccctg gagctcctga cgaggtggg aatcgagggc   1920
ctgactacca gaaagctcgc acagaagctg ggggtcgagc agccaacctt gtactggcac   1980
gtgaagaaca gagggccct ccttgacgct cttgcaatcg atgctggac aggcaccac    2040
acccacttct gccctcttga gggagagtcc tggcaggatt cctgaggaa caacgctaag   2100
agcttccggt gcgctctgct gtcccacagg gatggggcca aagtgcattt ggggacacgc   2160
cctacagaaa agcagtacga gactctggag aaccagctgg ccttcctgtg ccagcagggg   2220
tttagcctcg aaaatgccct ctatgccctc tctgccgtcg gccatttcac cctcgggtgt   2280
gtcttggaag atcaggagca ccaggtggcc aaggaagagc gggagacacc aacaactgac   2340
agtatgcccc ccttgttgcg gcaagccatt gagctgtttg atcatcaggg cgccgagccc   2400
gcctttctgt ttggcctgga gctgattatt tgcggcctgg agaagcagct gaagtgcgag   2460
```

```
tcaggtagcg ggtctggacg ggcagatgct ttggatgatt tcgaccttga catgctgggg   2520
agcgatgcct tggatgactt cgatctggac atgctcggct cagatgccct ggatgatttt   2580
gacctggaca tgctgggctc cgatgccctg gacgactttg acctcgacat gctcatcaac   2640
```

<210> SEQ ID NO 133
<211> LENGTH: 2196
<212> TYPE: DNA
<213> ORGANISM: artificial sequence
<220> FEATURE:
<223> OTHER INFORMATION: GG187

<400> SEQUENCE: 133

```
atggctcccg caatggagtc ccctacactg ctgtgcgtgg cactgctgtt ctttgcacca     60
gatggcgtgc tggcagaggt ccagctgcag cagtcaggac agaactgat caaacccgga    120 gcatctgtga aaatgagttg taaggcctca ggctatactt tcacctctta cgtgatgcac    180
tgggtcaagc agaaacctgg acagggcctg agtggatcg gctatattaa tcctacaac    240 gacgggacca agtacaacga aaagtttaaa ggcaaggcaa cactgactag tgataagagc    300
tcctctactg cttacatgga gctgagttca ctgaccagcg aggactccgc tgtgtactat    360
tgcgcaagag gaacctacta ttacggctct agggtgttcg attactgggg gcagggaacc    420
acactgacag tcagctccgg aggaggaggg tccggaggag agggtctgg aggcggggga    480 agtgacatcg tgatgacaca ggccgctcct agcattccag tgactcccgg cgagtcagtc    540
agcatctcct gtcggtctag taagagcctg ctgaactcca atggaaacac atatctgtac    600
tggtttctgc agaggcctgg ccagtcccca cagctgctga tctatcgcat gtctaacctg    660
gccagtggcg tgcccgatcg gttctctggc agtgggtcag gaaccgcctt tacactgagg    720
attagccgcg tcgaggctga ggacgtgggg gtctattact gcatgcagca tctggagtac    780
cctttcacat ttggcgccgg gactaaactg gaactgaagc ggtcggatcc caccacaacc    840
cccgctccaa ggccccctac ccccgcacca actattgcct cccagccact ctcactgcgg    900
cctgaggcct gtcggcccgc tgctggaggc gcagtgcata agggggcct cgatttcgcc    960 tgcgatatct ttatccccct gctggtggtc attctgttcg ccgtggacac tgggctgttt   1020
atctccaccc agcagcaggt cacattcctg ctgaaaatta gcggaccaga aaagggcttc   1080
cggctgctga atccccatcc taaaccaaac cccaagaaca cagaaggga ccgatgcctc   1140 caacacagct atgcaggtgc ctgggctgtg agtccggaga cagagctcac tggccacgtt   1200
ggatcaggga gcggctctgg gagcggtagt ggatctggtg gcatccctcc cgatcaacag   1260
cgccttatct tcgcaggaaa gcagctggag gacggccgga cattgtctga ctacaacatt   1320
cagaaagaat ccaccctcca cctggtgctg aggctccggg gggggatgca taggagcgcc   1380
tgcgggagaa tggctggctc tggaatgtcc agactcgaca agagcaaagt gatcaacagc   1440
gccctggagc tcctgaacga ggtgggaatc gagggcctga ctaccagaaa gctcgcacag   1500
aagctggggg tcgagcagcc aaccttgtac tggcacgtga gaacaagag ggccctcctt   1560 gacgctcttg caatcgagat gctggacagg caccacaccc acttctgccc tcttgaggga   1620
gagtcctggc aggatttcct gaggaacaac gctaagagct ccggtgcgc tctgctgtcc   1680 cacagggatg gggccaaagt gcatttgggg acacgcccta cagaaaagca gtacgagact   1740
ctggagaacc agctggcctt cctgtgccag cagggggttta gctcgaaaa tgccctctat   1800 gccctctctg ccgtcggcca tttcacctc gggtgtgtct tggaagatca ggagcaccag   1860
```

| | |
|---|---:|
| gtggccaagg aagagcggga gacaccaaca actgacagta tgccccccTT gttgcggcaa | 1920 |
| gccattgagc tgtttgatca tcagggcgcc gagcccgcct ttctgtttgg cctggagctg | 1980 |
| attatttgcg gcctggagaa gcagctgaag tgcgagtcag gtagcgggtc tggacgggca | 2040 |
| gatgctttgg atgatttcga ccttgacatg ctggggagcg atgccttgga tgacttcgat | 2100 |
| ctggacatgc tcggctcaga tgccctggat gattttgacc tggacatgct gggctccgat | 2160 |
| gccctggacg actttgacct cgacatgctc atcaac | 2196 |

<210> SEQ ID NO 134
<211> LENGTH: 2232
<212> TYPE: DNA
<213> ORGANISM: artificial sequence
<220> FEATURE:
<223> OTHER INFORMATION: GG188

<400> SEQUENCE: 134

| | |
|---|---:|
| atggctcccg caatggagtc ccctacactg ctgtgcgtgg cactgctgtt ctttgcacca | 60 |
| gatggcgtgc tggcagaggt ccagctgcag cagtcaggac cagaactgat caaacccgga | 120 |
| gcatctgtga aaatgagttg taaggcctca ggctatactt tcacctctta cgtgatgcac | 180 |
| tgggtcaagc agaaacctgg acagggcctg gagtggatcg gctatattaa tccatacaac | 240 |
| gacgggacca gtacaacga aaagtttaaa ggcaaggcaa cactgactag tgataagagc | 300 |
| tcctctactg cttacatgga gctgagttca ctgaccagcg aggactccgc tgtgtactat | 360 |
| tgcgcaagag gaacctacta ttacggctct agggtgttcg attactgggg gcagggaacc | 420 |
| acactgacag tcagctccgg aggaggaggg tccggaggag gagggtctgg aggcggggga | 480 |
| agtgacatcg tgatgacaca ggccgctcct agcattccag tgactcccgg cgagtcagtc | 540 |
| agcatctcct gtcggtctag taagagcctg ctgaactcca tggaaacac atatctgtac | 600 |
| tggtttctgc agaggcctgg ccagtcccca cagctgctga tctatcgcat gtctaacctg | 660 |
| gccagtggcg tgcccgatcg gttctctggc agtgggtcag gaaccgcctt tacactgagg | 720 |
| attagccgcg tcgaggctga ggacgtgggg gtctattact gcatgcagca tctggagtac | 780 |
| cctttcacat ttggcgccgg gactaaactg gaactgaagc ggtcggatcc caccacaacc | 840 |
| cccgctccaa ggcccctac ccccgcacca actattgcct cccagccact ctcactgcgg | 900 |
| cctgaggcct gtcggcccgc tgctggaggc gcagtgcata agggggcct cgatttcgcc | 960 |
| tgcgatatct ttatccccct gctggtggtc attctgttcg ccgtggacac tgggctgttt | 1020 |
| atctccaccc agcagcaggt cacattcctg ctgaaaatta gcggaccag aaagggcttc | 1080 |
| cggctgctga atccccatcc taaaccaaac cccaagaaca cagaatggga ggagagtgtc | 1140 |
| gtacggccct cagtgtttgt ggtggatgga cagaccgaca tcccattcac gaggctggga | 1200 |
| cgaagccacc ggagacagtc gtgcagtgtg gcccggggat cagggagcgg ctctgggagc | 1260 |
| ggtagtggat ctggtggcat ccctccccgat caacagcgcc ttatcttcgc aggaaagcag | 1320 |
| ctggaggacg gccggacatt gtctgactac aacattcaga agaatccac cctccacctg | 1380 |
| gtgctgaggc tccgggggg gatgcatagg agcgcctgcg ggagaatggc tggctctgga | 1440 |
| atgtccagac tcgacaagag caaagtgatc aacagcgccc tggagctcct gaacgaggtg | 1500 |
| ggaatcgagg gcctgactac cagaaagctc gcacagaagc tggggtcga gcagccaacc | 1560 |
| ttgtactggc acgtgaagaa caagagggc ctccttgacg ctcttgcaat cgagatgctg | 1620 |
| gacaggcacc acacccactt ctgccctctt gagggagagt cctggcagga tttcctgagg | 1680 |
| aacaacgcta agagcttccg gtgcgctctg ctgtcccaca gggatggggc caaagtgcat | 1740 |

| | |
|---|---|
| ttggggacac gccctacaga aaagcagtac gagactctgg agaaccagct ggccttcctg | 1800 |
| tgccagcagg ggtttagcct cgaaaatgcc ctctatgccc tctctgccgt cggccatttc | 1860 |
| accctcgggt gtgtcttgga agatcaggag caccaggtgg ccaaggaaga gcgggagaca | 1920 |
| ccaacaactg acagtatgcc ccccttgttg cggcaagcca ttgagctgtt tgatcatcag | 1980 |
| ggcgccgagc ccgcctttct gtttggcctg gagctgatta tttgcggcct ggagaagcag | 2040 |
| ctgaagtgcg agtcaggtag cgggtctgga cgggcagatg ctttggatga tttcgacctt | 2100 |
| gacatgctgg ggagcgatgc cttggatgac ttcgatctgg acatgctcgg ctcagatgcc | 2160 |
| ctggatgatt ttgacctgga catgctgggc tccgatgccc tggacgactt tgacctcgac | 2220 |
| atgctcatca ac | 2232 |

<210> SEQ ID NO 135
<211> LENGTH: 2181
<212> TYPE: DNA
<213> ORGANISM: artificial sequence
<220> FEATURE:
<223> OTHER INFORMATION: GG189

<400> SEQUENCE: 135

| | |
|---|---|
| atggctcccg caatggagtc ccctacactg ctgtgcgtgg cactgctgtt ctttgcacca | 60 |
| gatggcgtgc tggcagaggt ccagctgcag cagtcaggac cagaactgat caaacccgga | 120 |
| gcatctgtga aaatgagttg taaggcctca ggctatactt tcacctctta cgtgatgcac | 180 |
| tgggtcaagc agaaacctgg acagggcctg gagtggatcg gctatattaa tcccatacaac | 240 |
| gacgggacca agtacaacga aaagtttaaa ggcaaggcaa cactgactag tgataagagc | 300 |
| tcctctactg cttacatgga gctgagttca ctgaccagcg aggactccgc tgtgtactat | 360 |
| tgcgcaagag gaacctacta ttacggctct agggtgttcg attactgggg gcagggaacc | 420 |
| acactgacag tcagctccgg aggaggaggg tccggaggag agggtctgga aggcggggga | 480 |
| agtgacatcg tgatgacaca ggccgctcct agcattccag tgactcccgg cgagtcagtc | 540 |
| agcatctcct gtcggtctag taagagcctg ctgaactcca tggaaacac atatctgtac | 600 |
| tggtttctgc agaggcctgg ccagtcccca cagctgctga tctatcgcat gtctaacctg | 660 |
| gccagtggcg tgcccgatcg gttctctggc agtgggtcag gaaccgcctt tacactgagg | 720 |
| attagccgcg tcgaggctga ggacgtgggg gtctattact gcatgcagca tctggagtac | 780 |
| cctttcacat ttggcgccgg gactaaactg gaactgaagc ggtcggatcc caccacaacc | 840 |
| cccgctccaa ggccccctac ccccgcacca actattgcct cccagccact ctcactgcgg | 900 |
| cctgaggcct gtcggcccgc tgctggaggc gcagtgcata aaggggcct cgatttcgcc | 960 |
| tgcgatatct ttatccccct gctggtggtc attctgttcg ccgtggacac tgggctgttt | 1020 |
| atctccaccc agcagcaggt cacattcctg ctgaaaatta gcggaccag aaagggcttc | 1080 |
| cggctgctga atccccatcc taaaccaaac cccaagaaca cagaccacg ccgcagcccc | 1140 |
| gcccaagaag atggcaaagt ctacatcaac atgccaggca ggggcggatc agggagcggc | 1200 |
| tctgggagcg gtagtggatc tggtggcatc cctcccgatc aacagcgcct tatcttcgca | 1260 |
| ggaaagcagc tggaggacgg ccggacattg tctgactaca cattcagaa gaatccacc | 1320 |
| ctccacctgg tgctgaggct ccgggggggg atgcatagga gcgcctgcgg gagaatggct | 1380 |
| ggctctggaa tgtccagact cgacaagagc aaagtgatca cagcgccct ggagctcctg | 1440 |
| aacgaggtgg gaatcgaggg cctgactacc agaaagctcg cacagaagct ggggtcgag | 1500 |

| | |
|---|---|
| cagccaacct tgtactggca cgtgaagaac aagagggccc tccttgacgc tcttgcaatc | 1560 |
| gagatgctgg acaggcacca cacccacttc tgccctcttg agggagagtc ctggcaggat | 1620 |
| ttcctgagga acaacgctaa gagcttccgg tgcgctctgc tgtcccacag ggatggggcc | 1680 |
| aaagtgcatt tggggacacg ccctacagaa aagcagtacg agactctgga gaaccagctg | 1740 |
| gccttcctgt gccagcaggg gtttagcctc gaaaatgccc tctatgccct ctctgccgtc | 1800 |
| ggccatttca ccctcgggtg tgtcttggaa gatcaggagc accaggtggc caaggaagag | 1860 |
| cgggagacac caacaactga cagtatgccc cccttgttgc ggcaagccat tgagctgttt | 1920 |
| gatcatcagg gcgccgagcc cgcctttctg tttggcctgg agctgattat ttgcggcctg | 1980 |
| gagaagcagc tgaagtgcga gtcaggtagc gggtctggac gggcagatgc tttggatgat | 2040 |
| ttcgaccttg acatgctggg gagcgatgcc ttggatgact tcgatctgga catgctcggc | 2100 |
| tcagatgccc tggatgattt tgacctggac atgctgggct ccgatgccct ggacgacttt | 2160 |
| gacctcgaca tgctcatcaa c | 2181 |

<210> SEQ ID NO 136
<211> LENGTH: 1782
<212> TYPE: DNA
<213> ORGANISM: artificial sequence
<220> FEATURE:
<223> OTHER INFORMATION: GG220

<400> SEQUENCE: 136

| | |
|---|---|
| atggctttgc ctgtcactgc cttgctgctt ccacttgctc tgttgttgca cgccgcaaga | 60 |
| cccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccggtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat ataccctac accttcggcg gaggcacaaa gctcgaaata | 780 |
| aagcggtcgg atcccgagcc caaatctcct gacaaaactc acacatgccc accgtgccca | 840 |
| gcacctcccg tggcggccc gtcagtgttc ctcttccccc caaaacccaa ggacaccctc | 900 |
| atgatcgccc ggacccctga ggtcacatgc gtggtggtgg acgtgagcca cgaggaccct | 960 |
| gaggtcaagt tcaactggta cgtggacggc gtggaggtgc ataatgccaa gacaaagccg | 1020 |
| cgggaggagc agtacaacag cacgtaccgt gtggtcagcg tcctcaccgt cctgcaccag | 1080 |
| gactggctga atggcaagga gtacaagtgc aaggtgtcca acaaagccct cccagccccc | 1140 |
| atcgagaaaa ccatctccaa agccaaaggg cagccccgag aaccacaggt gtacaccctg | 1200 |
| cccccatccc gggatgagct gaccaagaac caggtcagcc tgacctgcct ggtcaaaggc | 1260 |
| ttctatccca gcgacatcgc cgtggagtgg gagagcaatg gcaaccgga gaacaactac | 1320 |
| aagaccacgc ctcccgtgct ggactccgac ggctccttct tcctctacag caagctcacc | 1380 |

| | |
|---|---|
| gtggacaaga gcaggtggca gcaggggaac gtgttctcat gctccgtgat gcatgaggcc | 1440 |
| ctgcacaatc actatacccca gaaatctctg agtctgagcc caggcaagaa ggatatttac | 1500 |
| atctgggcac ccctcgccgg cacctgcggg gtgcttctcc tctccctggt gattaccctg | 1560 |
| tattgcagaa gggaccgatg cctccaacac agctatgcag gtgcctgggc tgtgagtccg | 1620 |
| gagacagagc tcactggcca cgttggatca gggagcggct ctgggagcgg tagtggatct | 1680 |
| ggtatgcaaa tcttcgtgaa aaccctgacc gggaaaacag ccactctcga agtcgagccc | 1740 |
| agcgatacaa ttgagaacgt gaaggccaag attcaggaca ag | 1782 |

<210> SEQ ID NO 137
<211> LENGTH: 1842
<212> TYPE: DNA
<213> ORGANISM: artificial sequence
<220> FEATURE:
<223> OTHER INFORMATION: GG221

<400> SEQUENCE: 137

| | |
|---|---|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg ggaagtgggg gcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat aacagaaaac ccggtcaatc cccaaagctc | 600 |
| ctcatctact ctgcgagcaa tagatatacc ggtgtgcctg ataggttcac cggaagcggc | 660 |
| tccggaacag atttcacccct gactatcagc aatatgcaat ccgaggactt ggctgactac | 720 |
| ttttgccagc aatacgacat ataccccttac accttcggcg gaggcacaaa gctcgaaata | 780 |
| aagcggtcgg atcccgagcc caaatctcct gacaaaactc acacatgccc accgtgccca | 840 |
| gcacctcccg tggccggccc gtcagtgttc ctcttccccc caaaacccaa ggacaccctc | 900 |
| atgatcgccc ggaccctga ggtcacatgc gtggtggtgg acgtgagcca cgaggaccct | 960 |
| gaggtcaagt tcaactggta cgtggacggc gtggaggtgc ataatgccaa gacaaagccg | 1020 |
| cgggaggagc agtacaacag cacgtaccgt gtggtcagcg tcctcaccgt cctgcaccag | 1080 |
| gactggctga atggcaagga gtacaagtgc aaggtgtcca acaaagccct cccagccccc | 1140 |
| atcgagaaaa ccatctccaa agccaaaggg cagccccgag aaccacaggt gtacaccctg | 1200 |
| cccccatccc gggatgagct gaccaagaac caggtcagcc tgacctgcct ggtcaaaggc | 1260 |
| ttctatccca gcgacatcgc cgtggagtgg gagagcaatg ggcaaccgga gaacaactac | 1320 |
| aagaccacgc ctcccgtgct ggactccgac ggctccttct tcctctacag caagctcacc | 1380 |
| gtggacaaga gcaggtggca gcaggggaac gtgttctcat gctccgtgat gcatgaggcc | 1440 |
| ctgcacaatc actatacccca gaaatctctg agtctgagcc caggcaagaa ggatatcttt | 1500 |
| tgggtgctgg tggtggttgg tggagtcctg gcttgctata gcttgctagt aacagtggcc | 1560 |
| tttattattt tctgggtgag gagtaagcgc agaatggagg agagtgtcgt acggccctca | 1620 |

```
gtgtttgtgg tggatggaca gaccgacatc ccattcacga ggctgggacg aagccaccgg    1680
agacagtcgt gcagtgtggc ccggggatca gggagcggct ctgggagcgg tagtggatct    1740
ggtatgcaaa tcttcgtgaa acccctgacc gggaaaacag ccactctcga agtcgagccc    1800
agcgatacaa ttgagaacgt gaaggccaag attcaggaca ag                       1842
```

<210> SEQ ID NO 138
<211> LENGTH: 1209
<212> TYPE: DNA
<213> ORGANISM: artificial sequence
<220> FEATURE:
<223> OTHER INFORMATION: GG222

<400> SEQUENCE: 138

```
atggctttgc ctgtcactgc cttgctgctt ccacttgctc tgttgttgca cgccgcaaga     60
ccccaagtgc agcttcaaca gtctggggca gaactcgtaa gaccaggagc atcagtgaca    120
ctgtcttgta aagcctccgg ctataccttc tctgactacg agatgcattg ggtcatccag    180
acaccagtac atgggctcga atggatagga gccatagatc cagagacagg cggaacagca    240
tacaaccaga gttcaaagg caaggccatt ctcacagcgg acaagagcag tagcaccgct    300
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat aacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat atacccctac accttcggcg gaggcacaaa gctcgaaata    780
aagcggtcgg atcccaccac aaacccccgct ccaaggcccc ctaccccgc accaactatt    840 gcctcccagc cactctcact gcggcctgag gcctgtcggc ccgctgctgg aggcgcagtg    900
catacaaggg gcctcgatt cgcctgcgat attctcctgg caggcctcgt ggctgctgat    960
gcggtggcat cgctgctcat cgtgggggcg gtgttcctgt gcgcacgcag accacgccgc   1020 agcccccgcccc aagaagatgg caaagtctac atcaacatgc aggcagggg cggatcaggg   1080 agcggctctg ggagcggtag tggatctggt atgcaaatct tcgtgaaaac cctgaccggg   1140
aaaacagcca ctctcgaagt cgagcccagc gatacaattg agaacgtgaa ggccaagatt   1200
caggacaag                                                          1209
```

<210> SEQ ID NO 139
<211> LENGTH: 1893
<212> TYPE: DNA
<213> ORGANISM: artificial sequence
<220> FEATURE:
<223> OTHER INFORMATION: GG223

<400> SEQUENCE: 139

```
atggctttgc ctgtcactgc cttgctgctt ccacttgctc tgttgttgca cgccgcaaga     60
cccgaggtcc agcttcagca gtctggacct gacctggtga gcctggggc ttcagtgaag    120 atatcctgca aggcttctgg ttactcattc actggctact acatgcactg ggtgaagcag    180
agtcatggaa agagccttga gtggattgga cgtattaatc ctaacaatgg tgttactctc    240
tacaaccaga aattcaagga caaggccata ttaactgtag acaagtcatc caccacagcc    300
```

| | |
|---|---|
| tacatggagc tccgcagcct gacatctgag gactctgcgg tctattactg tgcaagatca | 360 |
| actatgatta cgaactatgt tatggactac tggggtcaag taacctcagt caccgtttcc | 420 |
| tcaggcggag gaggcagtgg cggagggggra agtgggggcg gcggcagcag tattgtgatg | 480 |
| acccagactc ccacattcct gcttgtttca gcaggagaca gggttaccat aacctgcaag | 540 |
| gccagtcaga gtgtgagtaa tgatgtagct tggtaccaac agaagccagg gcagtctcct | 600 |
| acactgctca tatcctatac atccagtcgc tacgctggag tccctgatcg cttcattggc | 660 |
| agtggatatg ggacggattt cactttcacc atcagcactt gcaggctga ggacctggca | 720 |
| gtttatttct gtcagcaaga ttataattct cctccgacgt tcggtggagg caccaagctg | 780 |
| gaaatcaaac ggtcggatcc cgagcccaaa tctcctgaca aaactcacac atgcccaccg | 840 |
| tgcccagcac ctcccgtggc cggcccgtca gtgttcctct tccccccaaa acccaaggac | 900 |
| accctcatga tcgcccggac ccctgaggtc acatgcgtgg tggtggacgt gagccacgag | 960 |
| gaccctgagg tcaagttcaa ctggtacgtg gacggcgtgg aggtgcataa tgccaagaca | 1020 |
| aagccgcggg aggagcagta acagcacg taccgtgtgg tcagcgtcct caccgtcctg | 1080 |
| caccaggact ggctgaatgg caaggagtac aagtgcaagg tgtccaacaa agccctccca | 1140 |
| gcccccatcg agaaaaccat ctccaaagcc aaagggcagc cccgagaacc acaggtgtac | 1200 |
| accctgcccc catcccggga tgagctgacc aagaaccagg tcagcctgac ctgcctggtc | 1260 |
| aaaggcttct atcccagcga catcgccgtg gagtgggaga gcaatgggca accggagaac | 1320 |
| aactacaaga ccacgcctcc cgtgctggac tccgacggct ccttcttcct ctacagcaag | 1380 |
| ctcaccgtgg acaagagcag gtggcagcag gggaacgtgt tctcatgctc cgtgatgcat | 1440 |
| gaggccctgc acaatcacta tcccagaaa tctctgagtc tgagcccagg caagaaggat | 1500 |
| attctcctgg caggcctcgt ggctgctgat gcggtggcat cgctgctcat cgtggggcg | 1560 |
| gtgttcctgt gcgcacgcag acagcttgga ctgcacatct ggcagctgag gagtcagtgc | 1620 |
| atgtggcccc gagagacaca gctgctgctg gaggtgccgc cgtcgaccga ggacgccaga | 1680 |
| agctgccagt tccccgagga agagcgggc gagcgatcgg cagaggagaa ggggcggctg | 1740 |
| ggagatctgt gggtgggatc agggagcggc tctgggagcg gtagtggatc tggtatgcaa | 1800 |
| atcttcgtga aaaccctgac cgggaaaaca gccactctcg aagtcgagcc cagcgataca | 1860 |
| attgagaacg tgaaggccaa gattcaggac aag | 1893 |

<210> SEQ ID NO 140
<211> LENGTH: 1386
<212> TYPE: DNA
<213> ORGANISM: artificial sequence
<220> FEATURE:
<223> OTHER INFORMATION: GG224

<400> SEQUENCE: 140

| | |
|---|---|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct ggtgactgt ctccgctggc | 420 |

| | |
|---|---|
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccggtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat ataccctac accttcggcg gaggcacaaa gctcgaaata | 780 |
| aagcggtcgg atcccgcccc cgtggggctg gtggcgcggt tggctgacga gagcggccac | 840 |
| gtagtgttgc gctggctccc gccgcctgag cacccatga cgtctcacat ccgctacgag | 900 |
| gtggacgtct cggccggcaa cggcgcaggg agcgtacaga gggtggagat cctggagggc | 960 |
| cgcaccgagt gtgtgctgag caacctgcgg ggccggacgc gctacacctt cgccgtccgc | 1020 |
| gcgcgtatgg ctgagccgag cttcggcggc ttctggagcg cctggtcgga gcctgtgtcg | 1080 |
| ctgctgacgc ctagcgatat ttacatctgg gcacccctcg ccggcacctg cggggtgctt | 1140 |
| ctcctctccc tggtgattac cctgtattgc agaagggacc gatgcctcca acacagctat | 1200 |
| gcaggtgcct gggctgtgag tccggagaca gagctcactg ccacgttgg atcagggagc | 1260 |
| ggctctggga gcgtagtgg atctggtatg caaatcttcg tgaaaccct gaccgggaaa | 1320 |
| acagccactc tcgaagtcga gcccagcgat acaattgaga cgtgaaggc caagattcag | 1380 |
| gacaag | 1386 |

<210> SEQ ID NO 141
<211> LENGTH: 1917
<212> TYPE: DNA
<213> ORGANISM: artificial sequence
<220> FEATURE:
<223> OTHER INFORMATION: GG225

<400> SEQUENCE: 141

| | |
|---|---|
| atggctttgc ctgtcactgc cttgctgctt ccacttgctc tgttgttgca cgccgcaaga | 60 |
| cccgaggtcc agcttcagca gtctggacct gacctggtga agcctggggc ttcagtgaag | 120 |
| atatcctgca aggcttctgg ttactcattc actggctact acatgcactg ggtgaagcag | 180 |
| agtcatggaa agagccttga gtggattgga cgtattaatc ctaacaatgg tgttactctc | 240 |
| tacaaccaga aattcaagga caaggccata ttaactgtag acaagtcatc caccacagcc | 300 |
| tacatggagc tccgcagcct gacatctgag gactctgcgg tctattactg tgcaagatca | 360 |
| actatgatta cgaactatgt tatggactac tggggtcaag taacctcagt caccgtttcc | 420 |
| tcaggcggag gaggcagtgg cggagggga agtggggcg gcggcagcag tattgtgatg | 480 |
| acccagactc ccacattcct gcttgtttca gcaggagaca gggttaccat aacctgcaag | 540 |
| gccagtcaga gtgtgagtaa tgatgtagct tggtaccaac agaagccagg gcagtctcct | 600 |
| acactgctca tatcctatac atccagtcgc tacgctggag tccctgatcg cttcattggc | 660 |
| agtggatatg ggacggattt cactttcacc atcagcactt gcaggctga ggacctggca | 720 |
| gtttatttct gtcagcaaga ttataattct cctccgacgt tcggtggagg caccaagctg | 780 |
| gaaatcaaac ggtcggatcc cgagcccaaa tctcctgaca aaactcacac atgcccaccg | 840 |
| tgcccagcac ctcccgtggc cggccgtca gtgttcctct ccccccaaa acccaaggac | 900 |
| accctcatga tcgcccggac ccctgaggtc acatgcgtgg tggtggacgt gagccacgag | 960 |
| gaccctgagg tcaagttcaa ctggtacgtg gacggcgtgg aggtgcataa tgccaagaca | 1020 |
| aagccgcggg aggagcagta caacagcacg taccgtgtgg tcagcgtcct caccgtcctg | 1080 |

```
caccaggact ggctgaatgg caaggagtac aagtgcaagg tgtccaacaa agccctccca    1140
gcccccatcg agaaaccat ctccaaagcc aagggcagc cccgagaacc acaggtgtac     1200
accctgcccc catcccggga tgagctgacc aagaaccagg tcagcctgac ctgcctggtc    1260
aaaggcttct atcccagcga catcgccgtg gagtgggaga gcaatgggca accggagaac    1320
aactacaaga ccacgcctcc cgtgctggac tccgacggct ccttcttcct ctacagcaag    1380
ctcaccgtgg acaagagcag gtggcagcag gggaacgtgt tctcatgctc cgtgatgcat    1440
gaggccctgc acaatcacta cccagaaaa tctctgagtc tgagcccagg caagaaggat    1500
atcttttggg tgctggtggt ggttggtgga gtcctggctt gctatagctt gctagtaaca    1560
gtggccttta ttattttctg ggtgaggagt aagcgcagat gtgtgaaaag aagaaagcca    1620
aggggtgatg tagtcaaggt gattgtctcc gtccagcgga aaagacagga ggcagaaggt    1680
gaggccacag tcattgaggc cctgcaagcc cctccggacg tcaccacggt ggccgtggag    1740
gagacaatac cctcattcac ggggaggagc ccaaaccacg gatcagggag cggctctggg    1800
agcggtagtg gatctggtat gcaaatcttc gtgaaaaccc tgaccgggaa aacagccact    1860
ctcgaagtcg agcccagcga tacaattgag aacgtgaagg ccaagattca ggacaag      1917

<210> SEQ ID NO 142
<211> LENGTH: 1782
<212> TYPE: DNA
<213> ORGANISM: artificial sequence
<220> FEATURE:
<223> OTHER INFORMATION: GG226

<400> SEQUENCE: 142
atggctttgc tgtcactgc cttgctgctt ccacttgctc tgttgttgca cgccgcaaga      60
ccccaagtgc agcttcaaca gtctggggca gaactcgtaa gaccaggagc atcagtgaca     120
ctgtcttgta aagcctccgg ctataccttc tctgactacg agatgcattg ggtcatccag     180
acaccagtac atgggctcga atggatagga gccatagatc cagagacagg cggaacagca     240
tacaaccaga agttcaaagg caaggccatt ctcacagcgg acaagagcag tagcaccgct     300
tacatggagt tgcgatccct gaccagtgag gactctgcag tctactattg tacagggtac     360
tatgactacg actcattcac atattggggg cagggtacct tggtgactgt ctccgctggc     420
ggaggaggca gtggcggagg gggaagtggg ggcggcggca gcgatatagt gatgacgcag     480
tcccagaaga tcatgtccac gaccgtcggg gatcgggtca gtataacatg taaggcatcc     540
cagaacgtgg acgcggccgt ggcttggtat caacagaaac ccggtcaatc cccaaagctc     600
ctcatctact ctgcgagcaa tagatatacc ggtgtgcctg ataggttcac cggaagcggc     660
tccggaacag atttcaccct gactatcagc aatatgcaat ccgaggactt ggctgactac     720
ttttgccagc aatacgacat ataccctac accttcggcg gaggcacaaa gctcgaaata     780
aagcggtcgg atcccgagcc caatctcct gacaaaactc acacatgccc accgtgccca    840
gcacctcccg tggccggccc gtcagtgttc ctcttccccc caaaacccaa ggacaccctc    900
atgatcgccc ggacccctga ggtcacatgc gtggtggtgg acgtgagcca cgaggaccct    960
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtgtcca acaaagccct cccagccccc   1140
atcgagaaaa ccatctccaa agccaagggg cagccccgag aaccacaggt gtacaccctg   1200
```

```
ccccatccc gggatgagct gaccaagaac caggtcagcc tgacctgcct ggtcaaaggc    1260
ttctatccca gcgacatcgc cgtggagtgg gagagcaatg ggcaaccgga gaacaactac    1320
aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc caggcaagaa ggatatttac    1500
atctgggcac ccctcgccgg cacctgcggg gtgcttctcc tctccctggt gattaccctg    1560
tattgcagaa gggaccgatg cctccaacac agctatgcag gtgcctgggc tgtgagtccg    1620
gagacagagc tcactggcca cgttggatca gggagcggct ctgggagcgg tagtggatct    1680
ggtatgcaaa tcttcgtgaa accctgacc gggaaaacag gcactctcga agtcgagccc    1740
agcgatacaa ttgagaacgt gaaggccaag attcaggaca ag                      1782
```

<210> SEQ ID NO 143
<211> LENGTH: 1842
<212> TYPE: DNA
<213> ORGANISM: artificial sequence
<220> FEATURE:
<223> OTHER INFORMATION: GG227

<400> SEQUENCE: 143

```
atggctttgc ctgtcactgc cttgctgctt ccacttgctc tgttgttgca cgccgcaaga      60
ccccaagtgc agcttcaaca gtctggggca gaactcgtaa gaccaggagc atcagtgaca     120
ctgtcttgta aagcctccgg ctataccttc tctgactacg agatgcattg ggtcatccag     180
acaccagtac atgggctcga atggatagga gccatagatc cagagacagg cggaacagca     240
tacaaccaga agttcaaagg caaggccatt ctcacagcgg acaagagcag tagcaccgct     300
tacatggagt tgcgatccct gaccagtgag gactctgcag tctactattg tacagggtac     360
tatgactacg actcattcac atattggggg cagggtacct tggtgactgt ctccgctggc     420
ggaggaggca gtggcggagg gggaagtggg ggcggcggca gcgatatagt gatgacgcag     480
tcccagaaga tcatgtccac gaccgtcggg gatcgggtca gtataacatg taaggcatcc     540
cagaacgtgg acgcggccgt ggcttggtat caacagaaac ccggtcaatc cccaaagctc     600
ctcatctact ctgcgagcaa tagatatacc ggtgtgcctg ataggttcac cggaagcggc     660
tccggaacag atttcaccct gactatcagc aatatgcaat ccgaggactt ggctgactac     720
ttttgccagc aatacgacat ataccctac accttcggcg gaggcacaaa gctcgaaata     780
aagcggtcgg atcccgagcc caaatctcct gacaaaactc acacatgccc accgtgccca     840
gcacctcccg tggcggccc gtcagtgttc ctcttccccc caaaacccaa ggacaccctc     900
atgatcgccc ggacccctga ggtcacatgc gtggtggtgg acgtgagcca cgaggaccct     960
gaggtcaagt tcaactggta cgtggacggc gtggaggtgc ataatgccaa gacaaagccg    1020
cgggaggagc agtacaacag cacgtaccgt gtggtcagcg tcctcaccgt cctgcaccag    1080
gactggctga atggcaagga gtacaagtgc aaggtgtcca acaaagccct cccagccccc    1140
atcgagaaaa ccatctccaa agccaaaggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg ggcaaccgga gaacaactac    1320
aagaccacgc ctcccgtgct ggactccgac ggctccttct tcctctacag caagctcacc    1380
gtggacaaga gcaggtggca gcaggggaac gtgttctcat gctccgtgat gcatgaggcc    1440
ctgcacaatc actataccca gaaatctctg agtctgagcc caggcaagaa ggatatcttt    1500
```

| | |
|---|---|
| tgggtgctgg tggtggttgg tggagtcctg gcttgctata gcttgctagt aacagtggcc | 1560 |
| tttattattt tctgggtgag gagtaagcgc agaatggagg agagtgtcgt acggccctca | 1620 |
| gtgtttgtgg tggatggaca gaccgacatc ccattcacga ggctgggacg aagccaccgg | 1680 |
| agacagtcgt gcagtgtggc ccgggggatca gggagcggct ctgggagcgg tagtggatct | 1740 |
| ggtatgcaaa tcttcgtgaa aaccctgacc gggaaaacag gcactctcga agtcgagccc | 1800 |
| agcgatacaa ttgagaacgt gaaggccaag attcaggaca ag | 1842 |

<210> SEQ ID NO 144
<211> LENGTH: 1209
<212> TYPE: DNA
<213> ORGANISM: artificial sequence
<220> FEATURE:
<223> OTHER INFORMATION: GG228

<400> SEQUENCE: 144

| | |
|---|---|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg ggtcatccag | 180 |
| acaccagtac atgggctcga atggatagga gccatagatc cagagacagg cggaacagca | 240 |
| tacaaccaga gttcaaagg caaggccatt ctcacagcgg acaagagcag tagcaccgct | 300 |
| tacatggagt tgcgatccct gaccagtgag gactctgcag tctactattg tacagggtac | 360 |
| tatgactacg actcattcac atattggggg cagggtacct tggtgactgt ctccgctggc | 420 |
| ggaggaggca gtggcggagg gggaagtggg ggcggcggca gcgatatagt gatgacgcag | 480 |
| tcccagaaga tcatgtccac gaccgtcggg gatcgggtca gtataacatg taaggcatcc | 540 |
| cagaacgtgg acgcggccgt ggcttggtat caacagaaac ccggtcaatc cccaaagctc | 600 |
| ctcatctact ctgcgagcaa tagatatacc ggtgtgcctg ataggttcac cggaagcggc | 660 |
| tccggaacag atttcaccct gactatcagc aatatgcaat ccgaggactt ggctgactac | 720 |
| ttttgccagc aatacgacat ataccctac accttcggcg gaggcacaaa gctcgaaata | 780 |
| aagcggtcgg atcccaccac aaccccgct ccaaggcccc ctaccccgc accaactatt | 840 |
| gcctcccagc cactctcact gcggcctgag gcctgtcggc ccgctgctgg aggcgcagtg | 900 |
| catacaaggg gcctcgattt cgcctgcgat attctcctgg caggcctcgt ggctgctgat | 960 |
| gcggtggcat cgctgctcat cgtggggggcg gtgttcctgt gcgcacgcag accacgccgc | 1020 |
| agccccgccc aagaagatgg caaagtctac atcaacatgc caggcaggg cggatcaggg | 1080 |
| agcggctctg ggagcggtag tggatctggt atgcaaatct tcgtgaaaac cctgaccggg | 1140 |
| aaaacaggca ctctcgaagt cgagcccagc gatacaattg agaacgtgaa ggccaagatt | 1200 |
| caggacaag | 1209 |

<210> SEQ ID NO 145
<211> LENGTH: 1893
<212> TYPE: DNA
<213> ORGANISM: artificial sequence
<220> FEATURE:
<223> OTHER INFORMATION: GG229

<400> SEQUENCE: 145

| | |
|---|---|
| atggctttgc ctgtcactgc cttgctgctt ccacttgctc tgttgttgca cgccgcaaga | 60 |
| cccgaggtcc agcttcagca gtctggacct gacctggtga agcctggggc ttcagtgaag | 120 |

| | |
|---|---|
| atatcctgca aggcttctgg ttactcattc actggctact acatgcactg ggtgaagcag | 180 |
| agtcatggaa agagccttga gtggattgga cgtattaatc ctaacaatgg tgttactctc | 240 |
| tacaaccaga aattcaagga caaggccata ttaactgtag acaagtcatc caccacagcc | 300 |
| tacatggagc tccgcagcct gacatctgag gactctgcgg tctattactg tgcaagatca | 360 |
| actatgatta cgaactatgt tatggactac tggggtcaag taacctcagt caccgtttcc | 420 |
| tcaggcggag gaggcagtgg cggaggggga agtgggggcg gcggcagcag tattgtgatg | 480 |
| acccagactc ccacattcct gcttgtttca gcaggagaca gggttaccat aacctgcaag | 540 |
| gccagtcaga gtgtgagtaa tgatgtagct tggtaccaac agaagccagg gcagtctcct | 600 |
| acactgctca tatcctatac atccagtcgc tacgctggag tccctgatcg cttcattggc | 660 |
| agtggatatg ggacggattt cactttcacc atcagcactt tgcaggctga ggacctggca | 720 |
| gtttatttct gtcagcaaga ttataattct cctccgacgt tcggtggagg caccaagctg | 780 |
| gaaatcaaac ggtcggatcc cgagcccaaa tctcctgaca aaactcacac atgcccaccg | 840 |
| tgcccagcac ctcccgtggc cggccgtca gtgttcctct ccccccaaa acccaaggac | 900 |
| accctcatga tcgcccggac ccctgaggtc acatgcgtgg tggtggacgt gagccacgag | 960 |
| gaccctgagg tcaagttcaa ctggtacgtg gacggcgtgg aggtgcataa tgccaagaca | 1020 |
| aagccgcggg aggagcagta caacagcacg taccgtgtgg tcagcgtcct caccgtcctg | 1080 |
| caccaggact ggctgaatgg caaggagtac aagtgcaagg tgtccaacaa agccctccca | 1140 |
| gcccccatcg agaaaaccat ctccaaagcc aaagggcagc ccgagaacc acaggtgtac | 1200 |
| accctgcccc catcccggga tgagctgacc aagaaccagg tcagcctgac ctgcctggtc | 1260 |
| aaaggcttct atcccagcga catcgccgtg gagtgggaga gcaatgggca accggagaac | 1320 |
| aactacaaga ccacgcctcc cgtgctggac tccgacggct ccttcttcct ctacagcaag | 1380 |
| ctcaccgtgg acaagagcag gtggcagcag gggaacgtgt tctcatgctc cgtgatgcat | 1440 |
| gaggccctgc acaatcacta cccagaaaa tctctgagtc tgagcccagg caagaaggat | 1500 |
| attctcctgg caggcctcgt ggctgctgat gcggtggcat cgctgctcat cgtggggcg | 1560 |
| gtgttcctgt gcgcacgcag acagcttgga ctgcacatct ggcagctgag gagtcagtgc | 1620 |
| atgtggcccc gagagacaca gctgctgctg gaggtgccgc cgtcgaccga ggacgccaga | 1680 |
| agctgccagt tccccgagga agagcggggc gagcgatcgg cagaggagaa ggggcggctg | 1740 |
| ggagatctgt gggtgggatc agggagcggc tctgggagcg gtagtggatc tggtatgcaa | 1800 |
| atcttcgtga aaaccctgac cgggaaaaca ggcactctcg aagtcgagcc cagcgataca | 1860 |
| attgagaacg tgaaggccaa gattcaggac aag | 1893 |

<210> SEQ ID NO 146
<211> LENGTH: 1386
<212> TYPE: DNA
<213> ORGANISM: artificial sequence
<220> FEATURE:
<223> OTHER INFORMATION: GG230

<400> SEQUENCE: 146

| | |
|---|---|
| atggctttgc ctgtcactgc cttgctgctt ccacttgctc tgttgttgca cgccgcaaga | 60 |
| ccccaagtgc agcttcaaca gtctggggca gaactcgtaa gaccaggagc atcagtgaca | 120 |
| ctgtcttgta aagcctccgg ctataccttc tctgactacg agatgcattg gtcatccag | 180 |
| acaccagtac atgggctcga atggatagga gccatagatc cagagacagg cggaacagca | 240 |
| tacaaccaga agttcaaagg caaggccatt ctcacagcgg acaagagcag tagcaccgct | 300 |

```
tacatggagt tgcgatccct gaccagtgag gactctgcag tctactattg tacagggtac    360
tatgactacg actcattcac atattggggg cagggtacct tggtgactgt ctccgctggc    420
ggaggaggca gtggcggagg gggaagtggg ggcggcggca gcgatatagt gatgacgcag    480
tcccagaaga tcatgtccac gaccgtcggg gatcgggtca gtataacatg taaggcatcc    540
cagaacgtgg acgcggccgt ggcttggtat caacagaaac ccggtcaatc cccaaagctc    600
ctcatctact ctgcgagcaa tagatatacc ggtgtgcctg ataggttcac cggaagcggc    660
tccggaacag atttcaccct gactatcagc aatatgcaat ccgaggactt ggctgactac    720
ttttgccagc aatacgacat ataccectac accttcggcg gaggcacaaa gctcgaaata    780
aagcggtcgg atcccgcccc cgtggggctg gtggcgcggt tggctgacga gagcggccac    840
gtagtgttgc gctggctccc gccgcctgag acacccatga cgtctcacat ccgctacgag    900
gtggacgtct cggccggcaa cggcgcaggg agcgtacaga gggtggagat cctggagggc    960
cgcaccgagt gtgtgctgag caacctgcgg ggccggacgc gctacacctt cgccgtccgc   1020
gcgcgtatgg ctgagccgag cttcggcggc ttctggagcg cctggtcgga gcctgtgtcg   1080
ctgctgacgc ctagcgatat ttacatctgg gcacccctcg ccggcacctg cggggtgctt   1140
ctcctctccc tggtgattac cctgtattgc agaagggacc gatgcctcca acacagctat   1200
gcaggtgcct gggctgtgag tccggagaca gagctcactg gccacgttgg atcagggagc   1260
ggctctggga gcggtagtgg atctggtatg caaatcttcg tgaaaaccct gaccgggaaa   1320
acaggcactc tcgaagtcga gcccagcgat acaattgaga acgtgaaggc caagattcag   1380
gacaag                                                              1386
```

```
<210> SEQ ID NO 147
<211> LENGTH: 1917
<212> TYPE: DNA
<213> ORGANISM: artificial sequence
<220> FEATURE:
<223> OTHER INFORMATION: GG231

<400> SEQUENCE: 147
```

```
atggctttgc ctgtcactgc cttgctgctt ccacttgctc tgttgttgca cgccgcaaga     60
cccgaggtcc agcttcagca gtctggacct gacctggtga agcctggggc ttcagtgaag    120
atatcctgca aggcttctgg ttactcattc actggctact acatgcactg ggtgaagcag    180
agtcatggaa agagccttga gtggattgga cgtattaatc ctaacaatgg tgttactctc    240
tacaaccaga aattcaagga caaggccata ttaactgtag acaagtcatc caccacagcc    300
tacatggagc tccgcagcct gacatctgag gactctgcgg tctattactg tgcaagatca    360
actatgatta cgaactatgt tatggactac tggggtcaag taacctcagt caccgtttcc    420
tcaggcggag gaggcagtgg cggagggggg agtgggggcg gcggcagcag tattgtgatg    480
acccagactc ccacattcct gcttgtttca gcaggagaca gggttaccat aacctgcaag    540
gccagtcaga gtgtgagtaa tgatgtagct tggtaccaac agaagccagg gcagtctcct    600
acactgctca tatcctatac atccagtcgc tacgctggag tccctgatcg cttcattggc    660
agtggatatg ggacggattt cactttcacc atcagcactt tgcaggctga ggacctggca    720
gtttatttct gtcagcaaga ttataattct cctccgacgt tcggtggagg caccaagctg    780
gaaatcaaac ggtcggatcc cgagcccaaa tctcctgaca aaactcacac atgcccaccg    840
tgcccagcac ctcccgtggc cggcccgtca gtgttcctct ccccccaaa acccaaggac    900
```

```
accctcatga tcgcccggac ccctgaggtc acatgcgtgg tggtggacgt gagccacgag    960
gaccctgagg tcaagttcaa ctggtacgtg gacggcgtgg aggtgcataa tgccaagaca   1020
aagccgcggg aggagcagta acagcacg taccgtgtgg tcagcgtcct caccgtcctg    1080
caccaggact ggctgaatgg caaggagtac aagtgcaagg tgtccaacaa agccctccca   1140
gcccccatcg agaaaaccat ctccaaagcc aagggcagc cccgagaacc acaggtgtac   1200
accctgcccc catcccggga tgagctgacc aagaaccagg tcagcctgac ctgcctggtc   1260
aaaggcttct atcccagcga catcgccgtg gagtgggaga gcaatgggca accggagaac   1320
aactacaaga ccacgcctcc cgtgctggac tccgacggct ccttcttcct ctacagcaag   1380
ctcaccgtgg acaagagcag gtggcagcag gggaacgtgt tctcatgctc cgtgatgcat   1440
gaggccctgc acaatcacta cccagaaaa tctctgagtc tgagcccagg caagaaggat   1500
atcttttggg tgctggtggt ggttggtgga gtcctggctt gctatagctt gctagtaaca   1560
gtggccttta ttattttctg ggtgaggagt aagcgcagat gtgtgaaaag aagaaagcca   1620
aggggtgatg tagtcaaggt gattgtctcc gtccagcgga aaagacagga ggcagaaggt   1680
gaggccacag tcattgaggc cctgcaagcc cctccggacg tcaccacggt ggccgtggag   1740
gagacaatac cctcattcac ggggaggagc ccaaaccacg gatcagggag cggctctggg   1800
agcggtagtg gatctggtat gcaaatcttc gtgaaaccc tgaccgggaa aacaggcact   1860
ctcgaagtcg agcccagcga tacaattgag aacgtgaagg ccaagattca ggacaag     1917

<210> SEQ ID NO 148
<211> LENGTH: 90
<212> TYPE: DNA
<213> ORGANISM: artificial sequence
<220> FEATURE:
<223> OTHER INFORMATION: T7 plasmid pCLS26376

<400> SEQUENCE: 148
taatacgact cactataggg ggcgcgccac tagcgctgtc acgcgccaag ccgccaccat    60
ggtttaacat gttgctataa gcttcgactg                                     90

<210> SEQ ID NO 149
<211> LENGTH: 56
<212> TYPE: DNA
<213> ORGANISM: artificial sequence
<220> FEATURE:
<223> OTHER INFORMATION: T7 oligo F1

<400> SEQUENCE: 149
gcatcgtaat acgactcact atagggcagg ccaccatggc tttgcctgtc actgcc        56

<210> SEQ ID NO 150
<211> LENGTH: 56
<212> TYPE: DNA
<213> ORGANISM: artificial sequence
<220> FEATURE:
<223> OTHER INFORMATION: T7 oligo F2

<400> SEQUENCE: 150
gcatcgtaat acgactcact atagggcagg ccaccatggc tcccgcaatg gagtcc        56

<210> SEQ ID NO 151
<211> LENGTH: 26
<212> TYPE: DNA
<213> ORGANISM: artificial sequence
<220> FEATURE:
<223> OTHER INFORMATION: T7 oligo R1
```

<400> SEQUENCE: 151
ctagaggatc gctcgagtta ggtctc                                              26

<210> SEQ ID NO 152
<211> LENGTH: 2541
<212> TYPE: DNA
<213> ORGANISM: artificial sequence
<220> FEATURE:
<223> OTHER INFORMATION: pCLS24707

<400> SEQUENCE: 152

| | | | | | |
|---|---|---|---|---|---|
| atgatcccag | ccgtggtcct | gctgctgctg | ctgctggtgg | agcaggcagc | tgcactggga | 60 |
| gaaccccagc | tgtgctacat | cctggacgcc | attctgttcc | tgtacggcat | tgtgctgaca | 120 |
| ctgctgtatt | gtaggctgaa | gatccaggtc | cgcaaagccg | ctattacttc | atatgagaag | 180 |
| agccgcgtga | agttcagccg | atccgctgac | gcaccagcat | accagcaggg | acagaaccag | 240 |
| ctgtataacg | agctgaatct | gggacggaga | gaggaatacg | acgtcctgga | taagaggcgc | 300 |
| ggcagggatc | ctgaaatggg | cgggaagcct | cgacggaaaa | acccacagga | ggggctgtac | 360 |
| aatgaactgc | agaaggacaa | aatggctgag | gcatatagtg | aaatcggaat | gaagggcgag | 420 |
| agaaggcgcg | ggaaaggaca | cgatggcctg | taccaggggc | tgtccaccgc | cacaaaagac | 480 |
| acttatgatg | cactgcatat | gcaggccctg | cccctcgcg | gcagcgggc | caccaacttc | 540 |
| tccctgctga | gcaggctgg | agacgtggag | gaaaatcccg | gccctatggc | tcccgcaatg | 600 |
| gagtccccta | cactgctgtg | cgtggcactg | ctgttctttg | caccagatgg | cgtgctggca | 660 |
| gaggtccagc | tgcagcagtc | aggaccagaa | ctgatcaaac | ccggagcatc | tgtgaaaatg | 720 |
| agttgtaagg | cctcaggcta | tactttcacc | tcttacgtga | tgcactgggt | caagcagaaa | 780 |
| cctggacagg | gcctggagtg | gatcggctat | attaatccat | acaacgacgg | gaccaagtac | 840 |
| aacgaaaagt | ttaaaggcaa | ggcaacactg | actagtgata | agagctcctc | tactgcttac | 900 |
| atggagctga | gttcactgac | cagcgaagac | tccgctgtgt | actattgcgc | aagaggaacc | 960 |
| tactattacg | gctctagggt | gttcgattac | tgggggcagg | gaaccacact | gacagtcagc | 1020 |
| tccggaggag | gaggatccgg | aggaggaggg | tctgaaggcg | ggggaagtga | catcgtgatg | 1080 |
| acacaggccg | ctcctagcat | tccagtgact | cccggcgagt | cagtcagcat | ctcctgtcgg | 1140 |
| tctagtaaga | gcctgctgaa | ctccaatgga | aacacatatc | tgtactggtt | tctgcagagg | 1200 |
| cctggccagt | ccccacagct | gctgatctat | cgcatgtcta | acctggccag | tggcgtgccc | 1260 |
| gatcggttct | ctggcagtgg | gtcaggaacc | gcctttacac | tgaggattag | ccgcgtcgag | 1320 |
| gctgaagacg | tggggtctat | ttactgcatg | cagcatctgg | agtacccttt | cacatttggc | 1380 |
| gccgggacta | aactggaact | gaagcgcgcc | gatactacca | caccagctcc | acgaccacct | 1440 |
| actcctgcac | caaccattgc | ttcacagcct | ctgagcctgc | gaccagaagc | ttgccggcca | 1500 |
| gcagcaggag | gagcagtgca | caccagaggc | ctggacttcg | cctgtgattt | ctttatcccc | 1560 |
| ctgctggtgg | tcattctgtt | cgccgtggac | actgggctgt | ttatctccac | ccagcagcag | 1620 |
| gtcacattcc | tgctgaaaat | taagcggacc | agaaagggct | tccggctgct | gaatccccat | 1680 |
| cctaaaccaa | accccaagaa | caatggaagc | ggagagggac | gaggatccct | gctgacctgc | 1740 |
| ggggacgtgg | aggaaaaccc | aggacctatg | gacactgagt | ctaaccggag | agccaatctg | 1800 |
| gctctgccac | aggaacccag | ctccgtgccc | gcattcgagg | tcctgaaat | ctctcctcag | 1860 |
| gaggtgtcta | gtgggcgcct | gctgaagagt | gcctcaagcc | cccctctgca | cacttggctg | 1920 |

-continued

```
accgtgctga agaaagagca ggaattcctg ggagtcaccc agatcctgac agctatgatt    1980
tgcctgtgtt ttggcacagt ggtctgcagt gtgctggaca tctcacatat tgagggggat    2040
atcttctcct cttttaaggc tgggtaccct ttttggggag caatcttctt tagcatttcc    2100
ggaatgctgt caatcattag cgaaaggcgc aacgcaacat atctggtgcg aggaagcctg    2160
ggcgcaaata ctgccagttc aatcgccggc gggacaggca tcactattct gatcattaac    2220
ctgaagaaaa gcctggctta catccacatt cattcctgcc agaagttctt tgagactaaa    2280
tgtttcatgg cctcttttag taccgaaatc gtggtcatga tgctgttcct gaccattctg    2340
gggctgggat ccgccgtgtc tctgacaatc tgcggcgctg gggaggaact gaagggcaac    2400
aaggtcccag agaagcgagg gcggaagaaa ctgctgtata ttttcaaaca gccttttatg    2460
agaccagtgc agaccacaca ggaggaagat ggctgctcct gtaggtttcc cgaggaagag    2520
gaaggaggct gtgagctgtg a                                              2541
```

<210> SEQ ID NO 153
<211> LENGTH: 54
<212> TYPE: DNA
<213> ORGANISM: artificial sequence
<220> FEATURE:
<223> OTHER INFORMATION: beta-chain-F

<400> SEQUENCE: 153

```
gcatcgtaat acgactcact atagggcagg ccaccatgga cactgagtct aacc           54
```

<210> SEQ ID NO 154
<211> LENGTH: 20
<212> TYPE: DNA
<213> ORGANISM: artificial sequence
<220> FEATURE:
<223> OTHER INFORMATION: beta-chain-R

<400> SEQUENCE: 154

```
tcacagctca cagcctcctt                                                 20
```

<210> SEQ ID NO 155
<211> LENGTH: 55
<212> TYPE: DNA
<213> ORGANISM: artificial sequence
<220> FEATURE:
<223> OTHER INFORMATION: gamma-chain-F

<400> SEQUENCE: 155

```
gcatcgtaat acgactcact atagggcagg ccaccatgat cccagccgtg gtcct          55
```

<210> SEQ ID NO 156
<211> LENGTH: 20
<212> TYPE: DNA
<213> ORGANISM: artificial sequence
<220> FEATURE:
<223> OTHER INFORMATION: gamma-chain-R

<400> SEQUENCE: 156

```
tcagcgaggg ggcagggcct                                                 20
```

<210> SEQ ID NO 157
<211> LENGTH: 689
<212> TYPE: DNA
<213> ORGANISM: artificial sequence
<220> FEATURE:
<223> OTHER INFORMATION: Gal4-RQR8 pCLS26301

<400> SEQUENCE: 157

```
gaattccgga gtactgtcct ccgagcggag tactgtcctc cgagcggagt actgtcctcc      60
gagcggagta ctgtcctccg agcggagtac tgtcctccga gcggaccgac gtatgtcgag     120
gtaggcgtgt acggtgggag gcctatataa gcagagctcg tttagtgaac cgtcagatcg     180
cctggaggta ccgccaccat gctgaccagc ctgctgtgct ggatggccct gtgcctgctg     240
ggcgccgacc acgccgatgc ctgcccctac agcaacccca gcctgtgcag cggaggcggc     300
ggcagcgagc tgcccaccca gggcaccttc tccaacgtgt ccaccaacgt gagcccagcc     360
aagcccacca ccaccgcctg tccttattcc aatccttccc tgtgtagcgg aggggaggc     420 agcccagccc ccagacctcc caccccagcc ccaccatcg ccagccagcc tctgagcctg     480
agacccgagg cctgccgccc agccgccggc ggcgccgtgc acaccagagg cctggatttc     540
gcctgcgata tctacatctg gcccccactg gccggcacct gtggcgtgct gctgctgagc     600
ctggtgatca ccctgtactg caaccaccgc aaccgcaggc gcgtgtgcaa gtgccccagg     660
cccgtggtga gagcctagtg acctgcagg                                       689
```

<210> SEQ ID NO 158
<211> LENGTH: 727
<212> TYPE: DNA
<213> ORGANISM: artificial sequence
<220> FEATURE:
<223> OTHER INFORMATION: TetO-RQR8 pCLS26303

<400> SEQUENCE: 158

```
gaattctccc tatcagtgat agagatccct atcagtgata gagatcccta tcagtgatag      60
agatccctat cagtgataga gatccctatc agtgatagag atccctatca gtgatagaga     120
tccctatcag tgatagagac ggaccgacgt atgtcgaggt aggcgtgtac ggtgggaggc     180
ctatataagc agagctcgtt tagtgaaccg tcagatcgcc tggaggtacc gccaccatgc     240
tgaccagcct gctgtgctgg atggccctgt gcctgctggg cgccgaccac gccgatgcct     300
gcccctacag caaccccagc ctgtgcagcg gaggcggcgg cagcgagctg cccacccagg     360
gcaccttctc caacgtgtcc accaacgtga gcccagccaa gcccaccacc accgcctgtc     420
cttattccaa tccttccctg tgtagcggag ggggaggcag cccagccccc agacctccca     480
ccccagcccc caccatcgcc agccagcctc tgagcctgag acccgaggcc tgccgcccag     540
ccgccggcgg cgccgtgcac accagaggcc tggatttcgc ctgcgatatc tacatctggc     600
ccccactggc cggcacctgt ggcgtgctgc tgctgagcct ggtgatcacc ctgtactgca     660
accaccgcaa ccgcaggcgc gtgtgcaagt gccccaggcc cgtggtgaga gcctagtgac     720
ctgcagg                                                               727
```

<210> SEQ ID NO 159
<211> LENGTH: 1148
<212> TYPE: DNA
<213> ORGANISM: artificial sequence
<220> FEATURE:
<223> OTHER INFORMATION: Gal4-Renilla pCLS27049

<400> SEQUENCE: 159

```
gaattccgga gtactgtcct ccgagcggag tactgtcctc cgagcggagt actgtcctcc      60
gagcggagta ctgtcctccg agcggagtac tgtcctccga gcggaccgac gtatgtcgag     120
gtaggcgtgt acggtgggag gcctatataa gcagagctcg tttagtgaac cgtcagatcg     180
cctggaggta ccgccaccat gggcacttcg aaagtttatg atccagaaca aaggaaacgg     240
```

```
atgataactg gtccgcagtg gtgggccaga tgtaaacaaa tgaatgttct tgattcattt    300
attaattatt atgattcaga aaaacatgca gaaaatgctg ttatttttt acatggtaac    360 gcggcctctt cttatttatg gcgacatgtt gtgccacata ttgagccagt agcgcggtgt    420
attataccag accttattgg tatgggcaaa tcaggcaaat ctggtaatgg ttcttatagg    480
ttacttgatc attacaaata tcttactgca tggtttgaac ttcttaattt accaaagaag    540 atcattttg tcggccatga ttgggtgct tgtttggcat ttcattatag ctatgagcat    600
caagataaga tcaaagcaat agttcacgct gaaagtgtag tagatgtgat tgaatcatgg    660
gatgaatggc ctgatattga agaagatatt gcgttgatca atctgaaga aggagaaaaa    720 atggttttgg agaataactt cttcgtggaa accatgttgc catcaaaaat catgagaaag    780
ttagaaccag aagaatttgc agcatatctt gaaccattca aagagaaagg tgaagttcgt    840
cgtccaacat tatcatggcc tcgtgaaatc ccgttagtaa aaggtggtaa acctgacgtt    900
gtacaaattg ttaggaatta taatgcttat ctacgtgcaa gtgatgattt accaaaaatg    960
tttattgaat cggacccagg attcttttcc aatgctattg ttgaaggtgc caagaagttt    1020
cctaatactg aatttgtcaa agtaaaaggt cttcattttt cgcaagaaga tgcacctgat    1080
gaaatgggaa aatatatcaa atcgttcgtt gagcgagttc tcaaaaatga acaatgatag    1140
cctgcagg                                                              1148

<210> SEQ ID NO 160
<211> LENGTH: 1186
<212> TYPE: DNA
<213> ORGANISM: artificial sequence
<220> FEATURE:
<223> OTHER INFORMATION: TetO-Renilla pCLS27050

<400> SEQUENCE: 160
gaattctccc tatcagtgat agagatccct atcagtgata gagatcccta tcagtgatag     60
agatccctat cagtgataga gatccctatc agtgatagag atccctatca gtgatagaga    120
tccctatcag tgatagagac ggaccgacgt atgtcgaggt aggcgtgtac ggtgggaggc    180
ctatataagc agagctcgtt tagtgaaccg tcagatcgcc tggaggtacc gccaccatgg    240
gcacttcgaa agtttatgat ccagaacaaa ggaaacggat gataactggt ccgcagtggt    300
gggccagatg taaacaaatg aatgttcttg attcatttat taattattat gattcagaaa    360
aacatgcaga aaatgctgtt atttttttac atggtaacgc ggcctcttct tatttatggc    420
gacatgttgt gccacatatt gagccagtag cgcggtgtat taccagac cttattggta    480 tgggcaaatc aggcaaatct ggtaatggtt cttataggtt acttgatcat tacaaatatc    540
ttactgcatg gtttgaactt cttaatttac caaagaagat cattttgtc ggccatgatt    600 ggggtgcttg tttggcattt cattatagct atgagcatca agataagatc aaagcaatag    660
ttcacgctga agtgtagta gatgtgattg aatcatggga tgaatggcct gatattgaag    720
aagatattgc gttgatcaaa tctgaagaag gagaaaaaat ggttttggag aataacttct    780
tcgtggaaac catgttgcca tcaaaaatca tgagaaagtt agaaccagaa gaatttgcag    840
catatcttga accattcaaa gagaaaggtg aagttcgtcg tccaacatta tcatggcctc    900
gtgaaatccc gttagtaaaa ggtggtaaac ctgacgttgt acaaattgtt aggaattata    960
atgcttatct acgtgcaagt gatgatttac caaaaatgtt tattgaatcg gacccaggat    1020
tcttttccaa tgctattgtt gaaggtgcca agaagtttcc taatactgaa tttgtcaaag    1080
taaaaggtct tcattttcg caagaagatg cacctgatga aatgggaaaa tatatcaaat    1140
```
cgttcgttga gcgagttctc aaaaatgaac aatgatagcc tgcagg         1186

<210> SEQ ID NO 161
<211> LENGTH: 1176
<212> TYPE: DNA
<213> ORGANISM: artificial sequence
<220> FEATURE:
<223> OTHER INFORMATION: Gal4_NF-Kb pCLS26593

<400> SEQUENCE: 161

| | | |
|---|---|---|
| atgaagctcc tgtcctctat cgagcaggca tgcgacatct gcagactcaa gaagctgaag | 60 |
| tgcagcaagg agaagcccaa gtgcgccaag tgccttaaga caactggga gtgtaggtac | 120 |
| tcccctaaga ccaagaggtc ccctctgacc agagctcacc ttactgaggt ggagtccagg | 180 |
| ttggagcggt tggaacaact gttcctgttg atcttcccca gggaggacct cgatatgatt | 240 |
| ctgaaaatgg actccctcca ggacattaag gccctgctga ccgggctctt tgtgcaggac | 300 |
| aatgtgaaca agatgccgt cacagatcgg ctcgccagcg tcgagactga tatgccactg | 360 |
| acactgcggc agcatcggat tagcgccaca agctcaagcg aggaaagttc taacaaaggc | 420 |
| cagcgccagc tgacagttag cgaaaccttc aagtccatca tgaagaagtc ccccttcagc | 480 |
| ggaccaaccg acccaaggcc cccacctcgc aggatcgccg tgccctccag atcctccgcc | 540 |
| tccgtgccta gcctgccccc tcagccatac cctttcacct ccagcctgtc caccatcaac | 600 |
| tacgacgagt tcccaactat ggtgttcccc agcggccaga ttagccaggc aagcgccctc | 660 |
| gcacctgccc ctcccccaggt gctccctcag gcacctgcac ctgctcctgc tccagctatg | 720 |
| gtcagcgccc tcgctcaggc tcctgctccc gtcccagtgc ttgctccagg accaccacaa | 780 |
| gccgtcgccc cacccgcccc caaacccaca caagccggag aaggcactct ttctgaggcc | 840 |
| tgttgcagt gcagtttga cgacgaggac ctggggggcc tgctgggcaa ttcaacagac | 900 |
| cccgccgtgt ttactgacct cgccagcgtg ataacagcg agtttcagca gctgctcaac | 960 |
| cagggcatcc ccgtcgcccc ccacaccaca gagcccatgc tcatggagta tcccgaggcc | 1020 |
| attacacggc tggtgacagg ggcccagcgg ccccccgatc ccgccccgc ccccctgggg | 1080 |
| gccccagggc tgcccaacgg cctgctgagt ggggatgagg attttttcatc tattgccgat | 1140 |
| atggatttta gtgccctgct gtctcagatt agctcg | 1176 |

<210> SEQ ID NO 162
<211> LENGTH: 612
<212> TYPE: DNA
<213> ORGANISM: artificial sequence
<220> FEATURE:
<223> OTHER INFORMATION: Gal4_VP64 pCLS26594

<400> SEQUENCE: 162

| | | |
|---|---|---|
| atgaagctcc tgtcctctat cgagcaggca tgcgacatct gcagactcaa gaagctgaag | 60 |
| tgcagcaagg agaagcccaa gtgcgccaag tgccttaaga caactggga gtgtaggtac | 120 |
| tcccctaaga ccaagaggtc ccctctgacc agagctcacc ttactgaggt ggagtccagg | 180 |
| ttggagcggt tggaacaact gttcctgttg atcttcccca gggaggacct cgatatgatt | 240 |
| ctgaaaatgg actccctcca ggacattaag gccctgctga ccgggctctt tgtgcaggac | 300 |
| aatgtgaaca agatgccgt cacagatcgg ctcgccagcg tcgagactga tatgccactg | 360 |
| acactgcggc agcatcggat tagcgccaca agctcaagcg aggaaagttc taacaaaggc | 420 |
| cagcgccagc tgacagttag cgggtctgga cgggcagatg ctttggatga tttcgacctt | 480 |

| | |
|---|---|
| gacatgctgg ggagcgatgc cttggatgac ttcgatctgg acatgctcgg ctcagatgcc | 540 |
| ctggatgatt ttgacctgga catgctgggc tccgatgccc tggacgactt tgacctcgac | 600 |
| atgctcatca ac | 612 |

<210> SEQ ID NO 163
<211> LENGTH: 1356
<212> TYPE: DNA
<213> ORGANISM: artificial sequence
<220> FEATURE:
<223> OTHER INFORMATION: tetR_NF-Kb pCLS26595

<400> SEQUENCE: 163

| | |
|---|---|
| atgtccagac tcgacaagag caaagtgatc aacagcgccc tggagctcct gaacgaggtg | 60 |
| ggaatcgagg gcctgactac cagaaagctc gcacagaagc tgggggtcga gcagccaacc | 120 |
| ttgtactggc acgtgaagaa caagagggcc ctccttgacg ctcttgcaat cgagatgctg | 180 |
| gacaggcacc acacccactt ctgccctctt gagggagagt cctggcagga tttcctgagg | 240 |
| aacaacgcta agagcttccg gtgcgctctg ctgtcccaca gggatggggc caaagtgcat | 300 |
| ttggggacac gccctacaga aaagcagtac gagactctgg agaaccagct ggccttcctg | 360 |
| tgccagcagg ggtttagcct cgaaaatgcc ctctatgccc tctctgccgt cggccatttc | 420 |
| accctcgggt gtgtcttgga agatcaggag caccaggtgg ccaaggaaga gcgggagaca | 480 |
| ccaacaactg acagtatgcc ccccttgttg cggcaagcca ttgagctgtt tgatcatcag | 540 |
| ggcgccgagc ccgcctttct gtttggcctg gagctgatta tttgcggcct ggagaagcag | 600 |
| ctgaagtgcg agtcaggtag cgaaaccttc aagtccatca tgaagaagtc ccccttcagc | 660 |
| ggaccaaccg acccaaggcc cccacctcgc aggatcgccg tgccctccag atcctccgcc | 720 |
| tccgtgccta agcctgcccc tcagccatac cctttcacct ccagcctgtc caccatcaac | 780 |
| tacgacgagt tcccaactat ggtgttcccc agcggccaga ttagccaggc aagcgccctc | 840 |
| gcacctgccc ctccccaggt gctccctcag gcacctgcac ctgctcctgc tccagctatg | 900 |
| gtcagcgccc tcgctcaggc tcctgctccc gtcccagtgc ttgctccagg accaccacaa | 960 |
| gccgtcgccc cacccgcccc caaacccaca caagccggag aaggcactct ttctgaggcc | 1020 |
| ttgttgcagt tgcagtttga cgacgaggac ctggggcccc tgctgggcaa ttcaacagac | 1080 |
| cccgccgtgt ttactgacct cgccagcgtg gataacagcg agtttcagca gctgctcaac | 1140 |
| cagggcatcc ccgtcgcccc ccacaccaca gagcccatgc tcatggagta cccgaggcc | 1200 |
| attacacggc tggtgacagg ggcccagcgg cccccgatc ccgcccccgc cccctgggg | 1260 |
| gcccagggc tgcccaacgg cctgctgagt ggggatgagg attttcatc tattgccgat | 1320 |
| atggatttta gtgccctgct gtctcagatt agctcg | 1356 |

<210> SEQ ID NO 164
<211> LENGTH: 792
<212> TYPE: DNA
<213> ORGANISM: artificial sequence
<220> FEATURE:
<223> OTHER INFORMATION: tetR_VP64 pCLS26596

<400> SEQUENCE: 164

| | |
|---|---|
| atgtccagac tcgacaagag caaagtgatc aacagcgccc tggagctcct gaacgaggtg | 60 |
| ggaatcgagg gcctgactac cagaaagctc gcacagaagc tgggggtcga gcagccaacc | 120 |
| ttgtactggc acgtgaagaa caagagggcc ctccttgacg ctcttgcaat cgagatgctg | 180 |
| gacaggcacc acacccactt ctgccctctt gagggagagt cctggcagga tttcctgagg | 240 |

-continued

```
aacaacgcta agagcttccg gtgcgctctg ctgtcccaca gggatggggc caaagtgcat      300
ttggggacac gccctacaga aaagcagtac gagactctgg agaaccagct ggccttcctg      360
tgccagcagg ggtttagcct cgaaaatgcc ctctatgccc tctctgccgt cggccatttc      420
accctcgggt gtgtcttgga agatcaggag caccaggtgg ccaaggaaga gcgggagaca      480
ccaacaactg acagtatgcc cccttgttg cggcaagcca ttgagctgtt tgatcatcag       540
ggcgccgagc ccgcctttct gtttggcctg gagctgatta tttgcggcct ggagaagcag      600
ctgaagtgcg agtcaggtag cgggtctgga cgggcagatg cttggatga tttcgacctt       660 gacatgctgg ggagcgatgc cttggatgac ttcgatctgg acatgctcgg ctcagatgcc      720
ctggatgatt ttgacctgga catgctgggc tccgatgccc tggacgactt tgacctcgac      780
atgctcatca ac                                                         792
```

<210> SEQ ID NO 165
<211> LENGTH: 497
<212> TYPE: DNA
<213> ORGANISM: artificial sequence
<220> FEATURE:
<223> OTHER INFORMATION: lenviral plasmid with SFFV promoter

<400> SEQUENCE: 165

```
gataaaataa aagattttat ttagtctcca gaaaaagggg ggaatgaaag accccacctg       60
taggtttggc aagctagctg cagtaacgcc attttgcaag gcatggaaaa ataccaaacc     120
aagaatagag aagttcagat caagggcggg tacatgaaaa tagctaacgt tgggccaaac     180
aggatatctg cggtgagcag tttcggcccc ggcccggggc caagaacaga tggtcaccgc     240
agtttcggcc ccggcccgag gccaagaaca gatggtcccc agatatggcc caaccctcag     300
cagtttctta agacccatca gatgtttcca ggctcccca aggacctgaa atgaccctgc      360
gccttatttg aattaaccaa tcagcctgct tctcgcttct gttcgcgcgc ttctgcttcc      420
cgagctctat aaaagagctc acaaccctc actcggcgcg ccagtcctcc gacagactga      480
gtcgcccggg ggccacc                                                    497
```

<210> SEQ ID NO 166
<211> LENGTH: 49
<212> TYPE: DNA
<213> ORGANISM: homo sapiens
<220> FEATURE:
<223> OTHER INFORMATION: LAT-1 Genomic locus

<400> SEQUENCE: 166

```
tgctgctgcc catcctggcc atgttgatgg cactgtgtgt gcactgcca                   49
```

<210> SEQ ID NO 167
<211> LENGTH: 45
<212> TYPE: DNA
<213> ORGANISM: homo sapiens
<220> FEATURE:
<223> OTHER INFORMATION: LAT-2 Genomic locus

<400> SEQUENCE: 167

```
tgcctaccca cctgtcacct cctacccacc cctgagccag ccaga                       45
```

<210> SEQ ID NO 168
<211> LENGTH: 49
<212> TYPE: DNA
<213> ORGANISM: homo sapiens
<220> FEATURE:

<223> OTHER INFORMATION: LcK-1 Genomic locus

<400> SEQUENCE: 168
tgactggatg gaaaacatcg atgtgtgtga gaactgccat tatcccata                49

<210> SEQ ID NO 169
<211> LENGTH: 46
<212> TYPE: DNA
<213> ORGANISM: homo sapiens
<220> FEATURE:
<223> OTHER INFORMATION: LcK-2 Genomic locus

<400> SEQUENCE: 169
tgcacagcta tgagccctct cacgacggag atctgggctt tgagaa                   46

<210> SEQ ID NO 170
<211> LENGTH: 45
<212> TYPE: DNA
<213> ORGANISM: homo sapiens
<220> FEATURE:
<223> OTHER INFORMATION: ZAP70-2 Genomic locus

<400> SEQUENCE: 170
tgtatgagag cccctacagc gacccagagg agctcaagga caaga                    45

<210> SEQ ID NO 171
<211> LENGTH: 49
<212> TYPE: DNA
<213> ORGANISM: homo sapiens
<220> FEATURE:
<223> OTHER INFORMATION: LFA1_1 Genomic locus

<400> SEQUENCE: 171
tgggagctcc aggggagggg aacagcacag gaagcctcta tcagtgcca                49

<210> SEQ ID NO 172
<211> LENGTH: 47
<212> TYPE: DNA
<213> ORGANISM: homo sapiens
<220> FEATURE:
<223> OTHER INFORMATION: CD28 Genomic locus

<400> SEQUENCE: 172
tagcccatcg tcaggacaaa gatgctcagg ctgctcttgg ctctcaa                  47

<210> SEQ ID NO 173
<211> LENGTH: 49
<212> TYPE: DNA
<213> ORGANISM: homo sapiens
<220> FEATURE:
<223> OTHER INFORMATION: TRAT1-1 Genomic locus

<400> SEQUENCE: 173
tttcctctgg ggacttctag cattgttggg cttggctttg gttatatca                49

<210> SEQ ID NO 174
<211> LENGTH: 49
<212> TYPE: DNA
<213> ORGANISM: homo sapiens
<220> FEATURE:
<223> OTHER INFORMATION: TRAT1-2 Genomic locus

<400> SEQUENCE: 174
tgttgggctt ggctttggtt atatcactga tcttcaatat ttcccacta                49

-continued

```
<210> SEQ ID NO 175
<211> LENGTH: 936
<212> TYPE: PRT
<213> ORGANISM: artificial sequence
<220> FEATURE:
<223> OTHER INFORMATION: pCLS25353 TALEN LAT-1_A

<400> SEQUENCE: 175
```

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser His Asp Gly
        195                 200                 205

Gly Lys Gln Ala Leu Glu Thr Val Gln Arg Leu Leu Pro Val Leu Cys
    210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Glu Gln Val Val Ala
    290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Asn Gly Gly Lys Gln Ala Leu Glu

```
        370                 375                 380
Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
                420                 425                 430

Leu Thr Pro Glu Gln Val Val Ala Ile Ala Ser His Asp Gly Gly Lys
                435                 440                 445

Gln Ala Leu Glu Thr Val Gln Arg Leu Leu Pro Val Leu Cys Gln Ala
450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
                500                 505                 510

Ile Gly Gly Lys Gln Ala Leu Glu Thr Val Gln Ala Leu Leu Pro Val
            515                 520                 525

Leu Cys Gln Ala His Gly Leu Thr Pro Gln Gln Val Val Ala Ile Ala
            530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser His Asp Gly Gly Lys Gln Ala Leu Glu Thr Val Gln Arg
                580                 585                 590

Leu Leu Pro Val Leu Cys Gln Ala His Gly Leu Thr Pro Glu Gln Val
            595                 600                 605

Val Ala Ile Ala Ser His Asp Gly Gly Lys Gln Ala Leu Glu Thr Val
            610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Gly Lys Gln Ala Leu Glu
                645                 650                 655

Thr Val Gln Arg Leu Leu Pro Val Leu Cys Gln Ala His Gly Leu Thr
                660                 665                 670

Pro Gln Gln Val Val Ala Ile Ala Ser Asn Gly Gly Gly Arg Pro Ala
            675                 680                 685

Leu Glu Ser Ile Val Ala Gln Leu Ser Arg Pro Asp Pro Ala Leu Ala
            690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
                740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
            770                 775                 780

Phe Phe Met Lys Val Tyr Gly Tyr Arg Gly Lys His Leu Gly Gly Ser
785                 790                 795                 800
```

-continued

```
Arg Lys Pro Asp Gly Ala Ile Tyr Thr Val Gly Ser Pro Ile Asp Tyr
            805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
            915                 920                 925

Gly Glu Ile Asn Phe Ala Ala Asp
            930                 935

<210> SEQ ID NO 176
<211> LENGTH: 936
<212> TYPE: PRT
<213> ORGANISM: artificial sequence
<220> FEATURE:
<223> OTHER INFORMATION: TALEN LAT-1_B pCLS25354

<400> SEQUENCE: 176

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
            35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
            195                 200                 205

Gly Lys Gln Ala Leu Glu Thr Val Gln Arg Leu Leu Pro Val Leu Cys
    210                 215                 220
```

```
Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
            245                 250                 255

Leu Cys Gln Ala His Gly Leu Thr Pro Glu Gln Val Val Ala Ile Ala
                260                 265                 270

Ser Asn Ile Gly Gly Lys Gln Ala Leu Glu Thr Val Gln Ala Leu Leu
        275                 280                 285

Pro Val Leu Cys Gln Ala His Gly Leu Thr Pro Gln Gln Val Val Ala
290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Asn Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser Asn Ile Gly Gly Lys
        435                 440                 445

Gln Ala Leu Glu Thr Val Gln Ala Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
        515                 520                 525

Leu Cys Gln Ala His Gly Leu Thr Pro Glu Gln Val Val Ala Ile Ala
530                 535                 540

Ser His Asp Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser Asn Ile Gly Gly Lys Gln Ala Leu Glu Thr Val Gln Ala
            580                 585                 590

Leu Leu Pro Val Leu Cys Gln Ala His Gly Leu Thr Pro Glu Gln Val
        595                 600                 605

Val Ala Ile Ala Ser His Asp Gly Gly Lys Gln Ala Leu Glu Thr Val
610                 615                 620

Gln Arg Leu Leu Pro Val Leu Cys Gln Ala His Gly Leu Thr Pro Glu
625                 630                 635                 640
```

-continued

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935

<210> SEQ ID NO 177
<211> LENGTH: 1065
<212> TYPE: PRT
<213> ORGANISM: artificial sequence
<220> FEATURE:
<223> OTHER INFORMATION: TALEN LAT-2_A pCLS25345

<400> SEQUENCE: 177

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

```
Asp Gly Leu Pro Ala Arg Arg Thr Met Ser Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Ala Leu Leu Pro Val Leu Cys Gln Ala
465                 470                 475                 480

His Gly Leu Thr Pro Glu Gln Val Val Ala Ile Ala Ser His Asp Gly
```

-continued

```
                485                 490                 495
Gly Lys Gln Ala Leu Glu Thr Val Gln Arg Leu Leu Pro Val Leu Cys
                500                 505                 510
Gln Ala His Gly Leu Thr Pro Glu Gln Val Val Ala Ile Ala Ser His
                515                 520                 525
Asp Gly Gly Lys Gln Ala Leu Glu Thr Val Gln Arg Leu Leu Pro Val
                530                 535                 540
Leu Cys Gln Ala His Gly Leu Thr Pro Glu Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Ala His Gly Leu Thr Pro Glu Gln Val Val Ala
                580                 585                 590
Ile Ala Ser Asn Ile Gly Gly Lys Gln Ala Leu Glu Thr Val Gln Ala
                595                 600                 605
Leu Leu Pro Val Leu Cys Gln Ala His Gly Leu Thr Pro Glu Gln Val
                610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Glu
                645                 650                 655
Gln Val Val Ala Ile Ala Ser His Asp Gly Gly Lys Gln Ala Leu Glu
                660                 665                 670
Thr Val Gln Arg Leu Leu Pro Val Leu Cys Gln Ala His Gly Leu Thr
                675                 680                 685
Pro Gln Gln Val Val Ala Ile Ala Ser Asn Gly Gly Lys Gln Ala
                690                 695                 700
Leu Glu Thr Val Gln Arg Leu Leu Pro Val Leu Cys Gln Ala His Gly
705                 710                 715                 720
Leu Thr Pro Gln Gln Val Val Ala Ile Ala Ser Asn Asn Gly Gly Lys
                725                 730                 735
Gln Ala Leu Glu Thr Val Gln Arg Leu Leu Pro Val Leu Cys Gln Ala
                740                 745                 750
His Gly Leu Thr Pro Gln Gln Val Val Ala Ile Ala Ser Asn Gly Gly
                755                 760                 765
Gly Lys Gln Ala Leu Glu Thr Val Gln Arg Leu Leu Pro Val Leu Cys
                770                 775                 780
Gln Ala His Gly Leu Thr Pro Glu Gln Val Val Ala Ile Ala Ser His
785                 790                 795                 800
Asp Gly Gly Lys Gln Ala Leu Glu Thr Val Gln Arg Leu Leu Pro Val
                805                 810                 815
Leu Cys Gln Ala His Gly Leu Thr Pro Gln Gln Val Val Ala Ile Ala
                820                 825                 830
Ser Asn Gly Gly Arg Pro Ala Leu Glu Ser Ile Val Ala Gln Leu
                835                 840                 845
Ser Arg Pro Asp Pro Ser Gly Ser Gly Ser Gly Asp Pro Ile Ser
850                 855                 860
Arg Ser Gln Leu Val Lys Ser Glu Leu Glu Glu Lys Ser Glu Leu
865                 870                 875                 880
Arg His Lys Leu Lys Tyr Val Pro His Glu Tyr Ile Glu Leu Ile Glu
                885                 890                 895
Ile Ala Arg Asn Ser Thr Gln Asp Arg Ile Leu Glu Met Lys Val Met
                900                 905                 910
```

```
Glu Phe Phe Met Lys Val Tyr Gly Tyr Arg Gly Lys His Leu Gly Gly
            915                 920                 925

Ser Arg Lys Pro Asp Gly Ala Ile Tyr Thr Val Gly Ser Pro Ile Asp
        930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
            995                 1000                1005

Gly Asn Tyr Lys Ala Gln Leu Thr Arg Leu Asn His Ile Thr Asn Cys
        1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 178
<211> LENGTH: 1065
<212> TYPE: PRT
<213> ORGANISM: artificial sequence
<220> FEATURE:
<223> OTHER INFORMATION: TALEN LAT-2_B pCLS25346

<400> SEQUENCE: 178

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205
```

Gly His Gly Phe Thr His Ala His Ile Val Ala Leu Ser Gln His Pro
210             215             220
Ala Ala Leu Gly Thr Val Ala Val Lys Tyr Gln Asp Met Ile Ala Ala
225             230             235             240
Leu Pro Glu Ala Thr His Glu Ala Ile Val Gly Val Gly Lys Gln Trp
            245             250             255
Ser Gly Ala Arg Ala Leu Glu Ala Leu Leu Thr Val Ala Gly Glu Leu
        260             265             270
Arg Gly Pro Pro Leu Gln Leu Asp Thr Gly Gln Leu Leu Lys Ile Ala
    275             280             285
Lys Arg Gly Gly Val Thr Ala Val Glu Ala Val His Ala Trp Arg Asn
290             295             300
Ala Leu Thr Gly Ala Pro Leu Asn Leu Thr Pro Glu Gln Val Val Ala
305             310             315             320
Ile Ala Ser His Asp Gly Gly Lys Gln Ala Leu Glu Thr Val Gln Arg
            325             330             335
Leu Leu Pro Val Leu Cys Gln Ala His Gly Leu Thr Pro Gln Gln Val
        340             345             350
Val Ala Ile Ala Ser Asn Gly Gly Lys Gln Ala Leu Glu Thr Val
    355             360             365
Gln Arg Leu Leu Pro Val Leu Cys Gln Ala His Gly Leu Thr Pro Gln
370             375             380
Gln Val Val Ala Ile Ala Ser Asn Asn Gly Gly Lys Gln Ala Leu Glu
385             390             395             400
Thr Val Gln Arg Leu Leu Pro Val Leu Cys Gln Ala His Gly Leu Thr
            405             410             415
Pro Gln Gln Val Val Ala Ile Ala Ser Asn Asn Gly Gly Lys Gln Ala
        420             425             430
Leu Glu Thr Val Gln Arg Leu Leu Pro Val Leu Cys Gln Ala His Gly
    435             440             445
Leu Thr Pro Glu Gln Val Val Ala Ile Ala Ser His Asp Gly Gly Lys
450             455             460
Gln Ala Leu Glu Thr Val Gln Arg Leu Leu Pro Val Leu Cys Gln Ala
465             470             475             480
His Gly Leu Thr Pro Gln Gln Val Val Ala Ile Ala Ser Asn Gly Gly
            485             490             495
Gly Lys Gln Ala Leu Glu Thr Val Gln Arg Leu Leu Pro Val Leu Cys
        500             505             510
Gln Ala His Gly Leu Thr Pro Gln Gln Val Val Ala Ile Ala Ser Asn
    515             520             525
Asn Gly Gly Lys Gln Ala Leu Glu Thr Val Gln Arg Leu Leu Pro Val
530             535             540
Leu Cys Gln Ala His Gly Leu Thr Pro Gln Gln Val Val Ala Ile Ala
545             550             555             560
Ser Asn Asn Gly Gly Lys Gln Ala Leu Glu Thr Val Gln Arg Leu Leu
            565             570             575
Pro Val Leu Cys Gln Ala His Gly Leu Thr Pro Glu Gln Val Val Ala
        580             585             590
Ile Ala Ser His Asp Gly Gly Lys Gln Ala Leu Glu Thr Val Gln Arg
    595             600             605
Leu Leu Pro Val Leu Cys Gln Ala His Gly Leu Thr Pro Gln Gln Val
610             615             620

```
Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Glu
            645                 650                 655

Gln Val Val Ala Ile Ala Ser His Asp Gly Gly Lys Gln Ala Leu Glu
        660                 665                 670

Thr Val Gln Arg Leu Leu Pro Val Leu Cys Gln Ala His Gly Leu Thr
        675                 680                 685

Pro Glu Gln Val Val Ala Ile Ala Ser Asn Ile Gly Gly Lys Gln Ala
690                 695                 700

Leu Glu Thr Val Gln Ala Leu Leu Pro Val Leu Cys Gln Ala His Gly
705                 710                 715                 720

Leu Thr Pro Gln Gln Val Val Ala Ile Ala Ser Asn Asn Gly Gly Lys
                725                 730                 735

Gln Ala Leu Glu Thr Val Gln Arg Leu Leu Pro Val Leu Cys Gln Ala
            740                 745                 750

His Gly Leu Thr Pro Gln Gln Val Val Ala Ile Ala Ser Asn Asn Gly
        755                 760                 765

Gly Lys Gln Ala Leu Glu Thr Val Gln Arg Leu Leu Pro Val Leu Cys
770                 775                 780

Gln Ala His Gly Leu Thr Pro Gln Gln Val Val Ala Ile Ala Ser Asn
785                 790                 795                 800

Asn Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Asp Pro Ile Ser
850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
        930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
        1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
```

<210> SEQ ID NO 179
<211> LENGTH: 936
<212> TYPE: PRT
<213> ORGANISM: artificial sequence
<220> FEATURE:
<223> OTHER INFORMATION: TALEN LcK-1_A pCLS25355

<400> SEQUENCE: 179

```
Asn Gly Glu Ile Asn Phe Ala Ala Asp
            1060            1065

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                      60

Ile Val Ala Leu Ser Gln His Pro Ala Ala Leu Gly Thr Val Ala Val
65                  70                      75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Gly Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
```

```
            340                 345                 350
Gln Arg Leu Leu Pro Val Leu Cys Gln Ala His Gly Leu Thr Pro Glu
        355                 360                 365
Gln Val Val Ala Ile Ala Ser Asn Ile Gly Gly Lys Gln Ala Leu Glu
        370                 375                 380
Thr Val Gln Ala Leu Leu Pro Val Leu Cys Gln Ala His Gly Leu Thr
385                 390                 395                 400
Pro Gln Gln Val Val Ala Ile Ala Ser Asn Gly Gly Lys Gln Ala
                405                 410                 415
Leu Glu Thr Val Gln Arg Leu Leu Pro Val Leu Cys Gln Ala His Gly
                420                 425                 430
Leu Thr Pro Gln Gln Val Val Ala Ile Ala Ser Asn Asn Gly Gly Lys
                435                 440                 445
Gln Ala Leu Glu Thr Val Gln Arg Leu Leu Pro Val Leu Cys Gln Ala
        450                 455                 460
His Gly Leu Thr Pro Gln Gln Val Val Ala Ile Ala Ser Asn Asn Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Glu Gln Val Val Ala Ile Ala Ser Asn
                500                 505                 510
Ile Gly Gly Lys Gln Ala Leu Glu Thr Val Gln Ala Leu Leu Pro Val
        515                 520                 525
Leu Cys Gln Ala His Gly Leu Thr Pro Glu Gln Val Val Ala Ile Ala
        530                 535                 540
Ser Asn Ile Gly Gly Lys Gln Ala Leu Glu Thr Val Gln Ala Leu Leu
545                 550                 555                 560
Pro Val Leu Cys Gln Ala His Gly Leu Thr Pro Glu Gln Val Val Ala
                565                 570                 575
Ile Ala Ser Asn Ile Gly Gly Lys Gln Ala Leu Glu Thr Val Gln Ala
                580                 585                 590
Leu Leu Pro Val Leu Cys Gln Ala His Gly Leu Thr Pro Glu Gln Val
                595                 600                 605
Val Ala Ile Ala Ser Asn Ile Gly Gly Lys Gln Ala Leu Glu Thr Val
        610                 615                 620
Gln Ala Leu Leu Pro Val Leu Cys Gln Ala His Gly Leu Thr Pro Glu
625                 630                 635                 640
Gln Val Val Ala Ile Ala Ser His Asp Gly Gly Lys Gln Ala Leu Glu
                645                 650                 655
Thr Val Gln Arg Leu Leu Pro Val Leu Cys Gln Ala His Gly Leu Thr
                660                 665                 670
Pro Gln Gln Val Val Ala Ile Ala Ser Asn Gly Gly Gly Arg Pro Ala
                675                 680                 685
Leu Glu Ser Ile Val Ala Gln Leu Ser Arg Pro Asp Pro Ala Leu Ala
                690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
                740                 745                 750
His Lys Leu Lys Tyr Val Pro His Glu Tyr Ile Glu Leu Ile Glu Ile
                755                 760                 765
```

```
Ala Arg Asn Ser Thr Gln Asp Arg Ile Leu Glu Met Lys Val Met Glu
    770             775                 780
Phe Phe Met Lys Val Tyr Gly Tyr Arg Gly Lys His Leu Gly Gly Ser
785             790                 795                 800
Arg Lys Pro Asp Gly Ala Ile Tyr Thr Val Gly Ser Pro Ile Asp Tyr
                805                 810                 815
Gly Val Ile Val Asp Thr Lys Ala Tyr Ser Gly Gly Tyr Asn Leu Pro
                820                 825                 830
Ile Gly Gln Ala Asp Glu Met Gln Arg Tyr Val Glu Glu Asn Gln Thr
                835                 840                 845
Arg Asn Lys His Ile Asn Pro Asn Glu Trp Trp Lys Val Tyr Pro Ser
    850                 855                 860
Ser Val Thr Glu Phe Lys Phe Leu Phe Val Ser Gly His Phe Lys Gly
865             870                 875                 880
Asn Tyr Lys Ala Gln Leu Thr Arg Leu Asn His Ile Thr Asn Cys Asn
                885                 890                 895
Gly Ala Val Leu Ser Val Glu Glu Leu Leu Ile Gly Gly Glu Met Ile
                900                 905                 910
Lys Ala Gly Thr Leu Thr Leu Glu Glu Val Arg Arg Lys Phe Asn Asn
    915                 920                 925
Gly Glu Ile Asn Phe Ala Ala Asp
    930                 935
```

<210> SEQ ID NO 180
<211> LENGTH: 936
<212> TYPE: PRT
<213> ORGANISM: artificial sequence
<220> FEATURE:
<223> OTHER INFORMATION: TALEN LcK-1_B pCLS25356

<400> SEQUENCE: 180

```
Met Gly Asp Pro Lys Lys Lys Arg Lys Val Ile Asp Tyr Pro Tyr Asp
1               5                   10                  15
Val Pro Asp Tyr Ala Ile Asp Ile Ala Asp Leu Arg Thr Leu Gly Tyr
                20                  25                  30
Ser Gln Gln Gln Glu Lys Ile Lys Pro Lys Val Arg Ser Thr Val
    35                  40                  45
Ala Gln His His Glu Ala Leu Val Gly His Gly Phe Thr His Ala His
    50                  55                  60
Ile Val Ala Leu Ser Gln His Pro Ala Ala Leu Gly Thr Val Ala Val
65                  70                  75                  80
Lys Tyr Gln Asp Met Ile Ala Ala Leu Pro Glu Ala Thr His Glu Ala
                85                  90                  95
Ile Val Gly Val Gly Lys Gln Trp Ser Gly Ala Arg Ala Leu Glu Ala
                100                 105                 110
Leu Leu Thr Val Ala Gly Glu Leu Arg Gly Pro Pro Leu Gln Leu Asp
    115                 120                 125
Thr Gly Gln Leu Leu Lys Ile Ala Lys Arg Gly Gly Val Thr Ala Val
    130                 135                 140
Glu Ala Val His Ala Trp Arg Asn Ala Leu Thr Gly Ala Pro Leu Asn
145                 150                 155                 160
Leu Thr Pro Glu Gln Val Val Ala Ile Ala Ser Asn Ile Gly Gly Lys
                165                 170                 175
Gln Ala Leu Glu Thr Val Gln Ala Leu Leu Pro Val Leu Cys Gln Ala
                180                 185                 190
```

```
His Gly Leu Thr Pro Gln Gln Val Ala Ile Ala Ser Asn Gly Gly
        195                 200                 205

Gly Lys Gln Ala Leu Glu Thr Val Gln Arg Leu Leu Pro Val Leu Cys
210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
            245                 250                 255

Leu Cys Gln Ala His Gly Leu Thr Pro Gln Gln Val Val Ala Ile Ala
        260                 265                 270

Ser Asn Asn Gly Gly Lys Gln Ala Leu Glu Thr Val Gln Arg Leu Leu
    275                 280                 285

Pro Val Leu Cys Gln Ala His Gly Leu Thr Pro Gln Gln Val Val Ala
290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
            325                 330                 335

Val Ala Ile Ala Ser Asn Ile Gly Gly Lys Gln Ala Leu Glu Thr Val
        340                 345                 350

Gln Ala Leu Leu Pro Val Leu Cys Gln Ala His Gly Leu Thr Pro Gln
    355                 360                 365

Gln Val Val Ala Ile Ala Ser Asn Gly Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Glu Gln Val Val Ala Ile Ala Ser Asn Ile Gly Gly Lys Gln Ala
            405                 410                 415

Leu Glu Thr Val Gln Ala Leu Leu Pro Val Leu Cys Gln Ala His Gly
        420                 425                 430

Leu Thr Pro Glu Gln Val Val Ala Ile Ala Ser Asn Ile Gly Gly Lys
    435                 440                 445

Gln Ala Leu Glu Thr Val Gln Ala Leu Leu Pro Val Leu Cys Gln Ala
450                 455                 460

His Gly Leu Thr Pro Gln Gln Val Val Ala Ile Ala Ser Asn Gly Gly
465                 470                 475                 480

Gly Lys Gln Ala Leu Glu Thr Val Gln Arg Leu Leu Pro Val Leu Cys
            485                 490                 495

Gln Ala His Gly Leu Thr Pro Gln Gln Val Val Ala Ile Ala Ser Asn
        500                 505                 510

Asn Gly Gly Lys Gln Ala Leu Glu Thr Val Gln Arg Leu Leu Pro Val
    515                 520                 525

Leu Cys Gln Ala His Gly Leu Thr Pro Gln Gln Val Val Ala Ile Ala
530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
            565                 570                 575

Ile Ala Ser His Asp Gly Gly Lys Gln Ala Leu Glu Thr Val Gln Arg
        580                 585                 590

Leu Leu Pro Val Leu Cys Gln Ala His Gly Leu Thr Pro Glu Gln Val
    595                 600                 605
```

Val Ala Ile Ala Ser Asn Ile Gly Gly Lys Gln Ala Leu Glu Thr Val
610                 615                 620

Gln Ala Leu Leu Pro Val Leu Cys Gln Ala His Gly Leu Thr Pro Gln
625                 630                 635                 640

Gln Val Val Ala Ile Ala Ser Asn Asn Gly Gly Lys Gln Ala Leu Glu
            645                 650                 655

Thr Val Gln Arg Leu Leu Pro Val Leu Cys Gln Ala His Gly Leu Thr
        660                 665                 670

Pro Gln Gln Val Val Ala Ile Ala Ser Asn Gly Gly Arg Pro Ala
            675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
            805                 810                 815

Gly Val Ile Val Asp Thr Lys Ala Tyr Ser Gly Gly Tyr Asn Leu Pro
        820                 825                 830

Ile Gly Gln Ala Asp Glu Met Gln Arg Tyr Val Glu Glu Asn Gln Thr
    835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
            885                 890                 895

Gly Ala Val Leu Ser Val Glu Glu Leu Leu Ile Gly Gly Glu Met Ile
        900                 905                 910

Lys Ala Gly Thr Leu Thr Leu Glu Glu Val Arg Arg Lys Phe Asn Asn
    915                 920                 925

Gly Glu Ile Asn Phe Ala Ala Asp
930                 935

<210> SEQ ID NO 181
<211> LENGTH: 1065
<212> TYPE: PRT
<213> ORGANISM: artificial sequence
<220> FEATURE:
<223> OTHER INFORMATION: TALEN LcK-2_A pCLS25347

<400> SEQUENCE: 181

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

```
Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
 50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125

Asp Glu Val Gln Ser Gly Leu Arg Ala Ala Asp Ala Pro Pro Pro Thr
130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
            210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
            275                 280                 285

Lys Arg Gly Gly Val Thr Ala Val Glu Ala Val His Ala Trp Arg Asn
290                 295                 300

Ala Leu Thr Gly Ala Pro Leu Asn Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Ala His Gly Leu Thr Pro Glu
370                 375                 380

Gln Val Val Ala Ile Ala Ser Asn Ile Gly Gly Lys Gln Ala Leu Glu
385                 390                 395                 400

Thr Val Gln Ala Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
```

```
            450                 455                 460
Gln Ala Leu Glu Thr Val Gln Ala Leu Leu Pro Val Leu Cys Gln Ala
465                 470                 475                 480
His Gly Leu Thr Pro Gln Gln Val Val Ala Ile Ala Ser Asn Asn Gly
                    485                 490                 495
Gly Lys Gln Ala Leu Glu Thr Val Gln Arg Leu Leu Pro Val Leu Cys
                500                 505                 510
Gln Ala His Gly Leu Thr Pro Glu Gln Val Val Ala Ile Ala Ser His
                515                 520                 525
Asp Gly Gly Lys Gln Ala Leu Glu Thr Val Gln Arg Leu Leu Pro Val
530                 535                 540
Leu Cys Gln Ala His Gly Leu Thr Pro Gln Gln Val Val Ala Ile Ala
545                 550                 555                 560
Ser Asn Gly Gly Gly Lys Gln Ala Leu Glu Thr Val Gln Arg Leu Leu
                    565                 570                 575
Pro Val Leu Cys Gln Ala His Gly Leu Thr Pro Glu Gln Val Val Ala
                580                 585                 590
Ile Ala Ser Asn Ile Gly Gly Lys Gln Ala Leu Glu Thr Val Gln Ala
                595                 600                 605
Leu Leu Pro Val Leu Cys Gln Ala His Gly Leu Thr Pro Gln Gln Val
        610                 615                 620
Val Ala Ile Ala Ser Asn Gly Gly Gly Lys Gln Ala Leu Glu Thr Val
625                 630                 635                 640
Gln Arg Leu Leu Pro Val Leu Cys Gln Ala His Gly Leu Thr Pro Gln
                    645                 650                 655
Gln Val Val Ala Ile Ala Ser Asn Asn Gly Gly Lys Gln Ala Leu Glu
                660                 665                 670
Thr Val Gln Arg Leu Leu Pro Val Leu Cys Gln Ala His Gly Leu Thr
                675                 680                 685
Pro Glu Gln Val Val Ala Ile Ala Ser Asn Ile Gly Gly Lys Gln Ala
        690                 695                 700
Leu Glu Thr Val Gln Ala Leu Leu Pro Val Leu Cys Gln Ala His Gly
705                 710                 715                 720
Leu Thr Pro Gln Gln Val Val Ala Ile Ala Ser Asn Asn Gly Gly Lys
                    725                 730                 735
Gln Ala Leu Glu Thr Val Gln Arg Leu Leu Pro Val Leu Cys Gln Ala
                740                 745                 750
His Gly Leu Thr Pro Glu Gln Val Val Ala Ile Ala Ser His Asp Gly
                755                 760                 765
Gly Lys Gln Ala Leu Glu Thr Val Gln Arg Leu Leu Pro Val Leu Cys
770                 775                 780
Gln Ala His Gly Leu Thr Pro Glu Gln Val Val Ala Ile Ala Ser His
785                 790                 795                 800
Asp Gly Gly Lys Gln Ala Leu Glu Thr Val Gln Arg Leu Leu Pro Val
                    805                 810                 815
Leu Cys Gln Ala His Gly Leu Thr Pro Gln Gln Val Val Ala Ile Ala
                820                 825                 830
Ser Asn Gly Gly Gly Arg Pro Ala Leu Glu Ser Ile Val Ala Gln Leu
                835                 840                 845
Ser Arg Pro Asp Pro Ser Gly Ser Gly Gly Asp Pro Ile Ser
        850                 855                 860
Arg Ser Gln Leu Val Lys Ser Glu Leu Glu Glu Lys Lys Ser Glu Leu
865                 870                 875                 880
```

```
Arg His Lys Leu Lys Tyr Val Pro His Glu Tyr Ile Glu Leu Ile Glu
            885                 890                 895

Ile Ala Arg Asn Ser Thr Gln Asp Arg Ile Leu Glu Met Lys Val Met
                900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 182
<211> LENGTH: 1065
<212> TYPE: PRT
<213> ORGANISM: artificial sequence
<220> FEATURE:
<223> OTHER INFORMATION: TALEN LcK-2_B pCLS25348

<400> SEQUENCE: 182

Met Gly Asp Pro Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
                20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
                100                 105                 110

Leu Pro Pro Phe Gly Ala His His Thr Glu Ala Ala Thr Gly Glu Trp
            115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175
```

```
Val Asp Leu Arg Thr Leu Gly Tyr Ser Gln Gln Gln Glu Lys Ile
            180                 185                 190

Lys Pro Lys Val Arg Ser Thr Val Ala Gln His His Glu Ala Leu Val
            195                 200                 205

Gly His Gly Phe Thr His Ala His Ile Val Ala Leu Ser Gln His Pro
            210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
                260                 265                 270

Arg Gly Pro Pro Leu Gln Leu Asp Thr Gly Gln Leu Leu Lys Ile Ala
            275                 280                 285

Lys Arg Gly Gly Val Thr Ala Val Glu Ala Val His Ala Trp Arg Asn
290                 295                 300

Ala Leu Thr Gly Ala Pro Leu Asn Leu Thr Pro Gln Gln Val Val Ala
305                 310                 315                 320

Ile Ala Ser Asn Gly Gly Gly Lys Gln Ala Leu Glu Thr Val Gln Arg
            325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Ala His Gly Leu Thr Pro Gln
            370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
450                 455                 460

Gln Ala Leu Glu Thr Val Gln Ala Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Ala Leu Leu Pro Val Leu Cys
            500                 505                 510

Gln Ala His Gly Leu Thr Pro Glu Gln Val Val Ala Ile Ala Ser Asn
            515                 520                 525

Ile Gly Gly Lys Gln Ala Leu Glu Thr Val Gln Ala Leu Leu Pro Val
            530                 535                 540

Leu Cys Gln Ala His Gly Leu Thr Pro Gln Gln Val Val Ala Ile Ala
545                 550                 555                 560

Ser Asn Asn Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590
```

```
Ile Ala Ser His Asp Gly Gly Lys Gln Ala Leu Glu Thr Val Gln Arg
            595                 600                 605

Leu Leu Pro Val Leu Cys Gln Ala His Gly Leu Thr Pro Glu Gln Val
        610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser Asn Ile Gly Gly Lys Gln Ala
    690                 695                 700

Leu Glu Thr Val Gln Ala Leu Leu Pro Val Leu Cys Gln Ala His Gly
705                 710                 715                 720

Leu Thr Pro Gln Gln Val Val Ala Ile Ala Ser Asn Asn Gly Gly Lys
                725                 730                 735

Gln Ala Leu Glu Thr Val Gln Arg Leu Leu Pro Val Leu Cys Gln Ala
            740                 745                 750

His Gly Leu Thr Pro Glu Gln Val Val Ala Ile Ala Ser Asn Ile Gly
        755                 760                 765

Gly Lys Gln Ala Leu Glu Thr Val Gln Ala Leu Leu Pro Val Leu Cys
    770                 775                 780

Gln Ala His Gly Leu Thr Pro Gln Gln Val Val Ala Ile Ala Ser Asn
785                 790                 795                 800

Gly Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Asp Pro Ile Ser
850                 855                 860

Arg Ser Gln Leu Val Lys Ser Glu Leu Glu Glu Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
```

```
                    1010                1015                1020
Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 183
<211> LENGTH: 1065
<212> TYPE: PRT
<213> ORGANISM: artificial sequence
<220> FEATURE:
<223> OTHER INFORMATION: TALEN ZAP70-2_A pCLS25349

<400> SEQUENCE: 183

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30

Pro Ser Pro Ala Arg Glu Leu Leu Pro Gly Pro Gln Pro Asp Gly Val
        35                  40                  45

Gln Pro Thr Ala Asp Arg Gly Val Ser Pro Ala Gly Gly Pro Leu
    50                  55                  60

Asp Gly Leu Pro Ala Arg Arg Thr Met Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Gln Phe Asp Pro Ser Leu Phe Asn Thr Ser Leu Phe Asp Ser
            100                 105                 110

Leu Pro Pro Phe Gly Ala His His Thr Glu Ala Ala Thr Gly Glu Trp
        115                 120                 125

Asp Glu Val Gln Ser Gly Leu Arg Ala Ala Asp Ala Pro Pro Pro Thr
    130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
                245                 250                 255

Ser Gly Ala Arg Ala Leu Glu Ala Leu Leu Thr Val Ala Gly Glu Leu
            260                 265                 270

Arg Gly Pro Pro Leu Gln Leu Asp Thr Gly Gln Leu Leu Lys Ile Ala
        275                 280                 285

Lys Arg Gly Gly Val Thr Ala Val Glu Ala Val His Ala Trp Arg Asn
    290                 295                 300

Ala Leu Thr Gly Ala Pro Leu Asn Leu Thr Pro Gln Gln Val Val Ala
```

-continued

```
           305                 310                 315                 320
Ile Ala Ser Asn Asn Gly Gly Lys Gln Ala Leu Glu Thr Val Gln Arg
                325                 330                 335
Leu Leu Pro Val Leu Cys Gln Ala His Gly Leu Thr Pro Gln Gln Val
            340                 345                 350
Val Ala Ile Ala Ser Asn Gly Gly Lys Gln Ala Leu Glu Thr Val
            355                 360                 365
Gln Arg Leu Leu Pro Val Leu Cys Gln Ala His Gly Leu Thr Pro Glu
370                 375                 380
Gln Val Val Ala Ile Ala Ser Asn Ile Gly Gly Lys Gln Ala Leu Glu
385                 390                 395                 400
Thr Val Gln Ala Leu Leu Pro Val Leu Cys Gln Ala His Gly Leu Thr
                405                 410                 415
Pro Gln Gln Val Val Ala Ile Ala Ser Asn Gly Gly Lys Gln Ala
            420                 425                 430
Leu Glu Thr Val Gln Arg Leu Leu Pro Val Leu Cys Gln Ala His Gly
            435                 440                 445
Leu Thr Pro Gln Gln Val Val Ala Ile Ala Ser Asn Asn Gly Gly Lys
450                 455                 460
Gln Ala Leu Glu Thr Val Gln Arg Leu Leu Pro Val Leu Cys Gln Ala
465                 470                 475                 480
His Gly Leu Thr Pro Glu Gln Val Val Ala Ile Ala Ser Asn Ile Gly
                485                 490                 495
Gly Lys Gln Ala Leu Glu Thr Val Gln Ala Leu Leu Pro Val Leu Cys
            500                 505                 510
Gln Ala His Gly Leu Thr Pro Gln Gln Val Val Ala Ile Ala Ser Asn
            515                 520                 525
Asn Gly Gly Lys Gln Ala Leu Glu Thr Val Gln Arg Leu Leu Pro Val
            530                 535                 540
Leu Cys Gln Ala His Gly Leu Thr Pro Glu Gln Val Val Ala Ile Ala
545                 550                 555                 560
Ser Asn Ile Gly Gly Lys Gln Ala Leu Glu Thr Val Gln Ala Leu Leu
                565                 570                 575
Pro Val Leu Cys Gln Ala His Gly Leu Thr Pro Gln Gln Val Val Ala
            580                 585                 590
Ile Ala Ser Asn Asn Gly Gly Lys Gln Ala Leu Glu Thr Val Gln Arg
            595                 600                 605
Leu Leu Pro Val Leu Cys Gln Ala His Gly Leu Thr Pro Glu Gln Val
            610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Glu
                645                 650                 655
Gln Val Val Ala Ile Ala Ser His Asp Gly Gly Lys Gln Ala Leu Glu
            660                 665                 670
Thr Val Gln Arg Leu Leu Pro Val Leu Cys Gln Ala His Gly Leu Thr
            675                 680                 685
Pro Glu Gln Val Val Ala Ile Ala Ser His Asp Gly Gly Lys Gln Ala
            690                 695                 700
Leu Glu Thr Val Gln Arg Leu Leu Pro Val Leu Cys Gln Ala His Gly
705                 710                 715                 720
Leu Thr Pro Glu Gln Val Val Ala Ile Ala Ser His Asp Gly Gly Lys
                725                 730                 735
```

```
Gln Ala Leu Glu Thr Val Gln Arg Leu Leu Pro Val Leu Cys Gln Ala
            740                 745                 750

His Gly Leu Thr Pro Gln Gln Val Ala Ile Ala Ser Asn Gly Gly
        755                 760                 765

Gly Lys Gln Ala Leu Glu Thr Val Gln Arg Leu Leu Pro Val Leu Cys
770                 775                 780

Gln Ala His Gly Leu Thr Pro Glu Gln Val Val Ala Ile Ala Ser Asn
785                 790                 795                 800

Ile Gly Gly Lys Gln Ala Leu Glu Thr Val Gln Ala Leu Leu Pro Val
                805                 810                 815

Leu Cys Gln Ala His Gly Leu Thr Pro Gln Gln Val Val Ala Ile Ala
                820                 825                 830

Ser Asn Gly Gly Gly Arg Pro Ala Leu Glu Ser Ile Val Ala Gln Leu
            835                 840                 845

Ser Arg Pro Asp Pro Ser Gly Ser Gly Ser Gly Asp Pro Ile Ser
            850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
                900                 905                 910

Glu Phe Phe Met Lys Val Tyr Gly Tyr Arg Gly Lys His Leu Gly Gly
                915                 920                 925

Ser Arg Lys Pro Asp Gly Ala Ile Tyr Thr Val Gly Ser Pro Ile Asp
            930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
            995                1000                1005

Gly Asn Tyr Lys Ala Gln Leu Thr Arg Leu Asn His Ile Thr Asn Cys
        1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 184
<211> LENGTH: 1065
<212> TYPE: PRT
<213> ORGANISM: artificial sequence
<220> FEATURE:
<223> OTHER INFORMATION: TALEN ZAP70-2_B pCLS25350

<400> SEQUENCE: 184

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Pro Ile Arg Ser Arg Thr
            20                  25                  30
```

Pro Ser Pro Ala Arg Glu Leu Leu Pro Gly Pro Gln Pro Asp Gly Val
         35                  40                  45

Gln Pro Thr Ala Asp Arg Gly Val Ser Pro Pro Ala Gly Gly Pro Leu
 50                  55                  60

Asp Gly Leu Pro Ala Arg Arg Thr Met Ser Arg Thr Arg Leu Pro Ser
 65                  70                  75                  80

Pro Pro Ala Pro Ser Pro Ala Phe Ser Ala Gly Ser Phe Ser Asp Leu
                 85                  90                  95

Leu Arg Gln Phe Asp Pro Ser Leu Phe Asn Thr Ser Leu Phe Asp Ser
             100                 105                 110

Leu Pro Pro Phe Gly Ala His His Thr Glu Ala Ala Thr Gly Glu Trp
         115                 120                 125

Asp Glu Val Gln Ser Gly Leu Arg Ala Ala Asp Ala Pro Pro Pro Thr
         130                 135                 140

Met Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                 165                 170                 175

Val Asp Leu Arg Thr Leu Gly Tyr Ser Gln Gln Gln Gln Glu Lys Ile
             180                 185                 190

Lys Pro Lys Val Arg Ser Thr Val Ala Gln His His Glu Ala Leu Val
         195                 200                 205

Gly His Gly Phe Thr His Ala His Ile Val Ala Leu Ser Gln His Pro
         210                 215                 220

Ala Ala Leu Gly Thr Val Ala Val Lys Tyr Gln Asp Met Ile Ala Ala
225                 230                 235                 240

Leu Pro Glu Ala Thr His Glu Ala Ile Val Gly Val Gly Lys Gln Trp
             245                 250                 255

Ser Gly Ala Arg Ala Leu Glu Ala Leu Leu Thr Val Ala Gly Glu Leu
             260                 265                 270

Arg Gly Pro Pro Leu Gln Leu Asp Thr Gly Gln Leu Leu Lys Ile Ala
         275                 280                 285

Lys Arg Gly Gly Val Thr Ala Val Glu Ala Val His Ala Trp Arg Asn
         290                 295                 300

Ala Leu Thr Gly Ala Pro Leu Asn Leu Thr Pro Glu Gln Val Val Ala
305                 310                 315                 320

Ile Ala Ser His Asp Gly Gly Lys Gln Ala Leu Glu Thr Val Gln Arg
                 325                 330                 335

Leu Leu Pro Val Leu Cys Gln Ala His Gly Leu Thr Pro Gln Gln Val
             340                 345                 350

Val Ala Ile Ala Ser Asn Gly Gly Lys Gln Ala Leu Glu Thr Val
         355                 360                 365

Gln Arg Leu Leu Pro Val Leu Cys Gln Ala His Gly Leu Thr Pro Gln
         370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Ala His Gly Leu Thr
             405                 410                 415

Pro Gln Gln Val Val Ala Ile Ala Ser Asn Asn Gly Gly Lys Gln Ala
                 420                 425                 430

Leu Glu Thr Val Gln Arg Leu Leu Pro Val Leu Cys Gln Ala His Gly
             435                 440                 445

-continued

Leu Thr Pro Gln Gln Val Val Ala Ile Ala Ser Asn Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser His
        515                 520                 525

Asp Gly Gly Lys Gln Ala Leu Glu Thr Val Gln Arg Leu Leu Pro Val
530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Lys Gln Ala Leu Glu Thr Val Gln Arg
        595                 600                 605

Leu Leu Pro Val Leu Cys Gln Ala His Gly Leu Thr Pro Gln Gln Val
610                 615                 620

Val Ala Ile Ala Ser Asn Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Ile Gly Gly Lys Gln Ala Leu Glu
            660                 665                 670

Thr Val Gln Ala Leu Leu Pro Val Leu Cys Gln Ala His Gly Leu Thr
        675                 680                 685

Pro Gln Gln Val Val Ala Ile Ala Ser Asn Asn Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Gln Gln Val Val Ala Ile Ala Ser Asn Gly Gly
        755                 760                 765

Gly Lys Gln Ala Leu Glu Thr Val Gln Arg Leu Leu Pro Val Leu Cys
770                 775                 780

Gln Ala His Gly Leu Thr Pro Glu Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Leu Thr Pro Gln Gln Val Val Ala Ile Ala
            820                 825                 830

Ser Asn Gly Gly Gly Arg Pro Ala Leu Glu Ser Ile Val Ala Gln Leu
        835                 840                 845

Ser Arg Pro Asp Pro Ser Gly Ser Gly Ser Gly Gly Asp Pro Ile Ser
    850                 855                 860

Arg Ser Gln Leu Val Lys Ser Glu Leu Glu Glu Lys Lys Ser Glu Leu

```
                865            870           875            880
Arg His Lys Leu Lys Tyr Val Pro His Glu Tyr Ile Glu Leu Ile Glu
                    885               890               895

Ile Ala Arg Asn Ser Thr Gln Asp Arg Ile Leu Glu Met Lys Val Met
                900               905               910

Glu Phe Phe Met Lys Val Tyr Gly Tyr Arg Gly Lys His Leu Gly Gly
                915               920               925

Ser Arg Lys Pro Asp Gly Ala Ile Tyr Thr Val Gly Ser Pro Ile Asp
                930               935               940

Tyr Gly Val Ile Val Asp Thr Lys Ala Tyr Ser Gly Gly Tyr Asn Leu
945                 950               955               960

Pro Ile Gly Gln Ala Asp Glu Met Gln Arg Tyr Val Glu Glu Asn Gln
                    965               970               975

Thr Arg Asn Lys His Ile Asn Pro Asn Glu Trp Trp Lys Val Tyr Pro
                980               985               990

Ser Ser Val Thr Glu Phe Lys Phe Leu Phe Val Ser Gly His Phe Lys
                    995               1000              1005

Gly Asn Tyr Lys Ala Gln Leu Thr Arg Leu Asn His Ile Thr Asn Cys
                1010              1015              1020

Asn Gly Ala Val Leu Ser Val Glu Glu Leu Leu Ile Gly Gly Glu Met
1025                1030              1035              1040

Ile Lys Ala Gly Thr Leu Thr Leu Glu Glu Val Arg Arg Lys Phe Asn
                    1045              1050              1055

Asn Gly Glu Ile Asn Phe Ala Ala Asp
                1060              1065

<210> SEQ ID NO 185
<211> LENGTH: 936
<212> TYPE: PRT
<213> ORGANISM: artificial sequence
<220> FEATURE:
<223> OTHER INFORMATION: TALEN LFA1_1_A pCLS25513

<400> SEQUENCE: 185

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
                35                  40                  45

Ala Gln His His Glu Ala Leu Val Gly His Gly Phe Thr His Ala His
                50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                    85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
                115                 120                 125

Thr Gly Gln Leu Leu Lys Ile Ala Lys Arg Gly Gly Val Thr Ala Val
                130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
```

```
                165                 170                 175
Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser Asn Ile Gly Gly Lys Gln Ala Leu Glu Thr Val Gln Ala Leu Leu
        275                 280                 285

Pro Val Leu Cys Gln Ala His Gly Leu Thr Pro Gln Gln Val Val Ala
    290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Gly Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser His Asp Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Gln Gln Val Val Ala Ile Ala Ser Asn
            500                 505                 510

Asn Gly Gly Lys Gln Ala Leu Glu Thr Val Gln Arg Leu Leu Pro Val
        515                 520                 525

Leu Cys Gln Ala His Gly Leu Thr Pro Gln Gln Val Val Ala Ile Ala
    530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590
```

Leu Leu Pro Val Leu Cys Gln Ala His Gly Leu Thr Pro Gln Gln Val
            595                 600                 605

Val Ala Ile Ala Ser Asn Asn Gly Gly Lys Gln Ala Leu Glu Thr Val
        610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
            645                 650                 655

Thr Val Gln Ala Leu Leu Pro Val Leu Cys Gln Ala His Gly Leu Thr
        660                 665                 670

Pro Gln Gln Val Val Ala Ile Ala Ser Asn Gly Gly Gly Arg Pro Ala
            675                 680                 685

Leu Glu Ser Ile Val Ala Gln Leu Ser Arg Pro Asp Pro Ala Leu Ala
        690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935

<210> SEQ ID NO 186
<211> LENGTH: 936
<212> TYPE: PRT
<213> ORGANISM: artificial sequence
<220> FEATURE:
<223> OTHER INFORMATION: TALEN LFA1_1_B pCLS25514

<400> SEQUENCE: 186

Met Gly Asp Pro Lys Lys Lys Arg Lys Val Ile Asp Tyr Pro Tyr Asp
1               5                   10                  15

```
Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
50                  55                  60

Ile Val Ala Leu Ser Gln His Pro Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
            130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
                180                 185                 190

His Gly Leu Thr Pro Gln Gln Val Val Ala Ile Ala Ser Asn Asn Gly
                195                 200                 205

Gly Lys Gln Ala Leu Glu Thr Val Gln Arg Leu Leu Pro Val Leu Cys
        210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
                260                 265                 270

Ser Asn Ile Gly Gly Lys Gln Ala Leu Glu Thr Val Gln Ala Leu Leu
            275                 280                 285

Pro Val Leu Cys Gln Ala His Gly Leu Thr Pro Glu Gln Val Val Ala
            290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Gln
            355                 360                 365

Gln Val Val Ala Ile Ala Ser Asn Asn Gly Gly Lys Gln Ala Leu Glu
        370                 375                 380

Thr Val Gln Arg Leu Leu Pro Val Leu Cys Gln Ala His Gly Leu Thr
385                 390                 395                 400

Pro Glu Gln Val Val Ala Ile Ala Ser Asn Ile Gly Gly Lys Gln Ala
                405                 410                 415

Leu Glu Thr Val Gln Ala Leu Leu Pro Val Leu Cys Gln Ala His Gly
                420                 425                 430
```

```
Leu Thr Pro Gln Gln Val Val Ala Ile Ala Ser Asn Gly Gly Lys
            435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Gln Gln Val Val Ala Ile Ala Ser Asn
            500                 505                 510

Asn Gly Gly Lys Gln Ala Leu Glu Thr Val Gln Arg Leu Leu Pro Val
            515                 520                 525

Leu Cys Gln Ala His Gly Leu Thr Pro Glu Gln Val Val Ala Ile Ala
            530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Gln Gln Val
            595                 600                 605

Val Ala Ile Ala Ser Asn Asn Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
                645                 650                 655

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
            675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
```

```
                850             855             860
Ser Val Thr Glu Phe Lys Phe Leu Phe Val Ser Gly His Phe Lys Gly
865             870             875             880

Asn Tyr Lys Ala Gln Leu Thr Arg Leu Asn His Ile Thr Asn Cys Asn
                885             890             895

Gly Ala Val Leu Ser Val Glu Leu Leu Ile Gly Gly Glu Met Ile
                900             905             910

Lys Ala Gly Thr Leu Thr Leu Glu Glu Val Arg Arg Lys Phe Asn Asn
                915             920             925

Gly Glu Ile Asn Phe Ala Ala Asp
    930             935
```

<210> SEQ ID NO 187
<211> LENGTH: 936
<212> TYPE: PRT
<213> ORGANISM: artificial sequence
<220> FEATURE:
<223> OTHER INFORMATION: TALEN CD28_A pCLS25618

<400> SEQUENCE: 187

```
Met Gly Asp Pro Lys Lys Lys Arg Lys Val Ile Asp Tyr Pro Tyr Asp
1               5               10              15

Val Pro Asp Tyr Ala Ile Asp Ile Ala Asp Leu Arg Thr Leu Gly Tyr
                20              25              30

Ser Gln Gln Gln Glu Lys Ile Lys Pro Lys Val Arg Ser Thr Val
        35              40              45

Ala Gln His His Glu Ala Leu Val Gly His Gly Phe Thr His Ala His
        50              55              60

Ile Val Ala Leu Ser Gln His Pro Ala Ala Leu Gly Thr Val Ala Val
65              70              75              80

Lys Tyr Gln Asp Met Ile Ala Ala Leu Pro Glu Ala Thr His Glu Ala
                85              90              95

Ile Val Gly Val Gly Lys Gln Trp Ser Gly Ala Arg Ala Leu Glu Ala
                100             105             110

Leu Leu Thr Val Ala Gly Glu Leu Arg Gly Pro Pro Leu Gln Leu Asp
        115             120             125

Thr Gly Gln Leu Leu Lys Ile Ala Lys Arg Gly Gly Val Thr Ala Val
    130             135             140

Glu Ala Val His Ala Trp Arg Asn Ala Leu Thr Gly Ala Pro Leu Asn
145             150             155             160

Leu Thr Pro Glu Gln Val Val Ala Ile Ala Ser Asn Ile Gly Gly Lys
                165             170             175

Gln Ala Leu Glu Thr Val Gln Ala Leu Leu Pro Val Leu Cys Gln Ala
                180             185             190

His Gly Leu Thr Pro Gln Gln Val Val Ala Ile Ala Ser Asn Asn Gly
        195             200             205

Gly Lys Gln Ala Leu Glu Thr Val Gln Arg Leu Leu Pro Val Leu Cys
    210             215             220

Gln Ala His Gly Leu Thr Pro Glu Gln Val Val Ala Ile Ala Ser His
225             230             235             240

Asp Gly Gly Lys Gln Ala Leu Glu Thr Val Gln Arg Leu Leu Pro Val
                245             250             255

Leu Cys Gln Ala His Gly Leu Thr Pro Glu Gln Val Val Ala Ile Ala
                260             265             270

Ser His Asp Gly Gly Lys Gln Ala Leu Glu Thr Val Gln Arg Leu Leu
```

```
            275                 280                 285
Pro Val Leu Cys Gln Ala His Gly Leu Thr Pro Glu Gln Val Val Ala
290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser Asn Ile Gly Gly Lys Gln Ala Leu Glu Thr Val
                340                 345                 350

Gln Ala Leu Leu Pro Val Leu Cys Gln Ala His Gly Leu Thr Pro Gln
                355                 360                 365

Gln Val Val Ala Ile Ala Ser Asn Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
                420                 425                 430

Leu Thr Pro Gln Gln Val Val Ala Ile Ala Ser Asn Gly Gly Lys
                435                 440                 445

Gln Ala Leu Glu Thr Val Gln Arg Leu Leu Pro Val Leu Cys Gln Ala
450                 455                 460

His Gly Leu Thr Pro Gln Gln Val Val Ala Ile Ala Ser Asn Gly Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser His
                500                 505                 510

Asp Gly Gly Lys Gln Ala Leu Glu Thr Val Gln Arg Leu Leu Pro Val
                515                 520                 525

Leu Cys Gln Ala His Gly Leu Thr Pro Glu Gln Val Val Ala Ile Ala
                530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
                580                 585                 590

Leu Leu Pro Val Leu Cys Gln Ala His Gly Leu Thr Pro Gln Gln Val
                595                 600                 605

Val Ala Ile Ala Ser Asn Asn Gly Gly Lys Gln Ala Leu Glu Thr Val
                610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
                660                 665                 670

Pro Gln Gln Val Val Ala Ile Ala Ser Asn Gly Gly Gly Arg Pro Ala
                675                 680                 685

Leu Glu Ser Ile Val Ala Gln Leu Ser Arg Pro Asp Pro Ala Leu Ala
690                 695                 700
```

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
            915                 920                 925

Gly Glu Ile Asn Phe Ala Ala Asp
930                 935

<210> SEQ ID NO 188
<211> LENGTH: 936
<212> TYPE: PRT
<213> ORGANISM: artificial sequence
<220> FEATURE:
<223> OTHER INFORMATION: TALEN CD28_B pCLS25619

<400> SEQUENCE: 188

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
            85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

```
Thr Gly Gln Leu Leu Lys Ile Ala Lys Arg Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
                180                 185                 190

His Gly Leu Thr Pro Gln Gln Val Val Ala Ile Ala Ser Asn Asn Gly
            195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                245                 250                 255

Leu Cys Gln Ala His Gly Leu Thr Pro Gln Gln Val Val Ala Ile Ala
                260                 265                 270

Ser Asn Asn Gly Gly Lys Gln Ala Leu Glu Thr Val Gln Arg Leu Leu
            275                 280                 285

Pro Val Leu Cys Gln Ala His Gly Leu Thr Pro Glu Gln Val Val Ala
    290                 295                 300

Ile Ala Ser Asn Ile Gly Gly Lys Gln Ala Leu Glu Thr Val Gln Ala
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
                340                 345                 350

Gln Arg Leu Leu Pro Val Leu Cys Gln Ala His Gly Leu Thr Pro Glu
            355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
                420                 425                 430

Leu Thr Pro Glu Gln Val Val Ala Ile Ala Ser Asn Ile Gly Gly Lys
            435                 440                 445

Gln Ala Leu Glu Thr Val Gln Ala Leu Leu Pro Val Leu Cys Gln Ala
    450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Gln Gln Val Val Ala Ile Ala Ser Asn
                500                 505                 510

Asn Gly Gly Lys Gln Ala Leu Glu Thr Val Gln Arg Leu Leu Pro Val
            515                 520                 525

Leu Cys Gln Ala His Gly Leu Thr Pro Glu Gln Val Val Ala Ile Ala
    530                 535                 540
```

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
            565                 570                 575

Ile Ala Ser Asn Asn Gly Gly Lys Gln Ala Leu Glu Thr Val Gln Arg
        580                 585                 590

Leu Leu Pro Val Leu Cys Gln Ala His Gly Leu Thr Pro Glu Gln Val
    595                 600                 605

Val Ala Ile Ala Ser His Asp Gly Gly Lys Gln Ala Leu Glu Thr Val
610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
            645                 650                 655

Thr Val Gln Ala Leu Leu Pro Val Leu Cys Gln Ala His Gly Leu Thr
        660                 665                 670

Pro Gln Gln Val Val Ala Ile Ala Ser Asn Gly Gly Arg Pro Ala
    675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
    755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
            805                 810                 815

Gly Val Ile Val Asp Thr Lys Ala Tyr Ser Gly Gly Tyr Asn Leu Pro
        820                 825                 830

Ile Gly Gln Ala Asp Glu Met Gln Arg Tyr Val Glu Asn Gln Thr
    835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
            885                 890                 895

Gly Ala Val Leu Ser Val Glu Glu Leu Leu Ile Gly Gly Glu Met Ile
        900                 905                 910

Lys Ala Gly Thr Leu Thr Leu Glu Glu Val Arg Arg Lys Phe Asn Asn
    915                 920                 925

Gly Glu Ile Asn Phe Ala Ala Asp
930                 935

<210> SEQ ID NO 189
<211> LENGTH: 936
<212> TYPE: PRT

<213> ORGANISM: artificial sequence
<220> FEATURE:
<223> OTHER INFORMATION: TALEN TRAT1-1_A pCLS25708

<400> SEQUENCE: 189

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Gly Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Gly Gly Gly Lys Gln Ala Leu Glu
    370                 375                 380

Thr Val Gln Arg Leu Leu Pro Val Leu Cys Gln Ala His Gly Leu Thr

-continued

```
385                 390                 395                 400
Pro Gln Gln Val Val Ala Ile Ala Ser Asn Asn Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Asn Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Asn Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Gln Gln Val Val Ala Ile Ala Ser Asn
            500                 505                 510
Asn Gly Gly Lys Gln Ala Leu Glu Thr Val Gln Arg Leu Leu Pro Val
        515                 520                 525
Leu Cys Gln Ala His Gly Leu Thr Pro Glu Gln Val Val Ala Ile Ala
    530                 535                 540
Ser Asn Ile Gly Gly Lys Gln Ala Leu Glu Thr Val Gln Ala Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Gly Gly Lys Gln Ala Leu Glu Thr Val
    610                 615                 620
Gln Arg Leu Leu Pro Val Leu Cys Gln Ala His Gly Leu Thr Pro Gln
625                 630                 635                 640
Gln Val Val Ala Ile Ala Ser Asn Gly Gly Gly Lys Gln Ala Leu Glu
                645                 650                 655
Thr Val Gln Arg Leu Leu Pro Val Leu Cys Gln Ala His Gly Leu Thr
            660                 665                 670
Pro Gln Gln Val Val Ala Ile Ala Ser Asn Gly Gly Gly Arg Pro Ala
        675                 680                 685
Leu Glu Ser Ile Val Ala Gln Leu Ser Arg Pro Asp Pro Ala Leu Ala
    690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
            740                 745                 750
His Lys Leu Lys Tyr Val Pro His Glu Tyr Ile Glu Leu Ile Glu Ile
        755                 760                 765
Ala Arg Asn Ser Thr Gln Asp Arg Ile Leu Glu Met Lys Val Met Glu
    770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
```

-continued

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Asn Gln Thr
                835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925

Gly Glu Ile Asn Phe Ala Ala Asp
        930                 935

<210> SEQ ID NO 190
<211> LENGTH: 936
<212> TYPE: PRT
<213> ORGANISM: artificial sequence
<220> FEATURE:
<223> OTHER INFORMATION: TALEN TRAT1-1_B pCLS25620

<400> SEQUENCE: 190

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Gln Glu Lys Ile Lys Pro Lys Val Arg Ser Thr Val
            35                  40                  45

Ala Gln His His Glu Ala Leu Val Gly His Gly Phe Thr His Ala His
        50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
        130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

```
Gly Gly Gly Lys Gln Ala Leu Glu Thr Val Gln Arg Leu Leu Pro Val
            245                 250                 255

Leu Cys Gln Ala His Gly Leu Thr Pro Glu Gln Val Val Ala Ile Ala
            260                 265                 270

Ser Asn Ile Gly Gly Lys Gln Ala Leu Glu Thr Val Gln Ala Leu Leu
            275                 280                 285

Pro Val Leu Cys Gln Ala His Gly Leu Thr Pro Gln Gln Val Val Ala
            290                 295                 300

Ile Ala Ser Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser Asn Ile Gly Gly Lys Gln Ala Leu Glu Thr Val
            340                 345                 350

Gln Ala Leu Leu Pro Val Leu Cys Gln Ala His Gly Leu Thr Pro Glu
            355                 360                 365

Gln Val Val Ala Ile Ala Ser Asn Ile Gly Gly Lys Gln Ala Leu Glu
            370                 375                 380

Thr Val Gln Ala Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser His Asp Gly Gly Lys
            435                 440                 445

Gln Ala Leu Glu Thr Val Gln Arg Leu Leu Pro Val Leu Cys Gln Ala
            450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
            485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
            515                 520                 525

Leu Cys Gln Ala His Gly Leu Thr Pro Glu Gln Val Val Ala Ile Ala
            530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Glu Gln Val
            595                 600                 605

Val Ala Ile Ala Ser His Asp Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
                645                 650                 655
```

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Arg Pro Ala
    675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
                770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Glu Asn Gln Thr
                835                 840                 845

Arg Asn Lys His Ile Asn Pro Asn Glu Trp Trp Lys Val Tyr Pro Ser
                850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925

Gly Glu Ile Asn Phe Ala Ala Asp
    930                 935

<210> SEQ ID NO 191
<211> LENGTH: 936
<212> TYPE: PRT
<213> ORGANISM: artificial sequence
<220> FEATURE:
<223> OTHER INFORMATION: TALEN TRAT1-2_A pCLS25621

<400> SEQUENCE: 191

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

-continued

```
Lys Tyr Gln Asp Met Ile Ala Ala Leu Pro Glu Ala Thr His Glu Ala
                85                  90                  95
Ile Val Gly Val Gly Lys Gln Trp Ser Gly Ala Arg Ala Leu Glu Ala
            100                 105                 110
Leu Leu Thr Val Ala Gly Glu Leu Arg Gly Pro Leu Gln Leu Asp
        115                 120                 125
Thr Gly Gln Leu Leu Lys Ile Ala Lys Arg Gly Gly Val Thr Ala Val
    130                 135                 140
Glu Ala Val His Ala Trp Arg Asn Ala Leu Thr Gly Ala Pro Leu Asn
145                 150                 155                 160
Leu Thr Pro Gln Gln Val Val Ala Ile Ala Ser Asn Asn Gly Gly Lys
                165                 170                 175
Gln Ala Leu Glu Thr Val Gln Arg Leu Leu Pro Val Leu Cys Gln Ala
            180                 185                 190
His Gly Leu Thr Pro Gln Gln Val Val Ala Ile Ala Ser Asn Gly Gly
        195                 200                 205
Gly Lys Gln Ala Leu Glu Thr Val Gln Arg Leu Leu Pro Val Leu Cys
    210                 215                 220
Gln Ala His Gly Leu Thr Pro Gln Gln Val Val Ala Ile Ala Ser Asn
225                 230                 235                 240
Gly Gly Gly Lys Gln Ala Leu Glu Thr Val Gln Arg Leu Leu Pro Val
                245                 250                 255
Leu Cys Gln Ala His Gly Leu Thr Pro Gln Gln Val Val Ala Ile Ala
            260                 265                 270
Ser Asn Asn Gly Gly Lys Gln Ala Leu Glu Thr Val Gln Arg Leu Leu
        275                 280                 285
Pro Val Leu Cys Gln Ala His Gly Leu Thr Pro Gln Gln Val Val Ala
    290                 295                 300
Ile Ala Ser Asn Asn Gly Gly Lys Gln Ala Leu Glu Thr Val Gln Arg
305                 310                 315                 320
Leu Leu Pro Val Leu Cys Gln Ala His Gly Leu Thr Pro Gln Gln Val
                325                 330                 335
Val Ala Ile Ala Ser Asn Asn Gly Gly Lys Gln Ala Leu Glu Thr Val
            340                 345                 350
Gln Arg Leu Leu Pro Val Leu Cys Gln Ala His Gly Leu Thr Pro Glu
        355                 360                 365
Gln Val Val Ala Ile Ala Ser His Asp Gly Gly Lys Gln Ala Leu Glu
    370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Gly Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Asn Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Gln Gln Val Val Ala Ile Ala Ser Asn
```

```
                    500                 505                 510
Asn Gly Gly Lys Gln Ala Leu Glu Thr Val Gln Arg Leu Leu Pro Val
                515                 520                 525

Leu Cys Gln Ala His Gly Leu Thr Pro Glu Gln Val Val Ala Ile Ala
                530                 535                 540

Ser His Asp Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Gly Gly Lys Gln Ala Leu Glu Thr Val Gln Arg
                580                 585                 590

Leu Leu Pro Val Leu Cys Gln Ala His Gly Leu Thr Pro Gln Gln Val
                595                 600                 605

Val Ala Ile Ala Ser Asn Gly Gly Lys Gln Ala Leu Glu Thr Val
                610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Lys Gln Ala Leu Glu
                645                 650                 655

Thr Val Gln Arg Leu Leu Pro Val Leu Cys Gln Ala His Gly Leu Thr
                660                 665                 670

Pro Gln Gln Val Val Ala Ile Ala Ser Asn Gly Gly Arg Pro Ala
                675                 680                 685

Leu Glu Ser Ile Val Ala Gln Leu Ser Arg Pro Asp Pro Ala Leu Ala
                690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
                740                 745                 750

His Lys Leu Lys Tyr Val Pro His Glu Tyr Ile Glu Leu Ile Glu Ile
                755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Asn Gln Thr
                835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925
```

-continued

Gly Glu Ile Asn Phe Ala Ala Asp
        930                 935

<210> SEQ ID NO 192
<211> LENGTH: 936
<212> TYPE: PRT
<213> ORGANISM: artificial sequence
<220> FEATURE:
<223> OTHER INFORMATION: TALEN TRAT1-2_B pCLS25622

<400> SEQUENCE: 192

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
            35                  40                  45

Ala Gln His His Glu Ala Leu Val Gly His Gly Phe Thr His Ala His
        50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser Asn Ile Gly Gly Lys
                165                 170                 175

Gln Ala Leu Glu Thr Val Gln Ala Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
            340                 345                 350

-continued

```
Gln Arg Leu Leu Pro Val Leu Cys Gln Ala His Gly Leu Thr Pro Glu
        355                 360                 365
Gln Val Val Ala Ile Ala Ser Asn Ile Gly Gly Lys Gln Ala Leu Glu
    370                 375                 380
Thr Val Gln Ala Leu Leu Pro Val Leu Cys Gln Ala His Gly Leu Thr
385                 390                 395                 400
Pro Glu Gln Val Val Ala Ile Ala Ser Asn Ile Gly Gly Lys Gln Ala
                405                 410                 415
Leu Glu Thr Val Gln Ala Leu Leu Pro Val Leu Cys Gln Ala His Gly
            420                 425                 430
Leu Thr Pro Glu Gln Val Val Ala Ile Ala Ser Asn Ile Gly Gly Lys
        435                 440                 445
Gln Ala Leu Glu Thr Val Gln Ala Leu Leu Pro Val Leu Cys Gln Ala
    450                 455                 460
His Gly Leu Thr Pro Gln Gln Val Val Ala Ile Ala Ser Asn Gly Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Glu Gln Val Val Ala Ile Ala Ser Asn
            500                 505                 510
Ile Gly Gly Lys Gln Ala Leu Glu Thr Val Gln Ala Leu Leu Pro Val
        515                 520                 525
Leu Cys Gln Ala His Gly Leu Thr Pro Gln Gln Val Val Ala Ile Ala
    530                 535                 540
Ser Asn Gly Gly Gly Lys Gln Ala Leu Glu Thr Val Gln Arg Leu Leu
545                 550                 555                 560
Pro Val Leu Cys Gln Ala His Gly Leu Thr Pro Gln Gln Val Val Ala
                565                 570                 575
Ile Ala Ser Asn Gly Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Asn Gly Gly Lys Gln Ala Leu Glu Thr Val
    610                 615                 620
Gln Arg Leu Leu Pro Val Leu Cys Gln Ala His Gly Leu Thr Pro Glu
625                 630                 635                 640
Gln Val Val Ala Ile Ala Ser Asn Ile Gly Gly Lys Gln Ala Leu Glu
                645                 650                 655
Thr Val Gln Ala Leu Leu Pro Val Leu Cys Gln Ala His Gly Leu Thr
            660                 665                 670
Pro Gln Gln Val Val Ala Ile Ala Ser Asn Gly Gly Gly Arg Pro Ala
        675                 680                 685
Leu Glu Ser Ile Val Ala Gln Leu Ser Arg Pro Asp Pro Ala Leu Ala
    690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
            740                 745                 750
His Lys Leu Lys Tyr Val Pro His Glu Tyr Ile Glu Leu Ile Glu Ile
        755                 760                 765
```

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Asn Gln Thr
        835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
930                 935

<210> SEQ ID NO 193
<211> LENGTH: 619
<212> TYPE: PRT
<213> ORGANISM: homo sapiens
<220> FEATURE:
<223> OTHER INFORMATION: ZAP70

<400> SEQUENCE: 193

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

```
Lys Glu Gln Gly Thr Tyr Ala Leu Ser Leu Ile Tyr Gly Lys Thr Val
            195                 200                 205
Tyr His Tyr Leu Ile Ser Gln Asp Lys Ala Gly Lys Tyr Cys Ile Pro
            210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Pro Thr Leu Pro Ala
                260                 265                 270
His Pro Ser Thr Leu Thr His Pro Gln Arg Arg Ile Asp Thr Leu Asn
            275                 280                 285
Ser Asp Gly Tyr Thr Pro Glu Pro Ala Arg Ile Thr Ser Pro Asp Lys
            290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                325                 330                 335
Leu Leu Ile Ala Asp Ile Glu Leu Gly Cys Gly Asn Phe Gly Ser Val
                340                 345                 350
Arg Gln Gly Val Tyr Arg Met Arg Lys Lys Gln Ile Asp Val Ala Ile
            355                 360                 365
Lys Val Leu Lys Gln Gly Thr Glu Lys Ala Asp Thr Glu Glu Met Met
            370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Met Glu Met
                405                 410                 415
Ala Gly Gly Gly Pro Leu His Lys Phe Leu Val Gly Lys Arg Glu Glu
                420                 425                 430
Ile Pro Val Ser Asn Val Ala Glu Leu Leu His Gln Val Ser Met Gly
            435                 440                 445
Met Lys Tyr Leu Glu Glu Lys Asn Phe Val His Arg Asp Leu Ala Ala
            450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
                500                 505                 510
Phe Arg Lys Phe Ser Ser Arg Ser Asp Val Trp Ser Tyr Gly Val Thr
            515                 520                 525
Met Trp Glu Ala Leu Ser Tyr Gly Gln Lys Pro Tyr Lys Lys Met Lys
            530                 535                 540
Gly Pro Glu Val Met Ala Phe Ile Glu Gln Gly Lys Arg Met Glu Cys
545                 550                 555                 560
Pro Pro Glu Cys Pro Pro Glu Leu Tyr Ala Leu Met Ser Asp Cys Trp
                565                 570                 575
Ile Tyr Lys Trp Glu Asp Arg Pro Asp Phe Leu Thr Val Glu Gln Arg
            580                 585                 590
Met Arg Ala Cys Tyr Tyr Ser Leu Ala Ser Lys Val Glu Gly Pro Pro
            595                 600                 605
Gly Ser Thr Gln Lys Ala Glu Ala Ala Cys Ala
```

<210> SEQ ID NO 194
<211> LENGTH: 13
<212> TYPE: DNA
<213> ORGANISM: artificial sequence
<220> FEATURE:
<223> OTHER INFORMATION: inverted palindrome
<220> FEATURE:
<221> NAME/KEY: misc_feature
<222> LOCATION: 7
<223> OTHER INFORMATION: n is a or c or t or g

<400> SEQUENCE: 194
gttaatnatt aac                                                        13

<210> SEQ ID NO 195
<211> LENGTH: 557
<212> TYPE: PRT
<213> ORGANISM: homo sapiens
<220> FEATURE:
<223> OTHER INFORMATION: HNF1B Transcription factor

<400> SEQUENCE: 195

Met Val Ser Lys Leu Thr Ser Leu Gln Gln Glu Leu Leu Ser Ala Leu
1               5                   10                  15

Leu Ser Ser Gly Val Thr Lys Glu Val Leu Val Gln Ala Leu Glu Glu
            20                  25                  30

Leu Leu Pro Ser Pro Asn Phe Gly Val Lys Leu Glu Thr Leu Pro Leu
        35                  40                  45

Ser Pro Gly Ser Gly Ala Glu Pro Asp Thr Lys Pro Val Phe His Thr
    50                  55                  60

Leu Thr Asn Gly His Ala Lys Gly Arg Leu Ser Gly Asp Glu Gly Ser
65                  70                  75                  80

Glu Asp Gly Asp Asp Tyr Asp Thr Pro Pro Ile Leu Lys Glu Leu Gln
                85                  90                  95

Ala Leu Asn Thr Glu Glu Ala Ala Glu Gln Arg Ala Glu Val Asp Arg
            100                 105                 110

Met Leu Ser Glu Asp Pro Trp Arg Ala Ala Lys Met Ile Lys Gly Tyr
        115                 120                 125

Met Gln Gln His Asn Ile Pro Gln Arg Glu Val Val Asp Val Thr Gly
    130                 135                 140

Leu Asn Gln Ser His Leu Ser Gln His Leu Asn Lys Gly Thr Pro Met
145                 150                 155                 160

Lys Thr Gln Lys Arg Ala Ala Leu Tyr Thr Trp Tyr Val Arg Lys Gln
                165                 170                 175

Arg Glu Ile Leu Arg Gln Phe Asn Gln Thr Val Gln Ser Ser Gly Asn
            180                 185                 190

Met Thr Asp Lys Ser Ser Gln Asp Gln Leu Leu Phe Leu Phe Pro Glu
        195                 200                 205

Phe Ser Gln Gln Ser His Gly Pro Gly Gln Ser Asp Asp Ala Cys Ser
    210                 215                 220

Glu Pro Thr Asn Lys Lys Met Arg Arg Asn Arg Phe Lys Trp Gly Pro
225                 230                 235                 240

Ala Ser Gln Gln Ile Leu Tyr Gln Ala Tyr Asp Arg Gln Lys Asn Pro
                245                 250                 255

Ser Lys Glu Glu Arg Glu Ala Leu Val Glu Glu Cys Asn Arg Ala Glu
            260                 265                 270

```
Cys Leu Gln Arg Gly Val Ser Pro Ser Lys Ala His Gly Leu Gly Ser
            275                 280                 285

Asn Leu Val Thr Glu Val Arg Val Tyr Asn Trp Phe Ala Asn Arg Arg
        290                 295                 300

Lys Glu Glu Ala Phe Arg Gln Lys Leu Ala Met Asp Ala Tyr Ser Ser
305                 310                 315                 320

Asn Gln Thr His Ser Leu Asn Pro Leu Leu Ser His Gly Ser Pro His
                325                 330                 335

His Gln Pro Ser Ser Pro Pro Asn Lys Leu Ser Gly Val Arg Tyr
            340                 345                 350

Ser Gln Gln Gly Asn Asn Glu Ile Thr Ser Ser Thr Ile Ser His
            355                 360                 365

His Gly Asn Ser Ala Met Val Thr Ser Gln Ser Val Leu Gln Gln Val
    370                 375                 380

Ser Pro Ala Ser Leu Asp Pro Gly His Asn Leu Leu Ser Pro Asp Gly
385                 390                 395                 400

Lys Met Ile Ser Val Ser Gly Gly Gly Leu Pro Pro Val Ser Thr Leu
                405                 410                 415

Thr Asn Ile His Ser Leu Ser His His Asn Pro Gln Gln Ser Gln Asn
            420                 425                 430

Leu Ile Met Thr Pro Leu Ser Gly Val Met Ala Ile Ala Gln Ser Leu
        435                 440                 445

Asn Thr Ser Gln Ala Gln Ser Val Pro Val Ile Asn Ser Val Ala Gly
    450                 455                 460

Ser Leu Ala Ala Leu Gln Pro Val Gln Phe Ser Gln Gln Leu His Ser
465                 470                 475                 480

Pro His Gln Gln Pro Leu Met Gln Gln Ser Pro Gly Ser His Met Ala
                485                 490                 495

Gln Gln Pro Phe Met Ala Ala Val Thr Gln Leu Gln Asn Ser His Met
            500                 505                 510

Tyr Ala His Lys Gln Glu Pro Pro Gln Tyr Ser His Thr Ser Arg Phe
        515                 520                 525

Pro Ser Ala Met Val Val Thr Asp Thr Ser Ser Ile Ser Thr Leu Thr
530                 535                 540

Asn Met Ser Ser Ser Lys Gln Cys Pro Leu Gln Ala Trp
545                 550                 555

<210> SEQ ID NO 196
<211> LENGTH: 631
<212> TYPE: PRT
<213> ORGANISM: homo sapiens
<220> FEATURE:
<223> OTHER INFORMATION: HNF1A Transcription factor

<400> SEQUENCE: 196

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80
```

```
Phe Thr Pro Pro Ile Leu Lys Glu Leu Glu Asn Leu Ser Pro Glu Glu
                 85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
            130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Leu Ile Glu Glu Pro Thr Gly Asp
            180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
            210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met Asp Thr Tyr Ser Gly
            275                 280                 285

Pro Pro Pro Gly Pro Gly Pro Gly Pro Ala Leu Pro Ala His Ser Ser
            290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
            355                 360                 365

Leu Val Ser Ala Ala Gly Gly Pro Leu Pro Pro Val Ser Thr Leu Thr
            370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
            435                 440                 445

Ile Asn Ser Met Gly Ser Ser Leu Thr Thr Leu Gln Pro Val Gln Phe
            450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
```

```
              500             505             510
Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Val Phe Thr
        530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
        610                 615                 620

Gln Met Ala Ser Ser Ser Gln
625                 630

<210> SEQ ID NO 197
<211> LENGTH: 1695
<212> TYPE: DNA
<213> ORGANISM: homo sapiens
<220> FEATURE:
<223> OTHER INFORMATION: HNF1B Transcription factor

<400> SEQUENCE: 197
gaagacactg gaatggtgtc caagctcacg tcgctccagc aagaactcct gagcgccctg      60
ctgagctccg gggtcaccaa ggaggtgctg gttcaggcct tggaggagtt gctgccatcc     120
ccgaacttcg gggtgaagct ggaaacgctg cccctgtccc ctggcagcgg ggccgagccc     180
gacaccaagc cggtgttcca tactctcacc aacggccacg ccaagggccg cttgtccggc     240
gacgagggct ccgaggacgg cgacgactat gacacacctc ccatcctcaa ggagctgcag     300
gcgctcaaca ccgaggaggc ggcggagcag cgggcggagg tggaccggat gctcagtgag     360
gacccttgga gggctgctaa aatgatcaag ggttacatgc agcaacacaa catccccag      420 agggaggtgg tcgatgtcac cggcctgaac cagtcgcacc tctcccagca tctcaacaag     480 ggcacccta tgaaaaccca gaagcgtgcc gctctgtaca cctggtacgt cagaaagcaa      540
cgagagatcc tccgacaatt caaccagaca gtccagagtt ctggaaatat gacagacaaa     600
agcagtcagg atcagctgct gtttctcttt ccagagttca gtcaacagag tcatgggcct     660
gggcagtccg atgatgcctg ctctgagccc accaacaaga gatgcgccg caaccggttc      720 aaatggggggc ccgcgtccca gcaaatcttg taccaggcct acgatcggca aaagaaccc     780 agcaaggaag agagagaggc cttagtggag gaatgcaaca gggcagaatg tttgcagcga     840
ggggtgtccc cctccaaagc ccacggcctg ggctccaact tggtcactga ggtccgtgtc     900
tacaactggt ttgcaaaccg caggaaggag gaggcattcc ggcaaaagct ggcaatggac     960
gcctatagct ccaaccagac tcacagcctg aaccctctgc tctcccacgg ctcccccac    1020 caccagccca gctcctctcc tccaaacaag ctgtcaggag tgcgctacag ccagcaggga    1080
aacaatgaga tcacttcctc ctcaacaatc agtcatcatg caacagcgc aatggtgacc     1140 agccagtcgg ttttacagca agtctcccca gccagcctgg acccaggcca caatctcctc    1200
tcacctgatg gtaaaatgat ctcagtctca ggaggaggtt tgcccccagt cagcaccttg    1260
acgaatatcc acagcctctc ccaccataat ccccagcaat ctcaaaacct catcatgaca    1320
```

| | |
|---|---|
| cccctctctg gagtcatggc aattgcacaa agcctcaaca cctcccaagc acagagtgtc | 1380 |
| cctgtcatca acagtgtggc cggcagcctg gcagccctgc agcccgtcca gttctcccag | 1440 |
| cagctgcaca gccctcacca gcagcccctc atgcagcaga gcccaggcag ccacatggcc | 1500 |
| cagcagccct tcatggcagc tgtgactcag ctgcagaact cacacatgta cgcacacaag | 1560 |
| caggaacccc cccagtattc ccacacctcc cggtttccat ctgcaatggt ggtcacagat | 1620 |
| accagcagca tcagtacact caccaacatg tcatcaagta aacagtgtcc tctacaagcc | 1680 |
| tgggaatacg tcttc | 1695 |

<210> SEQ ID NO 198
<211> LENGTH: 1917
<212> TYPE: DNA
<213> ORGANISM: homo sapiens
<220> FEATURE:
<223> OTHER INFORMATION: HNF1A Transcription factor

<400> SEQUENCE: 198

| | |
|---|---|
| gaagacactg gaatggtttc taaactgagc cagctgcaga cggagctcct ggcggccctg | 60 |
| ctcgagtcag ggctgagcaa agaggcactg atccaggcac tgggtgagcc ggggccctac | 120 |
| ctcctggctg agaaggccc cctggacaag ggggagtcct gcggcggcgg tcgaggggag | 180 |
| ctggctgagc tgcccaatgg gctgggggag actcggggct ccgaggacga acggacgac | 240 |
| gatgggggagg acttcacgcc acccatcctc aaagagctgg agaacctcag ccctgaggag | 300 |
| gcggcccacc agaaagccgt ggtggaaacc cttctgcagg aggacccgtg gcgtgtggcg | 360 |
| aagatggtca gtcctacct gcagcagcac aacatcccac agcgggaggt ggtcgatacc | 420 |
| actggcctca accagtccca cctgtcccaa cacctcaaca agggcactcc catgaaaacg | 480 |
| cagaagcggg ccgccctgta cacctggtac gtccgcaagc agcgagaggt ggcgcagcag | 540 |
| ttcacccatg cagggcaggg agggctgatt gaagagccca caggtgatga gctaccaacc | 600 |
| aagaagggc ggaggaaccg tttcaagtgg ggcccagcat cccagcagat cctgttccag | 660 |
| gcctatgaga ggcagaagaa ccctagcaag gaggagcgag aaacgctagt ggaggagtgc | 720 |
| aatagggcgg aatgcatcca gagaggggtg tccccatcac aggcacaggg gctgggctcc | 780 |
| aacctcgtca cggaggtgcg tgtctacaac tggtttgcca accggcgcaa agaagaagcc | 840 |
| ttccggcaca agctggcaat ggacacgtac agcgggcccc cccagggcc aggcccggga | 900 |
| cctgcgctgc ccgctcacag ctcccctggc ctgcctccac ctgccctctc ccccagtaag | 960 |
| gtccacggtg tgcgctatgg acagcctgcg ccagtgaga ctgcagaagt accctcaagc | 1020 |
| agcggcggtc ccttagtgac agtgtctaca cccctccacc aagtgtcccc cacgggcctg | 1080 |
| gagcccagcc acagcctgct gagtacagaa gccaagctgg tgtcagcagc tggggcccc | 1140 |
| ctccccccctg tcagcaccct gacagcactg cacagcttgg agcagacatc cccaggcctc | 1200 |
| aaccagcagc cccagaacct catcatggcc tcacttcctg gggtcatgac catcgggcct | 1260 |
| ggtgagcctg cctccctggg tcctacgttc accaacacag gtgcctccac cctggtcatc | 1320 |
| ggcctggcct ccacgcaggc acagagtgtg ccggtcatca acagcatggg cagcagcctg | 1380 |
| accaccctgc agcccgtcca gttctcccag ccgctgcacc cctcctacca gcagccgctc | 1440 |
| atgccacctg tgcagagcca tgtgacccag agcccttca tggcacgat ggctcagctg | 1500 |
| cagagccccc acgccctcta cagccacaag cccgaggtgg cccagtacac ccacacgggc | 1560 |
| ctgctcccgc agactatgct catcaccgac accaccaacc tgagcgccct ggccagcctc | 1620 |

```
acgcccacca agcaggtgtt cacctcagac actgaggcct ccagtgagtc cgggcttcac    1680
acgccggcat ctcaggccac cacccteca gtcecceagec aggacectge cggcateccag    1740 cacctgcagc cggeccaccg gctcagegec ageccacag tgtcctccag cagectggtg    1800 ctgtaccaga gctcagactc cagcaatggc cagagccacc tgctgccatc caaccacagc    1860
gtcatcgaaa ccttcatctc cacccagatg gcctcttcct cccaggaata cgtcttc       1917
```

METHOD OF ENGINEERING MULTI-INPUT SIGNAL SENSITIVE T CELL FOR IMMUNOTHERAPY

CROSS REFERENCE TO RELATED APPLICATION

This application is a 35 U.S.C. 371 National Phase of PCT Application No. PCT/EP2014/078876 filed Dec. 19, 2014 which claims priority to Danish Patent Application No. PA201370806 filed Dec. 20, 2013. The disclosure of these prior applications are hereby incorporated in their entirety by reference.

FIELD OF THE DESCRIPTION

The present invention relates to a method to engineer T cell for immunotherapy. In particular said T cells are engineered in order to be activated by the combination of input signals. The present invention relates to new designed chimeric antigen receptors which are able to redirect immune cell specificity and reactivity toward a selected target exploiting the ligand-binding domain properties. The present invention also relates to cells obtained by the present method, preferably comprising said chimeric antigen receptors for use in therapeutic or prophylactic treatment.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010). However, for example, cancer cells are unstable and some cells may no longer possess the target antigen. These cells, referred to as antigen loss escape variants, escape destruction by the therapy and may continue to grow and spread unchecked. Cancer and healthy cells may express the same antigen although at different levels. In such case, having the possibility to combine at least two antigens in order for the engineered T cell to discriminate between healthy tissue and cancer cells would present extremely valuable advantage over actual technology for therapeutic purposes. Bispecific tandem CAR has already been described (International application: WO2013123061, US. Patent application: US20130280220). However, in this design the bispecific chimeric antigen receptor comprises (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen. Such design may theoretically still lead to the T-cell activation independently to the recognition and binding of both antigens as one cannot exclude that the binding of one single chain Fv may trigger activation. Kloss, Condomines et al. 2013 described another combinatorial antigen recognition approach. A CAR comprising a signaling domain mediated the recognition of one antigen and another receptor comprising a co-stimulatory domain specific for a second antigen are expressed at the surface of a T cell. This dual targeting approach facilitates augmented T cell reactivity against tumor positive for two antigens. However this approach alone fails to prevent T cell reactivity to single-positive tumors. To remedy this failure, search of adapted configuration of CAR are required.

To avoid the tuning of CAR used for the combinatorial antigen recognition, the inventors developed a system wherein activation of T cell is only induced through the combination of at least two signals. Each input signal alone does not induce the activation of T cell. Environmental signal integration by a modular AND gate within a CAR design may provide the ultimate strategy to insure safety and expand the number of surface antigens available for therapeutic purposes.

Logic gates are the basic building blocks in electronic circuits that perform logical operations. These have input and output signals in the form of 0's and 1's; '0' signifies the absence of signal while '1' signifies its presence. Similar to the electronic logic gates, cellular signals can serve as logic gates.

Synthetic biology applies many of the principles of engineering to the field of biology in order to create biological devices which can ultimately be integrated into increasingly complex systems. These principles include standardization of parts, modularity, abstraction, reliability, predictability, and uniformity (Andrianantoandro, Basu et al. 2006). The application of engineering principles to biology is complicated by the inability to predict the functions of even simple devices and modules within the cellular environment. Some of the confounding factors are gene expression noise, mutation, cell death, undefined and changing extracellular environments, and interactions with the cellular context (Andrianantoandro, Basu et al. 2006). Thus, while synthetic biology offers much promise in developing systems to address challenges faced in the fields of manufacturing, environment and sustainability, and health and medicine, the realization of this potential is currently limited by the diversity of available parts and effective design frameworks (Wang, Wei et al. 2013).

SUMMARY OF THE INVENTION

The present invention is drawn to apply synthetic biology principles such as logic "AND GATE" to immune cell technology in order for the cells to be stimulated and/or activated only by the combinations of at least two input signals (FIG. 1). In particular, the present invention relates to a method of engineering immune cell for immunotherapy by render them sensitive to the combination of at least two input signals. Said input signals can be external stimuli such as hypoxia or the recognition of a ligand, preferably via the expression at the surface of the cell of a specific chimeric antigen receptor capable of recognizing said ligand. According to the present invention, the recognition of the input signals allow the combination of at least two transmitter domains which activate immune cell response, preferably via signaling protein. Each transmitter protein is independently inactive and thus does not activate immune cell response. Only the combination of these two transmitter domains allows T cell activation. The transmitter domains can be as non limiting examples, protease and an anchored membrane substrate domain comprising a protease cleavage site linked to a signaling protein, split proteins, scaffolding proteins, domains capable of dimerizing, autoinhibited protein with compound able to retrieve the inhibition, complementation of a prior inactivated gene. The present invention also relates to new design of chimeric antigen receptors, cells comprising said chimeric antigen receptors or obtained by the method of the invention, and therapeutic treatment using said engineered immune cell.

BRIEF DESCRIPTION OF THE FIGURES AND TABLES

FIG. 1: Logic "AND GATE" synthetic biology principle. Input (1,2) can be antigens expressed by tumor cells (and/or healthy cells) and/or tumor microenvironments. Output corresponds to the resulting activation of the immune cell.

Figure 2:
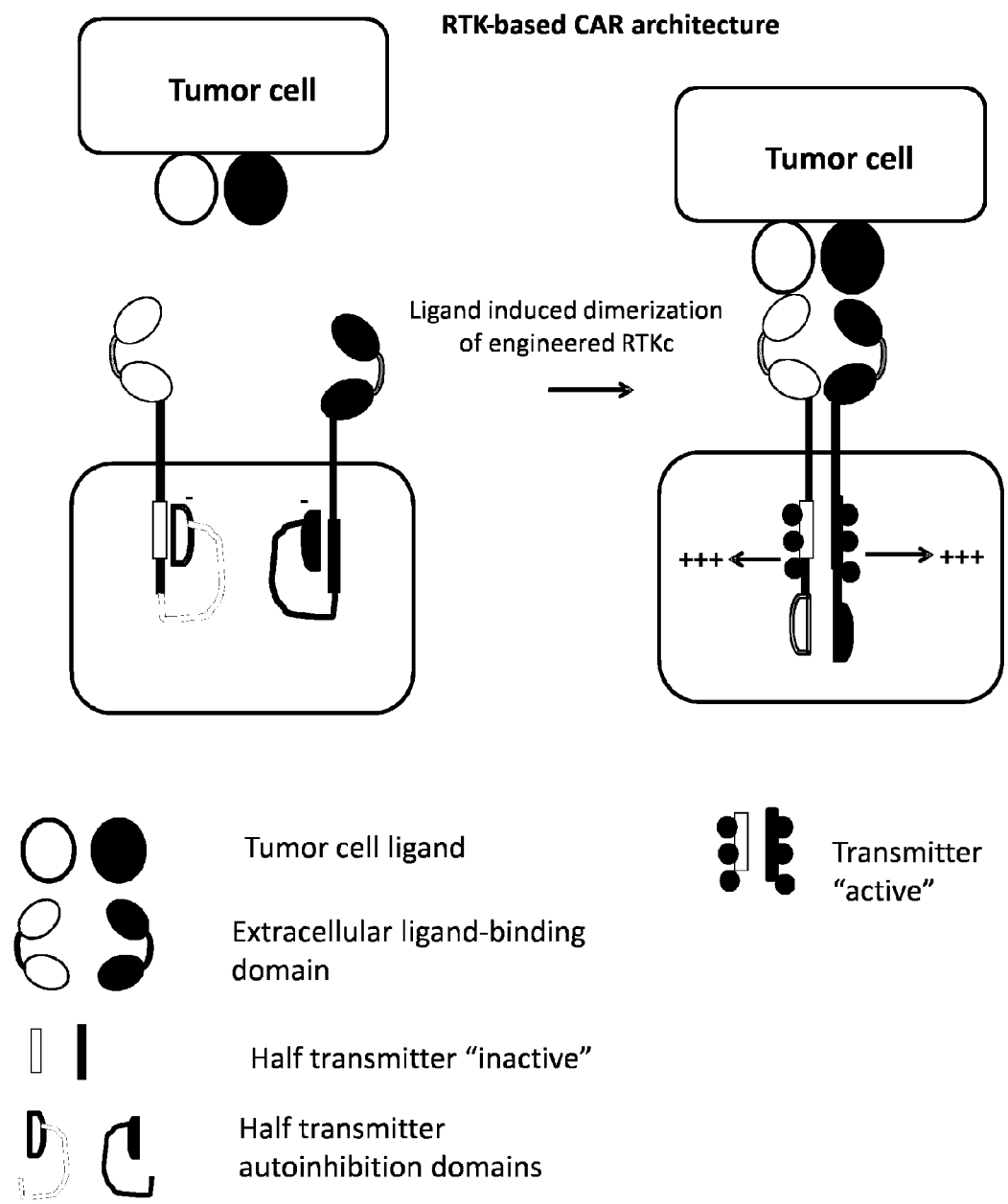

FIG. 2: AND GATE: Tumor antigen-driven dimerization and activation of receptor tyrosine kinase (RTK)-based chimeric antigen receptors. The simultaneous presence of two tumor cell ligands co localized at the tumor cell surface will drive the dimerization of two heterodimeric receptor tyrosine kinase-based chimeric antigen receptors, and lead to their activation via transphosphorylation. On both CARs, the transmitter domains are maintained in an inactive state by autoinhibition (e.g.: the kinase active site is masked by autoinhibitory domain). The presence of two tumor cell ligands colocalized at the tumor cell surface enable driving dimerization of the two CARs resulting in the relief of kinase autoinhibition and enabling activation of transmitter domain via transphosphorylation or its interaction with other molecules as non limiting examples.

Figure 3:
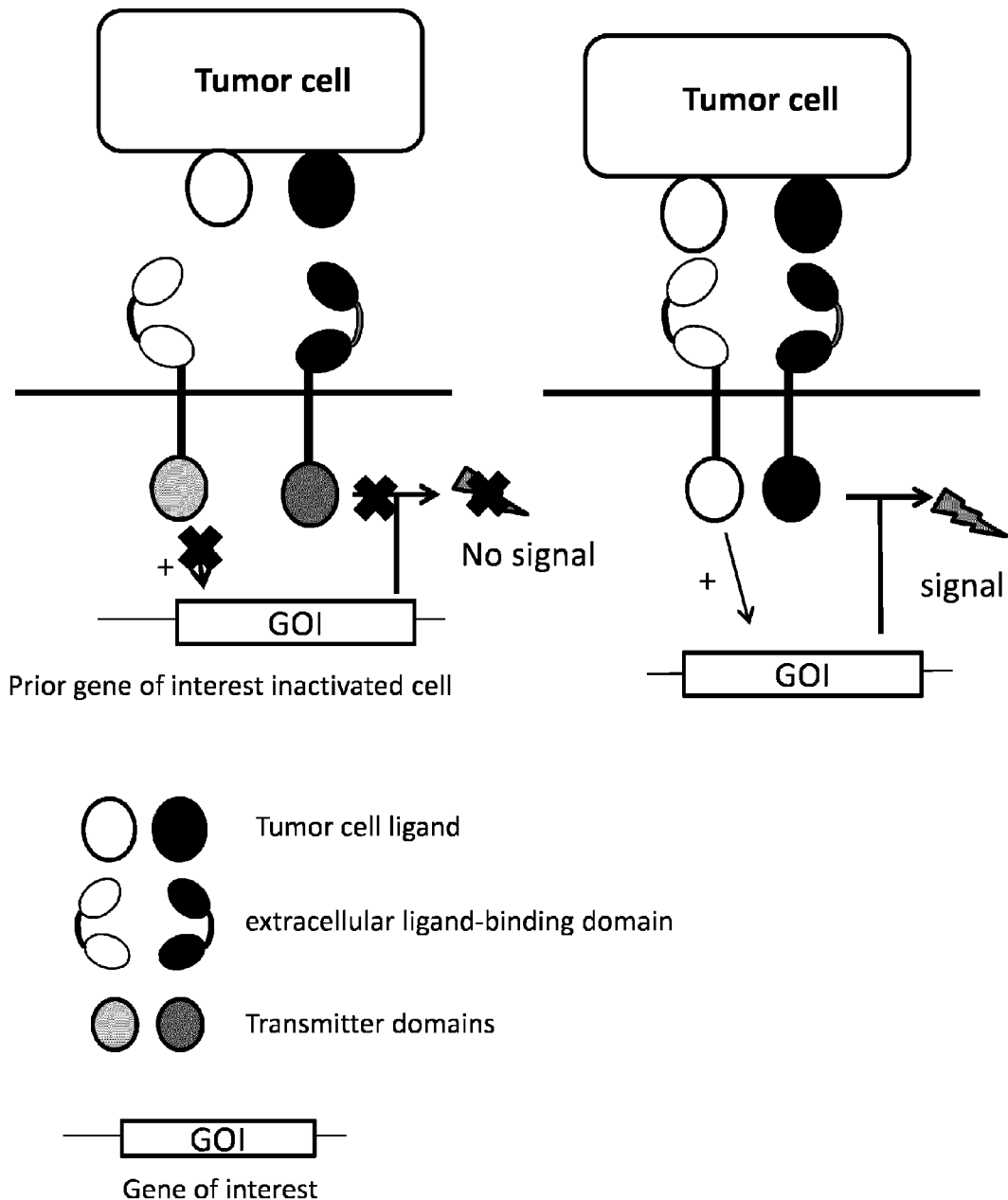

FIG. 3: AND GATE: prior inactivated gene complementation: in a simplified example two different tumor cell ligands can be recognized by two different CARs whose cytoplasmatic domains comprehend two different domains. Simultaneously the knock out of a key gene (GOI) in the signal pathway of the T cell has been performed. Upon the co-localization of the two CARs followed the recognition of the tumor ligand cells the first CAR can activate a factor which will enable the reactivation of the GOI necessary to the transmission of the signal mediated by the second CAR.

Figure 4:
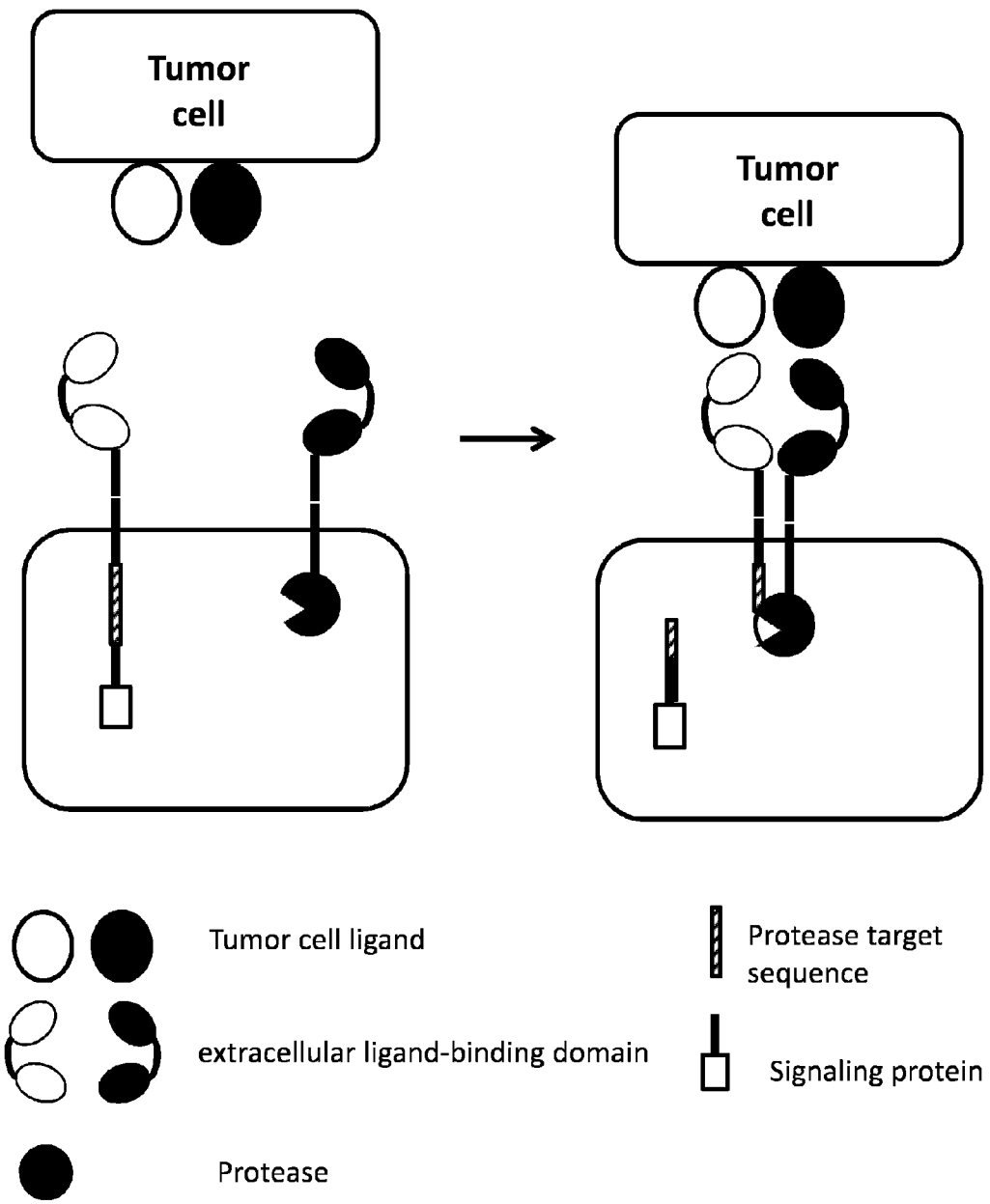

FIG. 4: AND GATE: Protease system. The simultaneous presence of two tumor cell ligands will activate the two CARs. The intracellular domain of the first CAR comprehends a protease target sequence linked to a signaling protein; the intracellular domain of the second CAR is harboring a protease. Each CAR independently is not activated by the presence of the single tumor ligand cell, the activation derives from the co-localization of the two CARs dues to the presence of both tumor ligand cells. The co-localization of the two CARs allows their activation mediated by the cleavage of the target sequence protease and the following release of the signaling protein.

Figure 5:
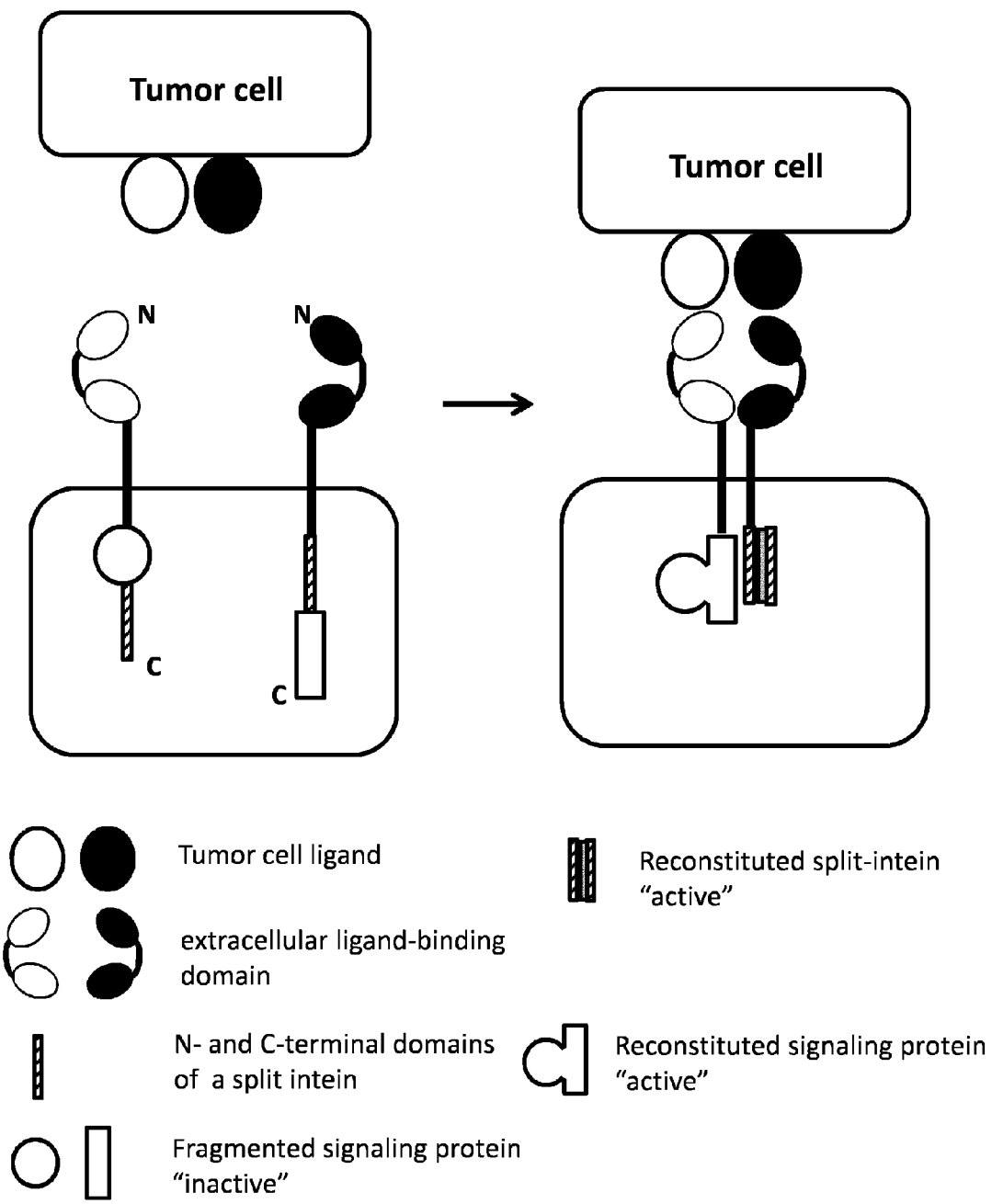

FIG. 5: AND GATE: Split protein system. The simultaneous presence of two tumor cell ligands will activate the two CARs. The intracellular domain of the first CAR comprehends a fragment of the "signaling domain" and C or N domain of the intein. The cytoplasmatic domain of the second CAR is harboring the complementary intein domain plus the complementary signaling domain fragment. Each CAR independently is not activated by the presence of the single tumor ligand cell, the activation derives from the co-localization of the two CARs dues to the presence of both tumor ligand cells. The co-localization of the two CARs allows their activation through the reconstitution of the full active split intein driving the reconstitution of the complete active form of the signaling protein which could initiate different pathways of activation of the T cell. Examples of signaling proteins are ZAP70, SH2 domains, and kinase domain.

Figure 6:
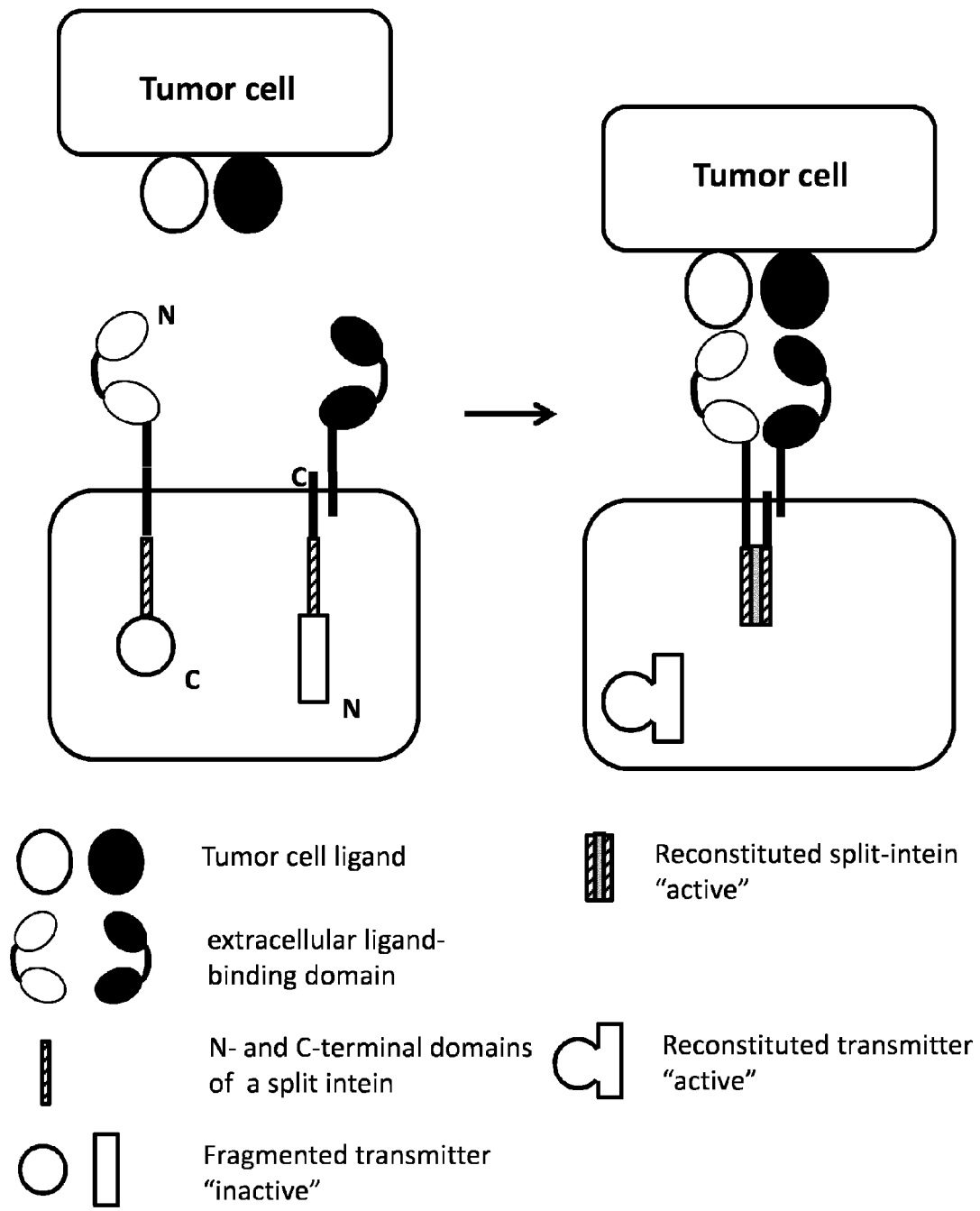

FIG. 6: AND GATE: Split protein system and release of the signaling protein. The simultaneous presence of two tumor cell ligands will activate the two CARs. The intracellular domain of the first CAR comprehends the C terminal inactive fragment of the "signaling protein" and C or N domain of the intein. The intracellular domain of the second CAR is harboring a dimerization domain which could homodimerize with an additional multi-domain. This multi-domain is constituted by the second intein domain and the N domain of the signaling protein fragment. Each CAR independently is not activated by the presence of the single tumor ligand cell, the activation derives from the co-localization of the two CARs dues to the presence of both tumor ligand cells. The co-localization of the two CARs allows their activation through the reconstitution of the full active split intein driving the reconstitution of the complete active form of the signaling protein, which could be released into the cytoplasm to initiate the activation of the T cell.

Figure 7:
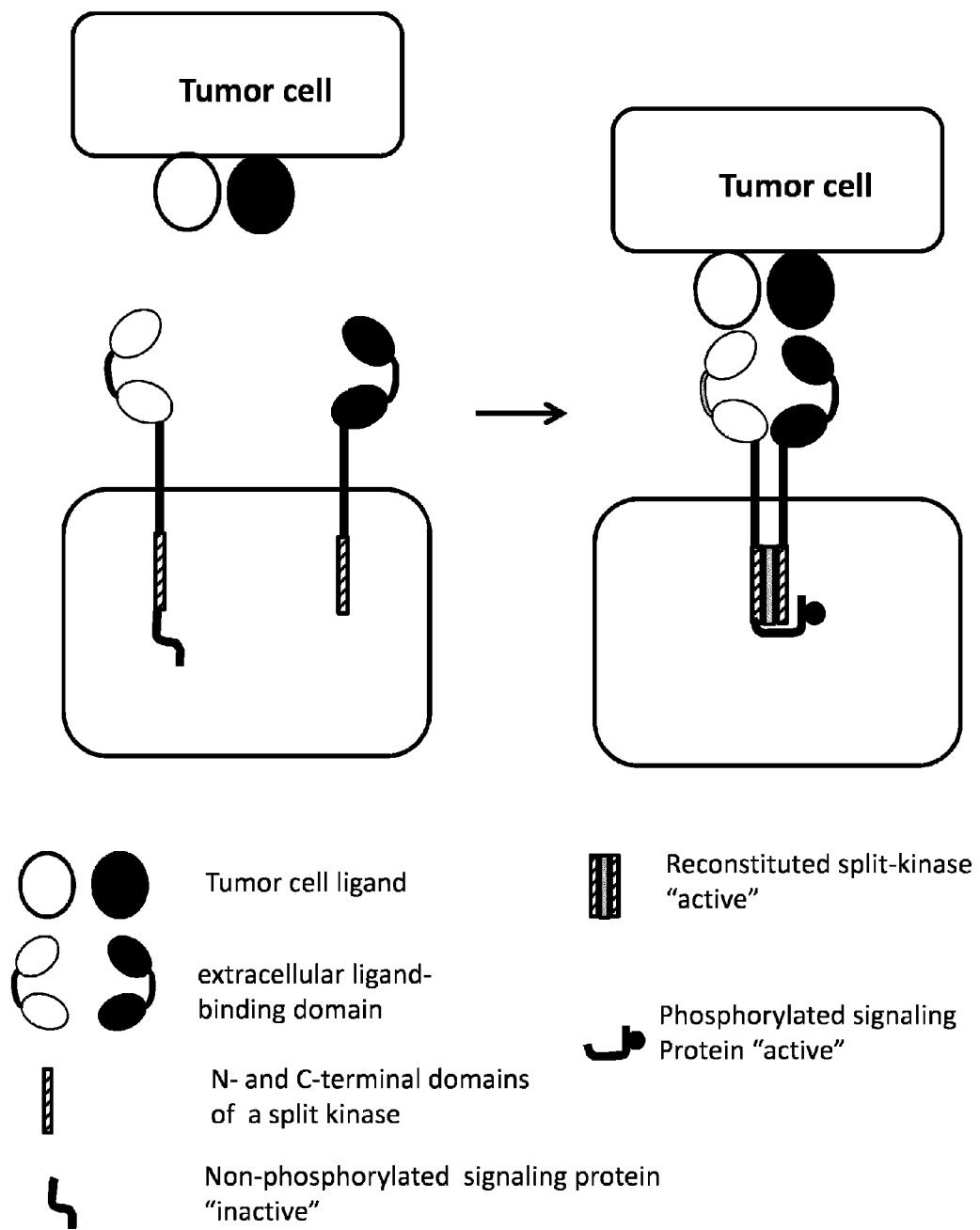

FIG. 7: AND GATE: Kinase based split protein system. The simultaneous presence of two tumor cell ligands will activate the two CARs. The intracellular domain of the first CAR comprehends a signaling protein binding region and C or N domain of a split kinase. The intracellular domain of the second CAR is harboring the complementary kinase domain. Each CAR independently is not activated by the presence of the single tumor ligand cell, the activation derives from the co-localization of the two CARs dues to the presence of both tumor ligand cells. The co-localization of the two CARs allows their activation through the reconstitution of the full active kinase which could be phosphorylated hence start the activation of the T cell. Example of split kinase could be LCK.

Figure 8:
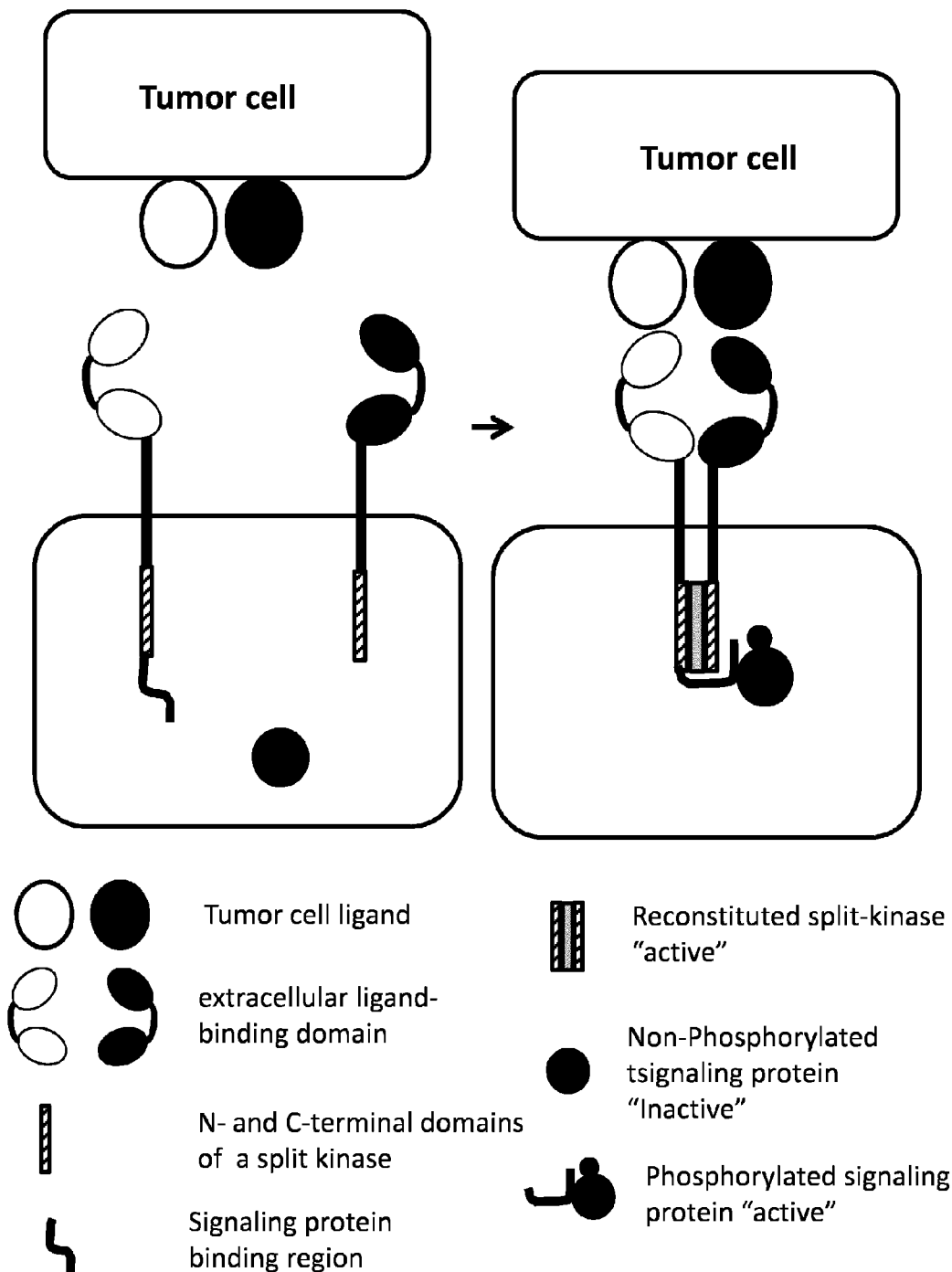

FIG. 8: AND GATE: Kinase based split protein system activation in trans. The simultaneous presence of two tumor cell ligands will activate the two CARs. The intracellular domain of the first CAR comprehends a signaling binding region and C or N domain of a split kinase. The intracellular domain of the second CAR is harboring the complementary kinase domain. Each CAR independently is not activated by the presence of the single tumor ligand cell; the activation derives from the co-localization of the two CARs dues to the presence of both tumor ligand cells.

The co-localization of the two CARs allows their activation through the reconstitution of the full active kinase which could cause a conformational modification on the signaling protein binding region allowing the binding of the signaling protein which could be activated by a phosphorylation in trans.

FIG. 9: AND GATE: Protease based split system and re-localization of the signaling protein. The simultaneous presence of two tumor cell ligands will activate the two CARs. The intracellular domain of the first CAR comprehends the C or N domain of a split protease, a protease target sequence and the signaling protein. The intracellular domain of the second CAR is harboring the complementary split protease domain. Each CAR independently is not activated by the presence of the single tumor ligand cell; the activation derives from the co-localization of the two CARs dues to the presence of both tumor ligand cells. The co-localization of the two CARs allows their activation through the reconstitution of the full active protease which could cleave the protease target sequence and cause the release of the signaling protein.

Figure 10:
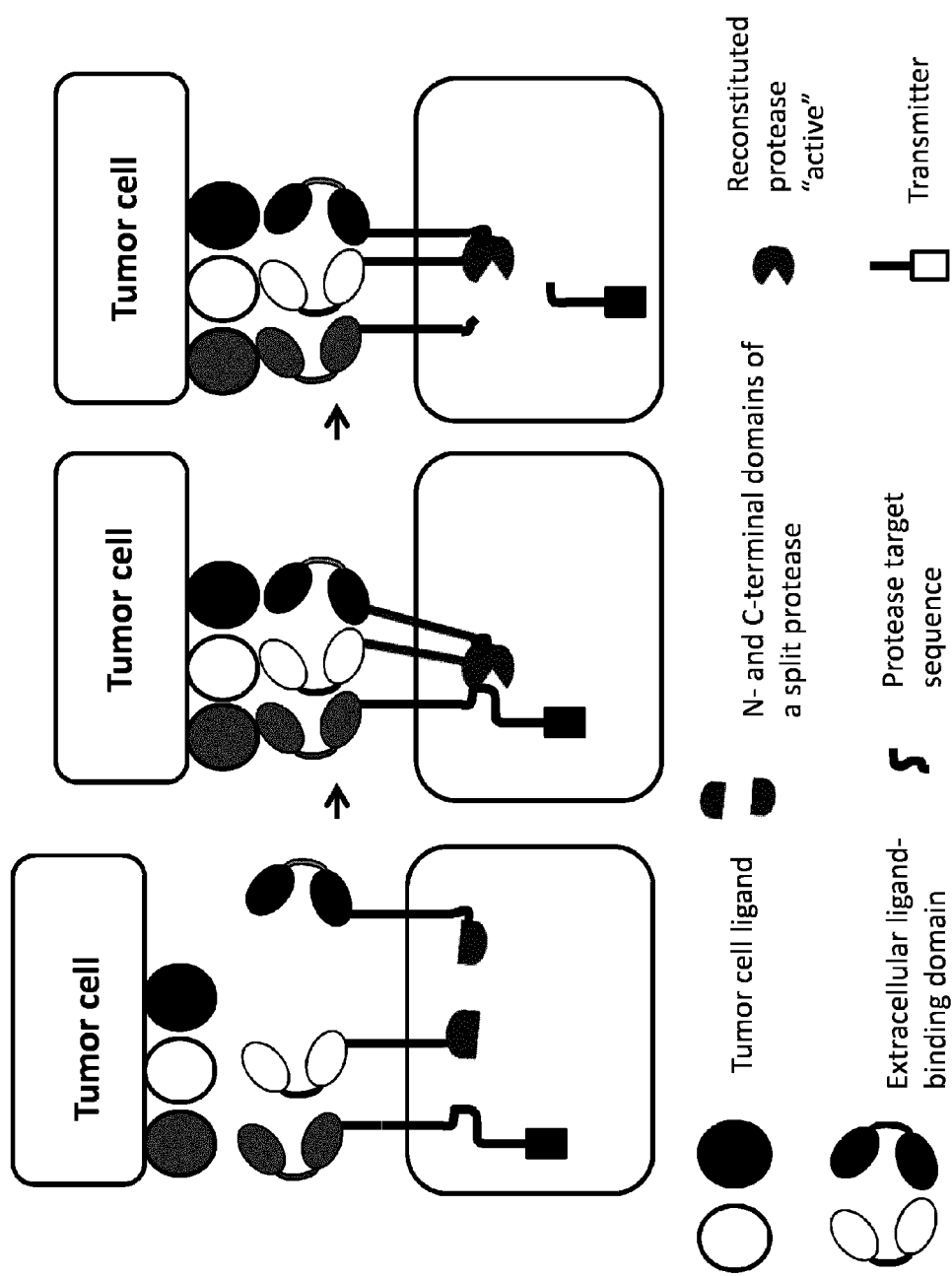

FIG. 10: AND GATE: Protease based split system using three CARs. The simultaneous presence of three tumor cell ligands will activate the CARs. The intracellular domain of the first CAR comprehends the protease target sequence and the signaling protein. The intracellular domains of the second and third CARs are constituted by the two complementary split protease domains. Each CAR independently is not activated by the presence of the single tumor ligand cell; the activation derives from the co-localization of three CARs dues to the presence of the three tumor ligand cells. The co-localization of three CARs allows their activation through the reconstitution of the full active protease which could cleave the protease target sequence and cause the release of the signaling protein.

Figure 11:
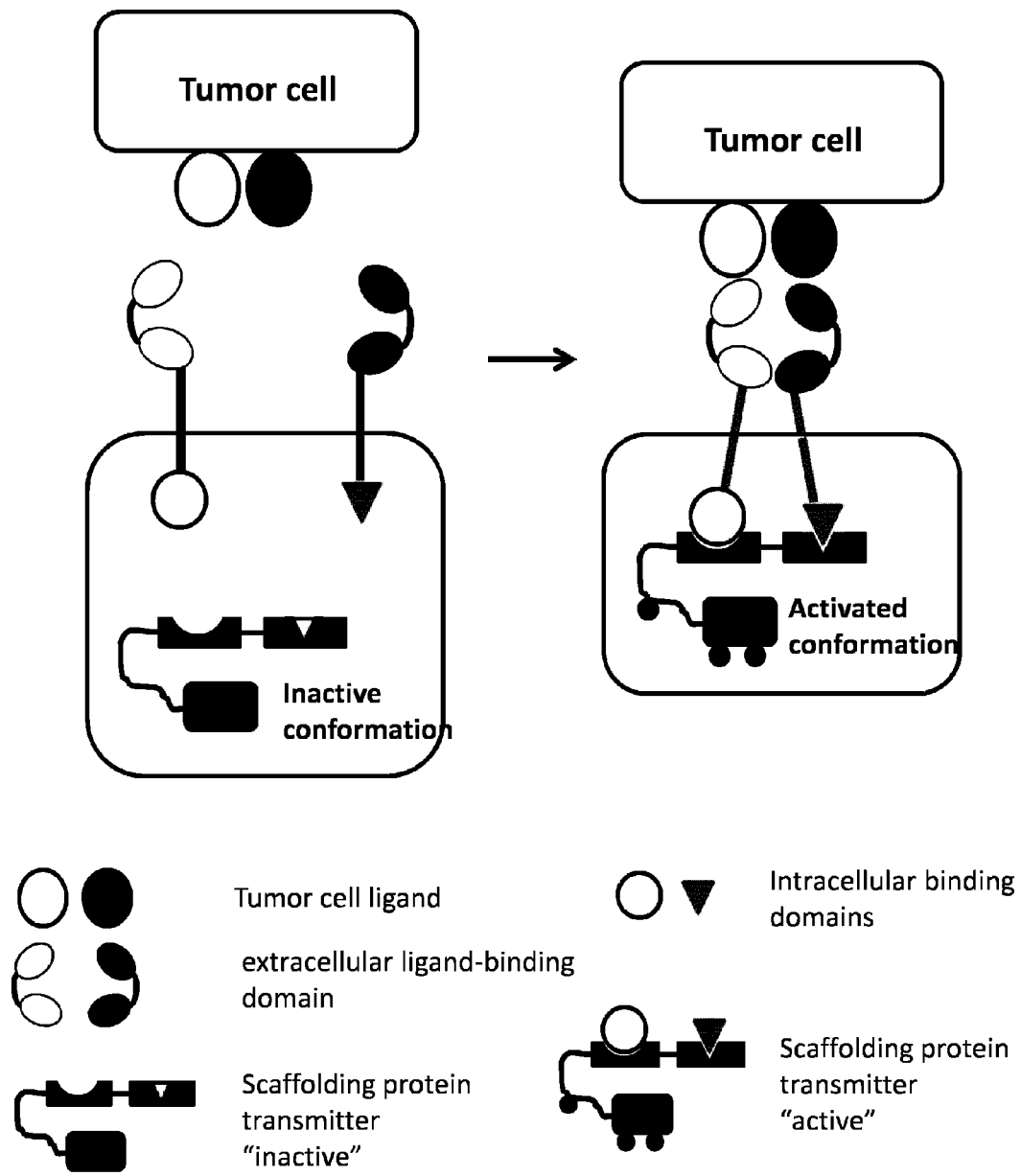

FIG. 11: AND GATE: Scaffolding protease based system. The simultaneous presence of two tumor cell ligands will activate the two CARs. The intracellular domain of the first CAR comprehends a first protein domain. The intracellular domain of the second CAR is harboring a second protein domain. Each CAR independently is not activated by the presence of the single tumor ligand cell, the activation derives from the co-localization of the two CARs dues to the presence of both tumor ligand cells. The co-localization of the two CARs allows their activation through the binding of the protein domain 1 and 2 to the inactive scaffolding protein. Upon the complex binding the active form of the scaffolding protein is reconstituted and the T cell can be activated. Examples of scaffolding proteins are Carma1, SP76, hemITAM, DLG1, KSR.

Figure 12:
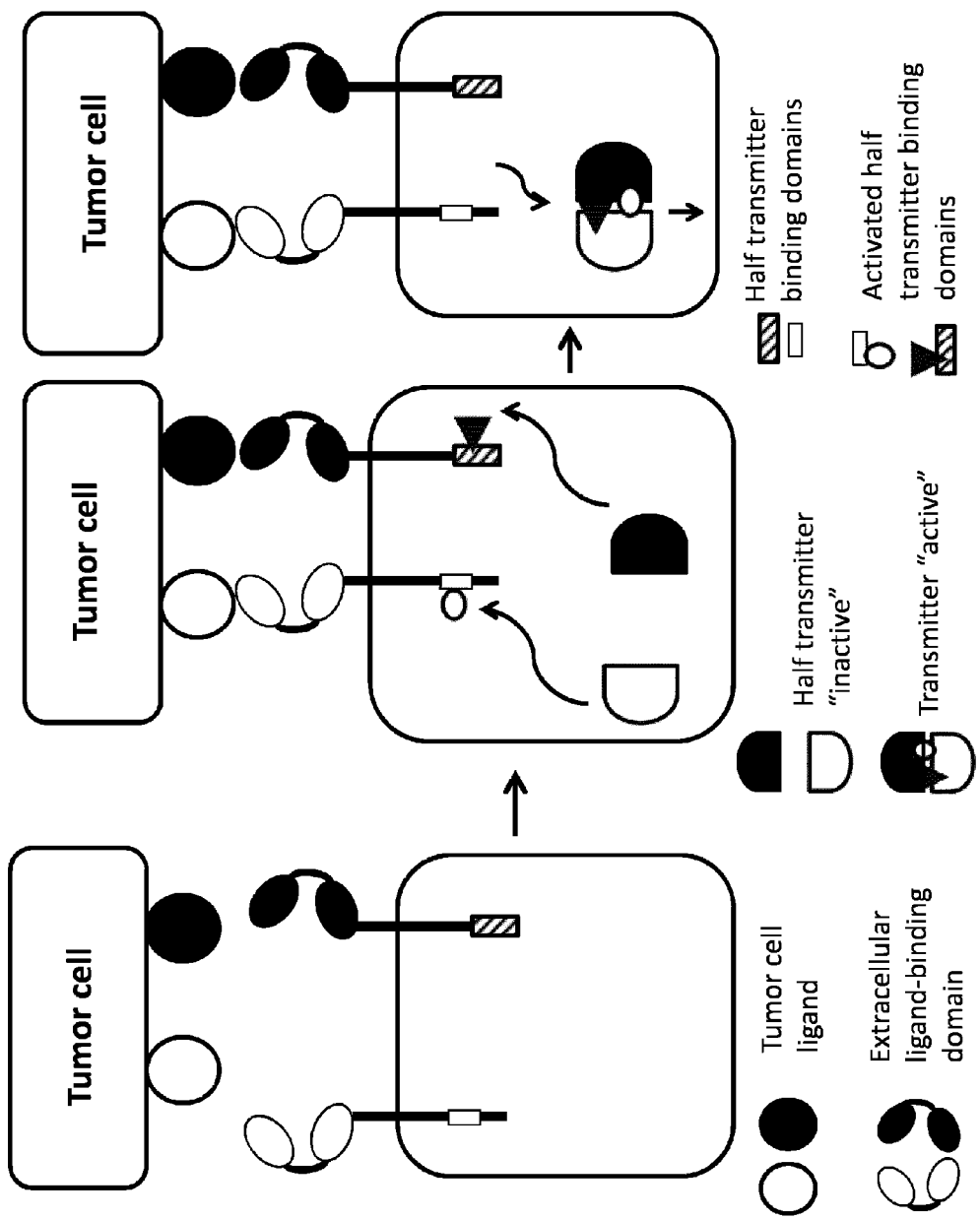

FIG. 12: AND GATE: Based on double activation of engineered heterodimeric domains. The simultaneous presence of two tumor cell ligands will activate the two CARs. The intracellular domain of the first CAR comprehends a first transmitter binding domain. The intracellular domain of the second CAR is harboring a second transmitter binding domain. Each Car independently is not activated by the presence of the single tumor ligand cell, the activation derives from the co-localization of the two CARs dues to the presence of both tumor ligand cells. The co-localization of the two CARs allows the activation of the two transmitter binding domains (e.g. phosphorylation and post-translation modifications) which can trigger the recruitment of a transmitter which can activate the T cell.

Figure 13:
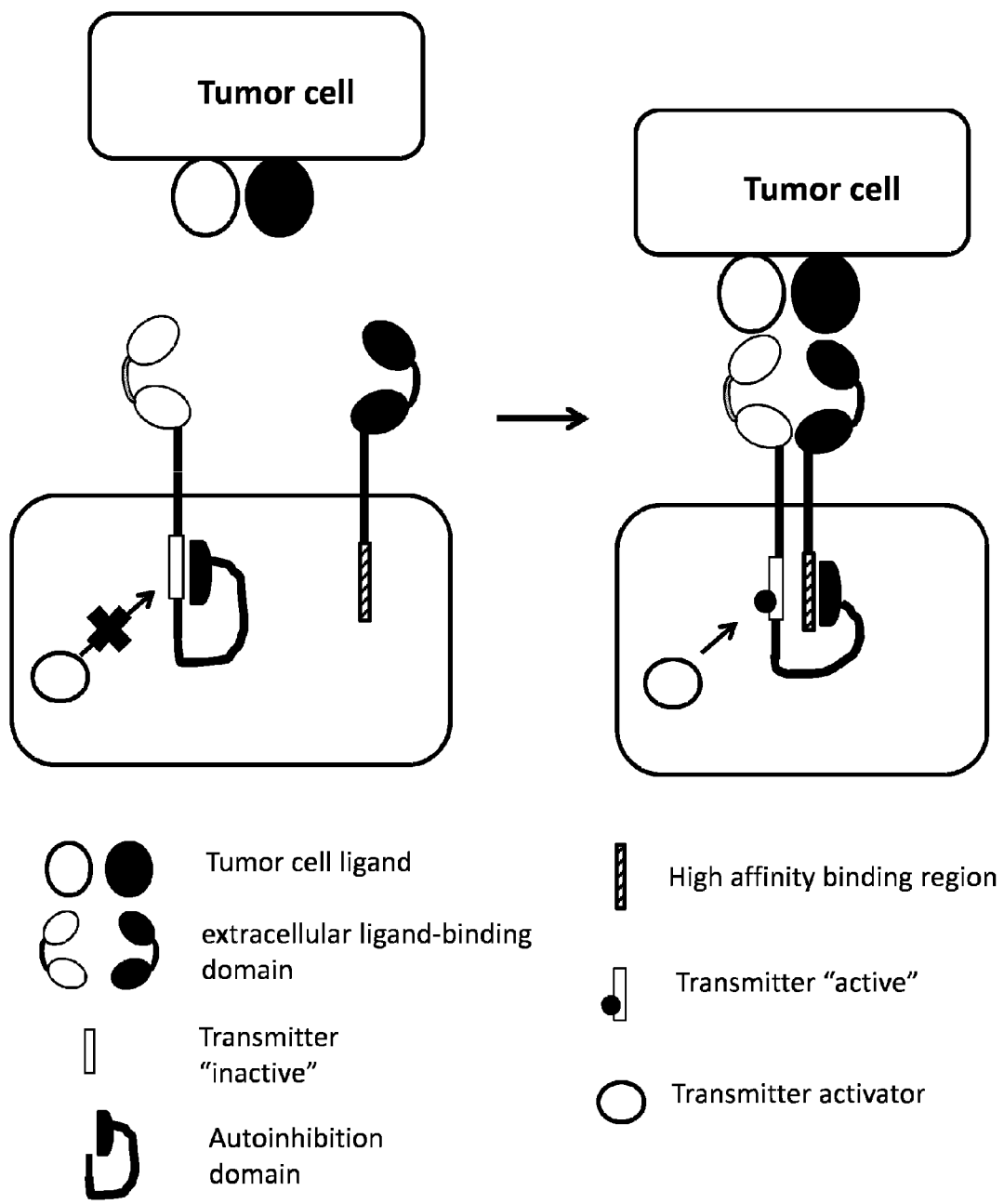

FIG. 13: AND GATE: Autoinhibition system: induced activation upon competitive binding. The simultaneous presence of two tumor cell ligands will activate the transmitter. On the first CAR, the transmitter domain is maintained in an inactive state by autoinhibition (e.g.: by interaction with a "shielding" protein or antibody). The colocalization of the second CAR upon binding to its ligand will displace the shielding molecule to itself on a domain of higher affinity (intermolecular displacement). The "unshielded" transmitter can then be activated (e.g.: by post-translational modifications or interaction with other molecules).

Figure 14:
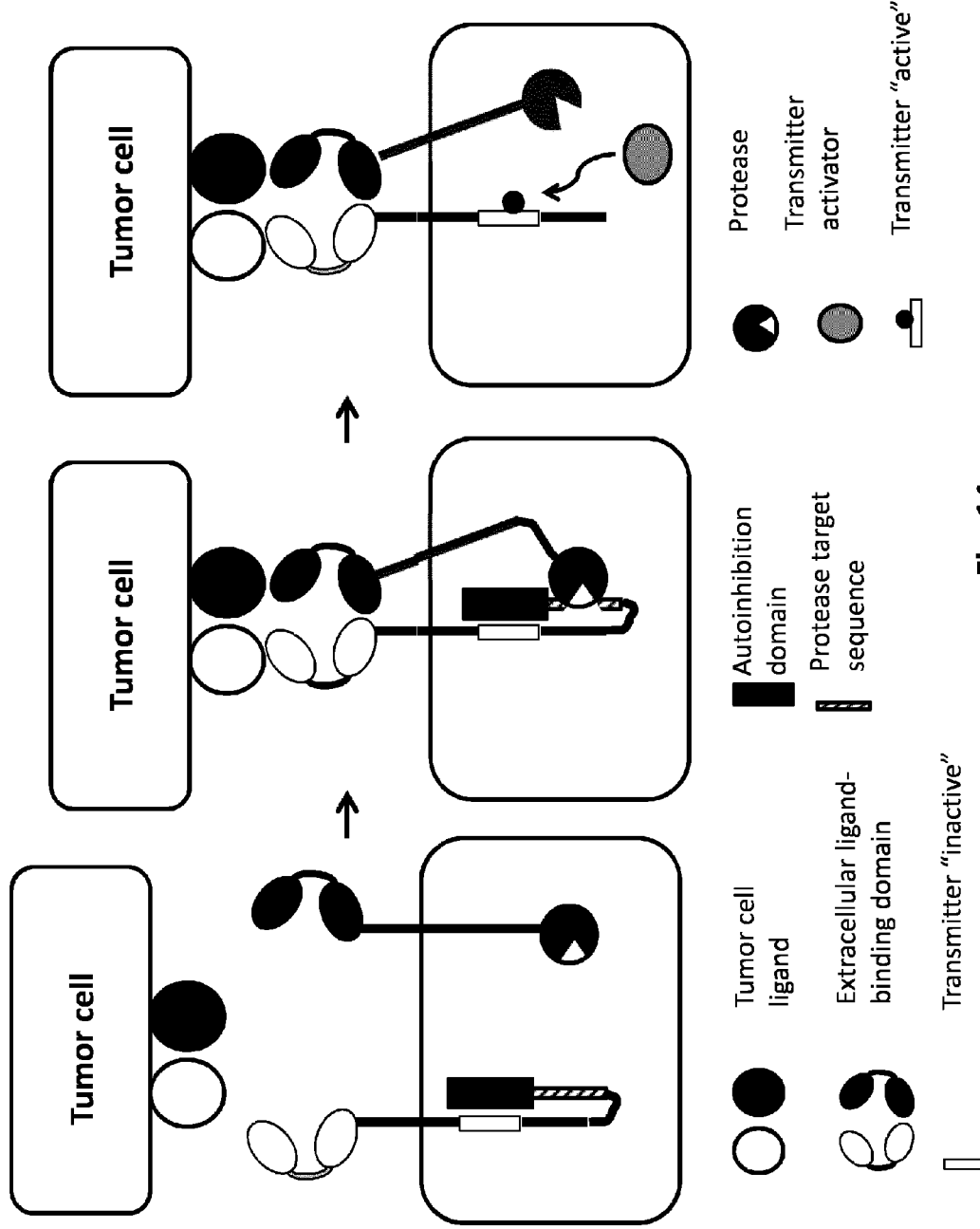

FIG. 14: AND GATE: Autoinhibition system: induced activation upon enzymatic cleavage of the inhibition domain. The simultaneous presence of two tumor cell ligands will activate the transmitter. On the first CAR, the transmitter domain is maintained in an inactive state by autoinhibition (e.g.: by interaction with a "shielding" protein or antibody). The colocalization of the second CAR upon binding to its ligand will bring a protease domain in close proximity of a protease target sequence present on the first car and thus allow to displace the shielding molecule. The "unshielded" transmitter can then be activated (e.g.: by post-translational modifications or interaction with other molecules).

Figure 15:
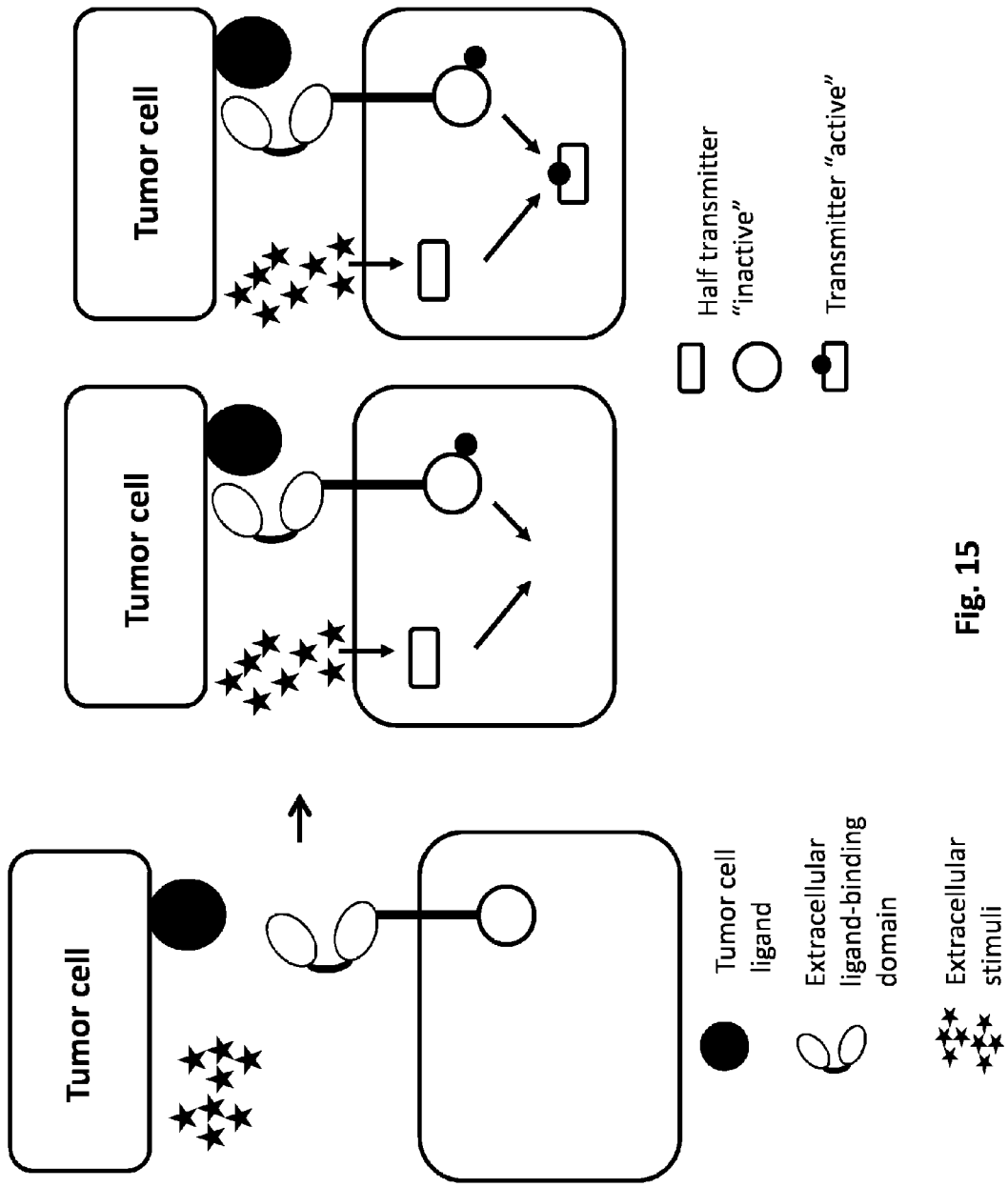

FIG. 15: AND GATE: Receptor binding and external stimuli to induce activation of the transmitter protein. The simultaneous binding of a CAR to its tumor cell ligand and the exposition of the engineered T cell to a tumor cell extracellular stimulus will activate the transmitter. External stimuli encompass variation in concentration of metabolites, small molecules, peptide, small proteins (chemokines, cytokines) and physico/chemical conditions (pH, hypoxia, redox potential).

Figure 16:
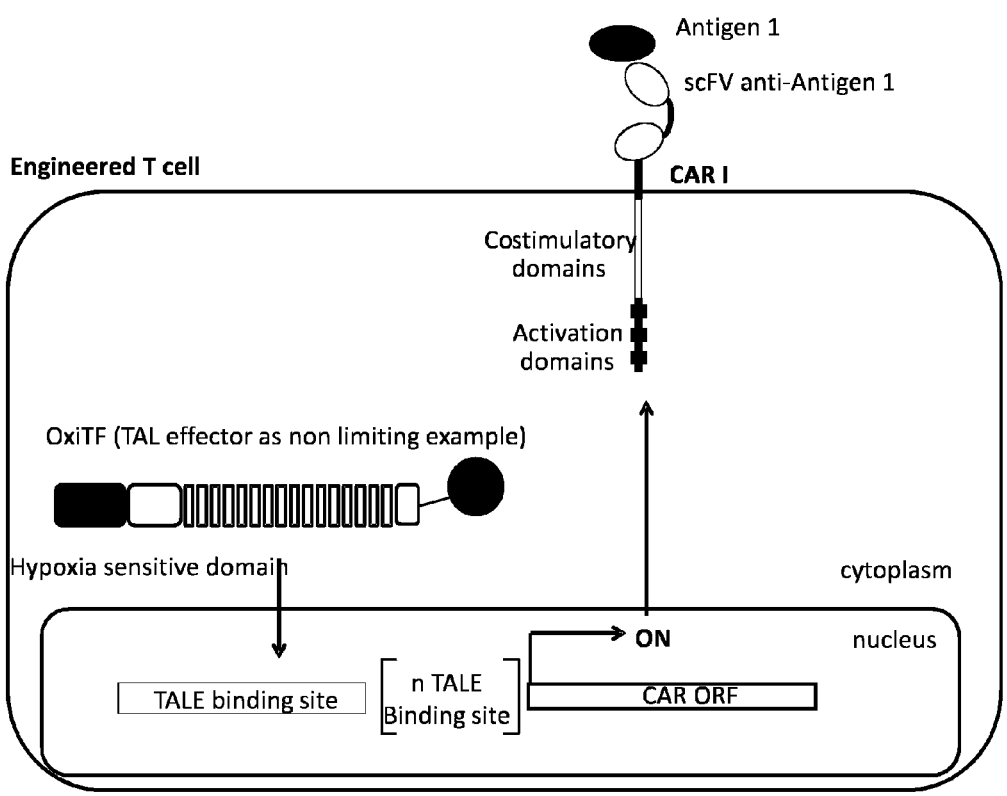

FIG. 16: AND GATE: Hypoxia dependent activation system in the presence of one tumor antigen.

The simultaneous presence of engineered T cells with one tumor cell ligand in an oxygen depleted environment, triggers T cells activation. To enable such logical AND gate activation system, T cell are engineered to harbor an oxygen-inducible synthetic activation pathway. Such synthetic pathway is made of three different elements including an engineered transcription factor sensitive to oxygen concentration (OxiTF), a synthetic promoter specific for the OxiTF driving the expression of the third element, a chimeric antigen receptor (CAR I). The OxiTF is design to activate a synthetic genetic element encoding a CAR specific for tumor antigen within engineered T cells. Upon solid tumor encounter, engineered T cells detect oxygen depletion and trigger CAR I production. Cell surface exposure of CARI enables the recognition of tumor antigen that eventually triggers T cells activation and proliferation via the activation and co-stimulatory domains present within CARI.

Figure 17:
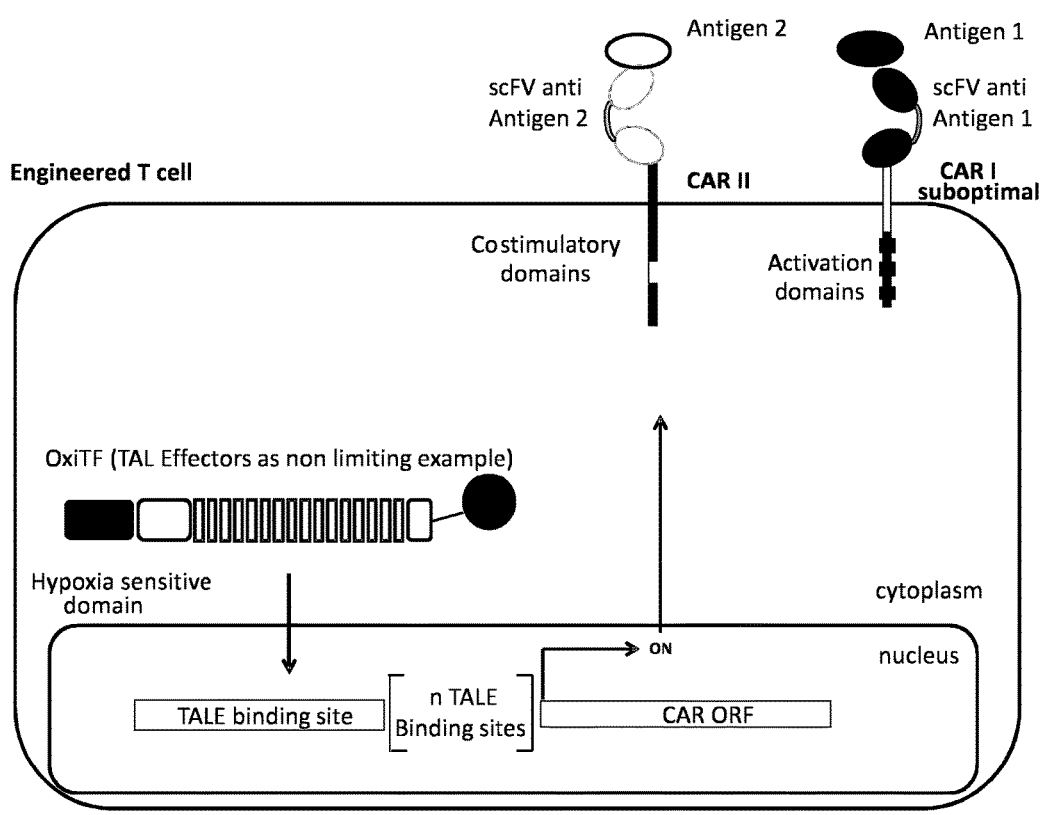

FIG. 17: AND GATE: Hypoxia dependent activation system in the presence of two tumor antigen.

The simultaneous presence of engineered T cells with two tumor cell ligands in an oxygen depleted environment, triggers T cells activation. To enable such logical AND gate activation system, T cells are engineered to harbor an oxygen-inducible synthetic activation pathway. Such synthetic pathway is made of four different elements including an engineered transcription factor sensitive to oxygen concentration (OxiTF), a synthetic promoter specific for the OxiTF driving the expression of the third element, a chimeric antigen receptor (CAR II) specific for tumor antigen II. The system is completed with a fourth element, consisting in a constitutively expressed CARI, specific for tumor antigen I. The OxiTF is design to activate a synthetic genetic element encoding a CARII within engineered T cells. Upon solid tumor encounter, engineered T cells detect oxygen depletion and trigger CAR I production. Cell surface exposure of CARII along with CARI enables the recognition of tumor antigen II in addition to the pre-existing CARI-tumor antigen I complex. Simultaneous presence of both CAR/

Tumor antigen complexes eventually triggers T cells activation and proliferation via the activation and co-stimulatory domains present within CARI and II.

FIG. 18: AND GATE: Illustration of the AND GATE principle applied to the T cell system activation. The extracellular of a CAR contains two ligand-binding domains that that exist under two conformations ("active" and "inactive"). In absence of the two tumor cell ligands, the equilibrium is strongly displaced towards the "inactive form". Only the simultaneous binding of the two ligand-binding domains to their respective tumor cell ligands (two inputs) will trigger a positive signal to the intracellular domain of the CAR (output).

Figure 19:
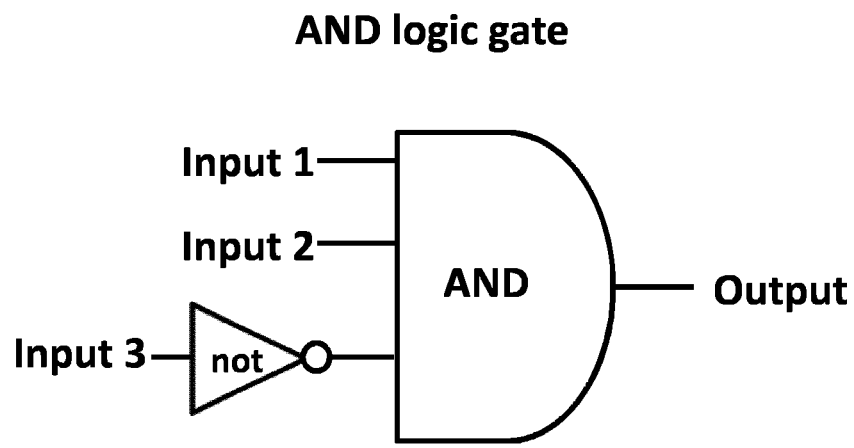

FIG. 19: AND NOT GATE: General schema. Illustration of the AND NOT GATE principle applied to the T cell system activation. The simultaneous presence of two tumor cell ligands and the absence of an healthy cell ligands will trigger a positive output. The input 1 and 2 corresponds to the presence of a tumor cell ligand while the third input should not be a healthy cell ligand. The first and the second CAR have a co-stimulatory cytoplasmatic domains while the third CAR is harboring an inhibitory domain whose inhibitor effect will be blocked in case of non recognition of the healthy cell ligand.

Figure 20:
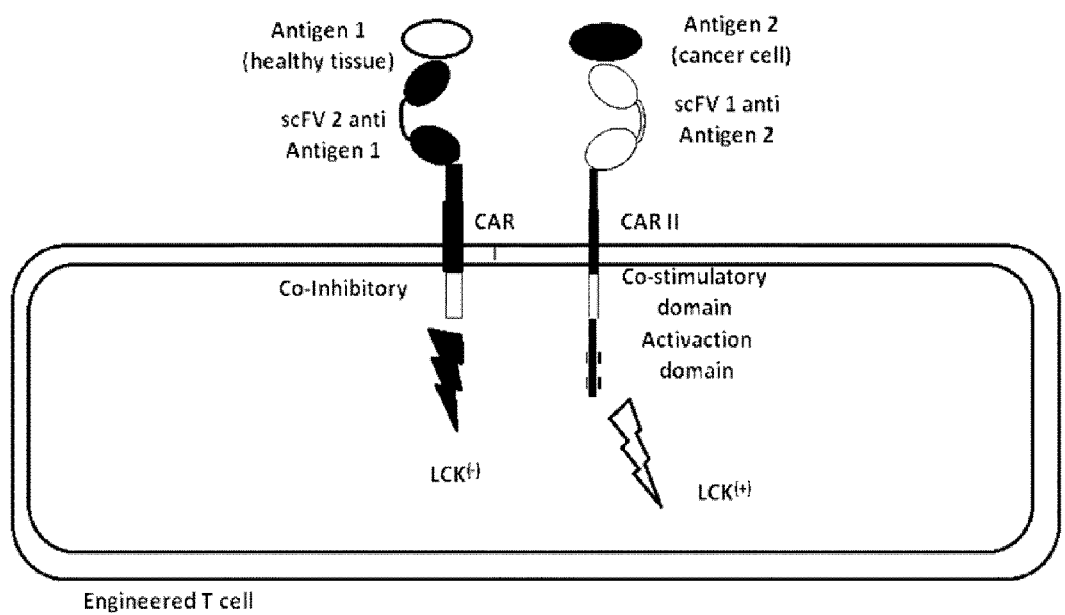

FIG. 20. Generation of two types of LCKs to inhibit and to stimulate the T cell signaling cascade The first CAR will recognize an antigen of an healthy cell with an inhibitory domain which will stimulate the transcription of a form constitutively negatively regulated of LCK$^{(-)}$. This first CAR will be coupled with a second one which contains a co-stimulatory domains which will activate the transcription of LCK$^{(+)}$ form, producing an high level of activation of the T cell.

Figure 21:
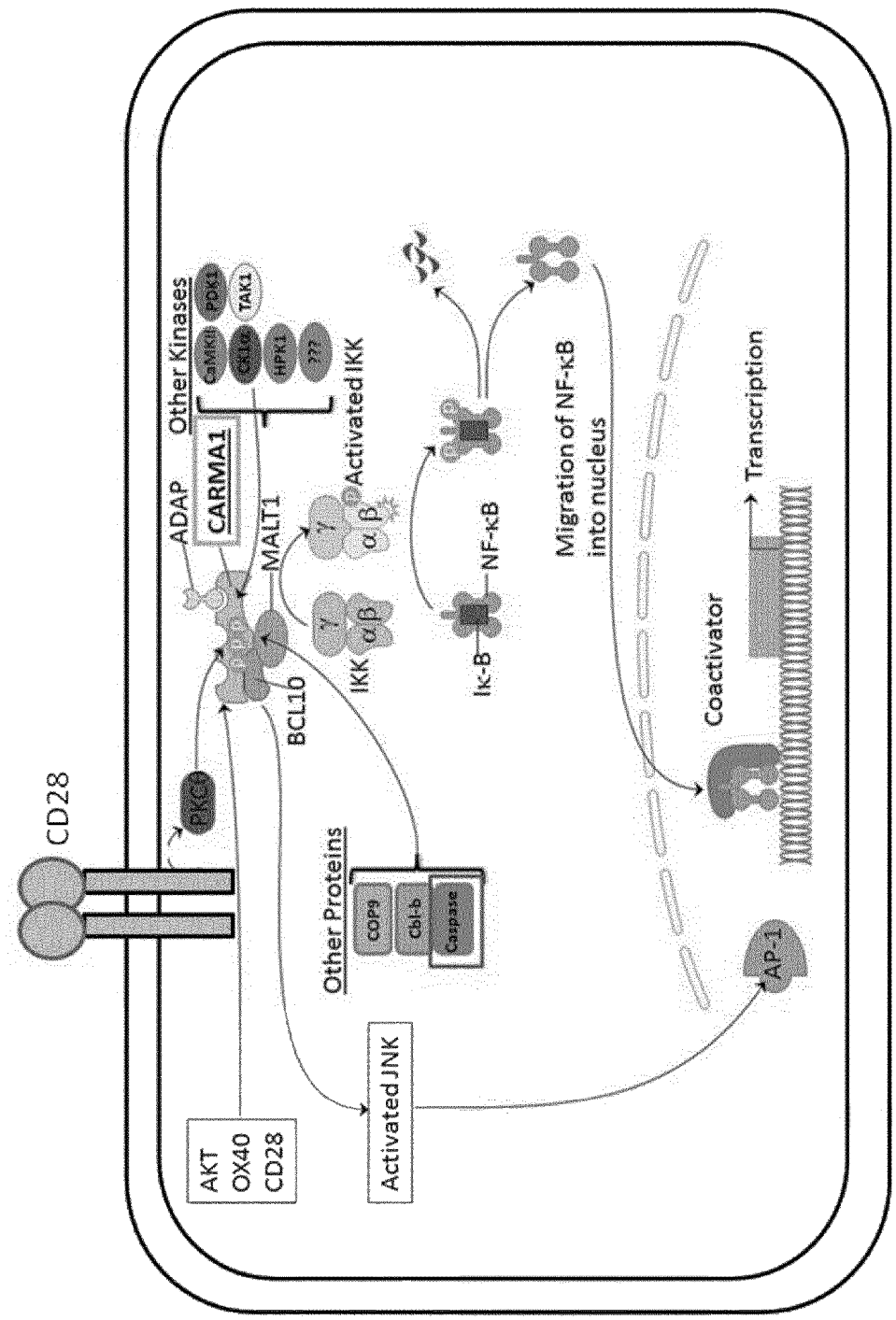

FIG. 21. Control of T cell activation through CAR-mediated regulation of CARMA1 protein. The stimulation of TCR after recognizing the antigen is linked to the recruitment of CD28 which leads to the activation of PKCθ, which in turn phosphorylates and activates CARMA1. CARMA1 constitutes a crucial signalosome for the transmission of the T cell Receptor (TCR) signaling and in general for T cell activation. CARMA1 recruits different proteins forming a multi-protein complexes that finally can activate two different signaling cascades: NF-κB and c-jun N-terminal kinase (JNK).

Figure 22:
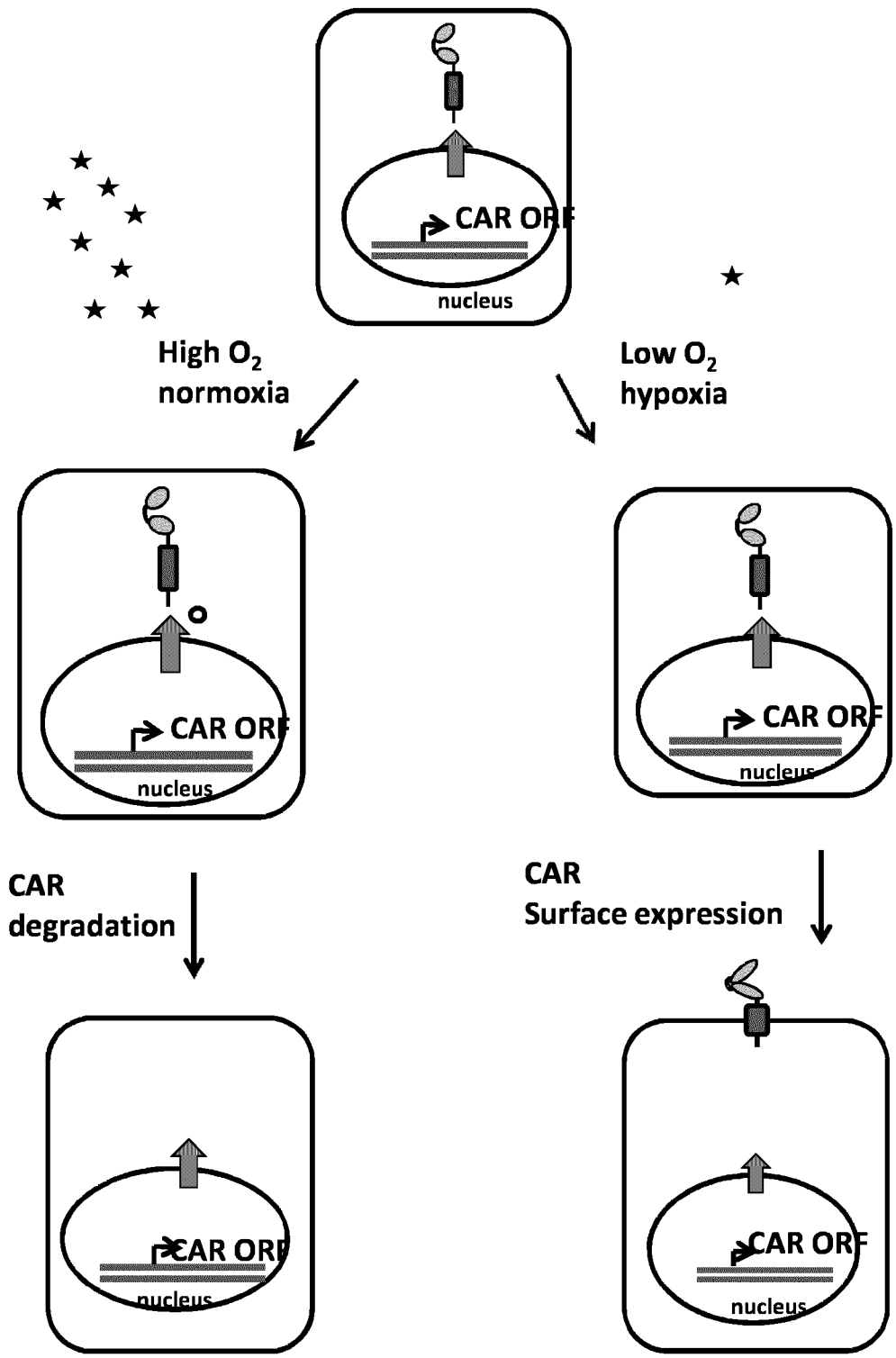

FIG. 22. Functioning of the HIF hypoxia System. In normoxia (high $O_2$), HIFα is hydroxylated by HIFα-specific prolyl hydroxylases (PHD1-3) which are oxygen sensing. Hydroxylation triggers poly-ubiquitylation of HIFα and targets the latter for proteosomal degradation by an E3 ubiquitin ligase. In hypoxia (low $O_2$), occur an inhibition of hydroxylation via TCA cycle intermediates, a stabilization of the HIFα protein and an impairment of HIF transcriptional activity.

Figure 23:
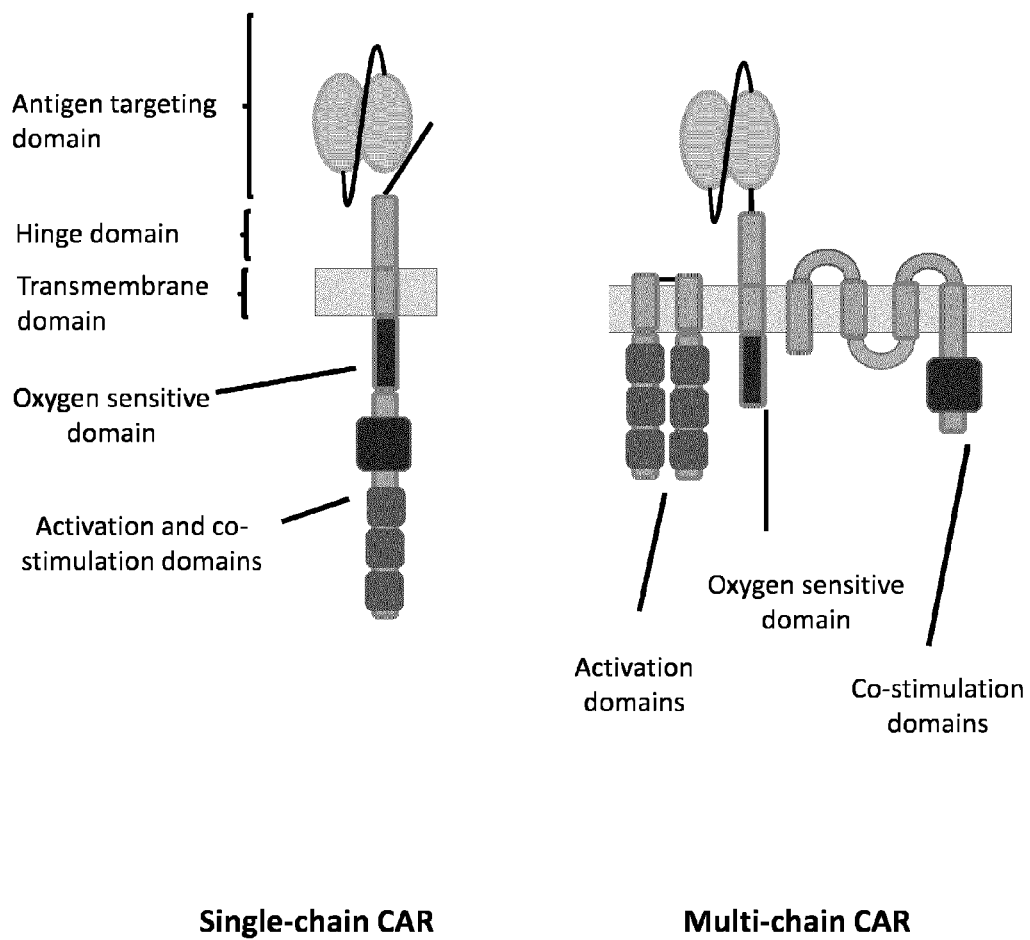

FIG. 23. Different chimeric antigen receptor (CAR) architectures carrying oxygen-sensitive domain such as HIFα. At left, a single-chain CAR (scCAR) carries on the same and unique chain the extracellular binding domain (here scFv), the oxygen domain (ex: HIF1) and the activation and co-activation domains. At right is shown as an exemplary conformation a multi-chain CAR (mcCAR) wherein the α-chain carries the scFv and the oxygen domain; the β-chain carries the co-stimulatory domain and the γ-chain carries the activation domain(s).

FIG. 24. A) Surface presentation of chain-HIF1 (a.a. 380-630) versus α-chain WT α-in normoxia or hypoxia. The surface exposition of CAR T-cells having HIF1 in hypoxia is similar to the one of control CAR T-cells (without α-HIF1), whereas the surface exposition is much reduced in normoxia condition, showing a good expression of CAR-αHIF1.

(B) Surface presentation of the α-chain-HIF1 (a.a. 380-630) versus α-chain WT after return from hypoxia to normoxia. The expression of CAR αHIF1 drops from hypoxia to normoxia condition. This is a reversible and dynamic system: in normoxia condition, the CAR expression is inhibited by the degradation of α-HIF1 and α-chain polypeptides in a temporally manner, and in hypoxia condition (i.e. tumor environment), the α-HIF1 and α-chain polypeptides are expressed.

FIG. 25. (A) Surface detection of α-HIF mcCAR versus control CAR in normoxia or hypoxia. In this experiment, less total RNA is used, the results obtained are similar to those of FIG. 23;

(B) Induced cytotoxicity in normoxia. The control multi-chain CAR (without α-HIF1) shows a high target cell killing, whereas the latter is null for the HIF-mcCAR in normoxia. In view of these results of cytotoxicity, as well as those of surface exposition, this indicates that the HIF system is fully functional within a chimeric antigen receptor.

FIG. 26. Surface presentation of various α-chain-HIF versus WT α-chain in normoxia or hypoxia. (A) HIF1-mcCAR (a.a. 380-630) construct with the -EA-linker; (B) HIF1-mcCAR (a.a. 344-417); (C) HIF3-mcCAR (a.a. 480-571); (D-E-F): same as for (A-B-C) but return from hypoxia to normoxia.

All the results obtained here by lentiviral delivery demonstrate that both HIF1 and HIF3 systems are functional and behave similarly. Also, it is shown that different parts of the HIF protein can be used with or without linker.

Legends:

| Sample | Conditions | Histogram |
|---|---|---|
| Isotype control | Hypoxia | solide line-Filled |
| α β γ | Normoxia | Dotted line |
| α β γ | Hypoxia | Dashed line |
| α-HIF β γ | Normoxia | Dotted line-Filled |
| α-HIF β γ | Hypoxia | Dashed line-Filled |

Figure 27:
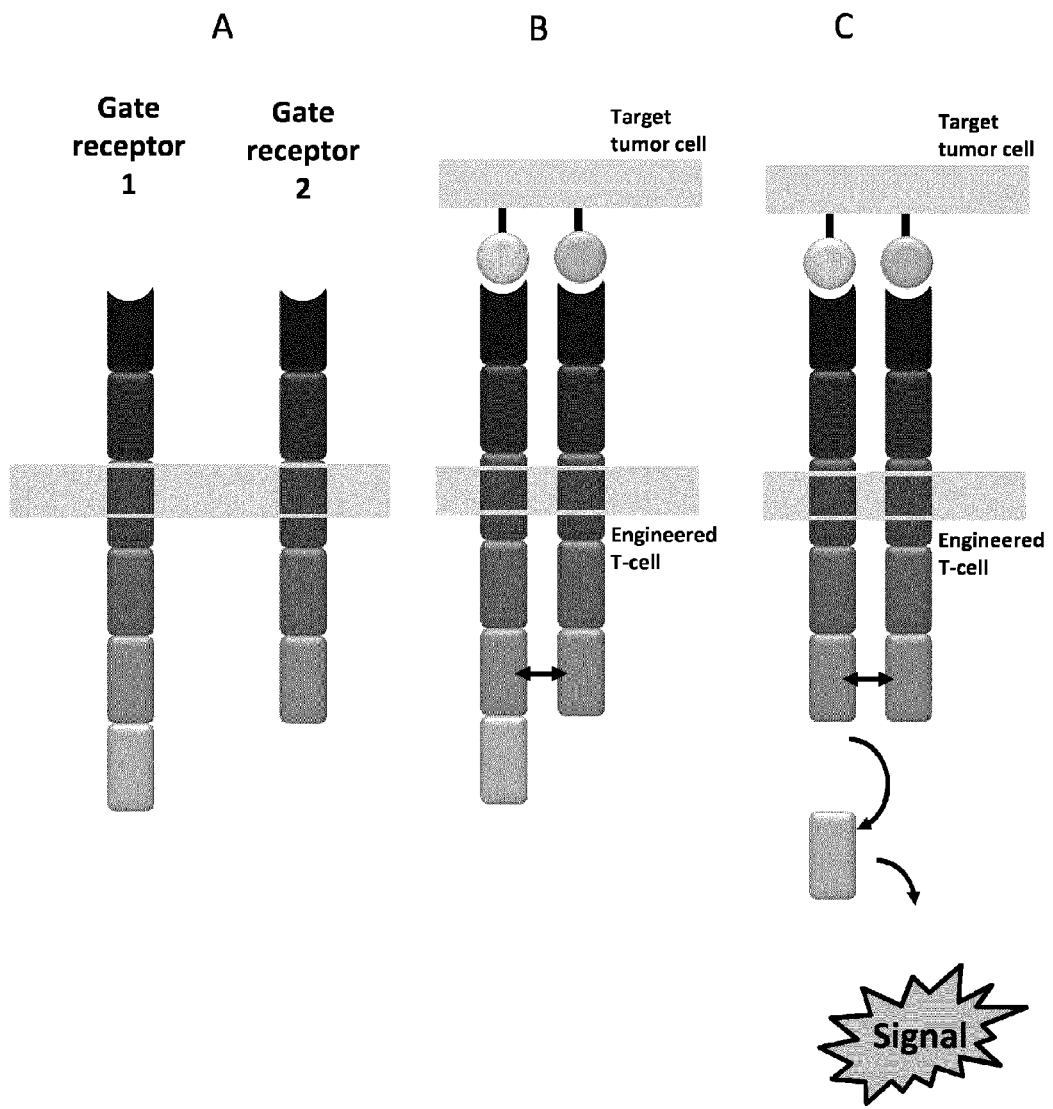

FIG. 27 (A) Schematic representation of the dual receptors logic AND gate. (B) Interaction of both membrane protein partners with their target ligand will trigger the colocalization of the intracellular interacting domains. (C) Release of the transmitter domain is triggering the output signal.

Figure 28:
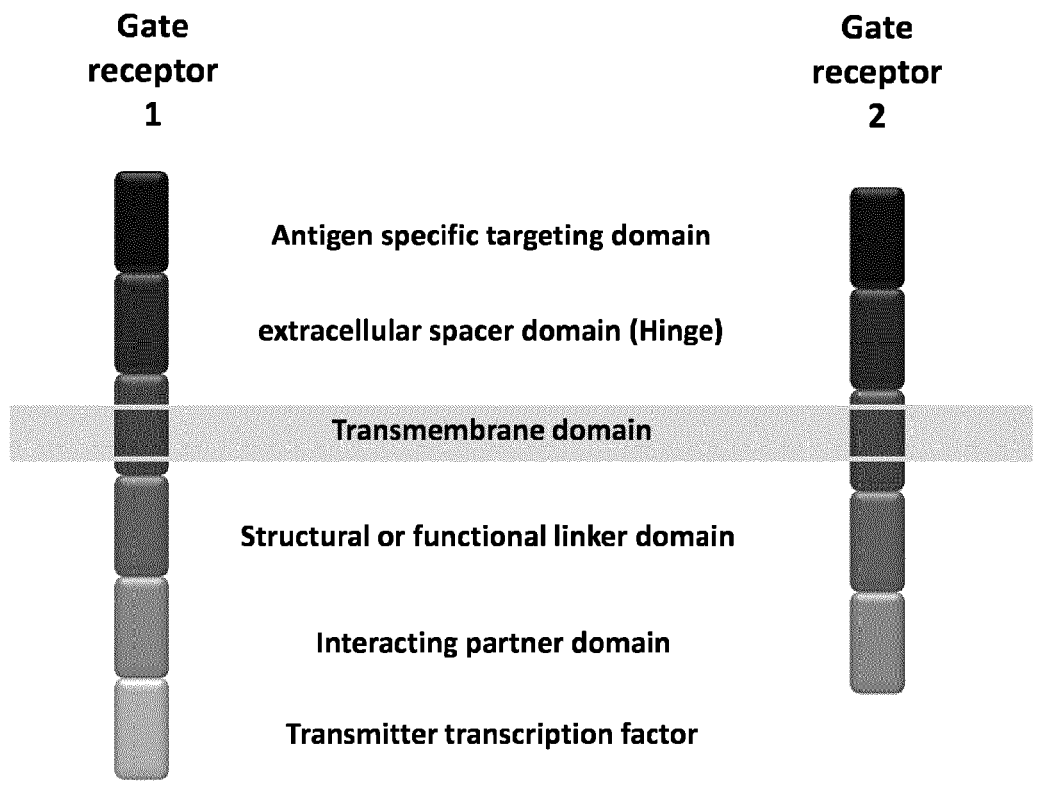

FIG. 28 Schematic representation of the composition of both gate receptors.

Figure 29:
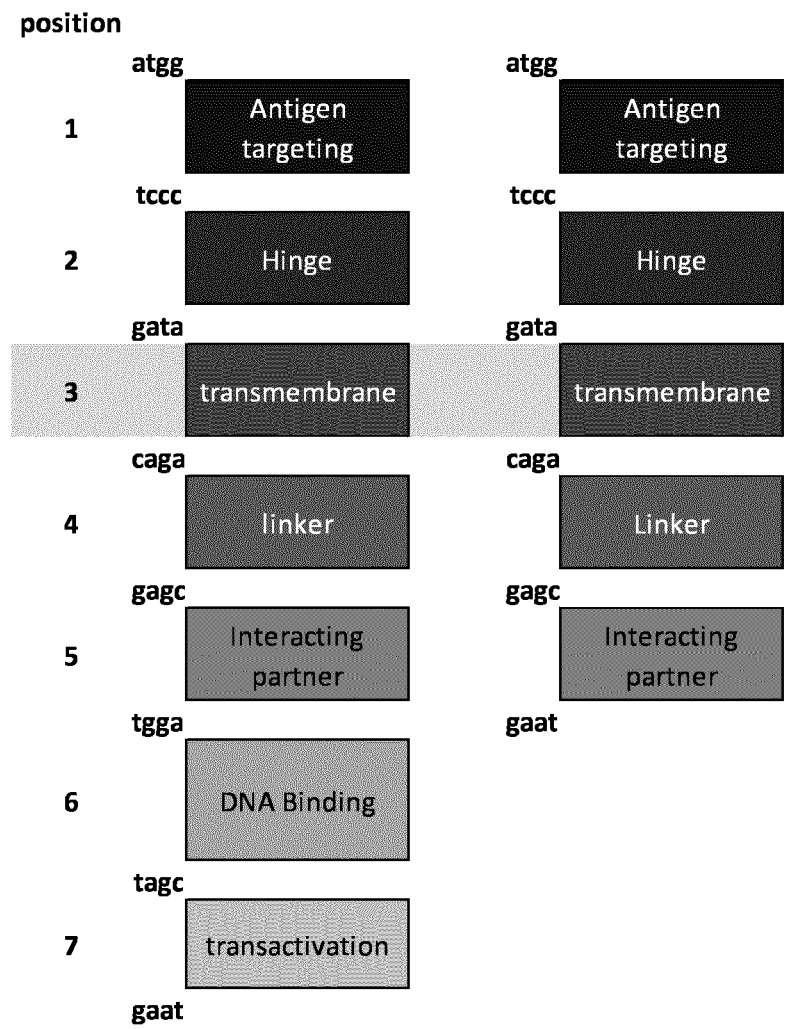

FIG. 29 Schematic representation of the molecular assembly strategy of the components for both gates, wherein the spacers are indicated.

FIG. 30 Surface expression of 7 membrane protein partners. GG83, GG111, GG121, GG152, GG153, GG155, GG156 and GG158 were tested; intensity of the signal (++: very good, +: good).

FIG. 31 Expression of the lentiviral delivered RQR8 cassette by mRNA transfection of different transactivators. These constructions are composed of a DNA binding domain (TetO or Gal4) and a transcription activation domain (VP64 or NF-kB), are transfected and are tested. The data obtained clearly indicated the expression of the lentiviral delivered RQR8 cassette by mRNA transfection of the adequate transactivator.

Figure 32A:
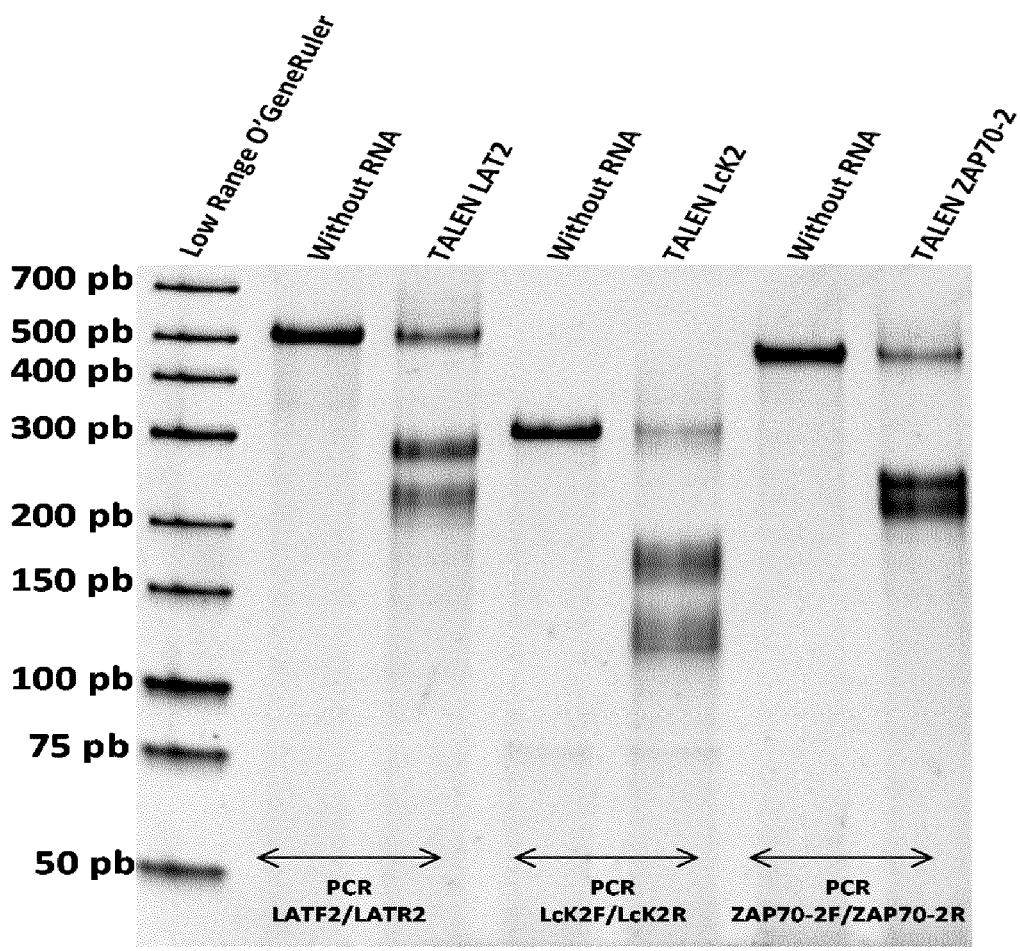
Figure 32B:
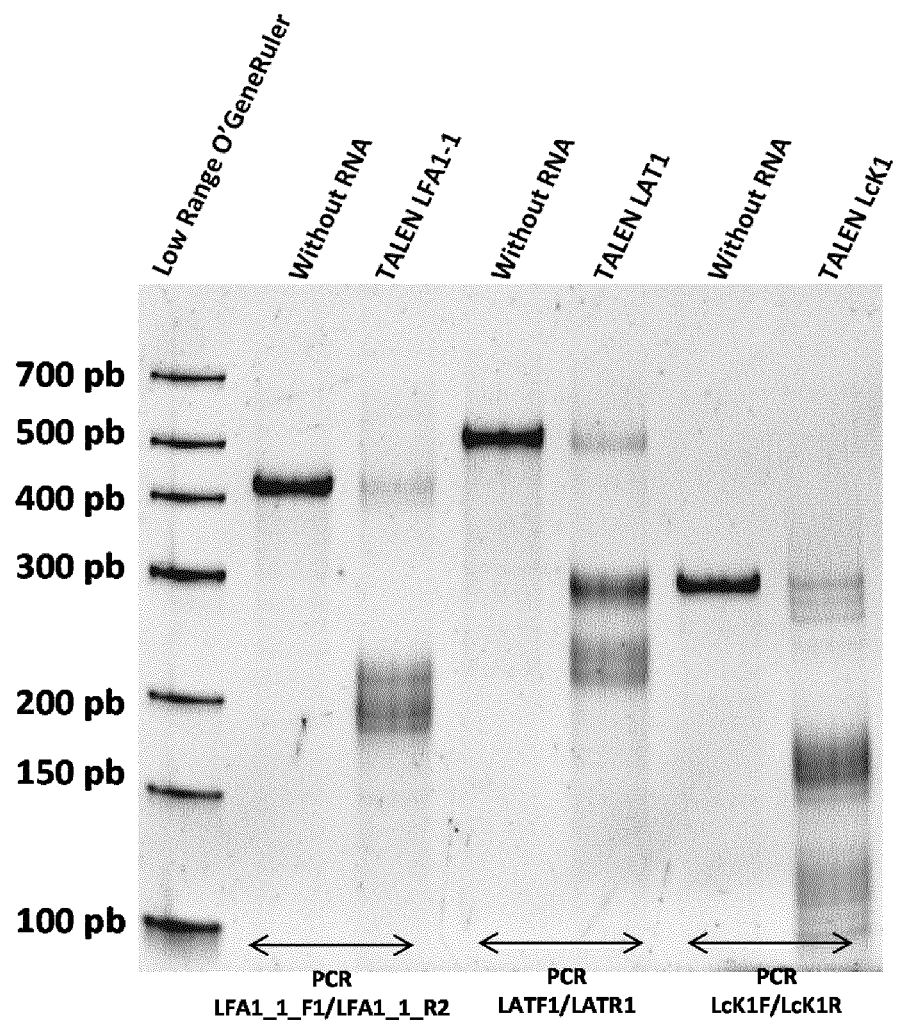
Figure 32C:
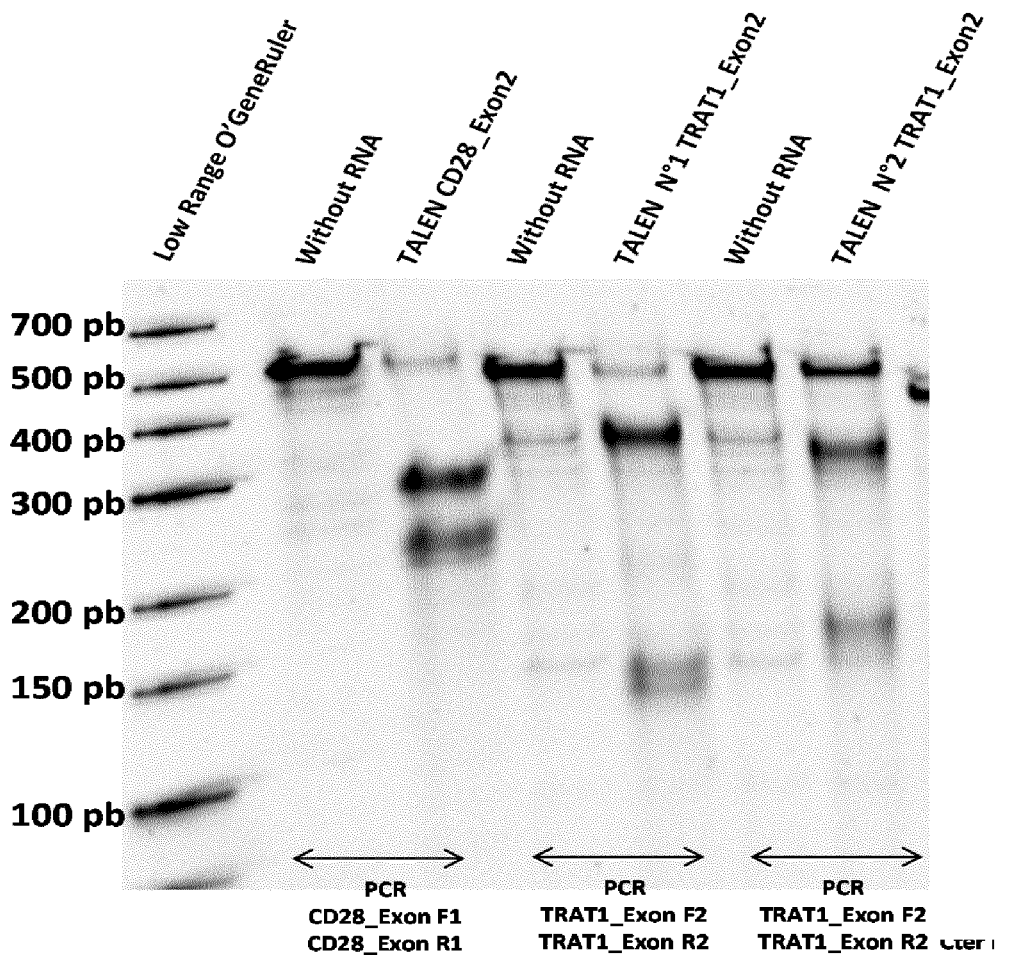

FIG. 32 T7 endonuclease assay demonstrating targeted mutagenesis at the endogenous loci using the designed TALEN: all the 3 panels A, B, C depict the knock-out (KO) of enzymes involved in T-cell signaling and/or functioning, such as LAT, LCK, ZAP70, LFA, TRAT or CD28. The data obtained clearly indicate a high level of targeted mutagenesis at all targeted loci using the designed TALEN.

Figure 33:
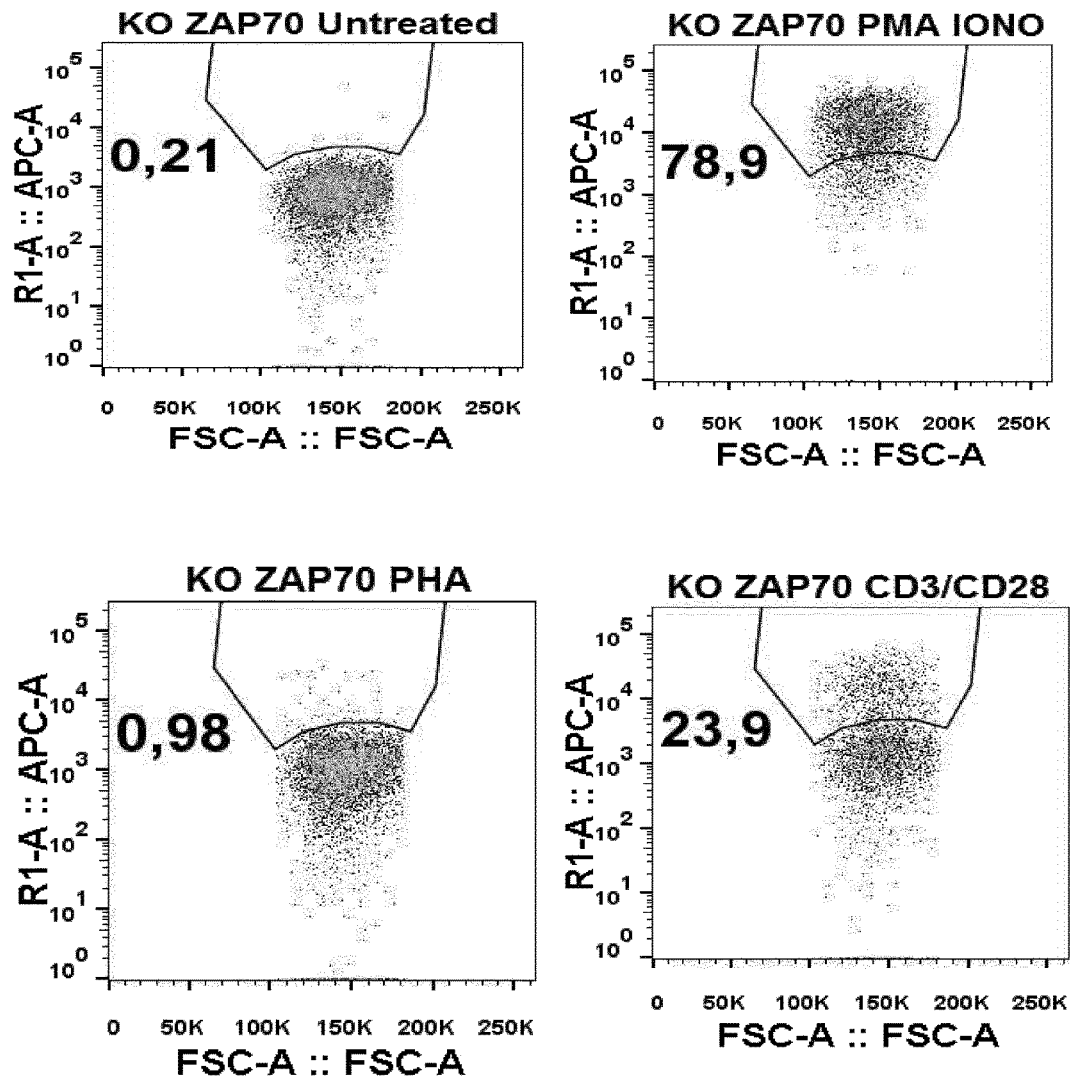
Figure 33:
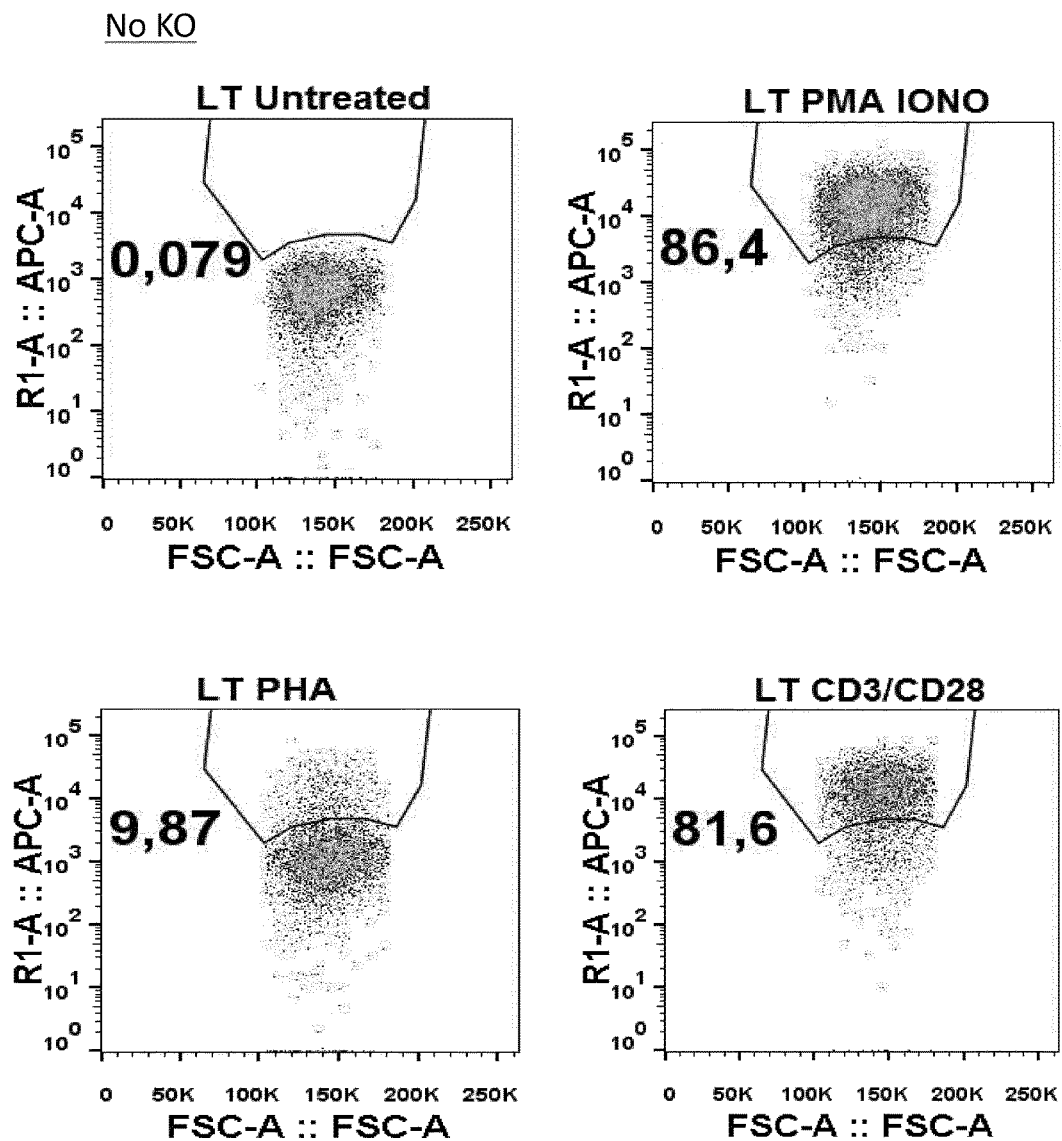
Figure 34:
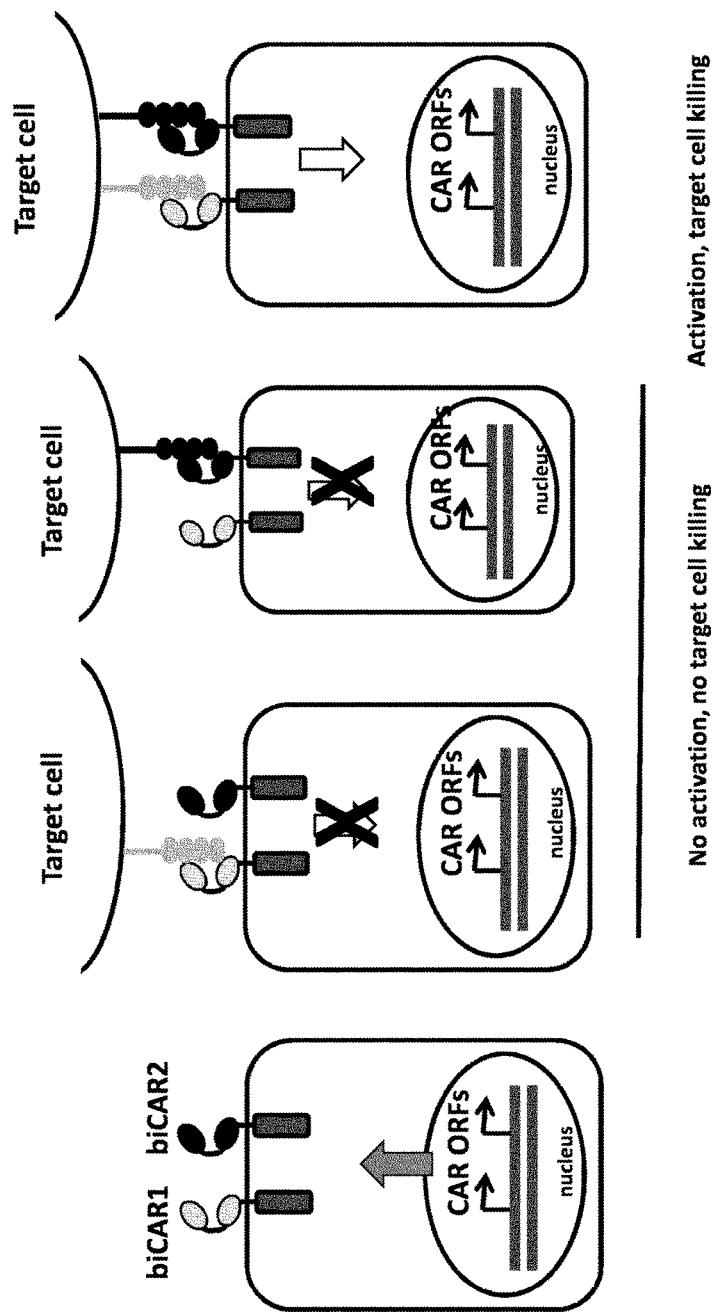

FIG. 33 Degranulation experiments following the Knockouts of ZAP70. The data obtained clearly indicate a strong staining decrease for the knock-out engineered T-cell relative to WT T-cells FIG. 34 Schematic representation of bi-specific CAR (biCAR) functioning. The bi-specific CAR (biCAR) is composed of two CARs (biCAR 1 and biCAR2) whose scFv have specific affinity to two different target cell antigens. When only one of these scFc binds to its specific antigen, there is no activation of the CAR and therefore no killing of the cell. When both scFv bind to their specific antigens, an activation of the CAR occurs and the target cell killed.

Table 1: Proteins that interact with the CARMA1 Signalosome

Table 2: CARMA1 Phosphorylation Sites

DETAILED DESCRIPTION OF THE INVENTION

The ability to control functional responses in adoptive T cell therapy is a key issue. In such therapeutic strategies, T cells are engineered by expressing surface-exposed chimeric antigen receptor (CAR) that achieves high tumor specific target cell recognition. However, to control and minimize potential toxic off-target effects, design of multi-input systems is highly desirable.

Depending of the type of "input signal", "the combination of at least two transmitter domains" can be performed by direct or indirect means.

For instance in case of the split-ubiquitin system, the combination of two input signals, which are the recognition of two different cell target ligands by the scFv from the 2 CARs, makes possible the co-localization of the two transmitter domains, i.e. the C- and N-terminal parts of the ubiquitin enzyme, therefore the activity of the latter can occur and a signal is produced.

The hypoxia HIFalpha system functions in a more indirect manner especially in regard to "the combination of transmitters". The combination of two input signals occurs between one hypoxia external signal and the other from the cell target ligand recognition by scFv of the CAR. At this stage, occurs a cascade of reactions such as inhibition of phosphorylation of HIF prolyl-hydroxylase, stabilization of the HIF-1α subunit, upregulation of several genes to promote survival in low-oxygen conditions, and ultimately binding of HIF-1 to HIF-responsive elements (HREs).

By "activation of immune cell", it is meant that the combination of two inputs signals triggers (directly or indirectly) the combination of two transmitters domains, which in its turn generates a signal (positive or negative) to the immune cell carrying the CAR, preferably by transduction means.

Consequently, a signal is emitted for the CAR expression and finally the lysis of the tumoral cells may happen.

Methods of Engineering Immune Cells

The inventors developed methods of engineering such immune cells based on the rational combination of regulatory modules in artificial circuits for performing tasks, including complex binary computation operations based on logic gates. The term "gate" is used to refer to a device or molecular mechanism that produces a particular (predetermined) output in response to two or more input signals.

According to the present invention, the logical AND gate refers to the immune cell activation, in particular T cell cytotoxicity against a target cell through the combination of different transmitter domains and activation of specific proteins (signaling proteins) resulting from the combination of at least two input signals. As non limiting examples, each signal can act together or separately to activate protein function or to remove an inhibiting protein. In another particular embodiment, said input signal can be the output signal resulting from prior input signals. In particular, the present invention relates to a method of engineering an immune cell for immunotherapy, in particular, method of engineering an immune cell for targeting specifically a cell comprising:

(a) Providing an immune cell;
(b) Engineering said immune cell to render said cell sensitive to at least two input signals such that the combination of input signals induces combination of at least two transmitter domains which results in activation of said immune cell, wherein each transmitter domain alone does not activate said immune cell.

This method is different from the combinatorial antigen recognition system described in (Kloss, Condomines et al. 2013) wherein said transmitter domains are signaling domain and co-stimulatory domains of a chimeric antigen receptor as described below, said signaling domain alone can activate T cell activation.

Input Signal: Recognition of a Ligand by Immune Cell

In a particular embodiment, said input signal can be the recognition of a ligand by said engineered immune cell, in particular by chimeric antigen receptor expressed at the surface of said engineered immune cell.

The chimeric antigen receptor (CAR) according to the present invention comprises an extracellular ligand-binding domain and an intracellular domain, more particularly, an extracellular ligand binding domain, a transmembrane domain and an intracellular domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells. In particular, the extracellular ligand-binding domain can comprise an antigen binding domain derived from an antibody against an antigen of the target. As non limiting examples, the antigen of the target can be a tumor-associated surface antigen as described above.

The extracellular ligand-binding domain can also comprise a peptide binding an antigen of the target, a peptide or a protein binding an antibody that binds an antigen of the target, a peptide or a protein ligand such as a growth factor, a cytokine or a hormone as non limiting examples binding a receptor on the target, or a domain derived from a receptor such as a growth factor receptor, a cytokine receptor or a hormone receptor as non limiting examples, binding a peptide or a protein ligand on the target. Preferably the target is a cell or a virus.

In a preferred embodiment, said extracellular ligand-binding domain is a single chain antibody fragment (scFv) comprising the light ($V_L$) and the heavy ($V_H$) variable fragment of a target antigen specific monoclonal antibody joined by a flexible linker. Other binding domain than scFv can also be used for predefined targeting of lymphocytes, such as camelid single-domain antibody fragments, receptor ligands like a vascular endothelial growth factor polypeptide, an integrin-binding peptide, heregulin or an IL-13 mutein, antibody binding domains, antibody hypervariable loops or CDRs as non limiting examples.

In another preferred embodiment, said extracellular binding domain can be a DARPin (designed ankyrin repeat protein). DARPins are genetically engineered antibody mimetic proteins typically exhibiting highly specific and high-affinity target protein binding. They are derived from natural ankyrin proteins and comprise at least three, usually four or five repeat motifs of these proteins. DARPins are small, single domain proteins which can be selected to bind any given target protein with high affinity and specificity (Epa, Dolezal et al. 2013; Friedrich, Hanauer et al. 2013; Jost, Schilling et al. 2013). According to the present invention, DARPins can be engineered to comprise multiple antigen recognition sites. Thus, said DARPins can be used to recognize a series of consecutive different antigens as well as a unique antigen. Thus, the present invention relates to a method comprising providing an immune cell, and expressing at the surface of said immune cell chimeric antigen receptor which comprises a designed ankyrin repeat protein capable of recognizing at least one specific ligand, preferably at two specific ligands.

As non limiting example, the ligand of the target can be a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, GD3, C-type lectin-like molecule-1 (CLL-1), ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap), LRP6, melanoma-associated Chondroitin Sulfate Proteoglycan (MCSP), CD38/CS1, MART1, WT1, MUC1, LMP2, Idiotype, NY-ESO-1, Ras mutant, gp100, proteinase 3, bcr-abl, tyrosinase, hTERT, EphA2, ML-TAP, ERG, NA17, PAX3, ALK, Androgen receptor; a lineage-specific or tissue specific antigen such as CD3, CD4, CD8, CD24, CD25, CD33, CD34, CD79, CD116, CD117, CD135, CD123, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. In specific cases, the ligand that the chimeric antigen receptor recognizes is present on the surface of a target cell, particularly cancer cell or viral cell. In some embodiments, the ligand that the chimeric antigen receptor recognizes is present in a tumor microenvironment. In some aspects of the invention, the ligand that the chimeric antigen receptor recognizes is a growth factor.

In a preferred embodiment, said input signals can be the recognition of at least two different ligands by chimeric antigen receptors expressed at the surface of engineered immune cells. Thus, the immune cell of the present method can be engineered by expressing at the surface of said immune cell at least two Chimeric Antigen Receptors (CAR) each comprising an extracellular domain capable of recognizing different ligands and an intracellular domain comprising transmitter domain. The combination of at least the two input signals corresponding to the recognition of different ligands by each extracellular domains of said CARs allows the combination of at least two transmitter domains and thus activation of said immune cell.

In a particular embodiment, the present method comprises the expression of at least two CARs comprising an extracellular ligand binding domain capable of recognizing the combination of several ligands such as non limiting examples the combination of HER2, MUC1, CD44, CD49f and/or epCAM to target breast cancer, the combination of mesothelin, folate receptor-alpha, CD44 and/or CD133 to target ovarian cancer cells, the combination of HER2 and IL13R-alpha2 for the treatment of glioblastoma, CD19 and CD20, Cd19 and CD22, CD20 and LI-CAM, LI-CAM and GD2, EGFR and LICAM, EGFR and C-MAT, EGFR and HER2, C-MET and HER2, EGFR and ROR1. In specific cases, at least one of the ligand that the chimeric antigen receptor recognizes is present on the surface of a target cell, particularly cancer cell. In some embodiments, at least one of the ligand that the chimeric antigen receptor recognizes is present in a tumor microenvironment. In some aspects of the invention, at least one of the ligand that the chimeric antigen receptor recognizes is a growth factor. In some embodiments, the first ligand is specific for an antigen present on a cancer cell surface and the second ligand is present in a tumor microenvironment.

The CAR according to the present invention is expressed on the surface membrane of the cell. Thus, the CAR comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source.

The transmembrane domain can be derived from any membrane-bound or transmembrane protein. As non limiting examples, the transmembrane polypeptide can be a subunit of the T cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1). Said transmembrane domain can also be a CD8 transmembrane domain (alpha and beta chains). Said Transmembrane domain can be engineered to create obligated hetero or homodimers. In particular embodiment said CARs can comprise transmembrane domains or intracellular domains which can only dimerize after ligand recognition. Another example of transmembrane domain can be NKG2-D receptor. NKG2D (natural killer cell group 2D) is a C-type lectin-like receptor expressed on NK cells, γδ-TcR$^+$ T cells, and CD8$^+$αβ-TcR$^+$ T cells (Bauer, Groh et al. 1999). NKG2D is associated with the transmembrane adapter protein DAP10 (Wu, Song et al. 1999), whose cytoplasmic domain binds to the p 85 subunit of the PI-3 kinase. In a preferred embodiment, two complementary architectures of CAR recognizing two different ligands can be expressed at the surface of the immune cell, a first CAR comprising an ITAM motif as described below and a second CAR comprising NKG2-D triggering an alternative signaling pathway.

Another example of transmembrane domain can be a receptor tyrosine kinase. Receptor tyrosine kinase are cell surface receptors involved in different critical cellular regulatory process including cell proliferation, cell differentiation, cell survival, cell migration, as well as cell cycle control. Receptor tyrosine kinase comprises an extracellular domain, a single transmembrane helix and an intracellular domain comprising tyrosine kinase function that is most of time autoregulated by additional carboxy-terminal and juxtamembrane domains. Activation of receptor tyrosine kinase is generally elicited by ligand-mediated dimerization. Thanks to their bivalence, growth hormone ligand has the capacity to simultaneously interact with two receptor monomers and promotes dimerization. Such dimerization induces the activation of intracellular kinase domains through conformational changes followed by trans-phosphorylation of different tyrosines located within their intracellular domain. The different phosphotyrosines generated eventually serve as docking site for the recruitment of downstream signaling partners that activate the cellular regulatory pathways. In a preferred embodiment, said CAR can comprise the extracellular domain, transmembrane, and/or the intracellular domain of a receptor tyrosine kinase, preferably selected from the group consisting of TrkA, c-Kit, FGFR and EGFR/Erb. Said tyrosine kinase transmembrane domain and/or intracellular domain can be linked to an extracellular ligand binding domain and intracellular domain according to the present invention (FIG. 2). In particular embodiment, said engineered cells comprise different CARs comprising different transmembrane domains.

Said transmembrane domain can also be an integrin. Integrins are heterodimeric integral membrane proteins composed of a α and β chains which combined together form the LFA-1 (integrin lymphocyte function-associated antigen-1) which is expressed on all leukocytes. LFA-1 plays a central role in leukocyte intercellular adhesion through interactions with its ligand, ICAMs 1-3 (intercellular adhesion molecules 1 through 3), and also it has an important role in lymphocyte co-stimulatory signaling (Chen and Flies 2013). The molecular details of the binding of LAF-1 to its immunoglobulin ICAM-1 are quite known allowing a careful engineering of LAF-1 binding site. The affinity of $α_L$ domain for ICAM-1 is regulated by the displacement of its C-terminal helix which is conformational linked to alterations of specific loops in LAF-1. The active and low conformations differ of 500 and 10,000 folds. It is also interesting to note that two types of antagonists are known for LFA-1 and their mechanism of action is known. Integrin cell surface adhesion receptors can transmit a signal from the outside to inside but also viceversa. There are cytoskeletal proteins as Talin which binds to the integrin tail LFA-1 to transfer a message from inside to outside.

Integrins are part of the immunological synapse and their spatial/location in the synapse seems to be strategically to the creation of an effective response to the T cell stimulation caused by the recognition of exposed antigens on the antigen presenting cells (Singleton, Roybal et al. 2009).

Indeed here we expose the idea to use the integrin scaffold to modulate the response of T cell exposing CAR. The integrin can be used to boost the activity of CAR engineered T cell enhancing its natural role of adhesion between the T cell and the tumoral cell allowing for a higher concentration of perforin and granzyme at the immunological synapse. More we can imagine to use the integrin to create a new generation of CAR whose scaffold could be a fusion between the integrin scaffold (i.e. the alpha and the beta chains but also other chains) and scFV domains (or any other type of antigen receptors). The possibility to modulate the 3D conformation of the integrins respects with the presence of small molecules in the cytoplasm creates remarkably opportunities. Indeed the integrin is naturally present in two forms: one low affinity form which hinders the active domains (the one responsible for the binding of the natural ligand i.e. ICAM) at the membrane surface and one active form with very high affinity for the natural ligand which is exposing the active domains in the extracellular milieu.

The transmembrane domain can further comprise a stalk region between said extracellular ligand-binding domain and said transmembrane domain. The term "stalk region" (also named hinge region) used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, CD28 or RTK, or from all or part of an antibody constant region. Alternatively the stalk region may be a synthetic sequence that corresponds to a naturally occurring stalk sequence, or may be an entirely synthetic stalk sequence.

The intracellular domain of the CAR according to the present invention comprises a transmitter domain. Indeed, according to the present invention, the input signals induce the combination of the transmitter domains leading to immune cell activation. In a particular embodiment, said transmitter domain is a signaling protein, and the combination of signaling protein function induces immune cell activation. In another particular embodiment, said transmitter domains are at least two molecules which can interact together, and the interaction induce immune cell activation.

In a particular embodiment, said CAR can be a multi-chain CAR comprising at least a transmembrane polypeptide which comprises at least one extracellular ligand binding domain; and a transmembrane polypeptide comprising at least one transmitter domain such that said polypeptides assemble together to form a multi-chain Chimeric Antigen Receptor (PCT/US2013/058005). Said multi-chain CAR can comprise several extracellular ligand binding domains, to simultaneously bind different ligands. In particular, said different extracellular ligand-binding domains can be placed on different transmembrane polypeptides composing the multi-chain CAR. In another embodiment, the present invention relates to a population of multi-chain CARs comprising each one different extracellular ligand binding domains.

In a particular embodiment, said chimeric antigen receptor comprises at least:
  an extracellular ligand binding domain capable of recognizing said specific ligand;
  a transmembrane domain;

an intracellular domain comprising at least an activation and co-activation domains and an oxygen-sensitive domain.

According to another embodiment, said extracellular domain contains additionally a hinge.

According to another embodiment, the scFv contained in said extracellular binding domain are directed to the CD19, 5T4, ROR1, CD123 or CD33 cell target antigens, and have respectively at least and identity of over 80%, preferably 90% or more preferably 95% with SEQ ID NO: 32, 35, 38; SEQ ID NO: 33; SEQ ID NO:34; SEQ ID NO:36 and SEQ ID NO:37.

According to another embodiment, said hinge is chosen from CD8a, IgG1 or EpoR-D2, and have an identity of over 80%, preferably 90% or more preferably 95% with respectively SEQ ID NO:39, 40 and 41.

According to another embodiment, said transmembrane domain is chosen from CD8a, 4-1BB, DAP10, CD28 or FceRIalpha, and have an identity of over 80%, preferably 90% or more preferably 95% with respectively SEQ ID NO:42, 43, 44, 45 and 46.

According to another embodiment, said oxygen-sensitive domain is chosen between HIF1 alpha or HIF3 alpha, and have an identity of over 80%, preferably 90% or more preferably 95% with respectively SEQ ID NO:22, 23, 85, and SEQ ID NO:26, 27.

According to another embodiment, said intracellular domain contains a linker chosen amongst CD3zeta, FceRIg, CD28, 4-1BB, OX40, DAP10, CD28, CD275, HVEM, LIGHT, CD40L, GITR, TIM1, SLAM, CD2, TLT-2, LAG3, DAP12, CD84, CD244, CD229, LTBR and CD278, and have an identity of over 80%, preferably 90% or more preferably 95% with respectively SEQ ID NO:47 to 70.

According to another embodiment, said activation domain is CD3zeta, and said activation domain is chosen between 4-1BB or CD28.

Complementation of a Prior Inactivated Gene

The transmitter proteins can also complement a prior inactivated gene or activate a gene in the nucleus to complement a prior inactivated gene. Thus, following combination of input signals, the combination of two transmitter signals allows the complementation of the inactivated gene and thus the activation of the T cell.

Domains involved in the formation of the immune synapse can be used as target for gene inactivation, and thus for complementation of this gene. Said immune cell inactivated for this gene can be used to engineer cell according to the present invention. Thus, following combination of input signals, the combination of transmitter domains induces the expression of a gene capable of complementing said inactivating gene. As non limiting examples, said domains which participate to the formation of the immunological synapse or to the transfer of the signal include as non-limiting examples: LCK, ZAP70, Itk, LAT, SLP76, GADS, GRB2, PLC-γ1, or VAV1. Other examples can be DOK1 and DOK2 proteins which negatively control the T cell receptor signaling by recruiting other negative regulators as RAS GTP, SHIP1 and CSK. Transcription factors modulated by the immunological synapse domains can also be activate to complement inactivated cell. Said transcription factors include as non-limiting examples: NFAT (nuclear factor of activated T cells), NE-κb (nuclear factor kappa-light chain enhancer of activated B cells), mTOR, AP1/2, ERK1/2, C-MAE. For example, ZAP-70 (Zeta-chain-associated protein kinase 70) is a protein normally expressed near the surface membrane of T cells. It is part of the T cell receptor, and plays a critical role in T cell signaling. Following antigen recognition by CAR comprising the CD3 zeta signaling domain in immune cell, ZAP70 binds to the CD3 zeta domain inducing activation of immune cell response. Thus, in inactivated ZAP70 gene T cell, the antigen recognition of only one antigen by CAR comprising CD3 zeta domain does not induce T cell activation. However, the recognition of a second ligand by another CAR comprising an intracellular ZAP70 domain can complement the prior inactivated ZAP70 gene and thus allows the activation of the T cell via CD3 zeta (FIG. 3).

Protease System

Transmitter domains according to the present invention can be a protease and a substrate protein comprising a signaling protein linked to a membrane anchoring domain via a protease cleavage site. The combination of the two transmitter domains results in activation of the immune cell. Indeed, cleavage of the substrate protein by the protease results in the release of signaling protein and thus in immune cell activation (FIG. 4). Said membrane anchoring domain can be a terminal extension which anchors the substrate protein to the membrane of the cell. In particular embodiment, said substrate protein is a part of the intracellular domain of a chimeric antigen receptor. Said protease can be as non-limiting examples: TEV protease, Factor Xa, thrombin, engineered viral proteases, enterokinase and HRV3C.

Split-Protein Based System

In another embodiment, the transmitter domains are split proteins. This system is based on protein complementation assays wherein a functional molecule is dissected into two non-functional fragments. Functionality is restored when the fragments are reassembled by attached protein-protein interaction domains. The functional molecule used in the protein complementation assays can be an active enzyme, or a signaling protein. Said split proteins encompass, as non-limiting examples, split kinases, split proteases and split inteins.

In a particular embodiment, said split proteins are split inteins which can reassemble together and restore the functionality of the intein. Inteins are internal protein sequences that catalyze a protein-splicing reaction, which precisely excise the intein sequence and join the flanking sequence with a peptide bond. Split intein is any intein in which the N-terminal domain of the intein and the C-terminal domain of the intein are not directly linked via a peptide bond. Natural split inteins have been identified in cyanobacteria and archaea, but split inteins can also be created artificially by separating an intein sequence into two fragments (International application WO2013/045632). According to the present invention, the protein splicing reaction precisely excises the intein sequence and joins the flanking sequence to reconstitute a signaling protein which induces immune cell activation (FIG. 5). In a particular embodiment, said signaling protein can be released upon spilt intein reassembly (FIG. 6).

In another particular embodiment, said split proteins can be split kinases which can assemble together to reconstitute a functional kinase (FIGS. 7 and 8). Said kinase can phosphorylate a signaling protein to induce immune cell activation. In a particular embodiment, said kinases can be as non limiting examples: CaMKII, Lck, PKCq, HPK1, PKθ, IKKβ, CK1α which will phosphorylate the serine residues on the linker region of the CARMA1 protein inducing NF-κβ and JNK signaling pathway.

In another particular embodiment, said split proteins can be split-protease which can interact together to form a functional protease as described above (FIGS. 9 and 10).

Said protease can interact with a substrate protein and cleave the target protease site to release the signaling protein.

Scaffolding Systems

Scaffold proteins are crucial regulators of many key signaling pathways. By Scaffold protein, it is meant a protein able to interact and/or bind with multiple members of a signaling pathway, tethering them into complexes. In the present invention, the transmitter domains can be members of the signaling pathway which can recruit a scaffold protein. This assembly may be able to enhance signaling specificity and efficiency by increasing the proximity and effective concentration of components in the scaffold complex resulting in the activation of the immune cell. As non limiting example, a scaffold protein can bind a protein kinase and its substrate thereby ensuring specific kinase phosphorylation or said scaffold protein can result in allosteric changes of the signaling members. Said scaffold protein can regulate signal transduction, can help localize pathway components (organized in complexes) to specific areas of the cell such as the plasma membrane, can coordinate signaling feedbacks, or can protect activated molecules from inactivation. Said scaffold protein according to the present invention can be as non-limiting example SH2 domain as in SYK tyrosine kinase or ZAP70 which can recognize and bind different ITAM domains (transmitter domains) as described for C-type lectin and hemITAM (FIG. 11) or CARMA-1 as described in example 2.

Double Activation System

Transmitter domains can also be a homo or heterodimeric proteins, in particular an intracellular domain of a receptor which can dimerize with another transmitter domain such as another intracellular domain of a receptor or a cytosolic protein. The dimerization of these transmitter domains transduces a signal downstream. One example of signaling proteins involving homo- or hetero-dimerization of proteins can be a tyrosine kinase receptor as described above involving the JAK/Stat signaling pathway. Activation of such components is generally elicited by ligand-mediated dimerization. Said transmitter domains that homodimerize can be engineered to form obligated heterodimer. In a particular embodiment, said CARs can comprise the transmembrane, and optionally the intracellular domains of a receptor tyrosine kinase, preferably selected from the group consisting of TrkA, c-Kit, FGFR and EGFR/Erb. The recognition of the ligands induces the dimerization of the receptor and thus activation of the signaling protein resulting in immune cell activation (FIG. 12).

Autoinhibited System

Transmitter domains can also be a non-activate form of an autoinhibited molecule. Autoinhibited compounds may exist in an autoinhibited state or an active state. The autoinhibited state results in perturbed catalytic function of the protein, or perturbs the ability of the protein to interact with another ligand. An autoinhibited state typically occurs in the absence of phosphorylation of the kinase. Activation of such autoinhibited protein can involve a conformational change of the compound. This conformational change can be the consequence of the interaction with another compound. Said inhibitory compounds can be allosteric inhibitory compounds. Allosteric inhibitory compounds bind and form a specific association with an autoinhibited compound so as to preserve a conserve non activated conformational state of the autoinhibited compound. Autoinhibition can be relieved by interacting with another transmitter domain which can have a higher affinity binding (FIG. 13) or which can induce for examples covalent modifications (e.g. de-/phosphorylation) of the interaction region or proteolysis (FIG. 14). As non limiting examples, said inhibitors can be class I and II of p21 activated kinase (pak) inhibitor, Rho activated protein inhibitors, autoinhibites non receptor serine/threonine kinase inhibitors, phosphatase inhibitor and autoinhibited small GTPase effector inhibitors.

The combination of transmitter domains according to the present invention is responsible for intracellular signaling following the binding of extracellular ligand binding domain and results in the activation of the immune cell and immune response. In other words, the signaling protein is responsible for the activation of at least one of the normal functions of the engineered immune cell. For example, the function of a T cell can be a cytolytic activity or helper activity including the secretion of cytokines. Thus, the term "signaling protein" refers to a protein which transduces the transmitter domain function signal and directs the cell to perform a specialized function. In a particular embodiment, said transmitter domain can be a signaling protein. Transmission of the signals can result from: protein/protein interactions, protein/DNA interaction, protein/RNA interaction, protein/small molecule interaction, post translational protein modification, conformational change, subcellular relocalization.

In particular, the signaling protein can complement a prior inactivated gene or activate a gene in the nucleus to complement a prior inactivated gene. Domains involved in the formation of the immune synapse can be used as target for gene inactivation, and thus for complementation of this gene. Said immune cell inactivated for this gene can be used to engineer cell according to the present invention. Thus, following combination of input signals, the combination of transmitter domains induces the expression of a gene capable of complementing said inactivating gene.

In another particular embodiment, the signaling protein can activate a gene in the nucleus. Examples of signaling protein can be members of NFAT transcription factor family which are inducible factor that could bind the interleukin-2 promoter in activated T cells. The regulation of NFAT proteins involves metabolites and proteins such as calcium, calcineurin and Homer scaffolding proteins. Said signaling protein can be an activated engineered form of NFAT avoiding regulation by calcineurin and Homer proteins. Said signaling protein can be a NF-κB engineered to avoid sequestration in the cytoplasm by Iκb allowing activation of T cells. Said signaling protein can also be the expression of the three IKK subunits (IKKα, IKKβ, IKKγ). Reconstituted IKK complex activated NF-κB pathway, by triggering the ubiquitination of the IκB. Also the activation of the JNK signaling could be triggered through the direct expression of signaling protein AP-1 (transcription factor). In another particular embodiment, said signaling protein can be an engineered transcription activator like effector (TALE) binding domain that will specifically target and activate transcription of the same gene as for the NFAT and NF-kb.

In another particular embodiment, said signaling protein can inhibit a signaling pathway through protein-protein interaction or can activate a gene in the nucleus to inhibit a signaling pathway.

Said signaling protein can be vaccinia H1 related proteins (VHR) a member of the mitogen-activated protein kinase phosphatases (MKPs) family which dephosphorylates and inactivates an extracellular signal regulated kinases (ERK) signaling proteins.

According to the present invention, said transmitter domains or signaling protein induced by transmitter domains can be a signal transducing domain. Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases or Ick. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d.

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A "co-stimulatory molecule" refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

External Stimuli

In another aspect of the invention, the input signal can be an external stimulus (FIG. 15). Said external stimuli encompass as non limiting examples variation upon presence of a tumor cell in the microenvironment of the engineered T cell of small molecules, peptide, small proteins, (chemokines, cytokines) and physicochemical conditions such as pH, hypoxia, redox potential. Redox regulatory elements can be oxygen or nitrogen such as reactive oxygen or nitrogen specied (NS and RNS) as non limiting examples.

In a particular embodiment, said external stimulus can be hypoxic environment.

In a preferred embodiment, the response to said hypoxia condition is triggered by the alpha hypoxia inducible factor 1 (HIF-1α) or by the alpha hypoxia inducible factor 3 (HIF-3α).

In a more preferred embodiment, the said HIF-1α polypeptide sequence has over 80% identity, preferably 90% identity or more preferably 95% identity with SEQ ID NO. 5 or to SEQ ID NO. 22-23, or the said HIF-3α polypeptide sequence has over 80% identity, preferably 90% identity or more preferably 95% identity with SEQ ID NO. 26-27.

Indeed, local tissue hypoxia is associated with many different disease states including certain tumors, certain inflammatory processes and conditions of neovascularization. Solid tumours, in particular, show relatively aberrant vascularization that causes intermittent/absent perfusion leading to hypoxia. A multifaceted adaptive response to hypoxia is facilitated by the stabilization and accumulation of the alpha subunit of hypoxia inducible factor 1 (HIF-1). Under normoxia, HIF1α is inhibited through the hydroxylation of specific proline residues located in its C-terminal region. Such hydroxylation is known to promote recruitment of VHL, an E3 ubiquitin ligase that triggers ubiquitinylation of HIF1α and its degradation by proteasome. In hypoxic conditions, HIF-1α forms a complex with its binding partner, aryl hydrocarbon receptor nuclear translocator (ARNT), as well as the p300/CBP transcriptional coactivators that bind to the hypoxia response element (HRE) in the untranslated regions of hypoxically regulated genes. This complex induces the transcription of genes that serve to maintain cellular homeostasis in the face of hypoxic conditions. For example, the HIF-1/p300/CBP complex plays a role in inducing expression of genes such as those encoding erythropoietin, which leads to erythropoiesis; vascular endothelial cell growth factor (VEGF), which is a primary mediator of angiogenesis; iNOS and heme oxygenase, which play roles in vasodilation; and the glucose transporter and glycolytic enzymes, which play roles in anaerobic metabolism. Beside HIF-1, the HIF-3 α system (ref Uniprot: Q9Y2N7 for human sequence) is also contemplated in the present invention. Also involved in adaptive response to hypoxia, its action is known to suppress hypoxia-inducible expression of HIF1A and EPAS, and to binds to core DNA sequence 5'-TACGTG-3' within the hypoxia response element (HRE) of target gene promoters. Its expression and characterization in human kidney are presented in Hara et al. (2001).

In a particular aspect of the invention, said input signal can be the hypoxic microenvironment which is detected by the engineered cell. Thus, according to the method of the present invention, the immune cell can be engineered to be sensitive to hypoxic environment. Said immune cell is engineered to trigger cytotoxicity via activation of synthetic hypoxia dependent activation pathways. In particular, said immune cell can be engineered to induce expression of a transmitter domain under hypoxia inducible promoter. Said hypoxia inducible promoter can be composed of HRE. The consensus sequence of HRE is (G/C/T)ACGTGC(G/C). Usually, multiple copies of HREs appear in a hypoxia inducible promoter. In a preferred embodiment, said hypoxia inducible promoter is composed of HREs and a basal promoter such as SV40 promoter. For example, said multiple copies of HRE can be derived from the PGK-1 promoter, the EPO, GAPDH, VEGF and survivin promoters.

In another particular embodiment, said immune cell is engineered by expressing a transcription factor sensitive to oxygen (oxiTF) and incorporating within the cell a synthetic promoter specific for the OxiTF driving the expression of a transmitter domain (FIG. 16). Said OxiTF can be an engineered transcription factor such as TAL effector, Zinc finger effector, CRISP effector, as non limiting examples, fused to an HIF1 alpha C-terminal domain. Under hypoxia, engineered immune cells sense oxygen depletion, in particular in tumor environment, and trigger the expression of a transmitter domain which induces immune cell activation. Said transmitter domain can be a transmitter domain or more particularly a chimeric antigen receptor comprising transmitter domains as described above. Said chimeric antigen receptor comprises an extracellular ligand binding domain capable of recognizing a specific ligand and the recognition of said ligand by said CAR is the second input signal. Said method of engineering immune cells can further comprise the step of expressing at the surface of said immune cell another chimeric antigen receptor. In a more preferred embodiment, such engineered cell can comprised a first CAR constitutively expressed at the surface of the immune cell and a second CAR expressed only in hypoxic conditions, the first and second CARs comprising extracellular binding domains capable of recognizing two different ligands (FIG. 17).

In another particular embodiment, the present invention encompasses a method of engineering an immune cell wherein the chimeric antigen receptor is a multi-chain CAR. In a preferred embodiment, α, β and γ chains of said multi-chain CAR have respectively an identity of over 80%, preferably 90% identity or more preferably 95% identity with SEQ ID NO. 7, 3 and 4.

In another particular embodiment, the present invention relates to a method of engineering an immune cell comprising a step of expressing a CAR which comprises at least two extracellular ligand binding domains. Bispecific tandem CAR previously described (International application: WO2013123061, US. Patent application: US20130280220), may theoretically still lead to the T cell activation independently to the recognition and binding of both antigen as one cannot exclude that the binding of one single chain Fv may trigger activation. So to avoid these drawbacks, the inventors sought to design new bispecific CAR comprising at least two extracellular ligand binding domains, which cannot induce T cell activation by the binding of only one ligand. Said CAR can comprise another domain which perturbs the ability the signaling function of the CAR, or perturbs the ability of the protein to interact with another ligand. The recognition of at least two ligands by the extracellular ligand binding domains can involve a conformational change of the CAR and thus the transduction of the signal of the CAR. The conformational change can occur for example by the interaction with a ligand which can have a higher affinity binding, such idiotypic antibody (FIG. 18).

Other AND Logic Gate System

In another aspect of the invention, the inventors also developed methods of engineering such immune cells based on logic gates, wherein only the presence of one specific input signal and not the other produces a particular output in response (FIG. 19). According to the present invention, the immune cell activation, in particular T cell cytotoxicity against a target cell is induced following the recognition of one of several input signals, in particular the recognition of a ligand on a cancer cell and not the recognition of a ligand present on the healthy cells. In particular, the present invention relates to a method of engineering an immune cell for immunotherapy, in particular, method of engineering an immune cell for targeting specifically a cell comprising:
  (a) Providing an immune cell;
  (b) Engineering said immune cell to render said cell sensitive to at least one among several input signals such that only the specific input signal induces activation of said immune cell response.

In a particular embodiment, the present invention relates to a method of engineering immune cell by expressing at the surface of the cell at least one first CAR comprising an extracellular ligand binding domain capable of recognizing a ligand at the surface of a tumor cell and another CAR comprising an extracellular ligand binding domain capable of recognizing a ligand at the surface of healthy cell, such that the recognition of the ligand at the surface of a healthy cell inhibits the activation of immune cell via an inhibitory transmitter domain, while the recognition of the ligand at the surface of the target cell induces the activation of the immune cell via transmitter domain. Inhibitory or activation transmitter domain can be derived from the SRC family kinase (SFK) member LCK. In a more preferred embodiment, inhibitory transmitter domain is a constitutively negatively regulated LCK, preferably comprising a mutation at the position Y394 (NCBI Reference Sequence: NP_005347.3) and activation domain is a constitutively active LCK form, preferably which comprises a mutation at position Y505 (NCBI Reference Sequence: NP_005347.3) (see example 2 and FIG. 20).

Delivery Methods

The different methods described above involve expressing CAR at the surface of a cell. As non-limiting example, said CAR can be expressed by introducing CAR into a cell. CAR can be introduced as transgene encoded by one plasmidic vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Chimeric Antigen Receptors, Polynucleotides and Vectors

The present invention also relates to a chimeric antigen receptor which comprises an extracellular ligand binding domain and an intracellular domain comprising a transmitter domain as described above. In particular, said transmitter domain is selecting from the group consisting of: protease, split protein, members of signaling pathway recruiting a scaffold protein, one monomer of the dimeric domain, an autoinhibited compound.

According to one embodiment, the chimeric antigen receptor comprises:
  the alpha-chain comprises extracellularly the CD8 hinge, FcRα as transmembrane domain, and intracellularly a part of FcRα combined with HIF1alpha or HIF3 alpha subunit;
  the beta-chain comprises the FcRβ as extracellular and transmembrane domain, and ΔITAM-41BB as intracellular co-stimulation domain;
  the gamma-chain comprises the FcRγ as transmembrane domain, and ΔITAM-CD3 as intracellular activation domain.

The present invention also relates to polynucleotides, vectors encoding the above described CAR according to the invention. The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Doronina, Wu et al. 2008). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct, transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830).

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Engineered Immune Cells

The present invention also relates to isolated cells or cell lines susceptible to be obtained by said method to engineer cells. In particular said isolated cell comprises at least one CAR as described above. In a preferred embodiment, said isolated cell comprises a population of CARs each one comprising different extracellular ligand binding domains. In particular, said isolated cell comprises exogenous polynucleotide sequence encoding CAR.

In the scope of the present invention is also encompassed an isolated immune cell, preferably a T cell obtained according to any one of the methods previously described. Said immune cell refers to a cell of hematopoietic origin functionally involved in the initiation and/or execution of innate and/or adaptive immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described.

In another embodiment, said isolated cell according to the present invention comprises a polynucleotide encoding CAR.

Therapeutic Applications

In another embodiment, isolated cell obtained by the different methods or cell line derived from said isolated cell as previously described can be used as a medicament. In another embodiment, said medicament can be used for treating cancer, autoimmune disease or infections in a patient in need thereof. In another embodiment, said isolated cell according to the invention or cell line derived from said isolated cell can be used in the manufacture of a medicament for treatment of a cancer, viral infection or autoimmune disease in a patient in need thereof.

In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise non solid tumors (such as hematological tumors, for example, leukemias and lymphomas) or may comprise solid tumors. Types of cancers to be treated with the multi-chain CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administered parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFv) fused to the intracellular signaling domain of the T cell antigen receptor complex zeta chain (scFv:ζ) and have the ability, when expressed in T cells, to redirect antigen recognition based on the monoclonal antibody's specificity.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The term "Hypoxia" refers to a condition wherein the oxygen concentration is below normal levels for a particular tissue (such as a tumor). Hypoxia in a particular tissue as, compared to surrounding tissue, is referred to as relative tissue hypoxia. An example of relative tissue hypoxia is tumor hypoxia in which a tumor has lower levels of $pO_2$ than that of surrounding non-tumor tissue. In some examples of the disclosed methods, the level of oxygen is for example 10% or less (for example, 9%, 8%, 7%, 6%, 5%, 4%, 3%, 2%, or 1%), or for example 50 mmHg or less (for example, 45 mmHg, 40 mmHg, 35 mmHg, 30 mmHg, 25 mmHg, 20 mmHg, 15 mmHg, 10 mmHg, 5 mmHg, 4 mmHg, 3 mmHg, 2 mmHg, or 1 mmHg). The body as a whole (generalized hypoxia) or a region of the body (tissue hypoxia) may be deprived of adequate oxygen. Those of skill in the art would be familiar with the measurement of oxygen levels in biological systems and that oxygen measurements may be expressed in "mmHg," wherein, for example, 10% $O_2$ is equal to 76 mmHg and 1% $O_2$ is equal to 7.6 mmHg.

By "Transcription Activator like Effector (TALE)" it is meant a binding domain protein wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base ($T_0$) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

The invention is more particularly related to the following objects:

1. A method of engineering an immune cell for specifically targeting a cell comprising:
   (a) Providing an immune cell;
   (b) Engineering said immune cell to render said cell sensitive to at least two input signals such that the combination of input signals induces combination of at least two transmitter domains which results in activation of said immune cell, wherein each transmitter domain alone does not activate said immune cell.
2. The method of claim 1 wherein at least one said input signal is the recognition of a specific ligand by said immune cell which is engineered by expressing at the surface of the cell a chimeric antigen receptor (CAR) comprising an extracellular ligand binding domain capable of recognizing said specific ligand and an intracellular domain comprising a transmitter domain capable of activating said immune cell in combination with another transmitter domain optionally via a signaling protein.
3. The method of claim 1 wherein at least said two input signals are the recognition of different specific ligands by said immune cell which is engineered by expressing at the surface of the cell chimeric antigen receptors (CARs) comprising extracellular ligand binding domains capable of recognizing said different specific ligands and intracellular domains comprising transmitter domains capable of activating immune cell in combination.
4. The method according to any one of claims 1 to 3 wherein said input signal is an external stimulus selected from the group consisting of: the presence of particular small molecules, chemokines, cytokines, physicochemical conditions, hypoxia.
5. The method of claim 4 wherein external stimulus is hypoxia and wherein said immune cell is engineered to express at least one transmitter domain under the control of a hypoxia inducible promoter.
6. The method of claim 4 wherein external stimulus is hypoxia and wherein said immune cell is engineered to express at least one chimeric antigen receptor comprising a transmitter domain under the control of a hypoxia inducible promoter and wherein the recognition of a ligand of said chimeric antigen receptor is another input signal.
7. The method according to any one of claims 1 to 6 wherein said transmitter domains are a protease and a substrate protein comprising a signaling protein linked to a membrane anchoring domain via a protease cleavage site such that said protease cleavage induces the release of the signaling protein capable of activating said immune cell.
8. The method of claim 7 wherein said protease is selected from the group consisting of: TEV protease, Factor Xa, thrombin, engineered viral proteases.
9. The method according to any one of claims 1 to 8 wherein said transmitter domains are split proteins which assemble to reconstitute a signaling protein capable of activating said immune cell.
10. The method of claim 9 wherein said split proteins are split proteases which assemble together to reconstitute a protease capable of cleaving a substrate protein and releasing a signaling protein capable of activating said immune cell.
11. The method of claim 9 wherein said split proteins are split kinases which assemble together to reconstitute a kinase which activates a signaling protein capable of activating said immune cell.
12. The method of claim 9 wherein said split proteins are a split-inteins which assemble together to reconstitute an intein which excises the intein sequence and join with a peptide bond flanking signaling protein sequences capable of activating said immune cell.
13. The method according to any one of claims 1 to 8 wherein said transmitter domains are members of a signaling pathway which can recruit a scaffold protein.
14. The method of claim 13 wherein said scaffold protein is SYK tyrosine kinase or ZAP70.

15. The method according to any one of claims 1 to 8 wherein said transmitter domains are dimeric proteins.
16. The method according to any one of claims 1 to 8 wherein said transmitter domain is an autoinhibited compound.
17. The method according to any one of claims 1 to 8 wherein said engineered immune cell is initially inactivating for a gene and wherein said combination of transmitter domains is capable of complementing said inactivated gene.
18. A chimeric antigen receptor comprising an extracellular ligand binding domain and an intracellular domain which comprise at least one transmitter domain.
19. The chimeric antigen receptor of claim 18 wherein said transmitter domains are selected from the group consisting of: a protease, split protein, dimeric protein, member of a signaling pathway which can recruit a scaffold protein and autoinhibited compound.
20. A polynucleotide encoding a chimeric antigen receptor of claim 18 or 19.
21. An isolated immune cell which comprises a chimeric antigen receptor of claim 18 or 19.
22. An isolated immune cell obtained by any one the method according to any one of claims 1 to 17.
23. An isolated immune cell of claim 21 or 22 for its use as a medicament.
24. An isolated immune cell according to any of claims 21 to 23 for treating a cancer, an autoimmune condition or an infection by a pathogen.
25. A method of treating a subject in need thereof comprising:
    (a) Providing a immune cell according to claim 21 or 22;
    (b) Administrating said immune cells to said patient.

EXAMPLES

Example 1

Control of T Cell Activation Through CAR-Mediated Regulation of CARMA1 Protein

The scaffold protein caspase recruitment domain-containing membrane-associated guanylate kinase protein-1 (CARMA1) is a member of the MAGUK family of kinases (Roche, Ramadas et al. 2013). CARMA1 constitutes a crucial signalosome for the transmission of the T cell Receptor (TCR) signaling and in general for T cell activation. The intracellular CARMA1 concentration is a key element in the regulation of its activity. An enhancement of the CARMA1 signaling has been observed at low and moderate concentrations while a decrease of the activity has been reported at high concentration dues to the sequestration of the different components away form each other (biphasic response). Following TCR engagement, CARMA1 recruits different proteins forming a multi-protein complexes that finally can activate two different signaling cascade: NF-κB and c-jun N-terminal kinase (JNK) (Blonska and Lin 2009).

CARMA1 is composed by five structural domains connected by linker regions. Among these five domains three constitute the membrane guanilate kinase domain (MAGUK): a PDZ homology domain (post synaptic density protein), a SRC homology domain (SH3) and a guanylate kinase domain (GUK). The MAGUK domain is necessary for cellular adhesion, formation of multi-domain complexes and signal transduction, thus this region is essential for CARMA1 regulating its localization at the membrane and its state of oligomerization. The N-terminal domain of CARMA1 is responsible for the activation and recruitment (CARD) of different proteins. Indeed the CARD domain is responsible for the interaction with B-cell CLL-lymphoma 10 (Bcl10) which per se mediates activation of NF-kB and JNK. The N-terminal domain is structurally followed by a coiled-coil domain which is responsible for the oligomerization state of CARMA1 and can regulate the binding of this last to the mucosa-associated lymphoma translocation gene1 (MALTA1) (essential for the activation of NF-kB). Finally the linker region between the coiled-coil domain and the MAGUK domain appears to play an important role in restraining the conformation of CARMA1 in a "closed" (inactive) form. On the contrary the phosphorylation of the serine residues of this zone produced by PKCθ (and other kinases see Table 1) promotes a high level of CARM1 activation with the following boost of the NF-κB signaling pathway. The negatively regulation of this pathway is operated by PP2A, which remove the phosphorylation of CARMA1 at the specific residue 5645.

The stimulation of TCR after recognizing the antigen is linked to the recruitment of CD28 which leads to the activation of PKCθ, which in turn phosphorylates and activates CARMA1. Once activated CARMA1 binds to Bcl10 via CARD-CARD interactions; this binary complex recruits MALT1 to form a ternary complex: CARMA1-Bcl10-MALT1 (CBM). The CBM complex is necessary for the activation of the NF-κB and JNK. All the proteins reported in Table 1 have been characterized for their interactions with CARMA1 at different level and in different roles (see FIG. 21).

TABLE 1

Proteins that Interact with the CARMA1 signalosome

| KINASES | UBIQUITIN LIGASES | OTHER |
| --- | --- | --- |
| PKCq | UBC13-UEV1A | Bcl10 |
| IKK Complex | TRAF6 | MALT1 |
| PDK1 | TRAF2 | ADAP |
| CaMKII | cIAP2 | Caspase 8 |
| HPK1 | NEDD4 | Net1 |
| CK1a | ITCH | |
| Akt | CBL-b | |
| TAK1 | COP9 | |
| RIP2 | STUB1 | |
| MKK7 (JNK activation) | CYLD | |
| | (de-ubiquitylating enzyme) | |
| Calcineurin (phosphatase) | A20 | |
| | (de-ubiquitylating enzyme) | |
| PP2A (phosphatase) | | |

Split-Protein Based Systems

In a first example, the inventor plan to use one of the kinases listed in Table 2 as system of split proteins which once reconstituted (after co-localization of two CARs) will phosphorylate the serine residues on the linker region of the CARMA1 protein giving the start signal to the NF-κB and JNK. The generation of a split kinase has been already reported with success in the case of a thymidine kinase (Massoud, Paulmurugan et al. 2010).

TABLE 2

| CARMA1 Phosphorylation Sites (Thome, Charton et al. 2010). | | | | | | | | | |
|---|---|---|---|---|---|---|---|---|---|
| Human CARMA1 | S109 | T110 | S551 | S552 | S555 | S565 | S608 | S637 | S645 |
| Kinase | CaMKII | PKCq | HPK1 | PKCθ | IKKβ | ? | CK1α | PKCθ | PKCθ |
| Effect of Mutation | | | | | | | | | |
| NF-κB | ↓ | ↓ | ↓ | ↓ | ↓ | ↓ | ↑ | Normal | ↓ |
| JNK | ? | ↓ | ? | ↓ | ↓ | ? | Normal | ? | ↓ |

Scaffolding Protein Systems

In addition to its carboxy-terminal MAGUK-like features, CARMA1 contains a CARD motif and a coiled coil domain that are functionally crucial. CARD motifs are protein-protein interaction domains that can mediate homotypic CARD/CARD interactions between two, or possibly even three CARD containing binding partners. The CARD of CARMA1 mediates homotypic interaction with the adaptor Bcl10 which contains an amino-terminal CARD motif and a Ser/Thr-rich carboxyl terminus of unknown structure. Bcl10 constitutively forms a complex with MALT1 necessary for the activation of JNK and NF-κB (see FIG. 21). Hence a fully reconstituted CARMA1 can be obtained after co-localization of two CARs once harboring the carboxy-terminal MAGUK-like features and a second one the CARD motif and the coiled coil domain; the reconstitution of the CARMA1 will allow the assembly of Bcl10 and MALT1 with the consequent activation of the two endogenous pathways JNK and NF-κB.

Example 2

Generation of Two Types of LCKs to Inhibit and to Stimulate the Signaling Cascade LCK (NCBI Reference Sequence: NP_005347.3) is one of the first molecules to be activated following TCR engagement (Borger, Filby et al. 2013; Borger, Zamoyska et al. 2013; Brownlie and Zamoyska 2013). LCK is constitutively active in T cell maintaining a low level of phosphorylation of the ζ chain of CD3 associated to TCR. LCK binds to the cytoplasmatic domain of CD8 following the interaction between TCR and peptide-MHC, the co-receptor CD8 drives LCK in proximity of the ζ chain of CD3 associated to TCR. The targets of LCK are the tyrosine residues on the ITAM of the TCR associated ζ chain of CD3 but also CD3δ chain, CD3ε chain and ZAP70. The phosphorylation of ZAP70 promotes a conformational change which actives its kinase activity leading to the phosphorylation of LAT (adaptor molecule linker for activation T cells). In turn Lat will recruit multiple downstream adaptors and signaling molecules.

LCK is positively regulates by phosphorylation of an active tyrosine (394 aa) in the catalytic centre which stabilizes an active conformation. On the contrary LCK is also negatively regulated by phosphorylation of a tyrosine in its C-terminal domain (505 aa). The activating tyrosine residue is auto phosphorylated by LCK and dephosphorylated by CD45 and other phosphatase (such as PTPN6, PTPN22). The negatively regulating tyrosine is phosphorylated by CSK and dephosphorylated by CD45.

The possibility to create a mutant of LCK which will be not phosphorylated on the C-terminal tyrosine (505 aa) gives the possibility to engineered LCK in a way to have a constitutively LCK$^{(+)}$ [Y505→X505+Y394]. On the contrary we could create a constitutively negatively regulated LCK$^{(-)}$ if we mutate the Y394 to any other residues (Y394→X394 and Y505). This mutation should avoid the phosphorylation of this position and the consequently it should create a LCK$^{(-)}$.

Thus we can plan a schema in which a first CAR will recognize an antigen of an healthy cell with an inhibitory domain which will stimulate the transcription of a form constitutively negatively regulated of LCK$^{(-)}$. This first CAR will be coupled with a second one which contains a co-stimulatory domains which will activate the transcription of LCK$^{(+)}$ form, producing an high level of activation of the T cell (FIG. 20).

Example 3

Use of Environmental Condition (Hypoxia) to Control HIF1α (a.a. 380-603) mcCAR Fusion Surface Presentation—mRNA Delivery The schematic functioning of the HIFα-system is depicted in FIG. 22 at both conditions (normoxia and hypoxia). In FIG. 23 is shown different CAR architectures (single-chain and multi-chain). In the following experiments, the multi-chain CAR conformation was used.

Constructs and mRNA Preparation

All constructs originated from the pCLS24707 (SEQ ID NO: 1) which encode the α-chain (SEQ ID NO: 2), β-chain (SEQ ID NO: 3) and γ-chain (SEQ ID NO: 4) of the multichain CAR (mcCAR). The sequence coding for the amino acids 380 to 603 of the Hypoxia-inducible factor 1-alpha (HIF1 accession number Q16665, (SEQ ID NO: 5) was synthesized, in two parts, de novo (GeneCust) and cloned, using classical molecular biology technics, downstream the α-chain, using a short -GS-linker (SEQ ID NO: 6) leading to pCLS26580 (SEQ ID NO: 7).

All individual chains were amplified by PCR using oligo pairs α-chain-F/α-chain-R, β-chain-F/β-chain-R, γ-chain-F/γ-chain-R and α-chain-F/α-chain-HIF-R (SEQ ID NO: 8 to 9) prior to mRNA synthesis. mRNA encoding the α-chain, β-chain, γ-chain or α-chain-HIF1 were in vitro transcribed from the PCR product and polyadenylated using the mMessage mMachine T7 Ultra kit (Life technologies) following the manufacturer's instructions. RNAs were purified with RNeasy columns (Qiagen), eluted in cytoporation medium T and quantified by measuring absorbance at 260 nm using a Nanodrop ND-1000 spectrophotometer. Quality of the RNA was verified on a denaturing formaldehyde/MOPS agarose gel.

Transfection

T lymphocytes were transfected by electrontransfer of messenger RNA using an AgilePulse MAX system (Harvard Apparatus) 3 to 6 days after activation. Following removal of activation beads, cells were pelleted, resuspended in cytoporation medium T at >28×106 cells/ml. 5×106 cells were mixed with 27.5 µg total RNA (10 µg α chain, 7.5 µg β chain and 10 µg γ chain) or with 32.5 µg total RNA (15 µg α chain-HIF1, 7.5 µg β chain and 10 µg γ chain) into a 0.4 cm cuvette. The electroporation consisted of two 0.1 ms pulses at 1200 V followed by four 0.2 ms pulses at 130V.

Following electroporation, cells were diluted into 2 mL culture medium and incubated either at 37° C./5% $CO_2$ (referred as normoxia) or at 37° C. with low $O_2$ concentration (referred as hypoxia) for 17 h. Hypoxic conditions were created using an atmosphere generation system (2.5 L AnaeroJAR assembly, Anaerogen 2.5 L, Anaerobic indicator BR0055 Oxoid) as described by the manufacturer. A fraction of the cells from the hypoxia condition were kept and incubated at 37° C./5% $CO_2$ (normoxia) for 4-6 h.

Flow Cytometry

First labelling for the detection of the α-chain was performed with anti-Fab'2-Biotin (goat anti-mouse IgG, Fab'2 fragment specific, 115-066-072, Jackson Immunoresearch) in PBS SVF2%, EDTA 2 mM, azide 0.1% for 20 min at 4° C. followed by a washing step with PBS SVF2% EDTA 2 mM azide 0.1%. Second labelling was performed with Streptavidin-APC in PBS SVF2% EDTA 2 mM azide 0.1% for 20 min at 4° C. followed by a washing step in PBS. Cell viability was monitored using the efluor450 (ebioscience 65-0863-14) in PBS for 20 min 4° C., followed by a washing step with PBS SVF2% EDTA 2 mM azide 0.1%. Flow cytometry was performed using the MACSQUANT (Miltenyi Biotec) and data analysis was performed with the FlowJo software.

The data obtained clearly indicated an improved surface exposition in hypoxic condition (vs normoxia) when the α-chain was fused the HIF1α fragment (FIG. 24).

Example 4

Use of Environmental Condition (Hypoxia) to Prevent Cytotoxicity Induced by HIF1α (a.a. 380-603) mcCAR Fusion Transfection of T-cells was performed as in example 1 with 2 μg total RNA (0.94 μg α chain, 0.47 μg β chain and 0.62 μg γ chain). Surface detection was performed in normoxia and hypoxia as described in Example 3 (FIG. 25A).

The cytolytic activity and specificity of engineered T-cells was assessed (1 day post transfection) using a flow cytometry-based cytotoxicity assay in normoxia. In this assay target cells presenting the CAR target antigen (target+) and target cells not presenting the CAR target antigen (target−) are labelled with either CellTrace™ CFSE or CellTrace™ violet. The mixed target cell populations (1:1 ratio) was co-incubate at 37° C. with various ratio of engineered effector CAR T cells (Effector/Target ratio of 10:1) in a final volume in X-Vivo-15 media, for a 4 h time periods. The whole cell population was recovered and labeled with eFluor780 viability marker before being fixed by 4% PFA. Fixed cells were analyzed by flow cytometry to determine their viability (target+, target- and effector T-cells). Flow cytometry and data analysis were performed as described in Example 3 (FIG. 25B).

Example 5

Use of Environmental Condition (Hypoxia) to Control HIF1α (a.a. 380-603) mcCAR Fusion Surface Presentation and Cytotoxicity—Lentiviral Delivery The alpha-HIF, beta, gamma chains were amplified by PCR, using oligo pairs GAα-chain-F/GAα-chain-HIF-R, GAβ-chain-F/GAβ-chain-R, GAγ-chain-F/GAγ-chain-R respectively (SEQ ID NO: 15 to 20). The three chains were assembled, using the Gibbson assembly protocol (New England Biolabs) in a lentiviral plasmid under the control of an SFFV promoter leading to pCLS26949 (SEQ ID NO: 21). Viral vectors were produced by GIGA-viral vectors (Belgium) from pCLS26949 (SEQ ID NO: 21) and pCLS24707 (SEQ ID NO: 1) encoding the alpha chain without the HIF domain.

Surface Labelling

Following lentiviral transduction, cells were incubated at 37° C./5% $CO_2$ (referred as normoxia). 3 to 10 days post transduction, engineered T-cells were incubated either at 37° C./5% $CO_2$ (referred as normoxia) or at 37° C. with low $O_2$ concentration (referred as hypoxia) for various time periods (1-24 hours). Hypoxic conditions were created as described by the manufacturers using either an atmosphere generation system (2.5 L AnaeroJAR assembly, Anaerogen 2.5 L, Anaerobic indicator BR0055 Oxoid) or the Oxyrase Enzyme System (EC-Oxyrase) or combination of the two methods. Detection of surface presentation of the CAR was performed as described in Example 3.

Induced Cytotoxicity

The cytolytic activity and specificity of engineered T-cells was assessed using a flow cytometry-based cytotoxicity assay in hypoxia or normoxia. In this assay target cells presenting the CAR target antigen (target+) and target cells not presenting the CAR target antigen (target−) are labelled with either CellTrace™ CFSE or CellTrace™ violet. The mixed target cell populations (1:1 ratio) was co-incubate at 37° C. with various ratio of engineered effector CAR T cells (Effector/Target ratio of 10:1 to 1:1) in a final volume in X-Vivo-15 media, for various time periods (4 h to 24 h).

The whole cell population was recovered and labeled with eFluor780 viability marker before being fixed by 4% PFA. Fixed cells were analyzed by flow cytometry to determine their viability (target+, target- and effector T-cells). Flow cytometry and data analysis were performed as described in Example 3.

Example 6

Use of Environmental Condition (Hypoxia) to Control mcCAR Surface Presentation by Alternative HIF1α or HIF3α Domains All constructs originated from the pCLS24707 (SEQ ID NO: 1) which encode the α-chain (SEQ ID NO: 2), β-chain (SEQ ID NO: 3) and γ-chain (SEQ ID NO: 4) of the multichain CAR (mcCAR). The sequence coding for the amino acids 344 to 417 (SEQ ID NO:22) or 530-652 (SEQ ID NO: 23) of the Hypoxia-inducible factor 1-alpha (HIF1 accession number Q16665) were assembled and cloned from de novo synthesized genes (GeneCust) as in Example 1, leading to pCLS26959 and pCLS26960 (SEQ ID NO: 24 to 25) respectively.

The sequence coding for the amino acids 480 to 571 (SEQ ID NO: 26) or 466-571 (SEQ ID NO: 27) of the Hypoxia-inducible factor 3-alpha (HIF3 accession number Q9Y2N7) were assembled and cloned from de novo synthesized genes (GeneCust) as in Example 3, leading to pCLS26961 and pCLS26962 (SEQ ID NO: 28 to 29) respectively.

The sequence coding for the amino acids 380 to 630 of the Hypoxia-inducible factor 1-alpha (HIF1 accession number Q16665, (SEQ ID NO: 5) was assembled and cloned from de novo synthesized genes (GeneCust), using classical molecular biology technics, downstream the α-chain, using a short -EA-linker (SEQ ID NO: 30) leading to pCLS26784 (SEQ ID NO:31).

Synthesis of mRNA, transfection, normoxia or hypoxia conditions, and flow cytometry in were generated and performed as described in Example 3.

The data obtained clearly indicated an improved surface exposition in hypoxic condition (vs normoxia) with the different fusions of HIF1α and HIF3α fragment to the alpha chain (FIG. 26 A-F).

Example 7

Design of a Dual Receptors Gate

In a general aspect, the system is composed of two membrane protein partners that are interacting upon co-localization (triggered by the binding to the two target antigens) and releasing a transmitter protein (FIG. 27).

Assembly of the Membrane Protein Partners

The first membrane protein partner is composed of different blocs (from the N- to the C-termini): (a) a signal sequence for the addressing to the membrane and an antigen-specific targeting regions (SEQ ID NO: 32 to 38), (b) an extracellular spacer domain (so-called hinge) (SEQ ID NO: 39 to 41), (c) a transmembrane domain (SEQ ID NO: 42 to 46), and (d) an intracellular structural and/or signaling linker domain (SEQ ID NO: 47 to 70) and (e1) one of the interacting partner domains (SEQ ID NO: 71 to 77) (FIG. 28).

The second membrane protein partner is composed of different blocs (from the N- to the C-termini): (a) a signal sequence for the addressing to the membrane and an antigen-specific targeting regions (SEQ ID NO: 32 to 38), (b) an extracellular spacer domain (so-called hinge) (SEQ ID NO: 39 to 41), (c) a transmembrane domain (SEQ ID NO: 42 to 46), (d) an intracellular structural and/or signaling linker domain (SEQ ID NO: 47 to 70), (e2) the second interacting partner domain (SEQ ID NO: 78 to 79), (f) a transcription factor composed of a DNA binding domain (SEQ ID NO: 80 to 81) and (g) a transactivation domain (SEQ ID NO: 82 to 82) (FIG. 28). The 2 parts of the split-ubiquitin system is the Nub/Cub in human is depicted by SEQ ID NO:72-77 and NO:79 respectively. The 2 interactor domains TEV of protease system from Tobacco Etch virus are depicted by SEQ ID NO:71 and 78.

The blocs are designed to incorporate at each extremity a type IIs restriction sites (BbsI) that allows enzymatic creation of unique overhangs for each position:

For the first membrane protein partner: atgg-(a)-tccc; tccc-(b)-gata; gata-(c)caga; caga-(d)-gagc; gagc-(e1)-gaat (FIG. 29).

For the second membrane protein partner: atgg-(a)-tccc; tccc-(b)-gata; gata-(c)caga; caga-(d)-gagc; gagc-(e2)-tgga; tgga-(f)-tagc; tagc-(g)-gaat (FIG. 29).

The different blocs are either synthesized de novo (GeneCust), assembled from oligos or amplified by PCR and inserted in either a pUC57 or pJET cloning vectors using classical molecular biology technics. Inserts containing the bloc of interest are amplified from the pUC57 or pJET by PCR with oligonucleotides located a few dozen base pairs upstream and downstream the cloned position (SEQ ID NO: 86 to 89). The PCR products are gel-purified and diluted to 1/40 of their size in base pairs (ng/μl). The sequences coding for the membrane protein partners are assembled in a one-pot reaction by iterative rounds of restriction and ligation (1 cycle: 37° C., 5 min, 45 cycles: 2 min at 37° C., 5 min at 16° C., 1 cycle: 5 min at 37° C., 1 cycle: 10 min at 80° C. and 1 cycle: 2 min at 25° C.) in presence of an pre-digested receiving plasmid (2 μl of each bloc, 1 μl receiving vector at 10 ng/μl, 1 μl ATP at 50 mM, 1 μl BbsI NEB, 1 μL T4 Ligase (5 U/μl), 2 μL T4 Ligase Buffer 10×, total volume 20 μl) (SEQ ID NO: 90) containing a kanamycin resistance gene marker. Examples of assembled membrane protein partners are given (SEQ ID NO: 92 to 147).

mRNA Preparation

The sequence coding for the assembled membrane protein partners are sub-cloned (NcoI and HindIII) in a plasmid under the control of a T7 promoter (SEQ ID NO: 202) using classical molecular biology technics. Alternatively, the sequence coding for the assembled membrane protein partners are amplified by PCR using oligonucleotides pairs bringing a T7 promoter (SEQ ID NO: 149 to 151) using classical molecular biology technics. Additionally, for the mcCAR-based membrane protein partner, the beta and gamma chains are amplified from pCLS24707 (SEQ ID NO: 152) using oligonucleotides β-chain-F/β-chain-R and γ-chain-F/γ-chain-R (SEQ ID NO: 153 to 156).

mRNA encoding the membrane protein partners are in vitro transcribed from the PCR product and polyadenylated using the mMessage mMachine T7 Ultra kit (Life technologies) following the manufacturer's instructions. RNAs are purified with RNeasy columns (Qiagen), eluted in cytoporation medium T and quantified by measuring absorbance at 260 nm using a Nanodrop ND-1000 spectrophotometer. Quality of the RNA is verified on a denaturing formaldehyde/MOPS agarose gel.

Transfection

T lymphocytes are transfected by electrontransfer of messenger RNA using an AgilePulse MAX system (Harvard Apparatus) 3 to 6 days after activation. Following removal of activation beads, cells are pelleted, resuspended in cytoporation medium T at >28×106 cells/ml. 5×106 cells are mixed with 1 to 30 μg total RNA into a 0.4 cm cuvette. The electroporation consisted of two 0.1 ms pulses at 1200 V followed by four 0.2 ms pulses at 130V. Following electroporation, cells are diluted into 2 ml culture medium and incubated either at 37° C./5% $CO_2$.

Flow Cytometry

First labelling for the detection of the membrane protein partners is performed with anti-Fab'2-Biotin conjugated (goat anti-mouse IgG, Fab'2 fragment specific, 115-066-072, Jackson Immunoresearch) in PBS SVF2%, EDTA 2 mM, azide 0.1% for 20 min at 4° C. followed by a washing step with PBS SVF2% EDTA 2 mM azide 0.1%. Second labelling is performed with Streptavidin-APC in PBS SVF2% EDTA 2 mM azide 0.1% for 20 min at 4° C. followed by a washing step in PBS. Cell viability is monitored using the efluor450 (ebioscience 65-0863-14) in PBS for 20 min 4° C., followed by a washing step with PBS SVF2% EDTA 2 mM azide 0.1%. Flow cytometry is performed using the MACSQUANT (Miltenyi Biotec) and data analysis is performed with the FlowJo software.

Examples of surface exposition of different membrane protein partners (SEQ ID NO: 96, 106, 110, 125, 126, 128, 129 and 131) are given in FIG. 30.

Example 8

Dual Receptors Gate Readouts—Lentiviral Delivery

To demonstrate the possibilities of the dual membrane protein partners' strategy, readouts based on the expression of a reporter gene are built. These reporter systems are composed of several repeats of either the TetO (7×) or the Gal4 (5×) operator sequence that are placed upstream of a minimal CMV promoter, allowing expression of an RQR8 or a renilla reporter gene placed downstream of this artificial promoter leading to pCLS26301, pCLS26303, pCLS27049 and pCLS27050 (SEQ ID NO: 157 to 160). These construct are cloned in a lentiviral expression vector. Viral vectors are prepared using the commercially available lentiviral expression systems according to the manufacturer protocols.

To evaluate the possibility to monitor the expression of the RQR8 gene, transactivators composed of a DNA binding domain (TetO or Gal4) and a transcription activation domain (VP64 or NF-kB) are constructed (SEQ ID NO: 161 to 164). Corresponding mRNAs are produced as described in Example 7 and T-cells previously transduced with the reporter systems (readouts) are transfected with these mRNAs coding for the transactivators.

The data obtained clearly indicated the expression of the lentiviral delivered RQR8 cassette by mRNA transfection of the adequate transactivator (FIG. 31).

The membrane protein partners are sub-cloned in a lentiviral plasmid under the control of an SFFV promoter (SEQ ID NO: 165). Alternatively, the assembled membrane protein partners are sub-cloned in a lentiviral production plasmid (under the control of an SFFV promoter (SEQ ID NO: 165)) upstream a 2A cis-acting hydrolase element followed by a reporter marker (e.g. fluorescent proteins). Standard molecular biology technics such as PCR, enzymatic restriction digestion and ligation are applied to create all constructions. Viral vectors are either obtained from commercial providers or prepared using commercially available lentiviral expression systems according to the manufacturer protocols.

The two interacting membrane protein partners are then delivered in T-cell previously transduced with the reporter systems (readouts) as either mRNA (Example 7) or lentiviral vectors or combination of the two. Expression of the reporter system is recorded in presence of target cells presenting antigens for (i) both interacting membrane protein partners, (ii) only one interacting membrane protein partner and (iii) none of the interacting membrane protein partners.

Example 9

Knock-Out of Proteins Involved in the TCR Signaling Pathway

To create a T-cell custom readout system for the dual membrane protein partners strategy, knock-outs of genes coding for proteins involved in the TCR pathway (SEQ ID NO: 166 to 174) are realized using TALEN (SEQ ID NO: 175 to 192). mRNA preparation and transfection is performed as described in Example 7. TALEN activity in T-cells is monitored at the endogenous locus using the enzymatic T7 assay using conventional protocols. The data obtained clearly indicated a high level of targeted mutagenesis at all targeted loci using the designed TALEN (FIG. 32).

The effect of the knock-out on the induced degranulation capacity of the engineered T-cell is assessed. Engineered T-cells are cultured in 96-well plates (80,000 cells/well) in a final volume of 100 µl of X-Vivo™-15 medium (Lonza) for 6 hours at 37° C. with 5% $CO_2$. Cell stimulation is performed with either Human T-Activator CDP/CD28 beads (Life Technologies, #11132D) or PMA (20 ng/ml) and ionomycin (1 uM) or PHA (1.5 µg/mL). CD107a staining was done during cell stimulation, by the addition of an APC-conjugated anti-CD107a antibody (BD Biosciences) together with 1 µg/ml of anti-CD49d (BD Biosciences), 1 µg/ml of anti-CD28 (Miltenyi), and 1× Monensin solution (eBioscience). After the 6 h incubation period, cells were stained with a fixable viability dye (eBioscience) and PE-conjugated anti-CD8 (Miltenyi) and analyzed by flow cytometry. The data obtained clearly indicated a strong staining decrease for the knock-out engineered T-cell relative to WT T-cells (FIG. 33).

Example 10

Complementation of Knock-Outs Using the Membrane Protein Partners Strategy

The gene coding for the KO protein (e.g. ZAP70) (SEQ ID NO: 193) are cloned in the readout systems described in Example 8 in place of the RQR8 or renilla genes. Alternatively, target DNA sequences (SEQ ID NO: 247) of human transcription factors (e.g.: HNF1B and HNF1A) (SEQ ID NO: 195 and 196) are cloned to replace the TetO or the Gal4 operator sequence in the readouts. DNA sequences coding for these human transcription factors (e.g.: HNF1B and HNF1A) are synthesized de novo to create blocs (SEQ ID NO: 197 to 198) compatible with the assembly process of membrane protein partners described in Example 7. Design of TALEN used to perform knock-out of genes (e.g. ZAP70), lentiviral vector production, mRNA preparation, T-cell transfection or transduction of the readouts and membrane protein partners is done as described in Examples 7, 8 and 9. The complementation of the knock-out is monitored using either the degranulation assay or a flow-based cytotoxicity assay in presence of target cells presenting antigens for (i) both interacting membrane protein partners, (ii) only one interacting membrane protein partner and (iii) none of the interacting membrane protein partners.

Example 11

Design of a Bispecific CAR (biCAR) Gate

Assembly of the biCAR Partners

The biCAR partners partner are composed of different blocs (from the N- to the C-termini): (a) a signal sequence for the addressing to the membrane and an antigen-specific targeting domain (b) an extracellular spacer domain (so-called hinge), (c) a transmembrane domain and (d) an intracellular activation and/or costimulatory domain (FIG. 23).

The functioning of such biCAR gates is shown in Figure

Antigen-specific targeting domains are selected from pools of candidates either based on biochemical criteria (e.g. equilibrium dissociation constants ($K_D$), on- and off-rates ($k_{off}$ and $k_{on}$) or randomly as collections or libraries.

The biCARs are either synthesized de novo or assembled as in previous examples. mRNA preparation, transfection and flow cytometry experiments are performed as in previous examples according to the manufacturer recommendations.

The biCAR partners are sub-cloned in a lentiviral plasmid either under the control of the adequate promoter or under the adequate promoter upstream a 2A cis-acting hydrolase element followed by a different reporter marker (e.g. fluorescent proteins) for each biCAR partners (one reporter marker per library). Standard molecular biology technics such as PCR, enzymatic restriction digestion and ligation are applied to create all constructs.

Viral vectors of individual biCARs, collection of biCARs or libraries of biCARs are either obtained from commercial providers or prepared using commercially available lentiviral expression systems according to the manufacturer protocols.

Example 12

Characterization of biCAR Gate System in Immortalized or in Primary T-Cells

Both biCAR partners composing the biCAR gate are delivered in immortalized human T-cells (Jurkat) or in primary T-cells as lentiviral vectors either individually or as libraries.

The transduced T-cells are purified for double positive surface biCAR expression or double positive reporter marker expression using bulk FACS sorting or magnetic separation.

The whole bulk double positive biCAR transduced population is then assessed for target cell driven activation (degranulation) using (i) a model cell line expressing only the $1^{st}$ CAR target antigens and (ii) a model cell line expressing only the $2^{nd}$ CAR target antigen. Populations that present no or weak activation induced by targets cells presenting only one antigen are isolated bulk using FACS sorting or magnetic separation.

These populations are then assessed for target cell driven activation (degranulation) using a model cell line expressing both CAR target antigens. Populations that present medium or strong activation induced by targets cells presenting both CAR antigens are isolated bulk using FACS sorting or magnetic separation.

The identity of both CARs is then confirmed by sequencing (or deep sequencing in case of libraries) using standard molecular biology procedure.

REFERENCES

Andrianantoandro, E., S. Basu, et al. (2006). "Synthetic biology: new engineering rules for an emerging discipline." Mol Syst Biol 2: 2006 0028.

Bauer, S., V. Groh, et al. (1999). "Activation of NK cells and T cells by NKG2D, a receptor for stress-inducible MICA." Science 285(5428): 727-9.

Bierer, B. E., G. Hollander, et al. (1993). "Cyclosporin A and FK506: molecular mechanisms of immunosuppression and probes for transplantation biology." Curr Opin Immunol 5(5): 763-73.

Blonska, M. and X. Lin (2009). "CARMA1-mediated NF-kappaB and JNK activation in lymphocytes." Immunol Rev 228(1): 199-211.

Boch, J., H. Scholze, et al. (2009). "Breaking the code of DNA binding specificity of TAL-type III effectors." Science 326(5959): 1509-12.

Borger, J. G., A. Filby, et al. (2013). "Differential polarization of C-terminal Src kinase between naive and antigen-experienced CD8+ T cells." J Immunol 190(7): 3089-99.

Borger, J. G., R. Zamoyska, et al. (2013). "Proximity of TCR and its CD8 coreceptor controls sensitivity of T cells." Immunol Lett 157(1-2): 16-22.

Brownlie, R. J. and R. Zamoyska (2013). "T cell receptor signalling networks: branched, diversified and bounded." Nat Rev Immunol 13(4): 257-69.

Chen, L. and D. B. Flies (2013). "Molecular mechanisms of T cell co-stimulation and co-inhibition." Nat Rev Immunol 13(4): 227-42.

Doronina, V. A., C. Wu, et al. (2008). "Site-specific release of nascent chains from ribosomes at a sense codon." Mol Cell Biol 28(13): 4227-39.

Epa, V. C., O. Dolezal, et al. (2013). "Structural model for the interaction of a designed Ankyrin Repeat Protein with the human epidermal growth factor receptor 2." PLoS One 8(3): e59163.

Friedrich, K., J. R. Hanauer, et al. (2013). "DARPin-targeting of measles virus: unique bispecificity, effective oncolysis, and enhanced safety." Mol Ther 21(4): 849-59.

Hara, S., Hamada J., Kobayashi C., Kondo Y., Imura N (2001). "Expression and characterization of hypoxia-inducible factor (HIF)-3alpha in human kidney: suppression of HIF-mediated gene expression by HIF-3alpha." Biochem Biophys Res Commun.; 287(4):808-13

Henderson, D. J., I. Naya, et al. (1991). "Comparison of the effects of FK-506, cyclosporin A and rapamycin on IL-2 production." Immunology 73(3): 316-21.

Jena, B., G. Dotti, et al. (2010). "Redirecting T-cell specificity by introducing a tumor-specific chimeric antigen receptor." Blood 116(7): 1035-44.

Jost, C., J. Schilling, et al. (2013). "Structural Basis for Eliciting a Cytotoxic Effect in HER2-Overexpressing Cancer Cells via Binding to the Extracellular Domain of HER2." Structure 21(11): 1979-91.

Kloss, C. C., M. Condomines, et al. (2013). "Combinatorial antigen recognition with balanced signaling promotes selective tumor eradication by engineered T cells." Nat Biotechnol 31(1): 71-5.

Liu, J., M. W. Albers, et al. (1992). "Inhibition of T cell signaling by immunophilin-ligand complexes correlates with loss of calcineurin phosphatase activity." Biochemistry 31(16): 3896-901.

Massoud, T. F., R. Paulmurugan, et al. (2010). "A molecularly engineered split reporter for imaging protein-protein interactions with positron emission tomography." Nat Med 16(8): 921-6.

Moscou, M. J. and A. J. Bogdanove (2009). "A simple cipher governs DNA recognition by TAL effectors." Science 326(5959): 1501.

Park, T. S., S. A. Rosenberg, et al. (2011). "Treating cancer with genetically engineered T cells." Trends Biotechnol 29(11): 550-7.

Roche, M. I., R. A. Ramadas, et al. (2013). "The role of CARMA1 in T cells." Crit Rev Immunol 33(3): 219-43.

Singleton, K. L., K. T. Roybal, et al. (2009). "Spatiotemporal patterning during T cell activation is highly diverse." Sci Signal 2(65): ra15.

Thome, M., J. E. Charton, et al. (2010). "Antigen receptor signaling to NF-kappaB via CARMA1, BCL10, and MALT1." Cold Spring Harb Perspect Biol 2(9): a003004.

Wang, Y. H., K. Y. Wei, et al. (2013). "Synthetic biology: advancing the design of diverse genetic systems." Annu Rev Chem Biomol Eng 4: 69-102.

Wu, J., Y. Song, et al. (1999). "An activating immunoreceptor complex formed by NKG2D and DAP10." Science 285(5428): 730-2.

The invention claimed is:

1. A method for treating cancer in a patient in need thereof comprising administering to said patient an immune cell comprising a multi-chain chimeric antigen receptor (CAR) comprising:
   - an extracellular ligand binding domain capable of recognizing a specific ligand expressed at the surface of a tumor cell, said extracellular ligand binding domain further comprising a hinge selected from CD8β, CD4, CD28, RTK, IgGI, and EpoR2-D2;
   - a transmembrane domain;
   - an intracellular domain comprising a CD3ζ domain; and
   - an oxygen-sensitive polypeptide domain,
   - wherein said multi-chain CAR comprises part of the alpha, beta, and gamma chains from an Fc receptor comprising an amino acid sequence identity greater than 80% to SEQ ID NO: 7, 3 and 4, respectively.

2. The method of claim 1, wherein the multi-chain CAR comprises:
   - part of an alpha-chain comprising a CD8 hinge region as an extracellular domain, an FcRα as a transmembrane domain, and a part of FcRα combined with HIF-Iα or HIF-3α subunit as an intracellular domain;
   - part of a beta-chain comprising an FcRβ as an extracellular domain, a FcRβ transmembrane domain, and a 4-1BB as an intracellular co-stimulation domain; and
   - part of a gamma-chain comprising an FcRγ transmembrane domain, and a CD3 as a intracellular activation domain.

3. The method according to claim 1, wherein the cancer is a solid tumor.

4. The method according to claim 1, wherein said oxygen-sensitive domain is HIF-Iα, HIF-3α, or an amino acid sequence comprising an amino acid sequence identity greater than 80% to SEQ ID NO: 22, 23, 85, or SEQ ID NO:26, 27.

5. The method according to claim 1, wherein said hinge is a CD8a, IgG1 or EpoR-D2 hinge.

6. The method according to claim 1, wherein said extracellular binding domain comprises a scFv directed to an epitope of a cell target antigen EGFRvIII, CS1, CT83, GD3, MSCP, CD19, 5T4, CD123, CD33, CD20, CD30, CD40, disialoganglioside GD2, C-type lectin-like molecule-1 (CLL-1), ductal-epithelial mucine, gp36, TAG-72, glycosphingolipids, glioma-associated antigen, 13-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostaste specific antigen (PSA), PAP, NY-ESO-1, LAGA-Ia, p53, protein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 514, ROR1, Nkp30, NKG2D, tumor stromal antigens, the extra domain A (EDA) and extra domain B (EDB) of fibronectin and the AI domain of tenascin-C (TnC AI) and fibroblast associated protein (fap), LRP6, melamona-associated Chondroitin Sulfate Proteoglycan (MCSP), CD38/CS1, MART1, WT1, MUC1, LMP2, Idiotype, NY-ESO-1, Ras mutant, gp100, proteinase 3, bcr-abl, tyrosinase, hTERT, EphA2, ML-TAP, ERG, NA17, PAX3, ALK, Androgen receptor; a lineage-specific or tissue specific antigen such as CD3, CD4, CD8, CD24, CD25, CD34, CD79, CD116, CD117, CD135, CD123, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV 120), an EBV-specific antigen, a CMV-specific antigen, a HPV-specific antigen, a Lasse Virus-specific antigen, or an Influenza Virus-specific antigen.

7. The method according to claim 1, wherein said extracellular binding domain comprises a scFv having a polypeptide sequence comprising an amino acid sequence identity greater than 80% to SEQ ID NO: 32, 35, 38; SEQ ID NO: 33; SEQ ID NO:34; SEQ ID NO:36 or SEQ ID NO:37.

8. The method according to claim 1, wherein said intracellular domain comprises a linker of a CD3 domain.

9. The method according to claim 1, wherein the CAR further comprises a co-stimulation domain of 4-1BB or CD28.

* * * * *